US012612384B2

(12) United States Patent
Ku et al.

(10) Patent No.: US 12,612,384 B2
(45) Date of Patent: Apr. 28, 2026

(54) HETEROCYCLIC CYP4A INHIBITOR COMPOUNDS AND COMPOSITIONS THEREOF

(71) Applicant: MBD CO., LTD., Suwon-si (KR)

(72) Inventors: Bo Sung Ku, Suwon-si (KR); Ho Sang Moon, Suwon-si (KR); Do Hyeong Na, Seoul (KR); Mi Sun Kim, Gwacheon-si (KR); Han Som Park, Suwon-si (KR)

(73) Assignee: MBD CO., LTD., Suwon-si (KR)

( * ) Notice: Subject to any disclaimer, the term of this patent is extended or adjusted under 35 U.S.C. 154(b) by 375 days.

(21) Appl. No.: 18/289,752

(22) PCT Filed: May 4, 2022

(86) PCT No.: PCT/KR2022/006432

§ 371 (c)(1),
(2) Date: Nov. 7, 2023

(87) PCT Pub. No.: WO2022/235091

PCT Pub. Date: Nov. 10, 2022

(65) Prior Publication Data

US 2024/0287032 A1 Aug. 29, 2024

(30) Foreign Application Priority Data

May 7, 2021 (KR) ........................ 10-2021-0059213

(51) Int. Cl.

| | |
|---|---|
| ***C07D 401/14*** | (2006.01) |
| ***A61K 31/496*** | (2006.01) |
| ***A61K 31/517*** | (2006.01) |
| ***A61P 1/16*** | (2006.01) |
| ***A61P 3/10*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |

(52) U.S. Cl.

CPC .......... *C07D 401/14* (2013.01); *A61K 31/496* (2013.01); *A61K 31/517* (2013.01); *A61P 1/16* (2018.01); *A61P 3/10* (2018.01); *C07D 405/14* (2013.01); *C07D 409/14* (2013.01); *C07D 413/14* (2013.01); *C07D 417/14* (2013.01)

(58) Field of Classification Search

None

See application file for complete search history.

(56) References Cited

U.S. PATENT DOCUMENTS

| | | | | |
|---|---|---|---|---|
| 7,943,768 | B2 * | 5/2011 | Bower | A61P 31/20 514/253.01 |
| 2013/0178458 | A1 | 7/2013 | Lindsley et al. | |

FOREIGN PATENT DOCUMENTS

| | | | | | |
|---|---|---|---|---|---|
| CN | 108358936 | A * | 8/2018 | | C07D 473/34 |
| KR | 10-2007-0031954 | A | 3/2007 | | |
| KR | 10-2013-0017643 | A | 2/2013 | | |
| KR | 10-1886118 | B1 | 9/2018 | | |
| WO | 2006/012173 | A1 | 2/2006 | | |
| WO | 2009/021868 | A2 | 2/2009 | | |
| WO | 2011/073277 | A1 | 6/2011 | | |

OTHER PUBLICATIONS

Korean Journal of Family Practice. 2015, pp. 375-420, 5(3), Republic of Korea.

Yoshihisa Nakatani, et al., Involvement of Endoplasmic Reticulum Stress in Insulin Resistance and Diabetes, The Journal of Biological Chemistry, Jan. 7, 2005, pp. 847-851, vol. 280, No. 1, USA.

Umut Özcan, et al. Endoplasmic Reticulum Stress Links Obesity, Insulin Action, and Type 2 Diabetes, Science, Oct. 15, 2004, pp. 457-461, vol. 306.

Carla J. H., et al. Endoplasmic reticulum stress-induced apoptosis in the development of diabetes: is there a role for adipose tissue and liver?, Apoptosis, Sep. 16, 2009, pp. 1424-1434, vol. 14, Springer.

Decio L. Eizirik, et al. The Role for Endoplasmic Reticulum Stress in Diabetes Mellitus, Endocrine Reviews, Feb. 2008, pp. 42-61, vol. 29(1).

Seung Kew Yoon, Diagnosis and treatment of fatty liver, The Korean Journal of Medicine: 2009, pp. 677-679, vol. 76, No. 6, Korea.

Gab Jin Cheon, et al., Role of pharmacologic treatment of nonalcoholic fatty liver disease: Constraint, Journals of Spring Conference, 2018, pp. 251-256, Korea.

John Willy Haukeland, et al., Metformin in patients with nonalcoholic fatty liver disease: A randomized, controlled trial, Scandinavian Journal of Gastroenterology, 2009, pp. 853-860, vol. 44.

Anna M. Diehl, et al., Cause, Pathogenesis, and Treatment of Nonalcoholic Steatohepatitis, The new england journal of medicine, Nov. 23, 2017, pp. 2063-2072, vol. 377, 21.

Arun J. Sanyal, et al., Pioglitazone, Vitamin E, or Placebo for Nonalcoholic Steatohepatitis, The new England journal of medicine, May 6, 2010, pp. 1675-1685, vol. 362, 18.

Huifang Gao, et al., CYP4A11 is involved in the development of nonalcoholic fatty liver disease via ROS-induced lipid peroxidation and inflammation, International Journal Of Molecular medicine, 2020, pp. 1121-1129, vol. 45.

N. L. Allinger, et al., Conformational Analysis. LXXVIIL the Conformation of Phenylcyclohexane, and Related Molecules, pp. 3259-3262, vol. 35, Jun. 8, 1971. Pergamon Press. Printed in Great Britain.

(Continued)

*Primary Examiner* — Sarah Pihonak
*Assistant Examiner* — Donna M Nestor
(74) *Attorney, Agent, or Firm* — Harvest IP LAW LLP

(57) ABSTRACT

The present invention relates to a novel quinoline or quinazoline compound and the use thereof. The compound according to the present invention shows an excellent inhibitory activity against cytochrome P450 4A (CYP4A) and thus may be utilized for preventing, relieving or treating metabolic diseases.

13 Claims, 2 Drawing Sheets

(56) References Cited

OTHER PUBLICATIONS

Norio Miyaura, et al. A New Stereospecific Cross-Coupling by the Palladium-Catalyzed Reaction of 1-Alkenylboranes With 1-Alkenyl or I-Alkynyl Halides, Jun. 2, 1979, pp. 3437-3440. vol. 36, Sapporo, Japan.

Norio Miyaura, et al., Stereoselective Synthesis of Arylated (E)-Alkenes by the Reaction of Alk-1-enylboranes with Aryl Halides in the Presence of Palladium Catalyst, J.C.S. Chem. Comm., Jan. 1, 1979, pp. 866-867, Japan.

Adam B. Mayerson, et al., The Effects of Rosiglitazone on Insulin Sensitivity, Lipolysis, and Hepatic and Skeletal Muscle Triglyceride Content in Patients With Type 2 Diabetes, Diabetes, Mar. 2002, pp. 797-802, vol. 51.

Kitt Falk Petersen, et al., Reversal of Nonalcoholic Hepatic Steatosis, Hepatic Insulin Resistance, and Hyperglycemia by Moderate Weight Reduction in Patients With Type 2 Diabetes, Diabetes, Mar. 2005, pp. 603-608, vol. 54.

* cited by examiner

[Figure 1]
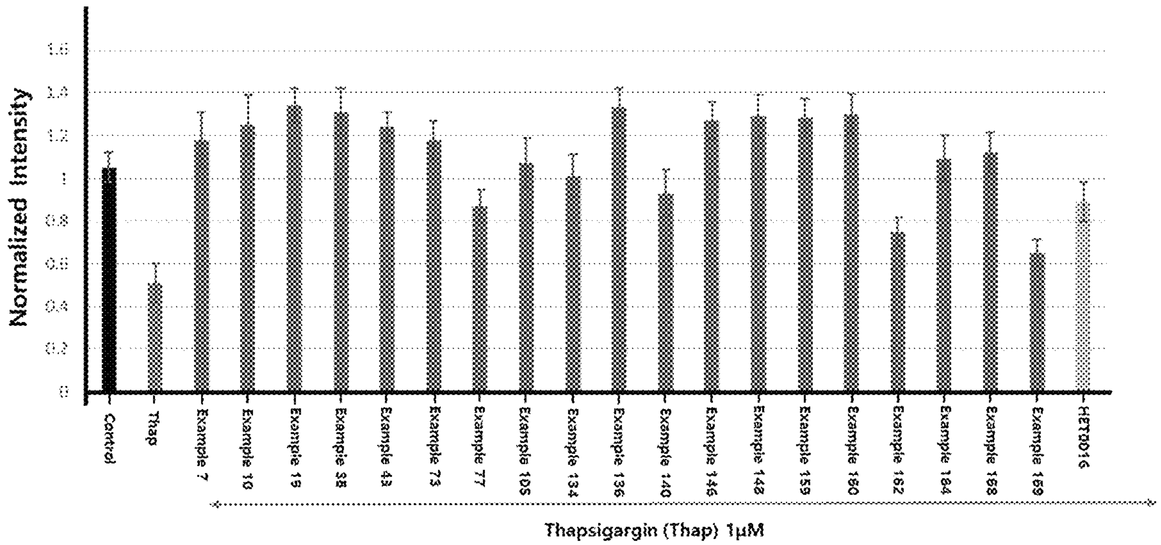
[Figure 2]
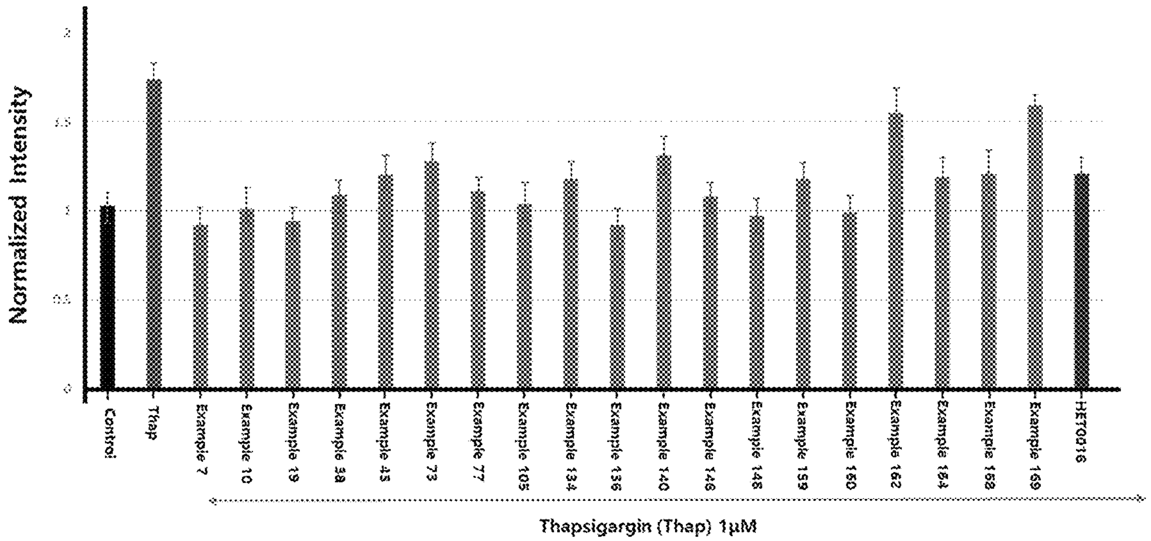

[Figure 3]
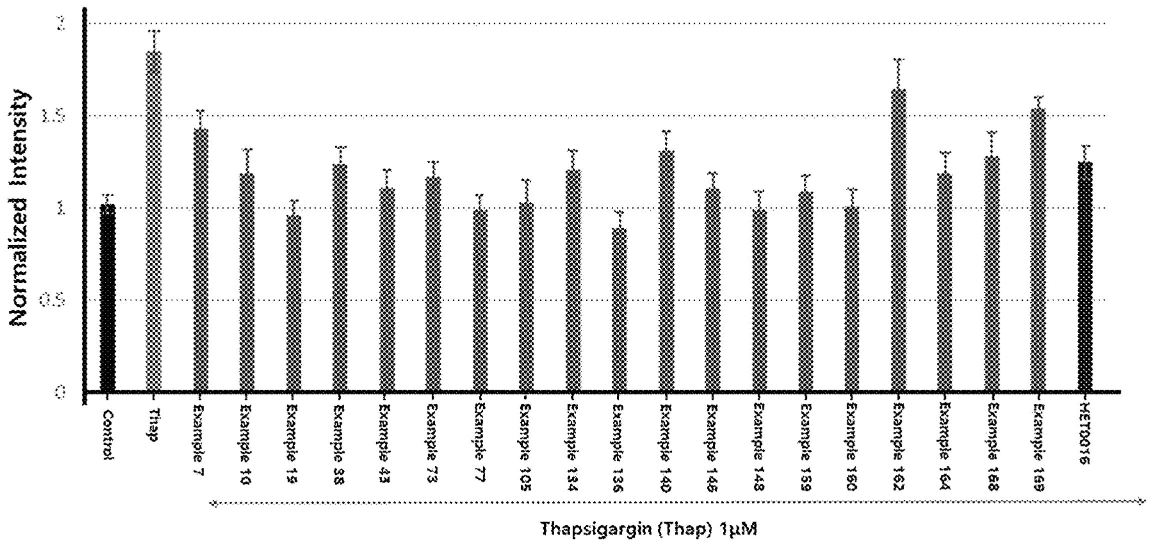

HETEROCYCLIC CYP4A INHIBITOR COMPOUNDS AND COMPOSITIONS THEREOF

CROSS-REFERENCE TO RELATED APPLICATIONS

This application claims the benefit under 35 U.S.C. section 371, of PCT International Application No. PCT/KR2022/006432, filed on May 4, 2022, which claims foreign priority to Korean Patent Application No. 10-2021-0059213, filed on May 7, 2021, in the Korean Intellectual Property Office, both of which are hereby incorporated by reference in their entireties.

TECHNICAL FIELD

The present invention relates to a novel quinoline or quinazoline compound and use thereof. The compound according to the present invention exhibits excellent inhibitory activity against cytochrome P450 4A (CYP4A) and can be effectively used in the prevention, improvement or treatment of metabolic diseases.

BACKGROUND ART

In accordance with an increase in the obese population due to eating habits and lifestyles in modern society, the prevalence of diabetes, fatty liver, dyslipidemia, hypertension and the like, which are classified as metabolic diseases (metabolic syndrome), is continuously increasing. The cause of metabolic diseases (metabolic syndrome) is not clear, but it is assumed that insulin resistance is the fundamental problem. Insulin resistance is when the body's response to insulin—a hormone that lowers blood sugar levels—is decreased, it is difficult for muscle and fat cells to absorb glucose. To solve this problem, more insulin is secreted, thereby increasing the risk of diseases such as diabetes and fatty liver (Korean J Fam Pract. 2015; 5; 375-420). Although the mechanisms underlying insulin resistance are unclear, it has been suggested that endoplasmic reticulum (ER) stress is a novel mechanism for the development of insulin resistance in obese individuals (Science 2004; 306; 457-461, J Biol Chem 2005; 280; 847-851). ER stress has been reported to be caused by disruption of $Ca^{2+}$ homeostasis, overload of protein/lipid biosynthesis, and oxidative stress. Recently, it has been shown that ER stress and the unfolded protein response (UPR) pathway play a role in the pathogenesis of diabetes (Apoptosis 2009; 14; 1424-1434, Endocr Rev 2008; 29; 42-61). However, the exact mechanism that directly regulates the UPR pathway has not yet been revealed.

Diabetes—which is one of the major metabolic diseases (metabolic syndrome)—is a disease in which the insulin secreted by the pancreas is insufficient or insulin does not function properly in the body. Therefore, the blood sugar in the blood cannot be used as energy and accumulates in the blood, causing symptoms of high blood sugar. There are two main types of diabetes. Type 1 diabetes is a disease in which the beta cells of the pancreas which secrete insulin are gradually destroyed and eventually no longer secrete insulin. It mainly occurs in children, but can also occur in adults. Treatment for type 1 diabetes mainly consists of injecting insulin several times a day, and testing blood sugar levels several times to adjust the insulin dosage. This is because excess insulin causes hypoglycemia and damage to the brain or other functions.

Type 2 diabetes patients account for more than 90% of all diabetes patients and are caused by insulin resistance and progressive insulin secretion defects. It is divided into cases where insulin resistance predominates (accompanied by obesity) and cases where insulin secretion deficiency predominates (accompanied by low body weight), and long-term blood sugar management that takes into account the complex etiology is required. Type 2 diabetes treatment includes 1) insulin-releasing drugs that directly stimulate insulin secretion but have the risk of causing hypoglycemia, 2) mealtime insulin-releasing drugs that stimulate glucose-stimulated insulin secretion but must be taken before each meal, 3) biguanides, including metformin, which inhibit hepatic gluconeogenesis (which is greatly elevated in diabetes), 4) insulin sensitizers such as ciglitazone and pioglitazone, which are thiazolidinedione derivatives that improve peripheral responsiveness to insulin but have side effects such as weight gain, edema, and hepatotoxicity, and 5) insulin injections, which are often required in the late stages of diabetes when pancreatic islets fail under chronic high stimulation (Korean Academy of Medical Sciences, 2014).

Fatty liver, another major metabolic disease (metabolic syndrome), refers to the accumulation of fat in liver cells due to excessive intake of fat or endogenous increase in fat synthesis or decrease in fat excretion within the liver. Fatty liver can be broadly divided into alcoholic fatty liver and non-alcoholic fatty liver. Alcoholic fatty liver disease can be influenced by alcohol intake, genetic ability to metabolize alcohol, and nutritional status. Alcoholic fatty liver disease may progress to alcoholic hepatitis or cirrhosis, eventually leading to liver cancer or end-stage liver failure. Non-alcoholic fatty liver disease (NAFLD) refers to a disease in which neutral fat accumulates in the liver regardless of drinking, and includes simple fatty liver (steatosis) and non-alcoholic steatohepatitis (NASH) (Non-patent document 3). Simple fatty liver disease is clinically considered a benign disease with a good prognosis, but NASH is a progressive liver disease and is recognized as a precursor disease that causes cirrhosis or liver cancer (Korean Journal of Medicine, 2009; 76; 6; 677-679).

Meanwhile, as described above, there are many reported cases of non-alcoholic fatty liver disease (NAFLD)/fatty liver, steatohepatitis, steatohepatitis-associated cirrhosis due to insulin resistance and diabetes. As such, the treatment mechanisms and strategies for the above diseases may be fundamentally similar, but there is controversy as to whether it can be shown the effective level of treatment efficacy for liver diseases such as steatohepatitis irrespective of the effect of reducing insulin resistance, depending on the specific treatment drugs. Up to now, there are no drugs approved as a treatment for non-alcoholic fatty liver disease. Therapeutic agents for steatohepatitis or non-alcoholic fatty liver-related cirrhosis are absolutely necessary. However, to date, there are no approved drugs that are effective and safe for improving fibrosis. Many studies are currently being conducted, and effects have been observed in some cases, but there are still limitations to clinical application. For example, in the case of metformin—which is used to treat type 2 diabetes, it was reported that there was no histological improvement effect on steatohepatitis in a study of adult and pediatric NASH (non-alcoholic steatohepatitis) patients (Non-patent document 1, Non-patent document 2). It was also reported that administration of pioglitazone did not improve liver fibrosis (Non-patent document 4).

Therefore, there is a need for the development of therapeutic agents that exhibit effective effects in various aspects for metabolic diseases (metabolic syndrome) such as diabetes and fatty liver disease.

CYP4A (cytochrome P450 4A) is mainly distributed in the endoplasmic reticulum (ER) membrane of the liver and is a representative membrane protein involved in liver detoxification and drug metabolism. It has been reported that CYP4A is overexpressed in patients with non-alcoholic fatty liver disease and animal models of various metabolic diseases. Through excessive fatty acid metabolism by CYP4A, ROS (reactive oxygen species) production and lipid peroxidation are abnormally induced, and this oxidative stress causes inflammation and endoplasmic reticulum stress (ER stress). It is known that this causes abnormalities in the metabolic function of the human body, thereby causing metabolic diseases such as type 2 diabetes and non-alcoholic steatohepatitis (Non-patent document 5).

Meanwhile, with respect to CYP4A, for example, Korean Patent Application Publication No. 10-2013-0017643 and Korean Patent Publication No. 10-1886118 disclose a pharmaceutical composition for the treatment or prevention of diabetes comprising a CYP4A inhibitor as an active ingredient and a composition for preventing or treating diabetes and fatty liver disease comprising a CYP4A inhibitory compound as an active ingredient, respectively.

PRIOR ART DOCUMENTS

Patent Documents

Patent document 1: Korean Patent Application Publication No. 10-2013-0017643

Patent document 2: Korean Patent Publication No. 10-1886118

Non-Patent Documents

Non-patent document 1: Gab Jin CHEON, Young Don KIM, Role of pharmacologic treatment of nonalcoholic fatty liver disease: Constraint, The Korean Association of Internal Medicine, Journals of Spring Conference 2018, 251-256

Non-patent document 2: Haukeland J W et al., Metformin in patients with nonalcoholic fatty liver disease: a randomized, controlled trial. Scand J Gastroenterol 2009; 44:853-860

Non-patent document 3: Anna M. Diehl et al., Cause, Pathogenesis, and Treatment of Nonalcoholic Steatohepatitis. The New England Journal of Medicine 2017; Nov. 23: 2063-2072

Non-patent document 4: Arun J. Sanyal et al., Pioglitazone, Vitamin E, or Placebo for Nonalcoholic Steatohepatitis, N Engl J Med 2010; 362:1675-1685

Non-patent document 5: HUIFANG GAO et al., CYP4A11 is involved in the development of nonalcoholic fatty liver disease via ROS-induced lipid peroxidation and inflammation. INTERNATIONAL JOURNAL OF MOLECULAR MEDICINE 2020; 45: 1121-1129

DISCLOSURE OF INVENTION

Technical Problem

Accordingly, the technical problem to be solved by the present invention is the provision of a novel heterocycle-based compound that exhibits excellent CYP4A inhibitory effects, or a racemate, a diastereomer, a geometric isomer, a stereoisomer, a tautomer, a hydrate or a pharmaceutically acceptable salt thereof.

In addition, another technical problem to be solved by the present invention is the provision of a pharmaceutical composition for the prevention or treatment of metabolic disease comprising the novel heterocycle-based compound, or a racemate, a diastereomer, a geometric isomer, a stereoisomer, a tautomer, a hydrate or a pharmaceutically acceptable salt thereof as an active ingredient.

Solution to Problem

To solve the above technical problem, the present invention provides a compound of the following Formula (1), or a racemate, a diastereomer, a geometric isomer, a stereoisomer, a tautomer, a hydrate or a pharmaceutically acceptable salt thereof:

[Formula (1)]

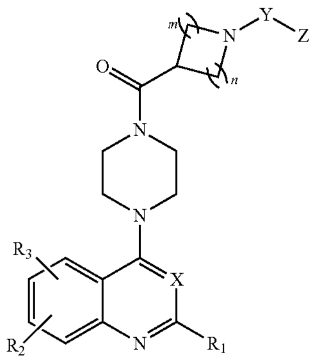

wherein $R_1$ and $R_2$ are each independently hydrogen, hydroxy, halo, amino, alkyl, haloalkyl or alkoxy;

$R_3$ is hydrogen or halo;

X is CH or N;

m and n are each independently an integer of 1 to 3;

Y is —S(═O)$_2$—, —C(═O)—, —S(═O)— or alkylene; wherein the alkylene may be substituted with one or more substituents selected from hydroxy, alkyl and alkoxy; and Z is alkyl, cycloalkyl, aryl or heteroaryl; wherein the alkyl, cycloalkyl, aryl and heteroaryl may be substituted with one or more substituents selected from halo; hydroxy; nitro; amino; alkyl; haloalkyl; hydroxyalkyl; alkylamino; dialkylamino; alkoxy; alkylcarbonyl; aminocarbonyl; carboxy; carboxyamino; carboxyalkyl; alkoxycarbonyl; alkoxyalkyl; aminoalkyl; alkylcarbonylamino; alkylcarbonylalkyl; alkylaminocarbonyl; dialkylaminocarbonyl; alkylaminoalkyl; dialkylaminoalkyl; aminocarbonylalkyl; alkylaminocarbonylalkyl; dialkylaminocarbonylalkyl; aryl unsubstituted or substituted with hydroxy, amino or alkyl; heterocycloalkyl unsubstituted or substituted with hydroxy, amino, alkyl, hydroxyalkyl, alkylcarbonyl or alkylcarbonyloxy; and heteroaryl unsubstituted or substituted with hydroxy or alkyl; and wherein the heteroaryl and heterocycloalkyl have one or more heteroatoms selected from N, O and S;

provided that when m or n is 3, Y is —S(═O)$_2$— and Z is phenyl; X is N.

The present invention is described in detail hereinafter.

The following terms in the present invention have the meanings described below unless otherwise indicated. Any undefined terms have meanings understood in the art.

In the present invention, the term "hydroxy" group refers to —OH.

In the present invention, the term "halo," either alone or in combination with additional terms (for example, haloalkyl), refers to a radical of fluorine (F), chlorine (Cl), bromine (Br) or iodine (I).

In the present invention, the term "nitro" group refers to —$NO_2$.

In the present invention, the term "carboxy" group refers to —COOH.

In the present invention, the term "carboxyamino" group refers to —NHCOOH.

In the present invention, the term "amino", alone or in combination, may refer to a primary, secondary or tertiary amino group bonded through a nitrogen atom. In the present invention, the secondary amino group may mean having an alkyl substituent, and the tertiary amino group may mean having two similar or different alkyl substituents. It is not limited thereto, but examples include —$NH_2$, methylamino, ethylamino, dimethylamino, diethylamino or methyl-ethyl-amino.

In the present invention, the term "alkyl," either alone or in combination with additional terms (for example, haloalkyl), refers to a radical of a linear or branched chain, saturated aliphatic hydrocarbon group having, for example, 1 to 7 carbon atoms or 1 to 5 carbon atoms. For example, the alkyl may include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl and the like, but is not limited thereto.

In the present invention, the term "alkoxy" refers to alkyloxy (—O-alkyl group) having, for example, 1 to 7 carbon atoms or 1 to 5 carbon atoms.

In the present invention, the term "alkylene" refers to a divalent straight or branched chain radical of a saturated aliphatic hydrocarbon group having, for example, 1 to 7 carbon atoms or 1 to 5 carbon atoms.

In the present invention, the term "hydroxyalkyl" refers to an alkyl group substituted with hydroxy.

In the present invention, the term "carbonyl" refers to —C(═O)—.

In the present invention, the term "sulfinyl" refers to —S(═O)—.

In the present invention, the term "sulfonyl" means to —S(═O)$_2$—.

In the present invention, the term "cycloalkyl" refers to a radical of a cyclic, saturated aliphatic hydrocarbon group having, for example, 3 to 10 carbon atoms or 3 to 8 carbon atoms.

Typical examples of cycloalkyl group may include cyclopropyl, cyclobutyl, cyclopentyl and cyclohexyl, but is not limited thereto.

In the present invention, the term "aryl" refers to an aromatic hydrocarbon group having, for example 6 to 10 carbon atoms. For example, the aryl may include phenyl and naphthyl, but is not limited thereto.

In the present invention, the term "heteroaryl" refers to, for example 5- to 10-membered or 5- to 9-membered aromatic hydrocarbons which form a single or fused ring—which may be fused with benzo or cycloalkyl-including one or more heteroatoms selected from N, O and S as a ring member. Examples of heteroaryl include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl or furopyridinyl.

According to one embodiment of the present invention, in the above Formula (1), $R_1$ and $R_2$ are each independently hydrogen, hydroxy, halo, amino, $C_1$-$C_7$ alkyl, halo-$C_1$-$C_7$ alkyl or $C_1$-$C_7$ alkoxy;

$R_3$ is hydrogen or halo;

X is CH or N;

m and n are each independently an integer of 1 to 3;

Y is —S(═O)$_2$—, —C(═O)—, —S(═O)— or $C_1$-$C_7$ alkylene; wherein the alkylene may be substituted with 1 to 4 substituents selected from hydroxy, $C_1$-$C_7$ alkyl and $C_1$-$C_7$ alkoxy;

Z is $C_1$-$C_7$ alkyl, $C_3$-$C_{10}$ cycloalkyl, $C_6$-$C_{10}$ aryl or 5- to 10-membered heteroaryl; wherein the alkyl, cycloalkyl, aryl and heteroaryl may be substituted with 1 to 4 substituents selected from halo; hydroxy; nitro; amino; $C_1$-$C_7$ alkyl; halo-$C_1$-$C_7$ alkyl; hydroxy-$C_1$-$C_7$ alkyl; $C_1$-$C_7$ alkylamino; di($C_1$-$C_7$ alkyl)amino; $C_1$-$C_7$ alkoxy; $C_1$-$C_7$ alkylcarbonyl; aminocarbonyl; carboxy; carboxyamino; carboxy-$C_1$-$C_7$ alkyl; $C_1$-$C_7$ alkoxycarbonyl; $C_1$-$C_7$ alkoxy-$C_1$-$C_7$ alkyl; amino-$C_1$-$C_7$ alkyl; $C_1$-$C_7$ alkylcarbonylamino; $C_1$-$C_7$ alkylcarbonyl-$C_1$-$C_7$ alkyl; $C_1$-$C_7$ alkylaminocarbonyl; di($C_1$-$C_7$ alkyl)aminocarbonyl; $C_1$-$C_7$ alkylamino-$C_1$-$C_7$ alkyl; di($C_1$-$C_7$ alkyl)amino-$C_1$-$C_7$ alkyl; aminocarbonyl-$C_1$-$C_7$ alkyl; $C_1$-$C_7$ alkylaminocarbonyl-$C_1$-$C_7$ alkyl; di($C_1$-$C_7$ alkyl)aminocarbonyl-$C_1$-$C_7$ alkyl; $C_6$-$C_{10}$ aryl unsubstituted or substituted with hydroxy, amino or $C_1$-$C_7$ alkyl; 5- to 10-membered heterocycloalkyl unsubstituted or substituted with hydroxy, amino, $C_1$-$C_7$ alkyl, hydroxy-$C_1$-$C_7$ alkyl, $C_1$-$C_7$ alkylcarbonyl or $C_1$-$C_7$ alkylcarbonyloxy; and 5- to 10-membered heteroaryl unsubstituted or substituted with hydroxy or $C_1$-$C_7$ alkyl; and wherein the heteroaryl and heterocycloalkyl have 1 to 4 heteroatoms selected from N, O and S;

provided that when m or n is 3, Y is —S(═O)$_2$— and Z is phenyl; X is N.

According to one embodiment of the present invention, in the above Formula (1), $R_1$ is hydrogen, halo, $C_1$-$C_5$ alkyl or halo-$C_1$-$C_5$ alkyl.

According to one embodiment of the present invention, in the above Formula (1), $R_2$ is hydrogen, hydroxy, halo, $C_1$-$C_5$ alkyl or $C_1$-$C_5$ alkoxy.

According to one embodiment of the present invention, in the above Formula (1),

Y is —S(═O)$_2$—, —C(═O)—, —S(═O)— or $C_1$-$C_5$ alkylene; wherein the alkylene is unsubstituted or substituted with 1 to 3 substituents selected from hydroxy, $C_1$-$C_5$ alkyl and $C_1$-$C_5$ alkoxy.

According to one embodiment of the present invention, in the above Formula (1),

Z is $C_1$-$C_5$ alkyl, $C_3$-$C_8$ cycloalkyl, $C_6$-$C_{10}$ aryl or 5- to 9-membered heteroaryl; wherein the alkyl, cycloalkyl, aryl and heteroaryl are unsubstituted or substituted with 1 to 3 substituents selected from halo; hydroxy; nitro; amino; $C_1$-$C_5$ alkyl; halo-$C_1$-$C_5$ alkyl; hydroxy-$C_1$-$C_5$ alkyl; $C_1$-$C_5$ alkylamino; di($C_1$-$C_5$ alkyl)amino; $C_1$-$C_5$ alkoxy; $C_1$-$C_5$ alkylcarbonyl; aminocarbonyl; carboxy;

carboxyamino; carboxy-$C_1$-$C_5$ alkyl; $C_1$-$C_5$ alkoxycarbonyl; $C_1$-$C_5$ alkoxy-$C_1$-$C_5$ alkyl; amino-$C_1$-$C_5$ alkyl; $C_1$-$C_5$ alkylcarbonylamino; $C_1$-$C_5$ alkylcarbonyl-$C_1$-$C_5$ alkyl; $C_1$-$C_5$ alkylaminocarbonyl; di($C_1$-$C_5$ alkyl)aminocarbonyl; $C_1$-$C_5$ alkylamino-$C_1$-$C_5$ alkyl; di($C_1$-$C_5$ alkyl)amino-$C_1$-$C_5$ alkyl; aminocarbonyl-$C_1$-$C_5$ alkyl; $C_1$-$C_5$ alkylaminocarbonyl-$C_1$-$C_5$ alkyl; di($C_1$-$C_5$ alkyl)aminocarbonyl-$C_1$-$C_5$ alkyl; $C_6$-$C_{10}$ aryl unsubstituted or substituted with hydroxy, amino or $C_1$-$C_5$ alkyl; 5- to 9-membered heterocycloalkyl unsubstituted or substituted with hydroxy, amino, $C_1$-$C_5$ alkyl, hydroxy-$C_1$-$C_5$ alkyl, $C_1$-$C_5$ alkylcarbonyl or $C_1$-$C_5$ alkylcarbonyloxy; and 5- to 9-membered heteroaryl unsubstituted or substituted with hydroxy or $C_1$-$C_5$ alkyl; and wherein the heteroaryl and heterocycloalkyl have 1 to 3 heteroatoms selected from N, O and S. According to one embodiment of the present invention, the aryl is phenyl; and the heteroaryl may be selected from imidazolyl, triazolyl, tetrazolyl, pyrazolyl, pyridinyl, thienyl, oxazolyl, isoxazolyl, thiazolyl, furyl and pyrimidinyl.

Representative examples of the compound of Formula (1) according to the present invention may include the following compounds, but are not limited thereto:

N-(4-((3-(4-(7-fluoroquinolin-4-yl)piperazine-1-carbonyl)pyrrolidin-1-yl)sulfonyl)phenyl)acetamide;

(R)—N-(4-((3-(4-(7-fluoroquinolin-4-yl)piperazine-1-carbonyl)pyrrolidin-1-yl)sulfonyl)phenyl)acetamide;

(1-((4-(dimethylamino)phenyl)sulfonyl)pyrrolidin-3-yl)(4-(7-fluoroquinolin-4-yl)piperazin-1-yl)methanone;

(4-(7-fluoroquinolin-4-yl)piperazin-1-yl)(1-((4-hydroxyphenyl)sulfonyl)pyrrolidin-3-yl)methanone;

(4-(7-fluoroquinolin-4-yl)piperazin-1-yl)(1-((1-methyl-1H-imidazol-2-yl)sulfonyl)pyrrolidin-3-yl)methanone;

(R)-(4-(7-fluoroquinolin-4-yl)piperazin-1-yl)(1-((1-methyl-1H-imidazol-2-yl)sulfonyl)pyrrolidin-3-yl)methanone;

(S)-(4-(7-fluoroquinolin-4-yl)piperazin-1-yl)(1-((1-methyl-1H-imidazol-2-yl)sulfonyl)pyrrolidin-3-yl)methanone;

(4-(7-fluoroquinolin-4-yl)piperazin-1-yl)(1-((4-nitrophenyl)sulfonyl)pyrrolidin-3-yl)methanone;

N-(3-((3-(4-(7-fluoroquinolin-4-yl)piperazine-1-carbonyl)pyrrolidin-1-yl)sulfonyl)phenyl)acetamide;

(1-((1H-1,2,4-triazol-5-yl)sulfonyl)pyrrolidin-3-yl)(4-(7-fluoroquinolin-4-yl)piperazin-1-yl)methanone;

(1-((3,5-dimethyl-1H-pyrazol-4-yl)sulfonyl)pyrrolidin-3-yl)(4-(7-fluoroquinolin-4-yl)piperazin-1-yl)methanone;

(4-(7-fluoroquinolin-4-yl)piperazin-1-yl)(1-((1,3,5-trimethyl-1H-pyrazol-4-yl)sulfonyl)pyrrolidin-3-yl)methanone;

(1-((1H-imidazol-2-yl)sulfonyl)pyrrolidin-3-yl)(4-(7-fluoroquinolin-4-yl)piperazin-1-yl)methanone;

(4-(7-fluoroquinolin-4-yl)piperazin-1-yl)(1-((1-methyl-1H-imidazol-5-yl)sulfonyl)pyrrolidin-3-yl)methanone;

(4-(7-fluoroquinolin-4-yl)piperazin-1-yl)(1-((4-(oxazol-5-yl)phenyl)sulfonyl)pyrrolidin-3-yl)methanone;

(1-((4-bromophenyl)sulfonyl)pyrrolidin-3-yl)(4-(7-fluoroquinolin-4-yl)piperazin-1-yl)methanone;

(4-(7-fluoroquinolin-4-yl)piperazin-1-yl)(1-((4-(pyridin-4-yl)phenyl)sulfonyl)pyrrolidin-3-yl)methanone;

(R)-(4-(7-fluoroquinolin-4-yl)piperazin-1-yl)(1-((4-(pyridin-4-yl)phenyl)sulfonyl)pyrrolidin-3-yl)methanone;

(S)-(1-((1H-1,2,4-triazol-5-yl)sulfonyl)pyrrolidin-3-yl)(4-(7-fluoroquinolin-4-yl)piperazin-1-yl)methanone;

(1-((5-(tert-butyl)-4H-1,2,4-triazol-3-yl)sulfonyl)pyrrolidin-3-yl)(4-(7-fluoroquinolin-4-yl)piperazin-1-yl)methanone;

N-(4-((3-(4-(quinolin-4-yl)piperazine-1-carbonyl)pyrrolidin-1-yl)sulfonyl)phenyl)acetamide;

(R)—N-(4-((3-(4-(quinolin-4-yl)piperazine-1-carbonyl)pyrrolidin-1-yl)sulfonyl)phenyl)acetamide;

(S)—N-(4-((3-(4-(quinolin-4-yl)piperazine-1-carbonyl)pyrrolidin-1-yl)sulfonyl)phenyl)acetamide;

(1-((6-chloropyridin-3-yl)sulfonyl)pyrrolidin-3-yl)(4-(quinolin-4-yl)piperazin-1-yl)methanone;

(1-((6-phenylpyridin-3-yl)sulfonyl)pyrrolidin-3-yl)(4-(quinolin-4-yl)piperazin-1-yl)methanone;

(1-([2,4'-bipyridin]-5-ylsulfonyl)pyrrolidin-3-yl)(4-(quinolin-4-yl)piperazin-1-yl)methanone;

(1-((6-(3-hydroxyphenyl)pyridin-3-yl)sulfonyl)pyrrolidin-3-yl)(4-(quinolin-4-yl)piperazin-1-yl)methanone;

(1-((6-(4-hydroxyphenyl)pyridin-3-yl)sulfonyl)pyrrolidin-3-yl)(4-(quinolin-4-yl)piperazin-1-yl)methanone;

(1-([2,3'-bipyridin]-5-ylsulfonyl)pyrrolidin-3-yl)(4-(quinolin-4-yl)piperazin-1-yl)methanone;

N-(5-((3-(4-(quinolin-4-yl)piperazine-1-carbonyl)pyrrolidin-1-yl)sulfonyl)pyridin-2-yl)acetamide;

(1-((4-bromophenyl)sulfonyl)pyrrolidin-3-yl)(4-(quinolin-4-yl)piperazin-1-yl)methanone;

(1-((4-(pyridin-3-yl)phenyl)sulfonyl)pyrrolidin-3-yl)(4-(quinolin-4-yl)piperazin-1-yl)methanone;

(1-((4-(2-methylpyrimidin-5-yl)phenyl)sulfonyl)pyrrolidin-3-yl)(4-(quinolin-4-yl)piperazin-1-yl)methanone;

(1-((4-(6-hydroxypyridin-3-yl)phenyl)sulfonyl)pyrrolidin-3-yl)(4-(quinolin-4-yl)piperazin-1-yl)methanone;

(1-((4-morpholinophenyl)sulfonyl)pyrrolidin-3-yl)(4-(quinolin-4-yl)piperazin-1-yl)methanone;

(4-(quinolin-4-yl)piperazin-1-yl)(1-(thiophen-2-ylsulfonyl)pyrrolidin-3-yl)methanone;

(1-((5-methylthiophen-2-yl)sulfonyl)pyrrolidin-3-yl)(4-(quinolin-4-yl)piperazin-1-yl)methanone;

(4-(quinolin-4-yl)piperazin-1-yl)(1-((1,3,5-trimethyl-1H-pyrazol-4-yl)sulfonyl)pyrrolidin-3-yl)methanone;

(1-((3,5-dimethylisoxazol-4-yl)sulfonyl)pyrrolidin-3-yl)(4-(quinolin-4-yl)piperazin-1-yl)methanone;

(1-((2,4-dimethylthiazol-5-yl)sulfonyl)pyrrolidin-3-yl)(4-(quinolin-4-yl)piperazin-1-yl)methanone;

(4-(quinolin-4-yl)piperazin-1-yl)(1-((5-(trifluoromethyl)pyridin-2-yl)sulfonyl)pyrrolidin-3-yl)methanone;

(1-((1H-imidazol-2-yl)sulfonyl)pyrrolidin-3-yl)(4-(quinolin-4-yl)piperazin-1-yl)methanone;

(1-((1H-1,2,4-triazol-5-yl)sulfonyl)pyrrolidin-3-yl)(4-(quinolin-4-yl)piperazin-1-yl)methanone;

(1-((1-methyl-1H-pyrazol-4-yl)sulfonyl)pyrrolidin-3-yl)(4-(quinolin-4-yl)piperazin-1-yl)methanone;

(1-((3,5-dimethyl-1H-pyrazol-4-yl)sulfonyl)pyrrolidin-3-yl)(4-(quinolin-4-yl)piperazin-1-yl)methanone;

(1-((1-methyl-1H-imidazol-4-yl)sulfonyl)pyrrolidin-3-yl)(4-(quinolin-4-yl)piperazin-1-yl)methanone;

N-(4-methyl-5-((3-(4-(quinolin-4-yl)piperazine-1-carbonyl)pyrrolidin-1-yl)sulfonyl)thiazol-2-yl)acetamide;

(R)—N-(4-methyl-5-((3-(4-(quinolin-4-yl)piperazine-1-carbonyl)pyrrolidin-1-yl)sulfonyl)thiazol-2-yl)acetamide;

(S)—N-(4-methyl-5-((3-(4-(quinolin-4-yl)piperazine-1-carbonyl)pyrrolidin-1-yl)sulfonyl)thiazol-2-yl)acetamide;

methyl 3-((3-(4-(quinolin-4-yl)piperazine-1-carbonyl)pyrrolidin-1-yl)sulfonyl)thiophene-2-carboxylate;

(1-((6-methoxypyridin-3-yl)sulfonyl)pyrrolidin-3-yl)(4-(quinolin-4-yl)piperazin-1-yl)methanone;

(1-((6-fluoropyridin-2-yl)sulfonyl)pyrrolidin-3-yl)(4-(quinolin-4-yl)piperazin-1-yl)methanone;

(4-(7-fluoroquinolin-4-yl)piperazin-1-yl)(1-(4-nitrobenzyl)pyrrolidin-3-yl)methanone;

(4-(7-fluoroquinolin-4-yl)piperazin-1-yl)(1-((4-nitrophenyl)sulfonyl)piperidin-4-yl)methanone;
N-(3-((4-(4-(7-fluoroquinolin-4-yl)piperazine-1-carbonyl)piperidin-1-yl)sulfonyl)phenyl)acetamide;
(1-((4-bromophenyl)sulfonyl)piperidin-4-yl)(4-(7-fluoroquinolin-4-yl)piperazin-1-yl)methanone;
(4-(7-fluoroquinolin-4-yl)piperazin-1-yl)(1-((4-(pyridin-4-yl)phenyl)sulfonyl)piperidin-4-yl)methanone;
(4-(7-fluoroquinolin-4-yl)piperazin-1-yl)(1-((4-(pyridin-3-yl)phenyl)sulfonyl)piperidin-4-yl)methanone;
(1-((6-chloropyridin-3-yl)sulfonyl)piperidin-3-yl)(4-(7-fluoroquinolin-4-yl)piperazin-1-yl)methanone;
N-(5-((3-(4-(7-fluoroquinolin-4-yl)piperazine-1-carbonyl)piperidin-1-yl)sulfonyl)pyridin-2-yl)acetamide;
(4-(7-fluoroquinolin-4-yl)piperazin-1-yl)(1-((6-morpholinopyridin-3-yl)sulfonyl)piperidin-3-yl)methanone;
(4-(7-fluoroquinolin-4-yl)piperazin-1-yl)(1-((6-(4-methylpiperazin-1-yl)pyridin-3-yl)sulfonyl)piperidin-3-yl)methanone;
(1-((4-bromophenyl)sulfonyl)piperidin-4-yl)(4-(quinolin-4-yl)piperazin-1-yl)methanone;
(1-((4-(pyridin-4-yl)phenyl)sulfonyl)piperidin-4-yl)(4-(quinolin-4-yl)piperazin-1-yl)methanone;
N-(4-((3-(4-(7-fluoroquinolin-4-yl)piperazine-1-carbonyl)azetidin-1-yl)sulfonyl)phenyl)acetamide;
(4-(7-fluoroquinolin-4-yl)piperazin-1-yl)(1-((4-hydroxyphenyl)sulfonyl)azetidin-3-yl)methanone;
(4-(7-fluoroquinolin-4-yl)piperazin-1-yl)(1-((4-nitrophenyl)sulfonyl)azetidin-3-yl)methanone;
(1-((4-bromophenyl)sulfonyl)azetidin-3-yl)(4-(7-fluoroquinolin-4-yl)piperazin-1-yl)methanone;
(4-(7-fluoroquinolin-4-yl)piperazin-1-yl)(1-((4-(pyridin-4-yl)phenyl)sulfonyl)azetidin-3-yl)methanone;
N-(4-((3-(4-(quinolin-4-yl)piperazine-1-carbonyl)azetidin-1-yl)sulfonyl)phenyl)acetamide;
(4-(7-fluoroquinolin-4-yl)piperazin-1-yl)(1-((3-nitrophenyl)sulfonyl)azetidin-3-yl)methanone;
(1-((3-aminophenyl)sulfonyl)azetidin-3-yl)(4-(7-fluoroquinolin-4-yl)piperazin-1-yl)methanone;
N-(3-((3-(4-(7-fluoroquinolin-4-yl)piperazine-1-carbonyl)azetidin-1-yl)sulfonyl)phenyl)acetamide;
N-(4-((3-(4-(quinazolin-4-yl)piperazine-1-carbonyl)piperidin-1-yl)sulfonyl)phenyl)acetamide;
(4-(quinazolin-4-yl)piperazin-1-yl)(1-tosylpiperidin-3-yl)methanone;
(1-((4-fluorophenyl)sulfonyl)piperidin-3-yl)(4-(quinazolin-4-yl)piperazin-1-yl)methanone;
1-((4-(dimethylamino)phenyl)sulfonyl)piperidin-3-yl)(4-(quinazolin-4-yl)piperazin-1-yl)methanone;
(1-((4-hydroxyphenyl)sulfonyl)piperidin-3-yl)(4-(quinazolin-4-yl)piperazin-1-yl)methanone;
N-(4-(3-(1-(2-methylquinazolin-4-yl)piperazine-4-carbonyl)piperidin-1-ylsulfonyl)phenyl)acetamide;
(4-(2-methylquinazolin-4-yl)piperazin-1-yl)(1-tosylpiperidin-3-yl)methanone;
(1-(4-fluorophenylsulfonyl)piperidin-3-yl)(4-(2-methylquinazolin-4-yl)piperazin-1-yl)methanone;
(1-(4-(dimethylamino)phenylsulfonyl)piperidin-3-yl)(4-(2-methylquinazolin-4-yl)piperazin-1-yl)methanone;
N-(4-(3-(1-(7-chloroquinolin-4-yl)piperazine-4-carbonyl)piperidine-1-carbonyl)phenyl)acetamide;
(4-(7-chloroquinolin-4-yl)piperazin-1-yl)(1-(4-fluorophenylcarbonyl)piperidin-3-yl)methanone;
(4-(7-chloroquinolin-4-yl)piperazin-1-yl)(1-(phenylcarbonyl)piperidin-3-yl)methanone;
(4-(7-chloroquinolin-4-yl)piperazin-1-yl)(1-(cyclohexylcarbonyl)piperidin-3-yl)methanone;
(4-(7-chloroquinolin-4-yl)piperazin-1-yl)(1-(pyridine-4-ylcarbonyl)piperidin-3-yl)methanone;
(4-(7-chloroquinolin-4-yl)piperazin-1-yl)(1-(4-methoxyphenylcarbonyl)piperidin-3-yl)methanone;
N-(4-(3-(4-(7-methoxyquinolin-4-yl)piperazine-1-carbonyl)piperidine-1-carbonyl)phenyl)acetamide;
(1-(4-fluorobenzoyl)piperidin-3-yl)(4-(7-methoxyquinolin-4-yl)piperazin-1-yl)methanone;
(1-benzoylpiperidin-3-yl)(4-(7-methoxyquinolin-4-yl)piperazin-1-yl)methanone;
(4-(7-methoxyquinolin-4-yl)piperazin-1-yl)(1-(cyclohexylcarbonyl)piperidin-3-yl)methanone;
(4-(7-methoxyquinolin-4-yl)piperazin-1-yl)(1-(pyridine-4-ylcarbonyl)piperidin-3-yl)methanone;
(4-(7-methoxyquinolin-4-yl)piperazin-1-yl)(1-(4-methoxyphenylcarbonyl)piperidin-3-yl)methanone;
N-(4-(3-(1-(2-(trifluoromethyl)quinolin-4-yl)piperazine-4-carbonyl)piperidine-1-carbonyl)phenyl)acetamide;
(1-(4-fluorobenzoyl)piperidin-3-yl)(4-(2-(trifluoromethyl)quinolin-4-yl)piperazin-1-yl)methanone;
(1-(cyclohexylcarbonyl)piperidin-3-yl)(4-(2-(trifluoromethyl)quinolin-4-yl)piperazin-1-yl)methanone;
(1-isonicotinoylpiperidin-3-yl)(4-(2-(trifluoromethyl)quinolin-4-yl)piperazin-1-yl)methanone;
(1-(4-methoxybenzoyl)piperidin-3-yl)(4-(2-(trifluoromethyl)quinolin-4-yl)piperazin-1-yl)methanone;
N-(4-(3-(1-(2-methylquinolin-4-yl)piperazine-4-carbonyl)piperidine-1-carbonyl)phenyl)acetamide;
(1-(4-fluorobenzoyl)piperidin-3-yl)(4-(2-methylquinolin-4-yl)piperazin-1-yl)methanone;
(1-benzoylpiperidin-3-yl)(4-(2-methylquinolin-4-yl)piperazin-1-yl)methanone;
(1-(cyclohexylcarbonyl)piperidin-3-yl)(4-(2-methylquinolin-4-yl)piperazin-1-yl)methanone;
(1-isonicotinoylpiperidin-3-yl)(4-(2-methylquinolin-4-yl)piperazin-1-yl)methanone;
N-(4-(3-(4-(7-fluoroquinolin-4-yl)piperazine-1-carbonyl)piperidine-1-carbonyl)phenyl)acetamide;
(1-(4-fluorobenzoyl)piperidin-3-yl)(4-(7-fluoroquinolin-4-yl)piperazin-1-yl)methanone;
(1-benzoylpiperidin-3-yl)(4-(7-fluoroquinolin-4-yl)piperazin-1-yl)methanone;
(1-(cyclohexylcarbonyl)piperidin-3-yl)(4-(7-fluoroquinolin-4-yl)piperazin-1-yl)methanone;
(4-(7-fluoroquinolin-4-yl)piperazin-1-yl)(1-isonicotinoylpiperidin-3-yl)methanone;
(4-(7-fluoroquinolin-4-yl)piperazin-1-yl)(1-(4-methoxybenzoyl)piperidin-3-yl)methanone;
N-(4-(3-(1-(quinolin-4-yl)piperazine-4-carbonyl)piperidine-1-carbonyl)phenyl)acetamide;
(1-(4-fluorophenylcarbonyl)piperidin-3-yl)(4-(quinolin-4-yl)piperazin-1-yl)methanone;
(1-benzoylpiperidin-3-yl)(4-(quinolin-4-yl)piperazin-1-yl)methanone;
(1-(cyclohexylcarbonyl)piperidin-3-yl)(4-(quinolin-4-yl)piperazin-1-yl)methanone;
(1-isonicotinoylpiperidin-3-yl)(4-(quinolin-4-yl)piperazin-1-yl)methanone;
(1-(4-methoxyphenylcarbonyl)piperidin-3-yl)(4-(quinolin-4-yl)piperazin-1-yl)methanone;
(1-(cyclohexylsulfonyl)piperidin-3-yl)(4-(7-fluoroquinolin-4-yl)piperazin-1-yl)methanone;
(4-(7-fluoroquinolin-4-yl)piperazin-1-yl)(1-(1-methyl-1H-imidazol-2-ylsulfonyl)piperidin-3-yl)methanone;
(1-(cyclopropylsulfonyl)piperidin-3-yl)(4-(7-fluoroquinolin-4-yl)piperazin-1-yl)methanone;

(1-(1-methyl-1H-imidazol-2-ylsulfonyl)piperidin-3-yl)(4-(quinolin-4-yl)piperazin-1-yl)methanone;

(1-(cyclohexylsulfonyl)piperidin-3-yl)(4-(quinolin-4-yl)piperazin-1-yl)methanone;

(1-(cyclopropylsulfonyl)piperidin-3-yl)(4-(quinolin-4-yl)piperazin-1-yl)methanone;

(4-(7-chloroquinolin-4-yl)piperazin-1-yl)(1-(furan-2-ylsulfonyl)piperidin-3-yl)methanone;

(4-(7-chloroquinolin-4-yl)piperazin-1-yl)(1-(pyridin-4-ylsulfonyl)piperidin-3-yl)methanone;

(4-(2-methylquinolin-4-yl)piperazin-1-yl)(1-(pyridin-3-ylsulfonyl)piperidin-3-yl)methanone;

(4-(2-methylquinolin-4-yl)piperazin-1-yl)(1-(pyridin-4-ylsulfonyl)piperidin-3-yl)methanone;

(4-(2-methylquinolin-4-yl)piperazin-1-yl)(1-(thiophen-2-ylsulfonyl)piperidin-3-yl)methanone;

(1-(pyridin-4-ylsulfonyl)piperidin-3-yl)(4-(2-(trifluoromethyl)quinolin-4-yl)piperazin-1-yl)methanone;

(1-(pyridin-3-ylsulfonyl)piperidin-3-yl)(4-(2-(trifluoromethyl)quinolin-4-yl)piperazin-1-yl)methanone;

methyl 3-((3-(4-(7-fluoroquinolin-4-yl)piperazine-1-carbonyl)piperidin-1-yl)sulfonyl)propanoate;

(4-(7-fluoroquinolin-4-yl)piperazin-1-yl)(1-((3-hydroxypropyl)sulfonyl)piperidin-3-yl)methanone;

methyl 3-((3-(4-(quinolin-4-yl)piperazine-1-carbonyl)piperidin-1-yl)sulfonyl)propanoate;

(1-((3-hydroxypropyl)sulfonyl)piperidin-3-yl)(4-(quinolin-4-yl)piperazin-1-yl)methanone;

(R)-(1-((1H-1,2,4-triazol-5-yl)sulfonyl)pyrrolidin-3-yl)(4-(7-fluoroquinolin-4-yl)piperazin-1-yl)methanone;

(1-((1H-1,2,4-triazol-5-yl)sulfonyl)piperidin-4-yl)(4-(7-fluoroquinolin-4-yl)piperazin-1-yl)methanone;

(S)-(1-((1H-1,2,4-triazol-5-yl)sulfonyl)pyrrolidin-3-yl)(4-(6-fluoroquinolin-4-yl)piperazin-1-yl)methanone;

(1-((1H-1,2,4-triazol-5-yl)sulfonyl)azetidin-3-yl)(4-(7-fluoroquinolin-4-yl)piperazin-1-yl)methanone;

(S)-(1-((1H-1,2,4-triazol-5-yl)sulfonyl)pyrrolidin-3-yl)(4-(8-fluoroquinolin-4-yl)piperazin-1-yl)methanone;

(S)-(4-(7-fluoroquinolin-4-yl)piperazin-1-yl)(1-((1-methyl-1H-1,2,4-triazol-3-yl)sulfonyl)pyrrolidin-3-yl)methanone;

(S)-(4-(7-fluoroquinolin-4-yl)piperazin-1-yl)(1-((1-(2-hydroxyethyl)-1H-1,2,4-triazol-3-yl)sulfonyl)pyrrolidin-3-yl)methanone;

(S)-(4-(7-fluoroquinolin-4-yl)piperazin-1-yl)(1-((1-isopropyl)-1H-1,2,4-triazol-3-yl)sulfonyl)pyrrolidin-3-yl)methanone;

(S)-1-(3-((3-(4-(7-fluoroquinolin-4-yl)piperazine-1-carbonyl)pyrrolidin-1-yl)sulfonyl)-1H-1,2,4-triazol-1-yl)propan-2-one;

(S)-(4-(7-fluoroquinolin-4-yl)piperazin-1-yl)(1-((1-(2-methoxyethyl)-1H-1,2,4-triazol-3-yl)sulfonyl)pyrrolidin-3-yl)methanone;

(S)-(1-((1-(2-aminoethyl)-1H-1,2,4-triazol-3-yl)sulfonyl)pyrrolidin-3-yl)(4-(7-fluoroquinolin-4-yl)piperazin-1-yl)methanone;

(S)-(4-(7-fluoroquinolin-4-yl)piperazin-1-yl)(1-((1-(2-hydroxyethyl)-1H-1,2,4-triazol-5-yl)sulfonyl)pyrrolidin-3-yl)methanone;

(S)-(1-((1H-imidazol-2-yl)sulfonyl)pyrrolidin-3-yl)(4-(7-fluoroquinolin-4-yl)piperazin-1-yl)methanone;

(R)-(1-((1H-imidazol-2-yl)sulfonyl)pyrrolidin-3-yl)(4-(7-fluoroquinolin-4-yl)piperazin-1-yl)methanone;

(S)-(4-(7-fluoroquinolin-4-yl)piperazin-1-yl)(1-((1-(2-hydroxyethyl)-1H-imidazol-2-yl)sulfonyl)pyrrolidin-3-yl)methanone;

(S)-(4-(7-fluoroquinolin-4-yl)piperazin-1-yl)(1-((1-(2-methoxyethyl)-1H-imidazol-2-yl)sulfonyl)pyrrolidin-3-yl)methanone;

(S)-(1-((1-(2-aminoethyl)-1H-imidazol-2-yl)sulfonyl)pyrrolidin-3-yl)(4-(7-fluoroquinolin-4-yl)piperazin-1-yl)methanone;

(S)-(4-(quinolin-4-yl)piperazin-1-yl)(1-((1,3,5-trimethyl-H-pyrazol-4-yl)sulfonyl)pyrrolidin-3-yl)methanone;

(R)-(4-(quinolin-4-yl)piperazin-1-yl)(1-((1,3,5-trimethyl-TH-pyrazol-4-yl)sulfonyl)pyrrolidin-3-yl)methanone;

(1-(4-nitrobenzyl)pyrrolidin-3-yl)(4-(quinolin-4-yl)piperazin-1-yl)methanone;

(S)-(4-(7-fluoroquinolin-4-yl)piperazin-1-yl)(1-((4-methyl-4H-1,2,4-triazol-3-yl)methyl)pyrrolidin-3-yl)methanone;

(1-((1H-tetrazol-5-yl)methyl)pyrrolidin-3-yl)(4-(7-fluoroquinolin-4-yl)piperazin-1-yl)methanone;

(S)-(4-(7-fluoroquinolin-4-yl)piperazin-1-yl)(1-(pyridin-3-ylsulfonyl)pyrrolidin-3-yl)methanone;

(S)-(4-(7-fluoroquinolin-4-yl)piperazin-1-yl)(1-(pyridin-2-ylsulfonyl)pyrrolidin-3-yl)methanone;

(S)-(4-(7-fluoroquinolin-4-yl)piperazin-1-yl)(1-((4-nitrophenyl)sulfonyl)pyrrolidin-3-yl)methanone;

(S)-(1-((1H-imidazol-2-yl)sulfonyl)pyrrolidin-3-yl)(4-(6-fluoroquinolin-4-yl)piperazin-1-yl)methanone;

(S)-(4-(6-fluoroquinolin-4-yl)piperazin-1-yl)(1-((1-(2-hydroxyethyl)-1H-imidazol-2-yl)sulfonyl)pyrrolidin-3-yl)methanone;

(S)-(1-(4H-1,2,4-triazole-3-carbonyl)pyrrolidin-3-yl)(4-(7-fluoroquinolin-4-yl)piperazin-1-yl)methanone;

(S)-(1-(2H-tetrazole-5-carbonyl)pyrrolidin-3-yl)(4-(7-fluoroquinolin-4-yl)piperazin-1-yl)methanone;

(S)-(1-((1H-1,2,4-triazol-5-yl)sulfonyl)pyrrolidin-3-yl)(4-(7-methylquinolin-4-yl)piperazin-1-yl)methanone;

(S)-(1-((1H-1,2,4-triazol-5-yl)sulfonyl)pyrrolidin-3-yl)(4-(7-hydroxyquinolin-4-yl)piperazin-1-yl)methanone;

(S)-(1-((1H-1,2,4-triazol-5-yl)sulfonyl)pyrrolidin-3-yl)(4-(7-methoxyquinolin-4-yl)piperazin-1-yl)methanone;

(S)-(4-(7-fluoroquinolin-4-yl)piperazin-1-yl)(1-((5-methyl-1H-1,2,4-triazol-3-yl)sulfonyl)pyrrolidin-3-yl)methanone;

(S)-(1-((1H-1,2,4-triazol-5-yl)sulfonyl)pyrrolidin-3-yl)(4-(2-(trifluoromethyl)quinolin-4-yl)piperazin-1-yl)methanone;

(S)-(1-((1H-1,2,4-triazol-5-yl)sulfonyl)pyrrolidin-3-yl)(4-(6,7-difluoroquinolin-4-yl)piperazin-1-yl)methanone; and (S)-(1-((1H-imidazol-2-yl)sulfonyl)pyrrolidin-3-yl)(4-(6,7-difluoroquinolin-4-yl)piperazin-1-yl)methanone.

In one embodiment of the present invention, it can be understood that any of the compounds of Formula (1) provided by the present invention contains more than one chiral center and thus exists in two or more stereoisomeric forms. Racemates of these isomers, individual isomers and mixtures enriched in one enantiomer, diastereomers with two chiral centers, and mixtures partially enriched in specific diastereomers are included within the scope of the present invention. A person skilled in the art will understand that the present invention includes all individual stereoisomers (e.g., enantiomers), racemates or partially resolved mixtures of compounds of formula (1) and, where appropriate, individual tautomers.

In one embodiment of the present invention, the present invention provides compounds containing various "ee" or "de" purities of various stereoisomers—i.e., diastereomeric or enantiomeric purities. In some embodiments, the compound of Formula (1) has an enantiomeric purity of at least 60% ee (e.g., 60%, 65%, 70%, 75%, 80%, 85%, 90%, 91%, 92%, 93%, 94%, 95%, 96%, 97%, 98%, 99%, 99.5%, 99.9% ee, or a range between these enumerated values). In one embodiment, the compound of Formula (1) has an enantiomeric purity of greater than 95% ee and up to 99.9% ee. In one embodiment, the compound of Formula (1) (e.g., as described herein) has a diastereomeric purity of at least 60% de (e.g., 60%, 65%, 70%, 75%, 80%, 85%, 90%, 91%, 92%, 93%, 94%, 95%, 96%, 97%, 98%, 99%, 99.5%, 99.9% de, or a range between these enumerated values). In one embodiment, the compound of Formula (1) (e.g., as described herein) has a diastereomeric purity of greater than 99.9% de.

In the present invention, the term "enantiomeric excess" or "ee" refers to the amount of one enantiomer present compared to other components. In a mixture of R and S enantiomers, it is defined as the percentage of enantiomeric excess, wherein R and S represent the mole or weight ratio of each enantiomer in the mixture and R+S=1. According to the knowledge about the optical rotation of chiral substances, the enantiomeric excess percentage is defined as ([a]obs/[a]max)*100, wherein [a]obs is the optical rotation of the enantiomeric mixture, and [a]max is the optical rotation of the pure enantiomer.

In the present invention, the term "diastereomeric excess" or "de" refers to the amount of one diastereomer present compared to other components, and is defined similarly to the case of enantiomeric excess above. Therefore, for a mixture of diastereomers D1 and D2, the percent diastereomeric excess is defined as wherein D1 and D2 are the mole or weight ratios of each diastereomer in the mixture, and D1+D2=1.

In one embodiment of the present invention, racemic mixture can be used in its own form or after it is resolved into individual isomers. Resolution may yield stereochemically pure compounds or a mixture enriched in one or more isomers. Methods for separating isomers are well known (cf. Allinger N. L. and Eliel E. L., "Topics in Stereochemistry", Vol. 6, Wiley Interscience, 1971), including physical methods such as chromatography using chiral adsorbents. Individual isomers in a chiral form can be prepared from chiral precursors. Alternatively, a diastereomer salt can be formed with a chiral acid (such as a single enantiomer of 10-camphorsulfonic acid, camphoric acid, alpha-bromocamphoric acid, tartaric acid, diacetyltartaric acid, malic acid, pyrrolidone-5-carboxylic acid), and then the mixture is chemically separated to obtain a single isomer. The salt is then graded and crystallized, and one or both of the split bases are freed. This process can be optionally repeated to obtain one or two isomers that essentially do not contain the other isomer, i.e., the desired stereoisomer with an optical purity of at least 91%, 92%, 93%, 94%, 95%, 96%, 97%, 98%, 99%, or 99.5% by weight. Alternatively, after the chiral auxiliary is chemically removed to give the pure enantiomer, the racemate can be covalently attached to the chiral compound (auxiliary) to obtain diastereomers that can be separated by chromatography or fractional crystallization, as is well known to those skilled in the art.

In the present invention, the term "tautomer" is a type of structural isomer of compounds that are easily interconverted by isomerization (tautomerization), which is a rearrangement of a hydrogen atom. A state of chemical equilibrium is achieved due to the rearrangement of hydrogen atoms. Examples include eno-keto, lactam-lactim, amide-eimidic acid, and amine-imine tautomers. Additionally, in the case of heteroaromatic compounds such as triazole, tautomers may be formed due to the movement of hydrogen atoms.

In one embodiment of the present invention, the compound of Formula (1) provided by the present invention includes its salt form, and the salt may preferably be in the form of a pharmaceutically acceptable salt. In the present invention, the term "pharmaceutically acceptable" refers to a property that does not impair the biological activity and physical properties of a compound. In the present invention, the pharmaceutically acceptable salt refers to a group of compounds represented by the Formula (1) that are pharmaceutically acceptable as defined above and have the desired pharmacological activity. Examples of such salts include, but are not limited to, acid addition salts formed with inorganic acids (e.g., hydrochloric acid, hydrobromic acid, sulfuric acid, phosphoric acid, nitric acid, etc.), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid and poly-galacturonic acid. The compounds may also be administered in the form of pharmaceutically acceptable quaternary salts known to those skilled in the art. Specifically, it may include chloride, bromide, iodide, —O— alkyl, toluenesulfonate, methylsulfonate, sulfonate, phosphate, or carboxylates (e.g., benzoate, succinate, acetate, glycolate, maleate, malate, fumarate, citrate, tartrate, ascorbate, cinnamate, mandelate and diphenylacetate).

The present invention also provides a process for preparing the compound of Formula (1). Hereinafter, to facilitate understanding of the present invention, a method for preparing the compound of Formula (1) will be described based on exemplary reaction schemes. However, a person skilled in the art to which the present invention pertains can obtain the compound of Formula (1) by various methods using known compounds or compounds that can be easily prepared therefrom based on the structure of Formula (1), and all of these methods should be construed as falling within the scope of the present invention. That is, the compound of Formula (1) can be prepared by arbitrarily combining various synthetic methods described herein or disclosed in the prior art. Therefore, the following description regarding the method for producing the compound of Formula (1) merely presents exemplary methods, and the order of unit operations, etc. can be selectively changed as needed, and is within the scope of the production method of the present invention. The scope of the preparation method of the present invention is not limited thereto.

[Reaction Scheme 1]
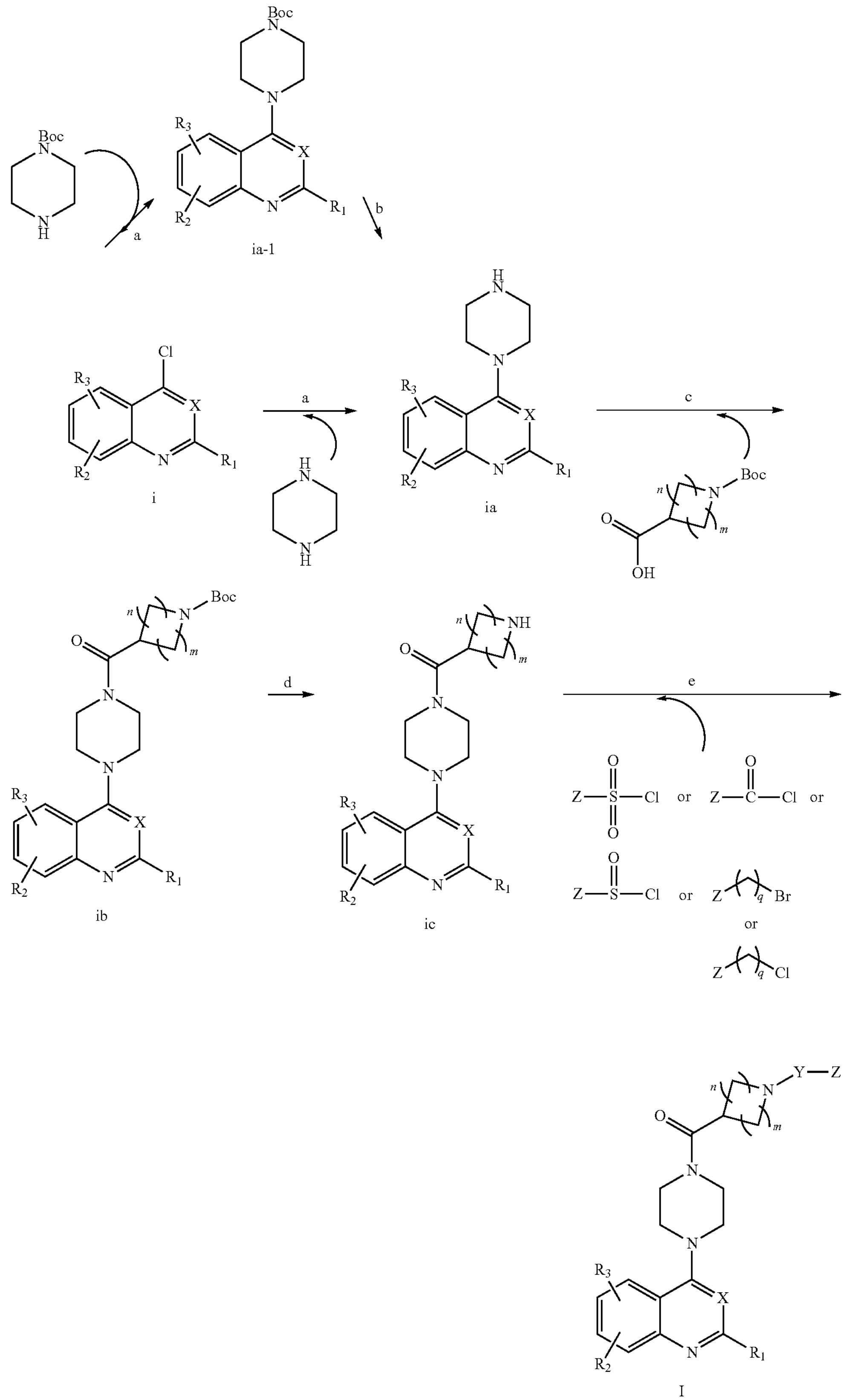

Reaction conditions, a) EtOH or NMP (N-Methyl-2-pyrrolidone), DIEA, 80-110° C., 6-24 hr. b) DCM, TFA or HCl in MeOH, rt, 1-6 hr. c) HATU, DIEA, DMF or DCM, rt, 2-4 hr. or EDCl (1-ethyl-3-(3-dimethylaminopropyl) carbodiimide), HOBt (hydroxybenzotriazole), DIEA, DMF, rt, 2-4 hr. d) TFA, DCM, 20-40° C., 1-3 hr. e) TEA or DIEA, DCM, rt, 2-12 hr.

In the above Reaction Scheme, q is an integer of 1 to 3.

[Reaction Scheme 1-1]

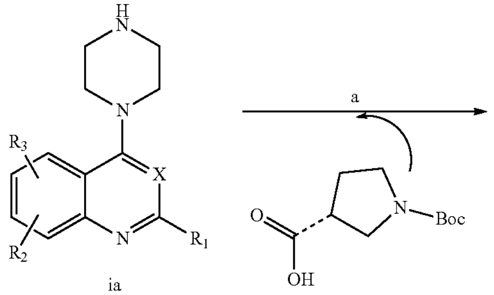

ia

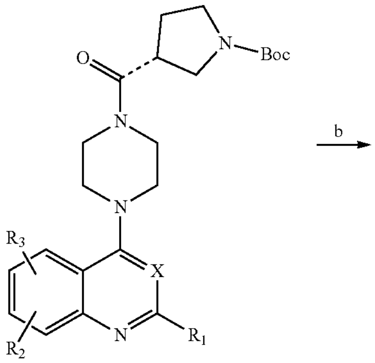

ia-1

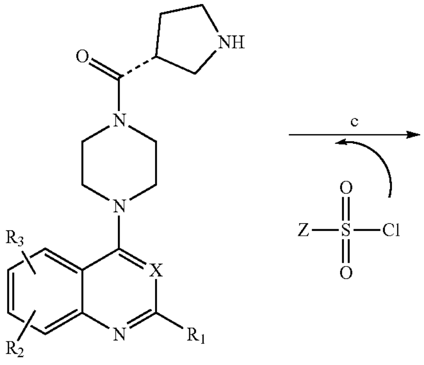

ic-1

-continued

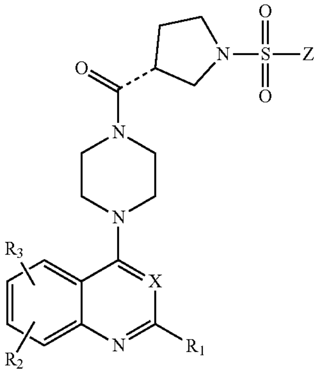
I-1

Reaction conditions, a) HATU, DIEA, DMF or DCM, rt, 1-4 hr. or EDCl (1-ethyl-3-(3-dimethylaminopropyl)carbodiimide), HOBt (hydroxybenzotriazole), DIEA, DMF, rt, 2-4 hr. b) TFA, DCM, 20-40° C., 1-3 hr. c) TEA or DIEA, DCM, rt, 2-12 hr.

Examples of a method for preparing a compound of Formula I-1 according to Reaction Scheme 1-1 is specifically presented in the Examples of the present specification.

[Reaction Scheme 1-2]

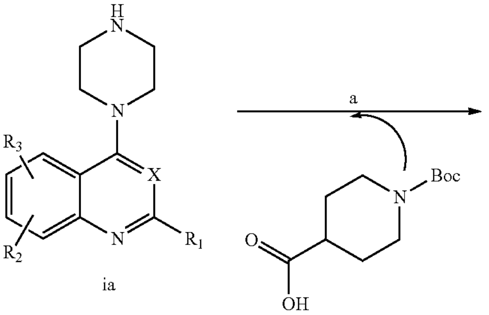

ia

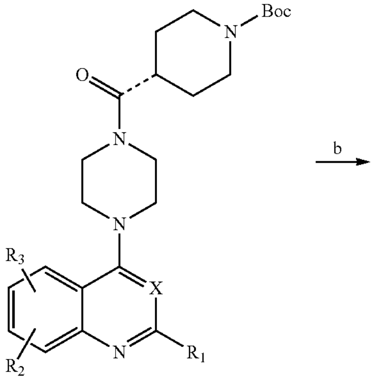

ia-2

-continued

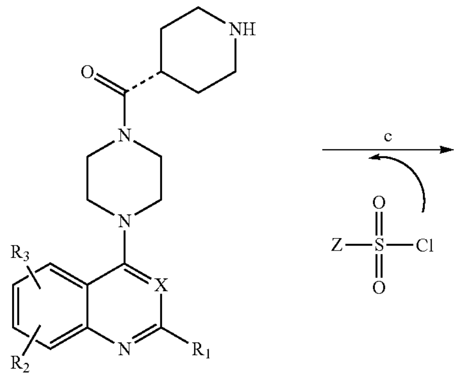

ib-1

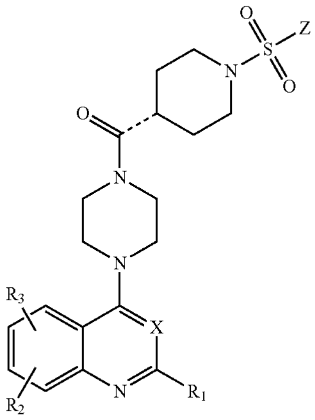

I-2

Reaction conditions, a) HATU, DIEA, DMF or DCM, rt, 1-4 hr. or EDCl (1-ethyl-3-(3-dimethylaminopropyl)carbodiimide), HOBt (hydroxybenzotriazole), DIEA, DMF, rt, 2-4 hr. b) TFA, DCM, 20-40° C., 1-3 hr. c) TEA or DIEA, DCM, rt, 2-12 hr.

[Reaction Scheme 1-3]

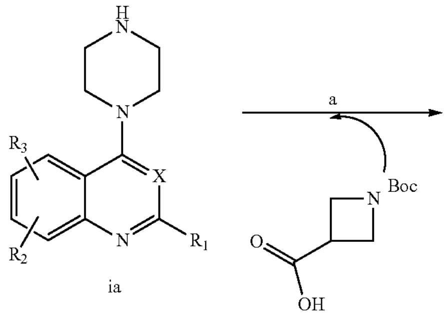

ia

-continued

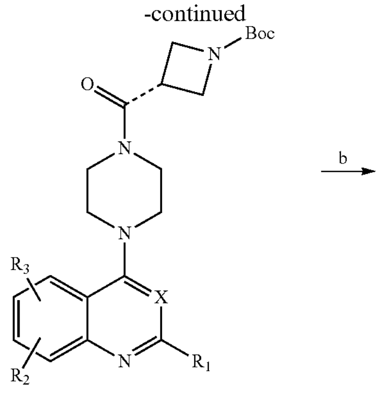

ia-3

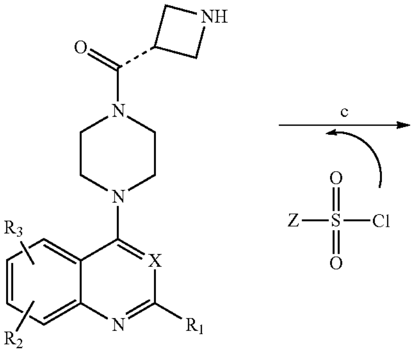

ib-3

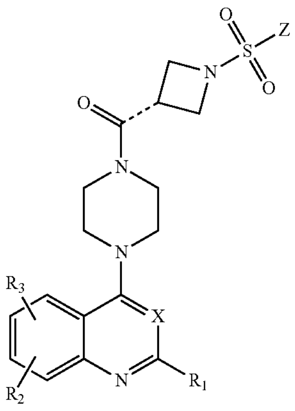

I-3

Reaction conditions, a) HATU, DIEA, DMF or DCM, rt, 1-4 hr. or EDCl (1-ethyl-3-(3-dimethylaminopropyl)carbodiimide), HOBt (hydroxybenzotriazole), DIEA, DMF, rt, 2-4 hr. b) TFA, DCM, 20-40° C., 1-3 hr. c) TEA or DIEA, DCM, rt, 2-12 hr.

[Reaction Scheme 1-4]

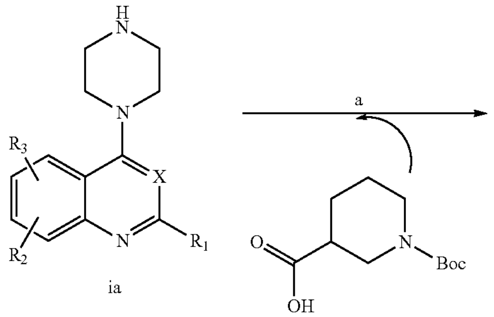

ia

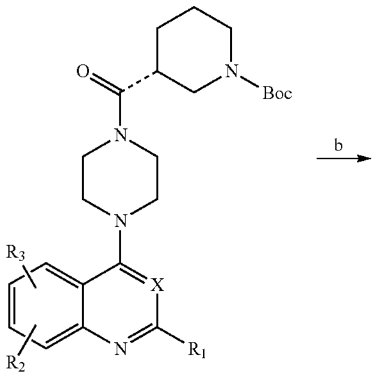

ia-4

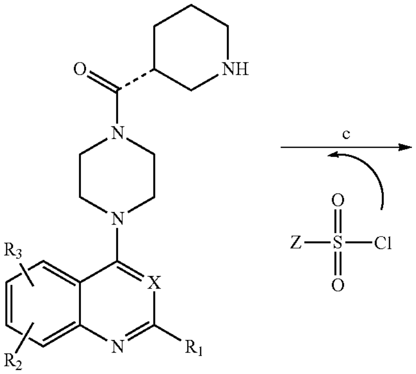

ib-4

-continued

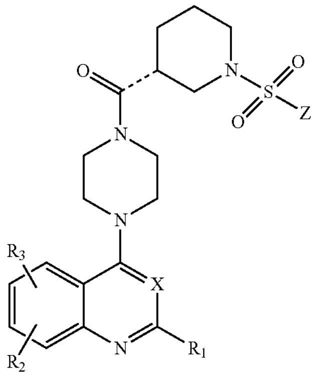

I-4

Reaction conditions, a) HATU, DIEA, DMF or DCM, rt, 1-4 hr. or EDCl (1-ethyl-3-(3-dimethylaminopropyl)carbodiimide), HOBt (hydroxybenzotriazole), DIEA, DMF, rt, 2-4 hr. b) TFA, DCM, 20-40° C., 1-3 hr. c) TEA or DIEA, DCM, rt, 2-12 hr.

[Reaction Scheme 1-5]

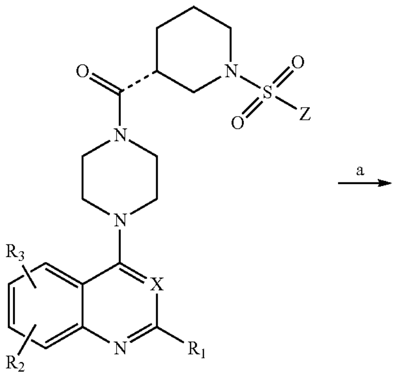

I-4

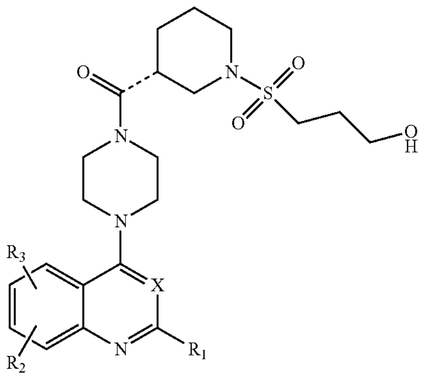

I-5

Reaction condition, a) MeOH, $NaBH_4$, rt, 2-12 hr.

The above Formula (I-5) can be obtained by a reaction in which an ester compound is converted into an alcohol group through a reduction reaction using sodium borohydride ($NaBH_4$). At this time, Z is an alkyl ester which belongs to that defined in the above Formula (1), and is preferably methyl propanoate.

[Reaction Scheme 1-6]

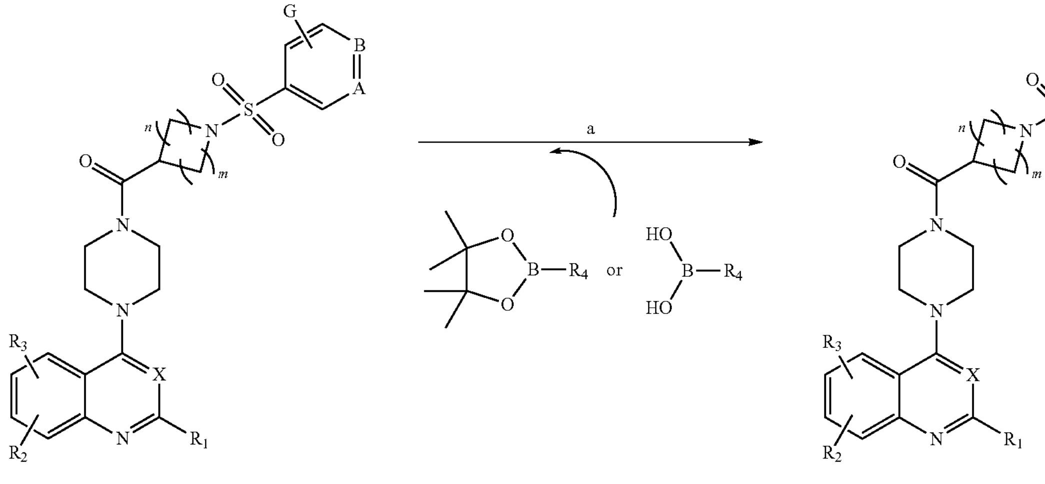

I-6

Reaction condition, a) Pd (dppf) $Cl_2$, $Na_2CO_3$, 70-110° C., 8-24 hr.

In the above Reaction Scheme, G is chloride (Cl) or bromine (Br), Formula I-6 is a compound included in the definition of Formula (1) above, A and B are each independently carbon or nitrogen, and $R_4$ belongs to Z defined in Formula (1).

Specifically, in step a) of Reaction Scheme 1-6, when it is aryl or heteroaryl having bromo: (Br) group, a compound (Formula I-6) can be synthesized by carrying out a carbon-carbon bond through a reaction between [1,1'-bis(diphenylphosphino) ferrocene] dichloropalladium (II) (hereinafter referred to as Pd (dppf) $Cl_2$) and a reagent in the form of dioxaboronane or boronic acid (References: Miyaura, Norio; Yamada, Kinji; Suzuki, Akira (1979). "A new stereospecific cross-coupling by the palladium-catalyzed reaction of 1-alkenylboranes with 1-alkenyl or 1-alkynyl halides". Tetrahedron Letters. 20 (36): 3437-3440. Miyaura, Norio; Suzuki, Akira (1979). "Stereoselective synthesis of arylated (E)-alkenes by the reaction of alk-1-enylboranes with aryl halides in the presence of palladium catalyst". Chem. Comm. 0 (19): 866-867.).

[Reaction Scheme 1-7]

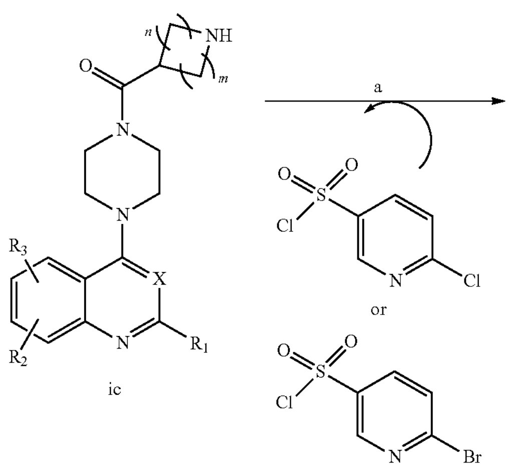

ic

-continued

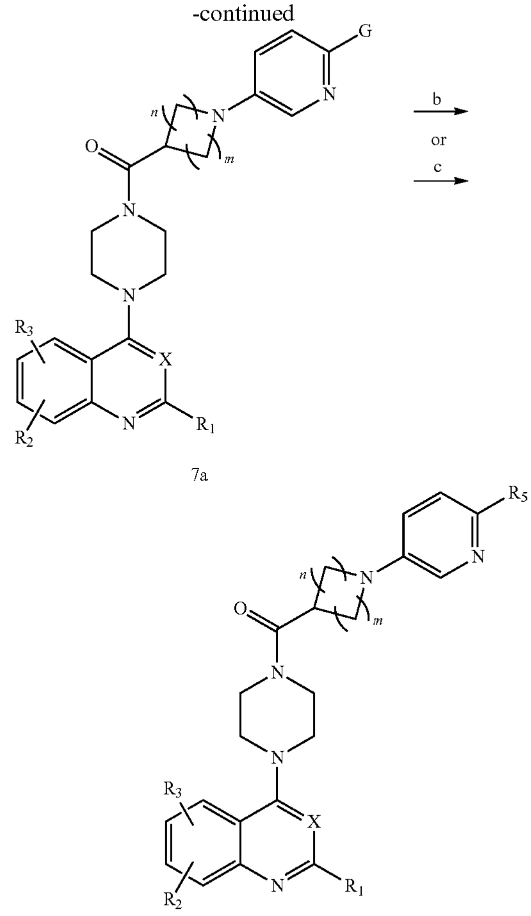

7a

I-7

Reaction conditions, a) TEA or DIEA, DCM, rt, 2-12 hr. b) $Ce_2CO_3$, DMF, RT-100° C., 8-24 hr. c) $Pd_2$ $(dba)_3$, Xanpos, $Ce_2CO_3$, DMF, RT-100° C., 2-24 hr.

In the above Reaction Scheme, G is chloride (Cl) or bromine (Br), wherein Rs is a substituent in the definition of Z in Formula (1) above.

[Reaction Scheme 1-8]
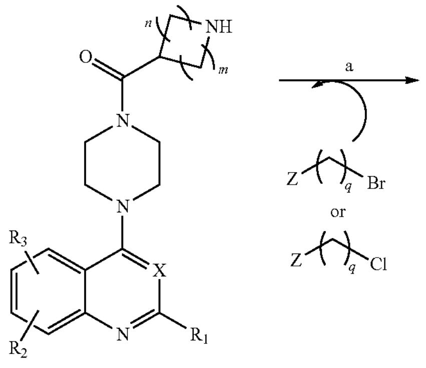
ic
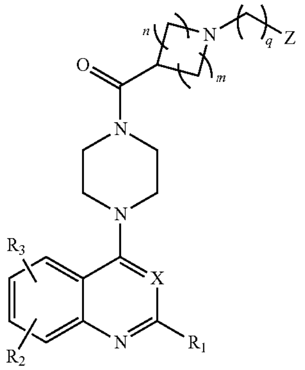
I-8
Reaction condition, a) TEA or 60% NaH, DCM or DMF, rt, 2-12 hr.
In the above Reaction Scheme, q is an integer of 1 to 3.
[Reaction Scheme 2]
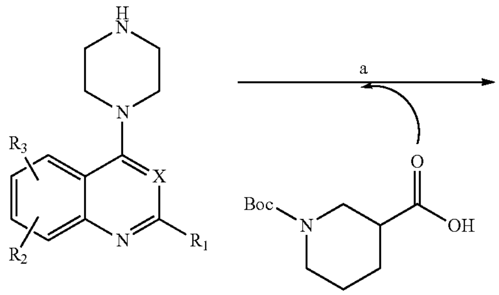
-continued
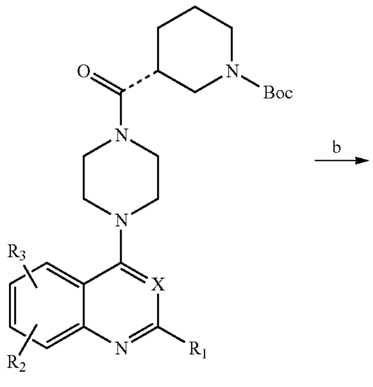
2a
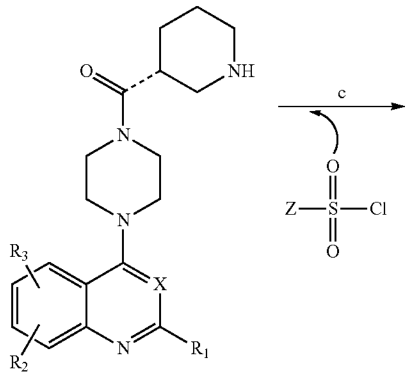
2b
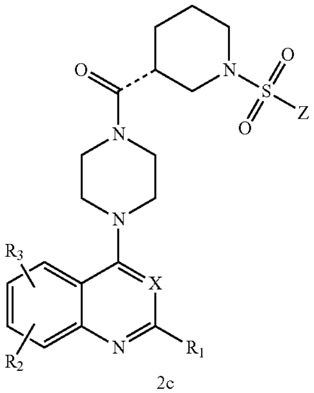
2c
Reaction conditions, a) HATU, DIEA, DMF, rt, 1-4 hr. or EDCl (1-ethyl-3-(3-dimethylaminopropyl)carbodiimide), HOBt (hydroxybenzotriazole), DIEA, DMF, rt, 2-4 hr. b) TFA, DCM, 20-40° C., 1-3 hr. c) TEA or DIEA, DCM, rt, 2-12 hr.

[Reaction Scheme 3]

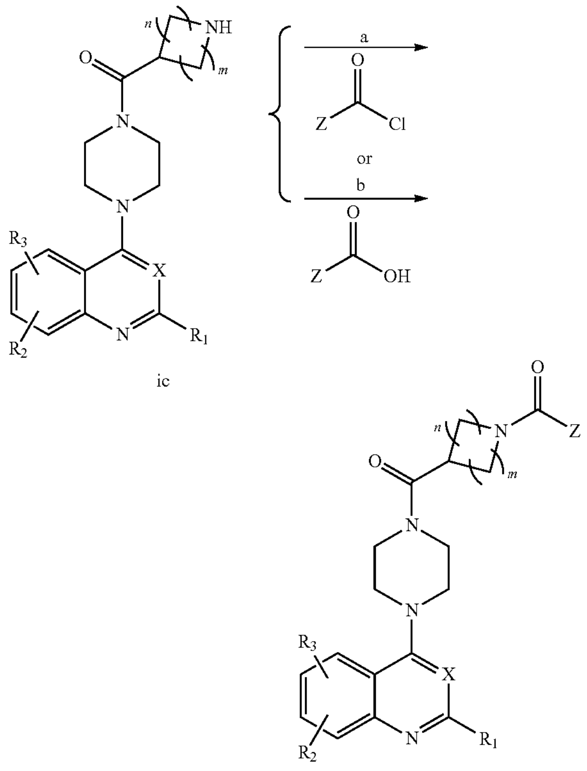

3a

Reaction conditions, a) TEA or DIEA, DCM, rt, 2-12 hr. b) HATU, DIEA, DMF, rt, 1-4 hr.

Reaction Scheme 3 is a method of synthesizing Formula 3a using ic as a starting material through a coupling reaction using carbonyl chloride or an amide coupling reaction using carboxylic acid. At this time, Z is a substituent belonging to that defined in the above Formula (1).

[Reaction Scheme 4]

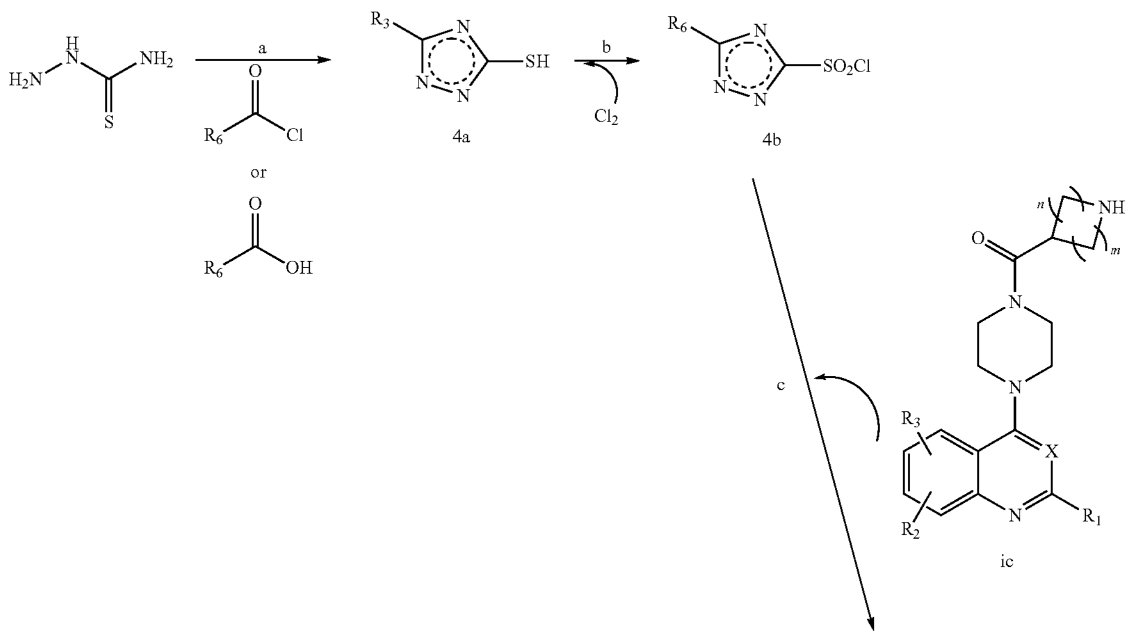

-continued

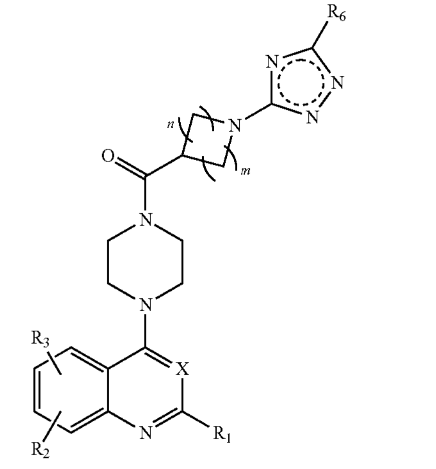

4c

Reaction conditions, a) NaOH or $CH_3ONa$, 1-4-dioxane or MeOH, water, 80-100° C., 8-24 hr. b) 2M-HCl, MeOH, 0° C., 1-4 hr. c) TEA or DIEA, DCM, rt, 2-12 hr.

Reaction Scheme 4 represents the synthesis of a triazole-type sulfonyl chloride intermediate and the synthesis of the desired compound (4c) through it. Triazole thiol is formed using hydrazine carbothioamide and $R_6$-carbonyl chloride or $R_6$-carboxylic acid, and then $Cl_2$ is used to convert the thiol to sulfonyl chloride. The formed sulfonyl chloride reacts with the intermediate and ic to obtain the desired compound. In the above Reaction Scheme, $R_6$ is alkyl, preferably methyl, ethyl, isopropyl or tert-butyl.

[Reaction Scheme 5]

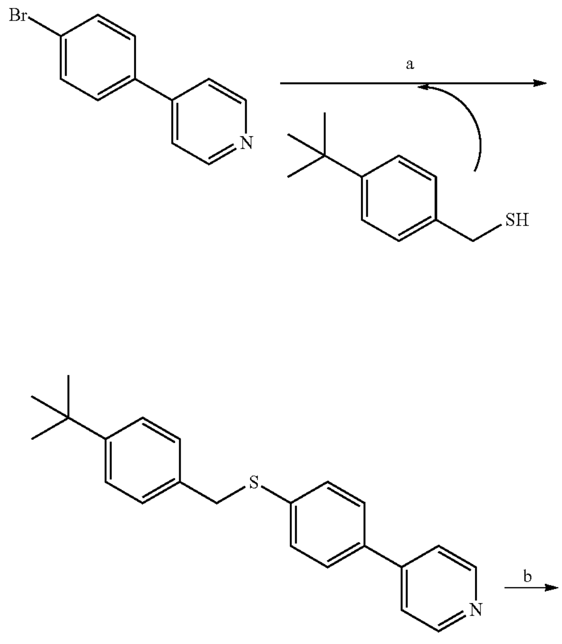

5a

-continued

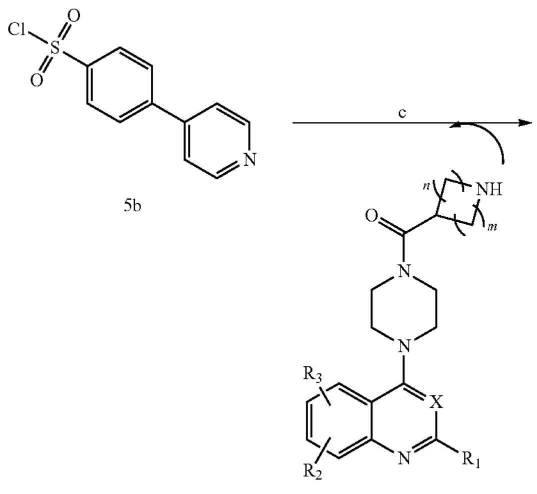

5b ic

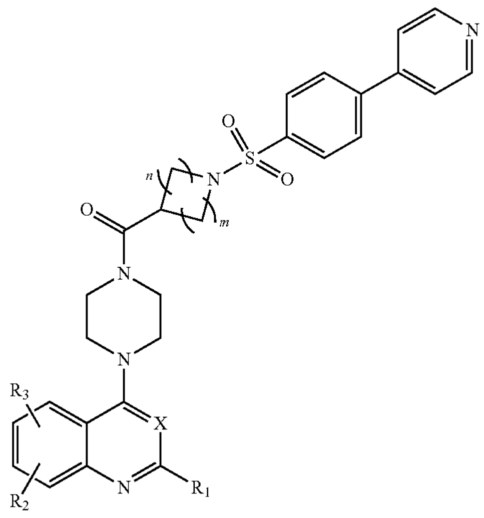

5c

Reaction conditions, a) $Pd_2(dba)_3$, Xanpos, DIEA, dioxane, 80-100° C., 2-24 hr. b) AcOH, water, N-Chloro-succinimide (NCS), RT–50° C., 8-24 hr. c) TEA or DIEA, DCM, rt, 2-12 hr.
[Reaction Scheme 6]
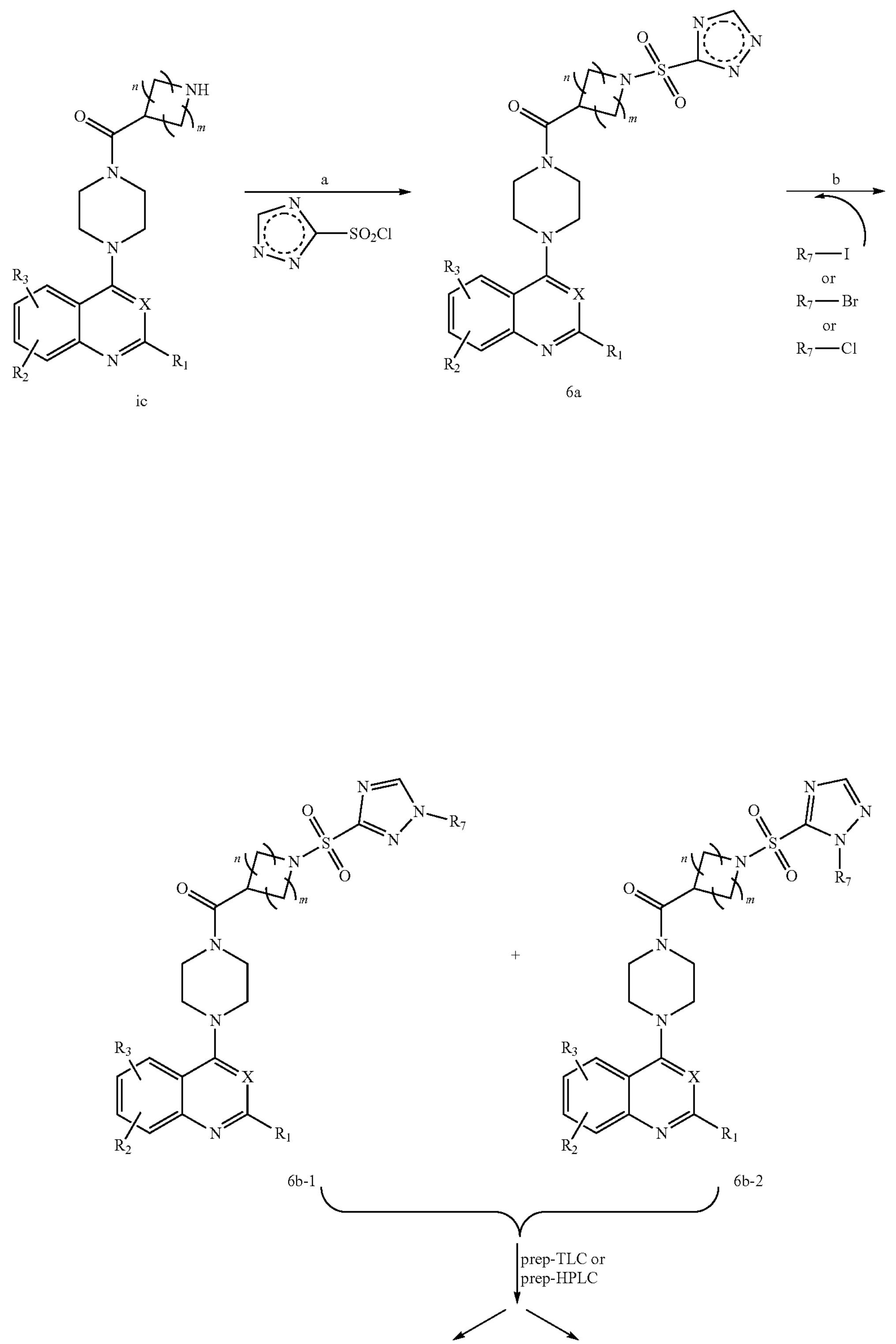
ic 6a 6b-1 6b-2

-continued

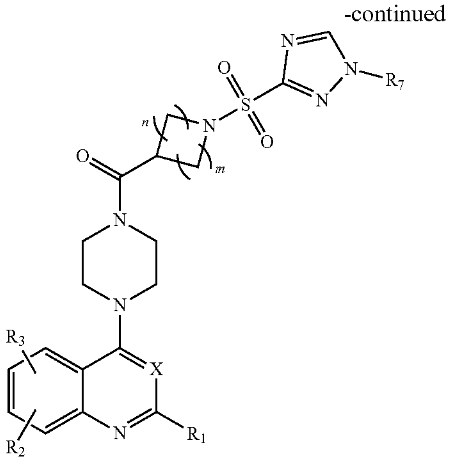

6b-1

+

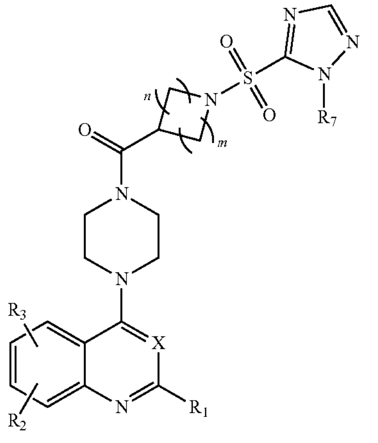

6b-2

Reaction conditions, a) Potassium carbonate, acetonitrile, rt–80° C., 2-24 hr. b) TEA or DIEA, DCM, rt, 2-12 hr.

Formula 6 is a compound included in the definition of Formula (1), and in Reaction Scheme 6, $R_7$ is alkyl, alkyl alcohol, alkylamine, alkylalkoxy or alkylketone, wherein alkyl is methyl, ethyl, propyl or isopropyl; alkoxy is methoxy; and alkyl ketone is propan-2-one.

The Formula 6 can be obtained by using 1c as a starting material and reacting with triazole sulfonyl chloride to produce formula (6a), and then introducing Re substituent to the triazole through a substitution reaction. In the above reaction, 6a-1 and 6b-2 are produced due to tautomerism of triazole hydrogen, and the two produced compounds can be separated through prep-TLC or prep-HPLC.

[Reaction Scheme 7]

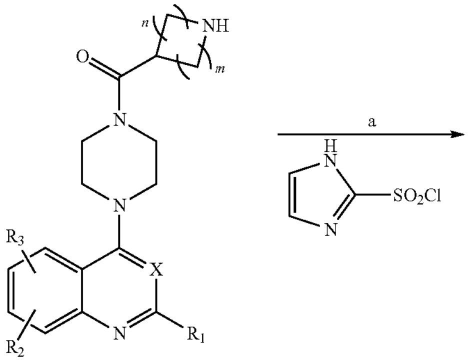

ic

-continued

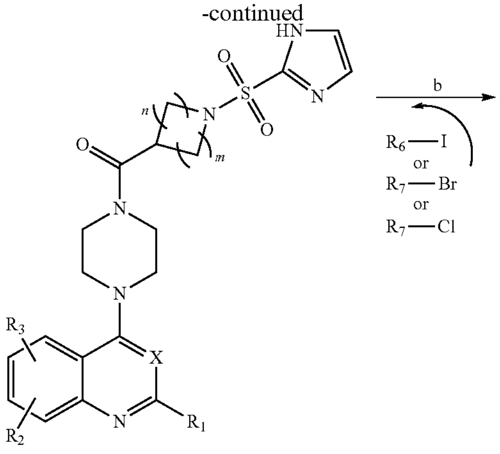

7a

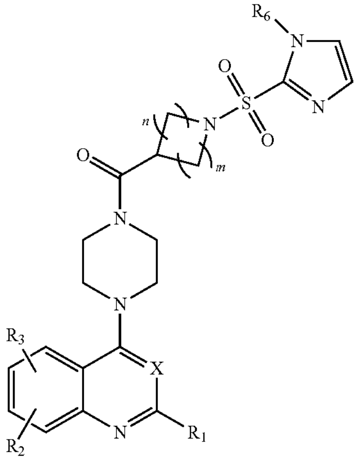

7b

Reaction conditions, a) Potassium carbonate, acetonitrile, rt–80° C., 2-24 hr. b) TEA or DIEA, DCM, rt, 2-12 hr.

Formula 7 is a compound included in the definition of Formula (1), and in Reaction Scheme 7, Rs is alkyl, alkyl alcohol, alkylamine, alkylalkoxy or alkylketone, wherein alkyl is methyl, ethyl, propyl or isopropyl, and alkoxy is methoxy. The Formula 7 can be obtained by using 1c as a starting material and reacting with imidazole sulfonyl chloride to produce Formula 7a, and then introducing $R_7$ substituent to imidazole through a substitution reaction.

The reagents used in Reaction Schemes 1, 1-1, 1-2, 1-3, 1-4, 1-5, 1-6, 2, 3, 4, 5, 6 and 7 are commercially available reagents, and they can be synthesized and used, if necessary. The solvent used in Reaction Schemes 1 and 2 may be commercially available solvents, and they are not particularly limited as long as they dissolve the starting material and do not inhibit the reaction. For example, ether-based solvents such as tetrahydrofuran, 1,2-dimethoxyethane, diethyl ether or 1,4-dioxane; aromatic hydrocarbon-based solvents such as benzene, toluene or xylene; amide-based solvents such as N,N-dimethylformamide, N,N-dimethylacetamide or N-methylpyrrolidone; organic solvents such as dimethyl sulfoxide; alcohol-based solvents such as methanol, ethanol, propanol, n-butanol or t-butanol; or a mixture thereof or a mixed solvent of the above solvent and water may be used. Preferably, a mixed solvent of ethanol or tetrahydrofuran (THF) and water can be used, but is not limited thereto.

In addition, to solve the above technical problem, the present invention provides a pharmaceutical composition for the prevention or treatment of metabolic disease comprising the compound of Formula (1), or a racemate, a diastereomer, a geometric isomer, a stereoisomer, a tautomer, a hydrate or a pharmaceutically acceptable salt thereof, together with a pharmaceutically acceptable carrier.

Metabolic disease (or metabolic syndrome) refers to a group of diseases in which various metabolic abnormalities occur in combination, including obesity, type 2 diabetes caused by insulin resistance, and various risk factors for cardiovascular diseases related to metabolism. This is a useful concept that can comprehensively explain insulin resistance, and complex and various metabolic abnormalities and clinical aspects related thereto. In the present invention, it refers to diseases or syndrome in which risk factors such as obesity, diabetes, fatty liver disease and the like increase together.

In the present invention, the term "metabolic disease" may include, but is not limited to, diabetes or fatty liver disease.

In the present invention, "diabetes" is a chronic disease characterized by abnormal glucose metabolism. The diabetes is either a result of an absolute deficiency in the production of insulin, the most important hormone that regulates blood glucose levels (insulin-dependent diabetes mellitus or type 1 diabetes), or is caused by a result of a decrease in the action of insulin in a target organ (non-insulin-dependent diabetes mellitus or type 2 diabetes).

Preferably, diabetes in the present invention refers to non-insulin-dependent diabetes mellitus (type 2 diabetes). The non-insulin-dependent diabetes mellitus generally exhibits abnormalities in glucose metabolism and lipid metabolism. That is, in the case of the non-insulin-dependent diabetes mellitus, insulin secretion is delayed or a sufficient amount is not secreted after food intake, so glucose production in the liver does not decrease, and the utilization of blood sugar by peripheral tissues such as muscle, liver, and fat does not increase. The postprandial hyperglycemia caused by this always stimulates insulin secretion, resulting in chronic hyperinsulinemia. If this condition continues, the beta cells can no longer maintain the increased rate of insulin secretion, ultimately resulting in insulin resistance. Persistent insulin resistance leads to problems with insulin production, leading to hypoinsulinemia. In particular, a decrease in the ratio of insulin to glucagon increases hepatic gluconeogenesis.

In addition, an increase in blood free fatty acids has been suggested as a cause of insulin resistance. An increase in free fatty acids in the blood increases the blood glucose level by inhibiting glucose utilization by insulin in peripheral tissues and interfering with gluconeogenesis in liver tissues. In the non-insulin-dependent diabetes mellitus, not only an increase in free fatty acids in the blood but also an increase in blood cholesterol and triglycerides and a decrease in HDL-cholesterol appear. The incidence of such dyslipidemia is 2 to 4 times higher than that of normal people.

Meanwhile, studies related to diabetes and diabetic complications have reported that diabetes is closely related to oxidative stress. Chronic hyperglycemia seen in diabetes increases the production of free radicals by various pathways such as auto-oxidation of glucose and protein glycation, and oxidative stress is increased by these highly reactive substances. Moreover, the expression and activity of antioxidant enzymes are insufficient to defend against oxidative stress induced by hyperglycemia, and the antioxidant enzyme activity is abnormally increased, and the balance maintained between these enzymes is broken.

In the present invention, the term "fatty liver disease" may refer to a group of diseases encompassing all aspects of the disease from fatty liver to steatohepatitis to fatty liver-associated cirrhosis.

The above-mentioned "fatty liver" is caused by the accumulation of fat in the liver due to excessive fat or alcohol intake, increased fat synthesis in the liver, excretion of triglycerides, and decreased burning, in general, fatty liver is defined when the proportion of fat accumulated in the liver is more than 5%. Most of the fat accumulated in the fatty liver is triglycerides.

Fatty liver can be divided into alcoholic fat caused by excessive drinking and non-alcoholic fatty liver caused by liver and obesity, diabetes, hyperlipidemia, or drugs. Alcoholic fatty liver occurs because excessive alcohol intake promotes fat synthesis in the liver and prevents normal energy metabolism. On the other hand, nonalcoholic fatty liver occurs more frequently in people suffering from obesity, insulin intolerance, and diabetes. This phenomenon suggests that nonalcoholic fatty liver may be caused by an increase in the concentration of free fatty acids in the blood due to insulin resistance or excessive lipolysis (A. B. Mayerson et al., Diabetes, 51: 797-802 (2002); K. F. Petersen et al., Diabetes, 54:603-608 (2005)).

In the present invention, the fatty liver may be any one or more selected from the group consisting of alcoholic fatty liver, non-alcoholic fatty liver, nutritive fatty liver, starvation fatty liver, obese fatty liver, and diabetic fatty liver, preferably, it may be non-alcoholic fatty liver, obese fatty liver, or diabetic fatty liver, and most preferably, it may be diabetic fatty liver, but is not limited thereto.

In the present invention, the term "steatohepatitis" refers to a case of inflammatory findings or fibrotic lesions accompanied by hepatocyte damage (balloon degeneration) while showing fat deposition in the liver. It is used to distinguish it from "fatty liver," which is a case in which fat deposition in the liver is shown but liver cell damage (balloon degeneration) and fibrosis are not found.

In the present invention, the term "fatty liver-associated liver cirrhosis" refers to liver cirrhosis accompanied by histological findings of fatty liver or steatohepatitis, or cirrhosis occurring in a patient with fatty liver or steatohepatitis histologically proven in the past.

In one embodiment of the present invention, fatty liver disease of the present invention refers to "non-alcoholic fatty liver disease." The non-alcoholic fatty liver disease is meant to include non-alcoholic fatty liver, non-alcoholic steatohepatitis, and non-alcoholic fatty liver-associated cirrhosis, and if it is known in the art as the disease group, the type is not limited thereto.

In addition, in the pharmaceutical composition according to the present invention, the compound represented by Formula (1), or a racemate, a diastereomer, a geometric isomer, a stereoisomer, a tautomer, a hydrate or a pharmaceutically acceptable salt thereof may be administered in various oral and parenteral formulations during clinical administration. In the case of formulations, it can be prepared using conventionally used pharmaceutically acceptable carrier—for example, diluents or excipients such as fillers, extenders, binders, wetting agents, disintegrants, and surfactants.

Solid preparations for oral administration include tablets, patients, powders, granules, capsules, troches, etc., such a solid preparation may be prepared by mixing one or more compounds of Formula (1) or a pharmaceutically acceptable salt thereof of the present invention with at least one excipient—for example, starch, calcium carbonate, sucrose or lactose or gelatin etc. In addition to simple excipients, lubricants such as magnesium stearate, talc and the like may also be used. Liquid formulations for oral administration include suspensions, oral solutions, emulsions, or syrup, in addition to water and liquid paraffin, which are commonly used simple diluents, various excipients—for example, wetting agents, sweetening agents, fragrances, preservatives and the like may be included.

Agents for parenteral administration include sterile aqueous solutions, non-aqueous solutions, suspension solutions, emulsions, lyophilized Formulations, and suppositories. Non-aqueous solvents and suspensions may include propylene glycol, polyethylene glycol, vegetable oils such as olive oil, and injectable esters such as ethyl oleate. As the base of the suppository, witepsol, macrogol, Tween 61, cacao butter, laurin fat, glycerol, gelatin, etc. may be used.

In addition, the dosage for the human body of the compound represented by the above Formula (1), or a racemate, a diastereomer, a geometric isomer, a stereoisomer, a hydrate or a pharmaceutically acceptable salt thereof may vary depending on the patient's age, weight, sex, dosage form, health status and disease degree, based on an adult patient weighing 70 kg, it is generally 0.01 to 1,000 mg/day, preferably 0.1 to 500 mg/day. In addition, according to the judgment of the doctor or pharmacist, divided administration may be administered once or several times a day at regular time intervals.

The pharmaceutical composition according to the present invention may be used alone or in combination with methods using surgery, hormone therapy, chemotherapy and biological response modifiers.

In the present invention, the term "prevention" is used to mean reducing or eliminating the possibility of contracting a disease.

In the present invention, the term "treatment" is used to mean deterring, delaying or ameliorating the progress of diseases in a subject exhibiting symptoms of diseases.

Effects of Invention

The compound according to the present invention has an excellent CYP4A inhibitory effect, and exhibits activities such as promoting glucose absorption into hepatocytes, inhibition of fat accumulation in liver cells, inhibition of reactive oxygen species by endoplasmic reticulum stress and treatment of steatohepatitis, which are important in diabetes and non-alcoholic steatohepatitis.

As such, the compound according to the present invention can be very usefully used in the development of therapeutic agents for metabolic diseases such as diabetes, steatohepatitis and obesity.

BRIEF DESCRIPTION OF DRAWINGS

FIG. 1 is a graph showing the results of measuring the effect of promoting glucose absorption.

FIG. 2 is a graph showing the results of measuring the effect of improving fat accumulation.

FIG. 3 is a graph showing the results of measuring active oxygen scavenging ability.

MODE FOR THE INVENTION

Hereinafter, the present invention is explained in more detail with the following examples. However, it must be understood that the protection scope of the present disclosure is not limited to the examples.

The present inventors confirmed the compound using the following analytical equipment to confirm the synthesized compound.

NMR (Nuclear Magnetic Resonance) was performed using a Bruker Avance Neo 400 MHz spectrometer, Bruker Avance III 400 MHz, or ZKNJ BIXI-1 300 MHz spectrometer, and the NMR solvent used was a commercially available NMR solvent substituted with deuterium. To confirm the molecular weight of the compound, an Agilent 1260 series LC/Mass system or a Waters Acquity UPLC/Mass system with a diode-array detector (DAD) or photo-diode array detector (PDA) was used, and as a mass detector, SQ Detector or SQ Detector 2 (electrospray ionization source) was used to measure the molecular weight. The column used was Sunfire C18 column (5 μm, 4.6×50 mm) or Waters Acquity UPLC BEH C18 column (1.7 μm, 2.1×50 mm). In addition, chiral HPLC was used to measure the e.e. (enantiomeric excess) of chiral compounds, and the instrument used was Agilent 1200 sense, SHIMADZU LC-20AD HPLC, Gilson-281 prep-HPLC or Waters-TharSFC (prep-SFC-80 and analysis-SFC), and the filler of the chiral column used was Type 1: IA, IB, IC, ID, IE, IF, IG, IH, IJ; Type 2: chiralpak or chiralcel column filled with AD-H, AS-H, OD-H, OJ-H.

Preparation Example 1: Synthesis of 7-fluoro-4-(piperazin-1-yl)quinolone

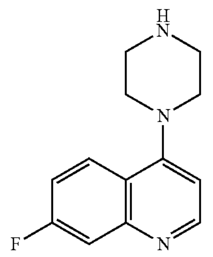 [SMILES: Fc1ccc2c(N3CCNCC3)ccnc2c1]

According to Reaction Scheme 1 above, 4-chloro-7-fluoroquinoline (6.0 g, 33.0 mmol) and piperazine (15.0 g, 116 mmole) were added to ethanol (250 ml) and DIEA (N,N-diisopropylethylamine, 3 ml), and heated, refluxed and stirred for 12 hours. Then, the obtained mixture was cooled to room temperature, saturated aqueous sodium hydrocarbon solution (sat. $NaHCO_3$, 150 ml) was added thereto, and extraction was carried out by adding dichloromethane (DCM, dichloromethane, 100 ml×3) to separate the organic layer. Water in the organic layer was removed using $Na_2SO_4$ (sodium bicarbonate), and the obtained product was filtered and concentrated under reduced pressure. The obtained product was purified by silica gel column chromatography using dichloromethane and methanol (MeOH, 1-10%) as developing solvents to obtain the title compound (5.1 g, 67% yield) as a white solid.

$^1$HNMR (400 MHz, DMSO-$d_6$): δ 8.82 (d, J=6.9 Hz, 1H), 8.36-8.81 (m, 1H), 8.04-8.00 (m, 1H), 7.67-7.61 (m, 1H), 7.34 (d, J=6.6 Hz, 1H), 4.03-3.90 (m, 4H), 3.59-3.38 (m, 4H). LC-MS (ESI): Rt=1.12 min, m/z 232.2 $[M+H]^+$. purity: 100% @ 254 nm, 100.0% @214 nm.

Preparation Example 2: Synthesis of tert-butyl 3-(4-(7-fluoroquinolin-4-yl)piperazine-1-carbonyl)pyrrolidine-1-carboxylate

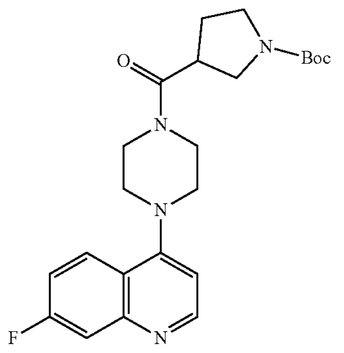 [SMILES: CC(C)(C)OC(=O)N1CCC(C(=O)N2CCN(c3ccnc4cc(F)ccc34)CC2)C1]

1-(Tert-butoxycarbonyl)pyrrolidine-3-carboxylic acid (717 mg, 3.33 mmol) was dissolved in dimethylformamide (DMF, 5 ml) and N,N-diisopropylethylamine (DIEA) (1.9). g, 15.2 mmol) was added thereto, and then 1-[bis(dimethylamino)methylene]-1H-1,2,3-triazo[4,5-b]pyridinium 3-oxide hexafluorophosphate (HATU)(1.7 g, 4.55 mmol) was added and stirred at room temperature for 5 minutes. Then, 7-Fluoro-4-(piperazin-1-yl)quinoline (700 mg, 3.03 mmol) was dissolved in DMF (5 ml) and added thereto, and the reaction solution was stirred at room temperature for 1 hour. After adding water (300 ml) to the reaction solution, extraction was carried out using ethyl acetate (EtOAc) (30 ml×3) to separate the organic layer. Water was removed from the organic layer using $Na_2SO_4$, and the obtained product was filtered and concentrated under reduced pressure. The concentrate was first purified using silica gel chromatography (developing solvent, dichloromethane: methanol=10-15:1), and then finally purified by C18 chromatography (5-90% $CH_3CN$ in water) to obtain the title compound (1.1 g, 85% yield) as a yellow solid.

LC-MS (ESI): Rt=1.28 min, m/z 429.6 $[M+H]^+$; purity: 100% @ 254 nm, 100% @214 nm.

Preparation Example 3: Synthesis of (4-(7-fluoroquinolin-4-yl)piperazin-1-yl)(pyrrolidin-3-yl)methanone)

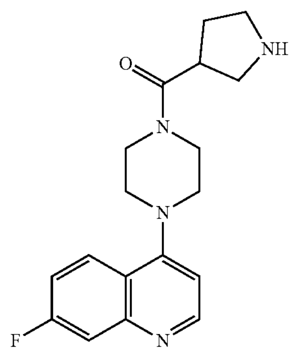 [SMILES: O=C(C1CCNC1)N1CCN(c2ccnc3cc(F)ccc23)CC1]

Tert-butyl 3-(4-(7-fluoroquinolin-4-yl)piperazine-1-carbonyl)piperidine-1-carboxylate (1.10 g, 2.57 mmol) was dissolved in dichloromethane (10 ml), and trifluoroacetic acid (TFA) (5 ml) was added thereto and stirred at room temperature for 3 hours. The reaction solution was concentrated and diluted in dichloromethane (10 ml), and saturated aqueous sodium bicarbonate solution (20 ml) was added to adjust the pH to 9. Extraction was carried out three times using a mixed solvent (20 ml) of dichloromethane:methanol=10:1. The organic layer was washed with brine (40 ml), dried over $Na_2SO_4$, filtered and concentrated under reduced pressure. The concentrate was first purified using silica gel column chromatography using a developing solvent of dichloromethane:methanol=10-5:1, and then crystallized using ethyl acetate (EtOAc) and n-hexane to obtain the title compound. (700 mg, 83% yield) as a yellow solid.

$^1$H NMR (400 MHz, DMSO-$d_6$): δ 8.70 (d, J=6.8 Hz, 1H), 8.34 (dd, J=9.6, 6.0 Hz 1H), 7.98 (dd, J=9.2, 2.4 Hz 1H), 7.64-7.59 (m, 1H), 7.17 (d, J=6.8 Hz, 1H), 3.97-3.92 (m, 4H), 3.87-3.86 (m, 2H), 3.78-3.77 (m, 2H), 3.60-3.53 (m, 2H), 3.39-3.34 (m, 2H), 3.21-3.18 (m, 1H), 2.25-2.18 (m, 1H), 2.01-1.92 (m, 1H), 1.32-1.27 (m, 1H). LC-MS (ESI): Rt=0.30 min, m/z 329.4 $[M+H]^+$ Preparation Example 4: Synthesis of (S)-tert-butyl 3-(4-(7-fluoroquinolin-4-yl)piperazine-1-carbonyl) pyrrolidine-1-carboxylate

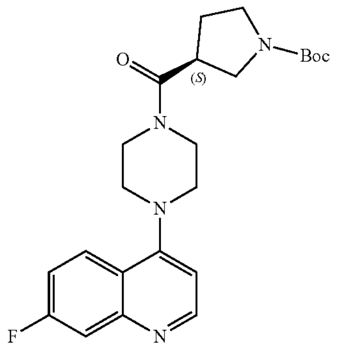

7-Fluoro-4-(piperazin-1-yl)quinoline (200 mg, 0.87 mmol) and (S)-1-(tert-butoxycarbonyl)pyrrolidine-3-carboxylic acid (224 mg, 1.04 mmol) were used in the same manner as in the synthesis method of Preparation Example 2 to obtain the title compound (300 mg, 81% yield) as a yellow solid.

LC-MS (ESI): Rt=1.40 min, m/z 429.3 $[M+H]^+$; purity: 100% @ 254 nm, 100% @214 nm.

Preparation Example 5: Synthesis of (S)-(4-(7-fluoroquinolin-4-yl)piperazin-1-yl)(pyrrolidin-3-yl) methanone

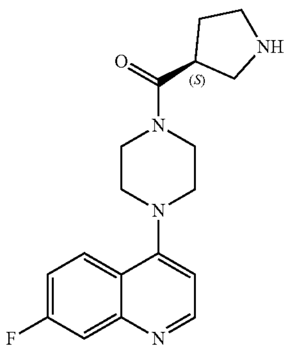

(S)-tert-butyl 3-(4-(7-fluoroquinolin-4-yl)piperazine-1-carbonyl)pyrrolidine-1-carboxylate (150 mg, 0.35 mmol) was dissolved in DCM (3 mL), and TFA (1 mL) was added thereto. Then, the same synthesis method as in Preparation Example 3 was carried out to obtain the title compound (190 mg, 810% yield) as a yellow solid.

LC-MS (ESI): Rt=1.08 min, m/z 329.3 $[M+H]^+$; purity: 100% @ 254 nm, 100% @ 214 nm.

Preparation Example 6: Synthesis of (R)-tert-butyl 3-(4-(7-fluoroquinolin-4-yl)piperazine-1-carbonyl) pyrrolidine-1-carboxylate

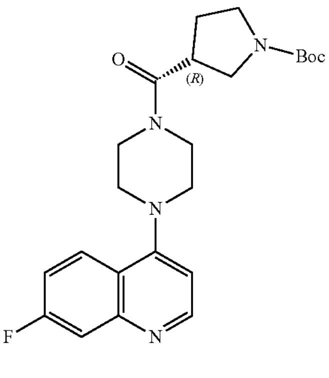

4-(Piperazin-1-yl)quinoline (2.00 g, 8.66 mmol) and (R)-1-(tert-butoxycarbonyl)pyrrolidine-3-carboxylic acid (2.10 g, 9.52 mmol) were used in the same manner as in the synthesis method of Preparation Example 2 to obtain the title compound (3.5 g, 95% yield) as a light yellow solid.

LC-MS (ESI): Rt=1.48 min., m/z 429.1 $[M+H]^+$; purity: 93% @254 nm, 97% @214 nm. chiral HPLC: Column: Chiralpak IC 5 µm 4.6×250 mm; Mobile Phase: Hex: EtOH=30:70 at 1 mL/min; Temp: 30° C.; Wavelength: 214 nm, Rt=15.671 min, 99.8% ee.

Preparation Example 7: Synthesis of (R)-(4-(7-fluoroquinolin-4-yl)piperazin-1-yl)(pyrrolidin-3-yl) methanone

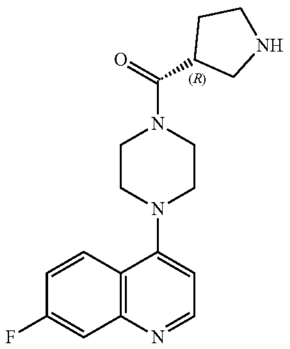

(R)-tert-butyl 3-(4-(7-fluoroquinolin-4-yl)piperazine-1-carbonyl)pyrrolidine-1-carboxylate (2.00 g, 4.67 mmol) and TFA (10 ml) were used in the same manner as in the synthesis method of Preparation Example 3 to obtain the title compound (950 mg, 62% yield) as a yellow solid.

Preparation Example 8: Synthesis of tert-butyl 4-(4-(7-fluoroquinolin-4-yl)piperazine-1-carbonyl)piperidine-1-carboxylate

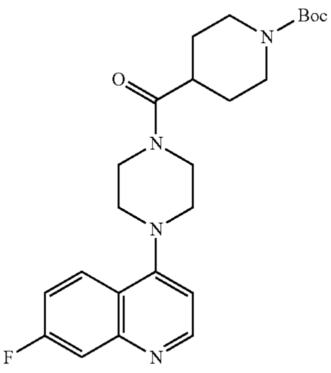 [SMILES: CC(C)(C)OC(=O)N1CCC(C(=O)N2CCN(c3ccnc4cc(F)ccc34)CC2)CC1]

According to the method of Reaction Scheme 1-2, 7-fluoro-4-(piperazin-1-yl)quinoline (800 mg, 3.46 mmol) and 1-(tert-butoxycarbonyl)piperidine-3-carboxylic acid (872 mg, 3.81 mmol) were used in the same manner as in the synthesis method of Preparation Example 2 to obtain the title compound (1.3 g, 85% yield) as a yellow solid.

$^1H$ NMR (400 MHz, $CDCl_3$): δ 8.74 (d, J=4.8 Hz, 1H), 8.03 (dd, J=9.2, 6.0 Hz 1H), 7.71 (dd, J=10.0, 2.4 Hz 1H), 7.32-7.27 (m, 1H), 6.83 (d, J=5.2 Hz, 1H), 4.17 (br s, 2H), 3.92-3.82 (m, 4H), 3.24-3.20 (m, 4H), 2.71-2.68 (m, 2H), 2.45 (br s, 1H), 1.80-1.71 (m, 4H), 1.49 (s, 9H). LC-MS (ESI): Rt=1.25 min, m/z 423.5 $[M+H]^+$; purity: 99.7% @ 254 nm, 99.8% @ 214 nm.

Preparation Example 9: Synthesis of (4-(7-fluoroquinolin-4-yl)piperazin-1-yl)(piperidin-4-yl)methanone

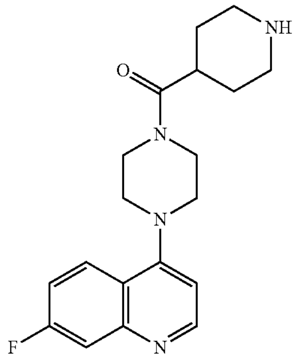 [SMILES: O=C(C1CCNCC1)N1CCN(c2ccnc3cc(F)ccc23)CC1]

Tert-butyl 4-(4-(7-fluoroquinolin-4-yl)piperazine-1-carbonyl)piperazine-1-carboxylate (1.3 g, 2.94 mmol) was used in the same manner as in the synthesis method of Preparation Example 3 to obtain the title compound (980 mg, 98% yield) as a yellow solid.

LC-MS (ESI): Rt=0.32, 0.46 min, m/z 343.5 $[M+H]^+$; purity: 99.5% @ 254 nm, 99.4% @ 214 nm.

Preparation Example 10: Synthesis of tert-butyl 3-(4-(7-fluoroquinolin-4-yl)piperazine-1-carbonyl)azetidine-1-carboxylate

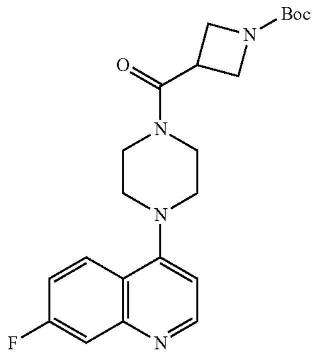 [SMILES: CC(C)(C)OC(=O)N1CC(C(=O)N2CCN(c3ccnc4cc(F)ccc34)CC2)C1]

According to the method of Reaction Scheme 1-3, 7-fluoro-4-(piperazin-1-yl)quinoline (1.5 g, 6.49 mmol) and 1-(tert-butoxycarbonyl)azetidine-3-carboxylic acid (1.7 g, 8.46 mmol) were used in the same manner as in the synthesis method of Preparation Example 2 to obtain the title compound (1.9 g, 70% yield) as a yellow solid.

$^1$H NMR (400 MHz, DMSO-$d_6$): δ 8.75 (d, J=4.8 Hz, 1H), 8.01 (dd, J=9.6, 6.0 Hz 1H), 7.70 (dd, J=9.6, 2.4 Hz 1H), 7.33-7.28 (m, 1H), 6.83 (d, J=5.2 Hz, 1H), 4.23 (br s, 2H), 4.11 (t, J=8.4 Hz, 2H), 4.00-3.86 (m, 2H), 3.58-3.52 (m, 3H), 3.26-3.19 (m, 4H), 1.45 (s, 9H).

Preparation Example 11: Synthesis of azetidin-3-yl (4-(7-fluoroquinolin-4-yl)piperazin-1-yl)methanone

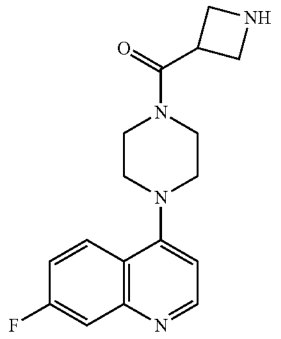 [SMILES: O=C(C1CNC1)N1CCN(c2ccnc3cc(F)ccc23)CC1]

According to the method of Reaction Scheme 1-3, tert-butyl 3-(4-(7-fluoroquinolin-4-yl)piperazine-1-carbonyl)azetidine-1-carboxylate (1.8 g, 4.35 mmol) was used in the same manner as in the synthesis method of Preparation Example 3 to obtain the title compound (1.1 g, 80% yield) as a yellow solid.

LC-MS (ESI): Rt=0.892 min, m/z 315.2 $[M+H]^+$; purity: 98.17% @ 254 nm.

Preparation Example 12: Synthesis of tert-butyl 3-(4-(quinolin-4-yl)piperazine-1-carbonyl)pyrrolidine-1-carboxylate

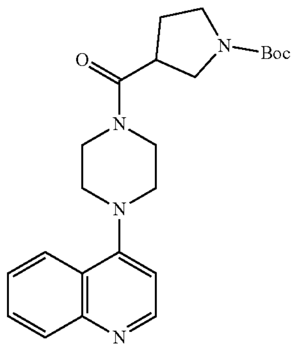 [SMILES: CC(C)(C)OC(=O)N1CCC(C(=O)N2CCN(c3ccnc4ccccc34)CC2)C1]

1-4-(Piperazin-1-yl)quinoline (33 g, 100 mmol) and 1-(tert-butoxycarbonyl)pyrrolidine-3-carboxylic acid (26 g, 0.12 mol) were used in the same manner as in the synthesis method of. Preparation Example 2 to obtain the title compound (32 g, 94% yield) as a yellow solid.

$^1$H NMR (400 MHz, $CDCl_3$): δ 8.74 (d, J=5.2 Hz, 1H), 8.08-8.02 (m, 2H), 7.73-7.69 (m, 1H), 7.56-7.52 (m, 1H), 6.89 (d, J=5.2 Hz, 1H), 3.95-3.83 (m, 4H), 3.59-3.54 (m, 3H), 3.39-3.29 (m, 6H), 2.34-2.09 (m, 2H), 1.47 (s, 9H).

Preparation Example 13: Synthesis of pyrrolidin-3-yl(4-(quinolin-4-yl)piperazin-1-yl)methanone

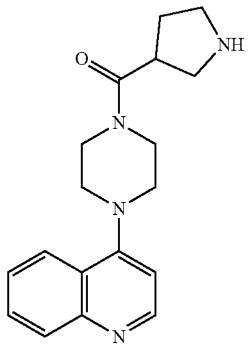 [SMILES: O=C(C1CCNC1)N1CCN(c2ccnc3ccccc23)CC1]

Tert-butyl 3-(4-(quinolin-4-yl)piperazine-1-carbonyl)pyrrolidine-1-carboxylate (43 g, 0.1 mol) was used in the same manner as in the synthesis method of Preparation Example 3 to obtain the title compound (40 g, 93% yield) as a light yellow solid.

$^1$H NMR (400 MHz, DMSO-$d_6$): δ 9.85 (br s, 1H), 9.49 (br s, 1H), 8.71 (d, J=6.8 Hz, 1H), 8.26-8.22 (m, 2H), 8.00 (t, J=7.6 Hz, 1H), 7.72 (t, J=7.6 Hz, 1H), 7.20 (d, J=6.8 Hz, 1H), 4.03-3.87 (m, 7H), 3.62-3.54 (m, 2H), 3.39-3.34 (m, 2H), 3.21-3.12 (m, 2H), 2.27-2.18 (m, 1H), 2.01-1.89 (m, 1H).

LC-MS (ESI): Rt=1.12 min., m/z 311.0 $[M+H]^+$; purity: 98% @ 254 nm, 83% @ 214 nm.

Preparation Example 14: Synthesis of (S)-tert-butyl 3-(4-(quinolin-4-yl)piperazine-1-carbonyl)pyrrolidine-1-carboxylate

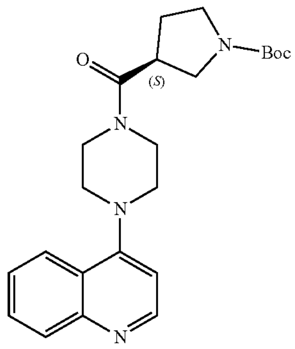

4-(Piperazin-1-yl)quinoline (300 mg, 1.41 mmol) and (S)-1-(tert-butoxycarbonyl)pyrrolidine-3-carboxylic acid (333 mg, 1.55 mmol) were used in the same manner as in the synthesis method of Preparation Example 2 to obtain the title compound (540 mg, 93% yield) as a white solid.

$^1$H NMR (400 MHz, $CDCl_3$): δ 8.77 (d, J=4.4 Hz, 1H), 8.10-8.08 (m, 1H), 8.04-8.02 (m, 1H), 7.72-7.68 (m, 1H), 7.55-7.51 (m, 1H), 6.86 (d, J=4.8 Hz, 1H), 3.96-3.83 (m, 4H), 3.59-3.50 (m, 3H), 3.38-3.24 (m, 6H), 2.23-2.02 (m, 2H), 1.47 (s, 9H).

Preparation Example 15: Synthesis of (S)-pyrrolidin-3-yl(4-(quinolin-4-yl)piperazin-1-yl)methanone

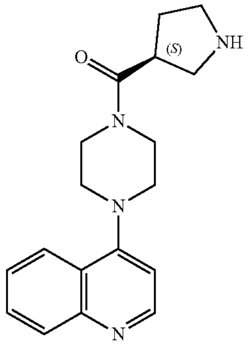

(S)-tert-butyl 3-(4-(quinolin-4-yl)piperazine-1-carbonyl) pyrrolidine-1-carboxylate (580 mg, 1.41 mmol) was used in the same manner as in the synthesis method of Preparation Example 3 to obtain the title compound (420 mg, 96% yield) as a yellow solid.

LC-MS (ESI): Rt=0.31 min., m/z 311.3 $[M+H]^+$

Preparation Example 16: Synthesis of (R)-tert-butyl 3-(4-(quinolin-4-yl)piperazine-1-carbonyl)pyrrolidine-1-carboxylate

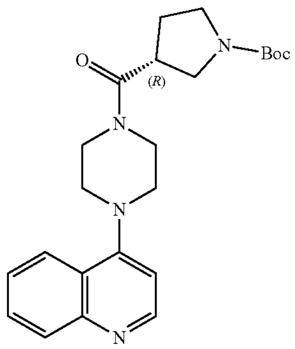

4-(Piperazin-1-yl)quinoline (300 mg, 1.41 mmol) and (R)-1-(tert-butoxycarbonyl)pyrrolidine-3-carboxylic acid (333 mg, 1.55 mmol) were used in the same manner as in the synthesis method of Preparation Example 2 to obtain the title compound (520 mg, 90% yield) as a white solid.

$^1$H NMR (400 MHz, $CDCl_3$): δ 8.77-8.75 (m, 1H), 8.10-8.07 (m, 1H), 8.04-8.02 (m, 1H), 7.71-7.67 (m, 1H), 7.55-7.50 (m, 1H), 6.89-6.81 (m, 1H), 3.95-3.82 (m, 4H), 3.66-3.45 (m, 3H), 3.38-3.23 (m, 6H), 2.17-2.09 (m, 2H), 1.47 (s, 9H). LC-MS (ESI): Rt=1.29 min, m/z 411.4 $[M+H]^+$; purity: 100% @ 254 nm, 90% @ 214 nm.

Preparation Example 17: Synthesis of (R)-pyrrolidin-3-yl(4-(quinolin-4-yl)piperazin-1-yl)methanone

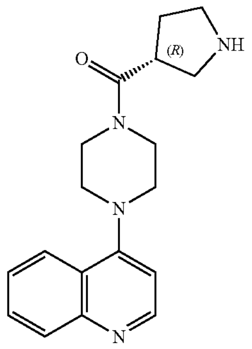

(R)-tert-butyl 3-(4-(quinolin-4-yl)piperazine-1-carbonyl) pyrrolidine-1-carboxylate (520 mg, 1.27 mmol) was used in the same manner as in the synthesis method of Preparation Example 3 to obtain the title compound (380 mg, 96% yield) as a yellow solid.

LC-MS (ESI): Rt=0.30 min, m/z 311.3 $[M+H]^+$

Preparation Example 18: Synthesis of tert-butyl 3-(4-(quinazolin-4-yl)piperazine-1-carbonyl)piperidine-1-carboxylate

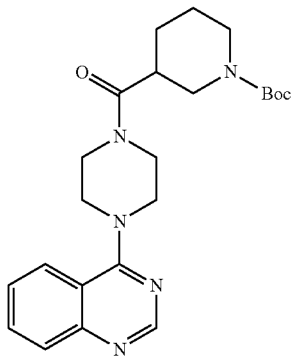 [SMILES: CC(C)(C)OC(=O)N1CCCC(C(=O)N2CCN(c3ncnc4ccccc34)CC2)C1]

1-(Tert-butoxycarbonyl)pyrrolidine-3-carboxylic acid (641 mg, 2.79 mmol) was dissolved in dimethylformamide (DMF, 15 ml), and DIEA (1.50 g, 11.65 mmol) and HATU (1.33 g), 3.49 mmol) were added thereto and stirred at room temperature for 20 minutes. 4-(Piperazin-1-yl)quinazoline hydrochloride (500 mg, 2.33 mmol) was dissolved in DMF (10 mL) and added to the reaction mixture, followed by stirring at room temperature for 2 hours. Water (150 ml) was added to the reaction solution, extraction was carried out using ethyl acetate (EtOAc) (30 ml×3), the organic layer was separated, water was removed using $Na_2SO_4$, filtered and concentrated under reduced pressure. The concentrate was purified using silica gel chromatography (developing solvent, dichloromethane:methanol=10-15:1) to obtain the title compound (600 mg, 60% yield) as a yellow solid.

LC-MS (ESI): Rt=1.46 min, m/z 426.6 $[M+H]^+$; purity: 80% @254 nm, 100% @214 nm.

Preparation Example 19: Synthesis of piperidin-3-yl (4-(quinazolin-4-yl)piperazin-1-yl)methanone

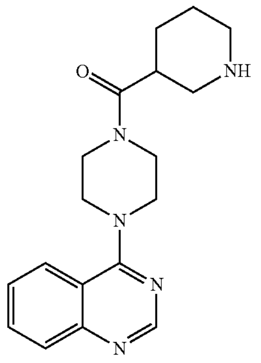 [SMILES: O=C(C1CCCNC1)N1CCN(c2ncnc3ccccc23)CC1]

Tert-butyl 3-(4-(quinazolin-4-yl)piperazine-1-carbonyl) piperidine-1-carboxylate (600 mg, 1.41 mmol) and TFA (5 mL) were used in the same manner as in the synthesis method of. Preparation Example 3 to obtain the title compound (450 mg, 98% yield) as a yellow.

$^1H$ NMR (400 MHz, DMSO-$d_6$): δ 8.68-8.64 (m, 1H), 8.10-8.07 (m, 1H), 7.87-7.81 (m, 2H), 7.62-7.57 (m, 1H), 3.77-3.44 (m, 10H), 3.07-2.91 (m, 3H), 2.71 (s, 1H), 1.84-1.54 (m, 3H), 1.28-1.19 (m, 1H). LC-MS (ESI): Rt=1.17 min, m/z 326.5 $[M+H]^+$; purity: 100% @ 254 nm, 100% @ 214 nm.

Preparation Example 20: Synthesis of tert-butyl 3-(4-(2-methylquinazolin-4-yl)piperazine-1-carbonyl)piperidine-1-carboxylate

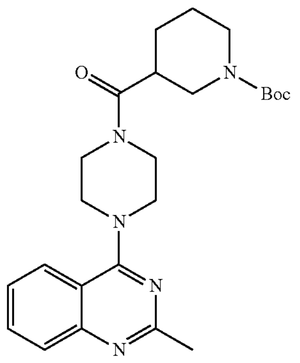 [SMILES: Cc1nc(N2CCN(C(=O)C3CCCN(C(=O)OC(C)(C)C)C3)CC2)c2ccccc2n1]

1-(Tert-butoxycarbonyl)piperidine-3-carboxylic acid (602 mg, 2.63 mmol) and 2-methyl-4-(piperazin-1-yl)quinazoline (500 mg, 2.19 mmol) were used in the same manner as in the synthesis method of Preparation Example 18 to obtain the title compound (700 mg, 73% yield) as a yellow solid.

LC-MS (ESI): Rt=1.48 min, m/z 440.6 $[M+H]^+$; purity: 100% @ 254 nm, 100% @214 nm.

Preparation Example 21: Synthesis of (4-(2-methylquinazolin-4-yl)piperazin-1-yl)(piperidin-3-yl) methanone

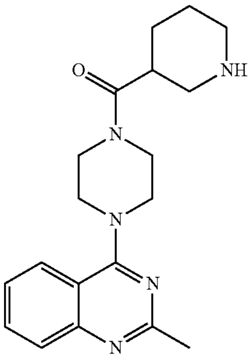

Tert-butyl 3-(4-(2-methylquinazolin-4-yl)piperazine-1-carbonyl)piperidine-1-carboxylate (700 mg, 1.59 mmol) and TFA (5 mL) were used in the same manner as in the synthesis method of Preparation Example 19 to obtain the title compound (530 mg, 98% yield) as a yellow solid.

$^1$H NMR (400 MHz, DMSO-$d_6$): δ 8.01-7.95 (m, 1H), 7.80-7.70 (m, 2H), 7.50-7.43 (m, 1H), 3.74-3.66 (m, 8H), 3.01 (t, J=12.8 Hz, 2H), 2.90-2.89 (m, 1H), 2.76-2.73 (m, 1H), 2.68 (s, 1H), 2.54 (s, 3H), 1.88-1.81 (m, 1H), 1.64-1.52 (m, 3H), 1.17-1.14 (m, 1H). LC-MS (ESI): Rt=1.22 min, m/z 340.5 $[M+H]^+$; purity: 100% @254 nm, 100% @214 nm.

Preparation Example 22: Synthesis of 5-(tert-butyl)-4H-1,2,4-triazole-3-thiol

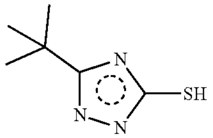

According to Reaction Scheme 4, hydrazine carbothioamide (5.0 g, 55.0 mmol) was dissolved in dioxane (10 mL), and then NaOH (2.2 g, 55.0 mmol) diluted in distilled water (9 mL) was slowly added thereto. Pivaloyl chloride (6.3 mL, 51 mmol) was slowly added over 20 minutes while maintaining the temperature of the reaction solution at about 25° C. The reactant was reacted for 2 hours and filtered to obtain a solid. The obtained solid was added to NaOH (4.5 g, 112.5 mmol) diluted in distilled water (15 mL) and stirred at 90° C. for 16 hours. The reaction mixture was cooled to room temperature and conc. HCl was added to adjust pH=3. A solid was formed, and the obtained solid was filtered and dried under reduced pressure to obtain the title compound (2.7 g, 45% yield) as a white solid.

$^1$H NMR (400 MHz, DMSO-$d_6$): δ 13.16 (s, 1H), 13.12 (s, 1H), 1.24 (s, 9H). LC-MS (ESI): Rt=0.69 min. m/z 158.0 $[M+H]^+$; purity: 100% @254 nm, 100% @214 nm.

Preparation Example 23: Synthesis of 5-(tert-butyl)-4H-1,2,4-triazole-3-sulfonyl chloride

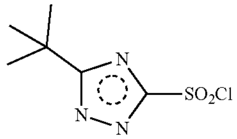

5-(Tert-butyl)-4H-1,2,4-triazole-3-thiol (500 mg, 3.18 mmol) was dissolved in 2 M HCl (20 mL) and MeOH (10 mL), and cooled to 0° C. and $C_{12}$ was slowly added thereto. The reaction mixture was diluted in EtOAc (200 mL) and washed with water (40 mL) and brine (40 mL). Water was removed from the organic layer using $Na_2SO_4$, and the obtained product was filtered and concentrated under reduced pressure to obtain the title compound (400 g, 47% yield) as a white solid.

LC-MS (ESI): Rt=1.46 min, m/z 224.0 $[M+H]^+$; purity: 100% @254 nm, 89.84% @214 nm.

Preparation Example 24: Synthesis of tert-butyl 3-(4-(7-fluoroquinolin-4-yl)piperazine-1-carbonyl) piperidine-1-carboxylate

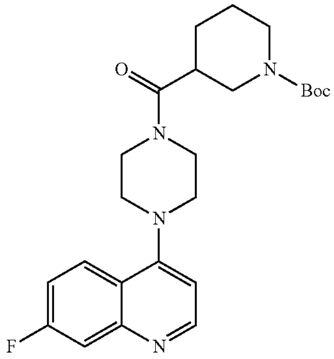 [SMILES: CC(C)(C)OC(=O)N1CCCC(C(=O)N2CCN(c3ccnc4cc(F)ccc34)CC2)C1]

1-(Tert-butoxycarbonyl)piperidine-3-carboxylic acid (2.41 g, 10.5 mmol) was dissolved in DMF (30 ml), and N,N-diisopropylethylamine (DIEA)(3.28 g, 25.4 mmol) was added thereto. 1-[Bis(dimethylamino)methylene]-1H-1,2,3-triazo[4,5-b]pyridinium 3-oxide hexafluorophosphate (HATU)(4.91 g, 12.9 mmol) was added thereto and stirred at room temperature for 20 minutes. Then, 7-fluoro-4-(piperazin-1-yl)quinoline (1.96 g, 8.50 mmol) was added thereto, and the reaction solution was stirred at room temperature for 2 hours. After adding water (150 ml) to the reaction solution, extraction was carried out using ethyl acetate (EtOAc) (30 ml×3) to separate the organic layer. Water was removed from the organic layer using $Na_2SO_4$, and the obtained product was filtered and concentrated under reduced pressure. The compound was purified using silica gel chromatography to obtain the title compound (1.9 g, 51% yield) as a yellow solid.

LC-MS (ESI): Rt=1.33 min, m/z 443.4 $[M+H]^+$; purity: 100% @ 254 nm, 100% @214 nm.

Preparation Example 25: Synthesis of (4-(7-fluoroquinolin-4-yl)piperazin-1-yl)(piperidin-3-yl)methanone

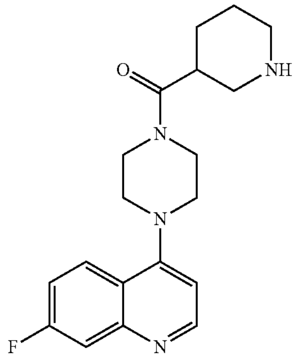 [SMILES: O=C(C1CCCNC1)N1CCN(c2ccnc3cc(F)ccc23)CC1]

Tert-butyl 3-(4-(7-fluoroquinolin-4-yl)piperazine-1-carbonyl)piperidine-1-carboxylate (1.80 g, 4.07 mmol) was dissolved in dichloromethane (10 ml), and trifluoroacetic acid (TFA) (3 ml) was added thereto and stirred at 30° C. for 1 hour. The reaction solution was concentrated and diluted in dichloromethane (10 ml), and saturated aqueous sodium bicarbonate solution (20 ml) was added thereto. Extraction was carried out three times using a mixed solvent of dichloromethane:methanol=10:1 (20 ml). The organic layer was dried over $Na_2SO_4$, filtered and concentrated under reduced pressure to obtain a yellow solid, and the obtained solid was then recrystallized using ethyl acetate (EtOAc) and n-hexane to obtain the title compound (1.32 g, 95% yield) as a yellow solid.

LC-MS (ESI): Rt=1.04 min, m/z 343.4 $[M+H]^+$; purity: 100% @ 254 nm, 100% @214 nm.

Preparation Example 26: Synthesis of (R)-tert-butyl 3-(4-(7-fluoroquinolin-4-yl)piperazine-1-carbonyl)piperidine-1-carboxylate

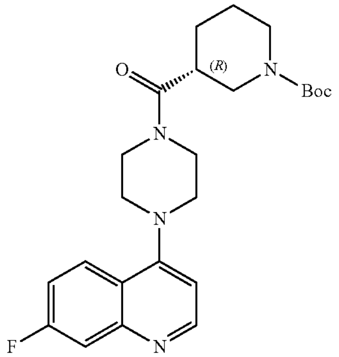

7-Fluoro-4-(piperazin-1-yl)quinoline (600 mg, 2.59 mmol) and (R)-1-(tert-butoxycarbonyl)piperidine-3-carboxylic acid (900 mg, 3.93 mmol) were used in the same manner as in the synthesis method of Preparation Example 24 to obtain the title compound (1.1 g, 96% yield) as a white solid.

$^1$HNMR (400 MHz, $CDCl_3$): δ 8.76-8.74 (m, 1H), 8.05-8.01 (m, 1H), 7.72-7.69 (m, 1H), 7.33-7.27 (m, 1H), 6.84-6.82 (m, 1H), 4.20-4.08 (m, 2H), 3.90-3.84 (m, 4H), 3.25-3.19 (m, 4H), 2.87-2.67 (m, 3H), 1.94-1.91 (m, 1H), 1.84-1.74 (m, 3H), 1.47 (s, 9H). LC-MS (ESI): Rt=1.64 min, m/z 443.6 $[M+H]^+$; purity: 100% @ 254 nm, 100% @ 214 nm.

Preparation Example 27: Synthesis of (R)-(4-(7-fluoroquinolin-4-yl)piperazin-1-yl)(piperidin-3-yl)methanone

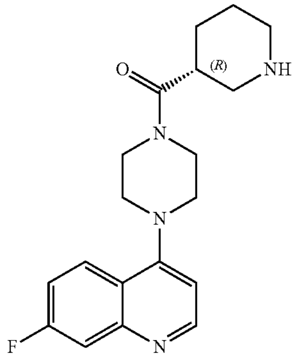

(R)-tert-butyl 3-(4-(7-fluoroquinolin-4-yl)piperazine-4-carbonyl)piperidine-1-carboxylate (500 mg, 1.13 mmol) was used in the same manner as in the synthesis method of Preparation Example 25 to obtain the title compound (350 mg, 90% yield) as a white solid.

$^1$HNMR (400 MHz, DMSO-$d_6$): δ 8.73-8.67 (m, 2H), 8.36-8.33 (m, 1H), 7.81-7.78 (m, 1H), 7.65-7.60 (m, 1H), 7.18 (d, J=7.2 Hz, 1H), 3.98-3.94 (m, 4H), 3.84-3.76 (m, 4H), 3.23-2.98 (m, 5H), 1.92-1.54 (m, 4H). LC-MS (ESI): Rt=1.30 min, m/z 343.5 $[M+H]^+$; purity: 100% @ 254 nm, 100% @ 214 nm.

Preparation Example 28: Synthesis of (S)-tert-butyl 3-(4-(7-fluoroquinolin-4-yl)piperazine-1-carbonyl)piperidine-1-carboxylate

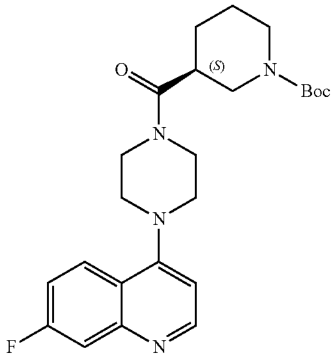

7-Fluoro-4-(piperazin-1-yl)quinoline (200 mg, 0.86 mmol) and (S)-1-(tert-butoxycarbonyl)piperidine-3-carboxylic acid (300 mg, 1.3 mmol) were used in the same manner as in the synthesis method of Preparation Example 24 to obtain the title compound (180 mg, 47% yield) as a white solid.

$^1$HNMR (400 MHz, $CDCl_3$): δ 8.75 (d, J=4.8 Hz, 1H), 8.05-8.01 (m, 1H), 7.72-7.69 (m, 1H), 7.33-7.28 (m, 1H), 6.83 (d, J=4.8 Hz, 1H), 4.21-4.06 (m, 2H), 3.99-3.81 (m,

4H), 3.25-3.19 (m, 4H), 2.98-2.68 (m, 3H), 2.04-1.95 (m, 1H), 1.91-1.74 (m, 3H), 1.47 (s, 9H). LC-MS (ESI): Rt=1.57 min, m/z 443.5 $[M+H]^+$; purity: 100% @ 254 nm, 97.39% @ 214 nm.

Preparation Example 29: Synthesis of (S)-(4-(7-fluoroquinolin-4-yl)piperazin-1-yl)(piperidin-3-yl) methanone

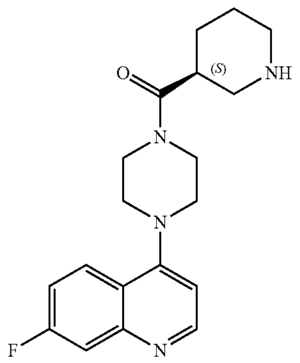

(S)-tert-butyl 3-(4-(7-fluoroquinolin-4-yl)piperazine-4-carbonyl)piperidine-1-carboxylate (380 mg, 0.86 mmol) was used in the same manner as in the synthesis method of Preparation Example 25 to obtain the title compound (140 mg) as a light yellow solid.

$^1$HNMR (400 MHz, $CDCl_3$): δ 8.73-8.71 (m, 2H), 8.37-8.33 (m, 1H), 7.81-7.78 (m, 1H), 7.65-7.60 (m, 1H), 7.19 (d, J=6.8 Hz, 1H), 4.00-3.77 (m, 8H), 3.24-2.94 (m, 5H), 1.96-1.59 (m, 4H). LC-MS (ESI): Rt=1.38 min, m/z 343.5 $[M+H]^+$; purity: 98% @ 254 nm, 100% @ 214 nm.

Preparation Example 30: Synthesis of tert-butyl 3-(4-(quinolin-4-yl)piperazine-1-carbonyl)piperidine-1-carboxylate

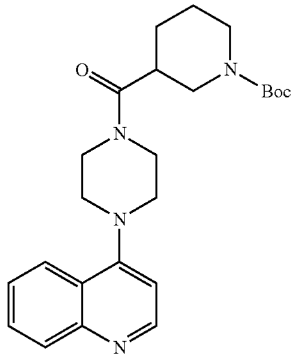

4-(Piperazin-1-yl)quinoline di-HCl salt (1.50 g, 5.24 mmol) and 1-(tert-butoxycarbonyl)piperidine-3-carboxylic acid (2.41 g, 10.5 mmol) were used in the same manner as in the synthesis method of Preparation Example 24 to obtain the title compound (2.1 mg, 80% yield) as a yellow solid.

LC-MS (ESI): Rt=1.31 min, m/z 425.4 $[M+H]^+$; purity: 100% @ 254 nm, 95.1% @ 214 nm.

Preparation Example 31: Synthesis of piperidin-3-yl (4-(quinolin-4-yl)piperazin-1-yl)methanone

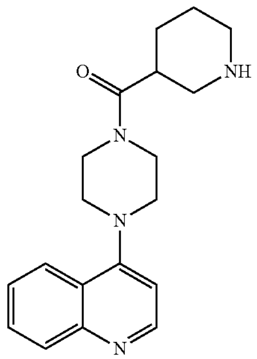

Tert-butyl 3-(4-(quinolin-4-yl)piperazine-1-carbonyl)piperidine-1-carboxylate (2.2 g, 5.18 mmol) was used in the same manner as in the synthesis method of Preparation Example 25 to obtain the title compound (1.6 g) as a yellow solid.

$^1$H MNR (400 MHz, $CDCl_3$): δ 8.76 (d, J=4.8 Hz, 1H), 8.08 (d, J=8.4 Hz, 1H), 8.02 (d, J=8.8 Hz, 1H), 7.71-7.67 (m, 1H), 7.55-7.51 (m, 1H), 6.85 (d, J=5.2 Hz, 1H), 3.91-3.83 (m, 4H), 3.24-3.17 (m, 5H), 3.13-3.09 (m, 2H), 3.04-2.98 (m, 1H), 2.95-2.88 (m, 1H), 2.81-2.75 (m, 1H), 1.95-1.92 (m, 1H), 1.82-1.75 (m, 1H), 1.72-1.65 (m, 1H). LC-MS (ESI): Rt=1.00 min, m/z 325.3 $[M+H]^+$; purity: 100% @ 254 nm, 100% @ 214 nm.

Preparation Example 32: Synthesis of (R)-tert-butyl 3-(4-(quinolin-4-yl)piperazine-1-carbonyl)piperidine-1-carboxylate

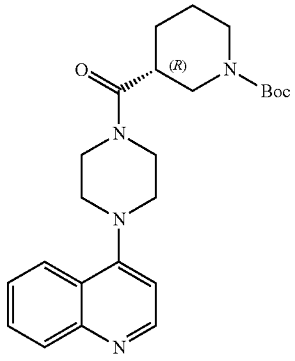

4-(Piperazin-1-yl)quinoline di-HCl salt (320 mg, 1.1 mmol) and (R)-1-(tert-butoxycarbonyl)piperidine-3-carboxylic acid (500 mg, 2.2 mmol) were used in the same manner as in the synthesis method of Preparation Example 24 to obtain the title compound (400 mg) as a white solid.

$^1$HNMR (400 MHz, $CDCl_3$): δ 8.76 (d, J=4.8 Hz, 1H), 8.09 (d, J=8.4 Hz, 1H), 8.03 (d, J=8.4 Hz, 1H), 7.69 (t, J=8.0 Hz, 1H), 7.53 (t, J=8.0 Hz, 1H), 6.86 (d, J=5.2 Hz, 1H), 4.27-4.05 (m, 2H), 3.92-3.83 (m, 4H), 3.31-3.21 (m, 4H), 2.94-2.65 (m, 3H), 1.95-1.92 (m, 1H), 1.84-1.73 (m, 3H), 1.47 (s, 9H). LC-MS (ESI): Rt=1.28 min, m/z 425.4 $[M+H]^+$; purity: 100% @ 254 nm, 95.10% @214 nm.

Preparation Example 33: Synthesis of (R)-piperidin-3-yl(4-(quinolin-4-yl)piperazin-1-yl)methanone

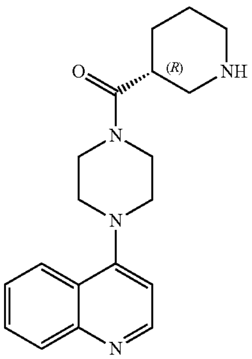

(R)-tert-butyl 3-(4-(quinolin-4-yl)piperazine-1-carbonyl) piperidine-1-carboxylate (600 mg, 1.41 mmol) was used in the same manner as in the synthesis method of Preparation Example 25 to obtain the title compound (2,800 mg) as a light yellow solid.

LC-MS (ESI): Rt=0.28 min, m/z 325.3 $[M+H]^+$; purity: 100% @ 254 nm, 100% @ 214 nm.

Preparation Example 34: Synthesis of (S)-tert-butyl 3-(4-(quinolin-4-yl)piperazine-1-carbonyl)piperidine-1-carboxylate

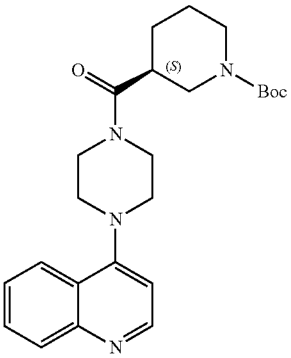

(S)-1-(tert-butoxycarbonyl)piperidine-3-carboxylic acid (500 mg, 2.2 mmol) was used in the same manner as in the synthesis method of Preparation Example 24 to obtain the title compound (380 mg) as a white solid.

$^1$HNMR (400 MHz, $CDCl_3$): $^1$HNMR (400 MHz, $CDCl_3$): δ 8.76 (d, J=4.8 Hz, 1H), 8.10-8.02 (m, 2H), 7.69 (t, J=7.2 Hz, 1H), 7.53 (t, J=8.0 Hz, 1H), 6.86 (d, J=5.2 Hz, 1H), 4.25-4.11 (m, 2H), 3.91-3.80 (m, 4H), 3.62-3.21 (m, 4H), 2.94-2.84 (m, 1H), 2.68-2.63 (m, 2H), 1.97-1.92 (m, 1H), 1.88-1.73 (m, 3H), 1.47 (s, 9H). LC-MS (ESI): Rt=1.27 min, m/z 425.4 $[M+H]^+$; purity: 100% @ 254 nm, 95.1% @ 214 nm.

Preparation Example 35: Synthesis of (S)-piperidin-3-yl(4-(quinolin-4-yl)piperazin-1-yl)methanone

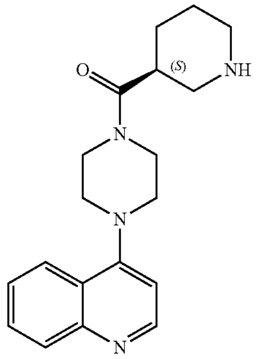

(S)-tert-butyl 3-(4-(quinolin-4-yl)piperazine-1-carbonyl) piperidine-1-carboxylate (600 mg, 1.41 mmol) was used in the same manner as in the synthesis method of Preparation Example 25 to obtain the title compound (250 mg) as a light yellow solid.

LC-MS (ESI): Rt=0.28 min, m/z 325.3 $[M+H]^+$; purity: 100% @ 254 nm, 99.5% @ 214 nm.

Preparation Example 36: Synthesis of 7-chloro-4-(piperazin-1-yl)quinolone

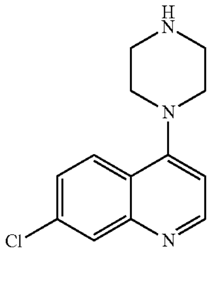 [SMILES: Clc1ccc2c(N3CCNCC3)ccnc2c1]

As shown in Reaction Scheme 1-4, 4,7-dichloroquinoline (5.0 g, 25.25 mmol) and piperazine (10.0 g, 116 mmol) were added to ethanol (250 ml), and heated and refluxed for 12 hours. Then, the mixture was cooled to room temperature, saturated aqueous sodium hydrocarbon solution (sat. $NaHCO_3$, 100 ml) was added thereto, and extraction was carried out adding dichloromethane (DCM, 60 ml×3) to separate the organic layer. The organic layer was dried over $Na_2SO_4$ (sodium bicarbonate), filtered and concentrated under reduced pressure. The obtained product was purified by silica gel column chromatography using dichloromethane and methanol (MeOH, 1-10%) as developing solvents to obtain the title compound (4.94 g) as a white solid.

White solid (80%), $^1$H NMR (400 MHz, $CDCl_3$) δ 8.72 (d, J=5.0 Hz, 1H), 8.04 (d, J=2.0 Hz, 1H), 7.96 (d, J=9.0 Hz, 1H), 7.42 (dd, J=9.0, 2.1 Hz, 1H), 6.84 (d, J=5.0 Hz, 1H), 3.49 (s, 1H), 3.18 (m, 8H).

Preparation Example 37: Synthesis of tert-butyl 3-(4-(7-chloroquinolin-4-yl)piperazine-1-carbonyl) piperidine-1-carboxylate

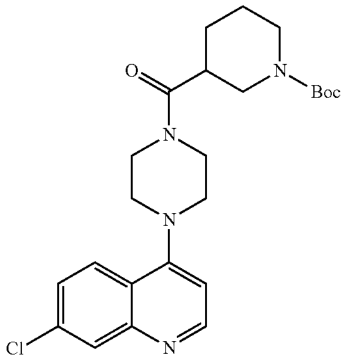 [SMILES: CC(C)(C)OC(=O)N1CCCC(C(=O)N2CCN(c3ccnc4cc(Cl)ccc34)CC2)C1]

1-(Tert-butoxycarbonyl)piperidine-3-carboxylic acid (2.33 g, 10.2 mmol) and 7-chloro-4-(piperazin-1-yl)quinoline (Preparation Example 36, 2.10 g, 8.47 mmol) were used, and they were stirred at room temperature for 2 hours. After adding water (150 ml) to the reaction solution, extraction was carried out using ethyl acetate (EtOAc) (30 ml×3) to separate the organic layer. Water was removed from the organic layer using $Na_2SO_4$, and the obtained product was filtered and concentrated under reduced pressure. The compound was purified using silica gel chromatography to obtain the title compound (3.87 g) as a yellow solid.

1H MNR: (400 MHz, $CDCl_3$): δ 8.75 (d, J=4.8 Hz, 1H), 8.07 (d, J=1.8 Hz, 1H), 7.96 (d, J=9.0 Hz, 1H), 7.47 (dd, J=9.0, 1.8 Hz, 1H), 6.85 (d, J=4.8 Hz, 1H), 4.25-4.06 (m, 2H), 3.90-3.79 (m, 4H), 3.26-3.20 (m, 4H), 2.96-2.68 (m, 4H), 1.95-1.91 (m, 1H), 1.81-1.73 (m, 2H), 1.47 (s, 9H).

Preparation Example 38: Synthesis of (4-(7-chloroquinolin-4-yl)piperazin-1-yl)(piperidin-3-yl)methanone

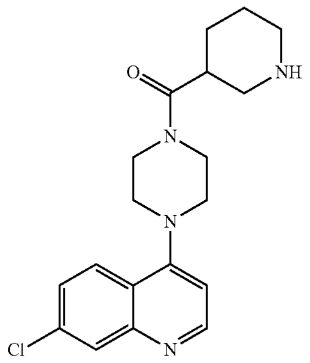 [SMILES: O=C(C1CCCNC1)N1CCN(c2ccnc3cc(Cl)ccc23)CC1]

Tert-butyl 3-(4-(7-chloroquinolin-4-yl)piperazine-1-carbonyl)piperidine-1-carboxylate (2.00 g, 4.36 mmol) was dissolved in dichloromethane (10 ml), and trifluoroacetic acid (TFA)(4 ml) was added thereto and stirred at 30° C. for 1 hour. The reaction solution was concentrated and diluted in dichloromethane (10 ml), and saturated aqueous sodium bicarbonate solution (20 ml) was added thereto. Extraction was carried out three times using a mixed solvent of dichloromethane:methanol=10:1 (20 ml). The organic layer was dried over $Na_2SO_4$, filtered and concentrated under reduced pressure to obtain a yellow solid. The obtained solid was then recrystallized using ethyl acetate (EtOAc) and n-hexane to obtain the title compound (1.55 g, 88% yield) as a yellow solid.

$^1H$ MNR: (400 MHz, $CDCl_3$): δ 8.76 (d, J=5.2 Hz, 1H), 8.07 (d, J=2.4 Hz, 1H), 7.95 (d, J=9.2 Hz, 1H), 7.47 (dd, J=9.6, 2.4 Hz, 1H), 6.85 (d, J=4.8 Hz, 1H), 3.90-3.82 (m, 4H), 3.49-3.41 (br s, 1H), 3.22-3.13 (m, 6H), 3.07-3.02 (m, 1H), 2.99-2.94 (m, 1H), 2.85-2.79 (m, 1H), 1.96-1.92 (m, 1H), 1.85-1.69 (m, 3H). LC-MS (ESI): m/z 359.3 $[M+H]^+$; Purity: 100% @254 nm, 100% @214 nm.

Preparation Example 39: Synthesis of 2-methyl-4-(piperazin-1-yl)quinolone

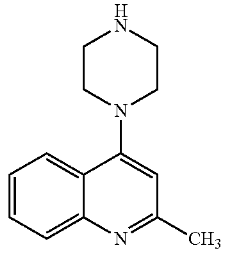 [SMILES: Cc1cc(N2CCNCC2)c2ccccc2n1]

4-Chloro-2-methylquinoline (3.0 g, 16.9 mmol) was used in the same manner as in the synthesis method of Preparation Example 36 to obtain the title compound (3.1 g) as a white solid. White solid (86%), $^1H$ NMR (400 MHz, $CDCl_3$) δ 7.97 (d, J=8.6 Hz, 2H), 7.62 (ddd, J=8.4, 6.9, 1.4 Hz, 1H), 7.42 (ddd, J=8.1, 6.9, 1.1 Hz, 1H), 6.74 (s, 1H), 3.49 (s, 2H), 3.25-3.09 (m, 8H), 2.68 (s, 3H). LC-MS (ESI): Rt=0.93 min, m/z 228.2 $[M+H]^+$; purity: 100% @ 254 nm, 100% @ 214 nm.

Preparation Example 40: Synthesis of tert-butyl 3-(1-(2-methylquinolin-4-yl)piperazine-4-carbonyl) piperidine-1-carboxylate

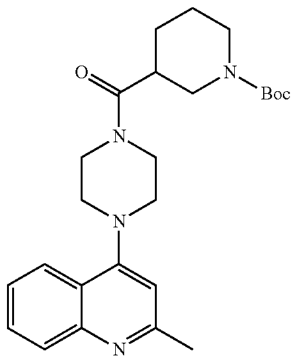 [SMILES: Cc1cc(N2CCN(C(=O)C3CCCN(C(=O)OC(C)(C)C)C3)CC2)c2ccccc2n1]

2-Methyl-4-(piperazin-1-yl)quironline (2.50 g, 11.0 mmol) was used in the same manner as in the synthesis method of Preparation Example 37 to obtain the title compound (4.8 g) as a yellow solid.

LC-MS (ESI): Rt=1.56 min, m/z 439.5 $[M+H]^+$; purity: 100% @ 254 nm, 100% @ 214 nm.

Preparation Example 41: Synthesis of (4-(2-methylquinolin-4-yl)piperazin-1-yl)(piperidin-3-yl) methanone

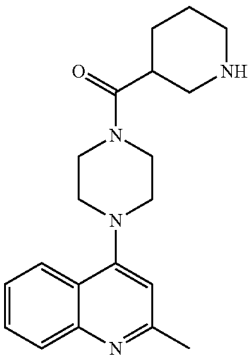 [SMILES: Cc1cc(N2CCN(C(=O)C3CCCNC3)CC2)c2ccccc2n1]

Tert-butyl 3-(1-(2-methylquinolin-4-yl)piperazine-4-carbonyl)piperidine-1-carboxylate (4.83 g, 11.0 mmol) was used in the same manner as in the synthesis method of Preparation Example 38 to obtain the title compound (3.7 g) as a yellow solid.

LC-MS (ESI): Rt=1.22 min, m/z 339.4 $[M+H]^+$; purity: 100% @ 254 nm, 100% @ 214 nm.

Preparation Example 42: Synthesis of (R)-tert-butyl 3-(4-(2-methylquinolin-4-yl)piperazine-1-carbonyl) piperidine-1-carboxylate

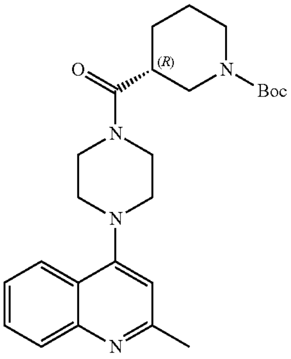

(R)-1-(tert-butoxycarbonyl)piperidine-3-carboxylic acid (111 mg, 0.48 mmol) was used in the same manner as in the synthesis method of Preparation Example 40 to obtain the title compound (190 mg) as a white solid.

LC-MS (ESI): Rt=1.55 min, m/z 439.4 $[M+H]^+$; purity: 100% @ 254 nm, 100% @ 214 nm.

Preparation Example 43: Synthesis of (R)-(4-(2-methylquinolin-4-yl)piperazin-1-yl)(piperidin-3-yl) methanone

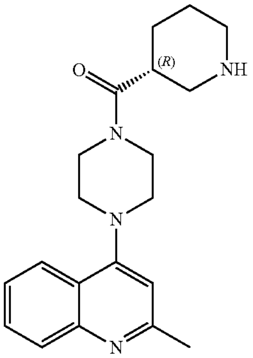

(R)-tert-butyl 3-(1-(2-methylquinolin-4-yl)piperazine-4-carbonyl)piperidine-1-carboxylate (190 mg, 0.43 mmol) was used in the same manner as in the synthesis method of Preparation Example 38 to obtain the title compound (140 mg) as a white solid.

LC-MS (ESI): Rt=1.32 min, m/z 339.2 $[M+H]^+$; purity: 100% @ 254 nm, 100% @ 214 nm.

Preparation Example 44: Synthesis of (S)-tert-butyl 3-(4-(2-methylquinolin-4-yl)piperazine-1-carbonyl) piperidine-1-carboxylate

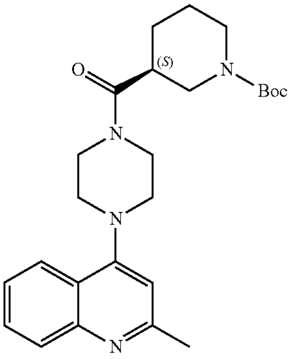

(S)-1-(tert-butoxycarbonyl)piperidine-3-carboxylic acid (111 mg, 0.48 mmol) was used in the same manner as in the synthesis method of Preparation Example 40 to obtain the title compound (180 mg) as a white solid.

LC-MS (ESI): Rt=1.62 min, m/z 439.3 $[M+H]^+$; purity: 100% @ 254 nm, 97.39% @ 214 nm.

Preparation Example 45: Synthesis of (S)-(4-(2-methylquinolin-4-yl)piperazin-1-yl)(piperidin-3-yl) methanone

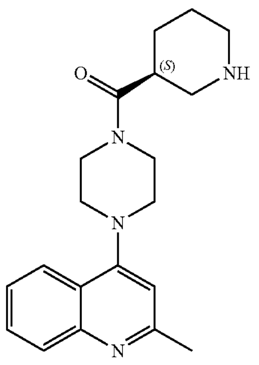

(S)-tert-butyl 3-(1-(2-methylquinolin-4-yl)piperazine-4-carbonyl)piperidine-1-carboxylate (188 mg, 0.43 mmol) was used in the same manner as in the synthesis method of Preparation Example 38 to obtain the title compound (140 mg) as a yellow solid.

LC-MS (ESI): Rt=1.28 min, m/z 339.2 $[M+H]^+$; purity: 100% @ 254 nm, 100% @ 214 nm.

Preparation Example 46: Synthesis of 4-(piperazin-1-yl)-2-(trifluoromethyl)quinolone

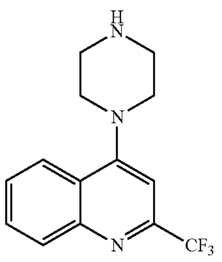 [SMILES: FC(F)(F)c1cc(N2CCNCC2)c2ccccc2n1]

4-Chloro-2-(trifluoromethyl)quinoline (3.0 g, 12.9 mmol) was used in the same manner as in the synthesis method of Preparation Example 36 to obtain the title compound (3.3 mg) as a yellow solid.

1H MNR: (300 MHz, $CDCl_3$): δ 8.16 (d, J=8.4 Hz, 1H), 8.05 (d, J=8.4 Hz, 1H), 7.76-7.71 (m, 1H), 7.61-7.56 (m, 1H), 7.14 (s, 1H), 3.31-3.28 (m, 4H), 3.21-3.18 (m, 4H). LC-MS (ESI): Rt=1.40 min, m/z 282.2 $[M+H]^+$; purity: 100% @ 254 nm, 100% @ 214 nm.

Preparation Example 47: Synthesis of tert-butyl 3-(4-(2-(trifluoromethyl)quinolin-4-yl)piperazine-1-carbonyl) piperidine-1-carboxylate

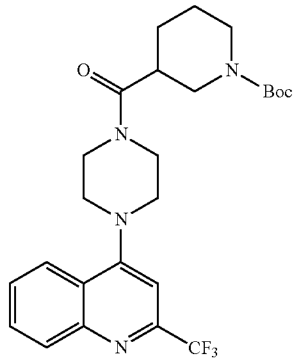 [SMILES: CC(C)(C)OC(=O)N1CCCC(C(=O)N2CCN(c3cc(C(F)(F)F)nc4ccccc34)CC2)C1]

4-(Piperazin-1-yl)-2-(trifluoromethyl)quinoline (2.5 g, 8.90 mmol) was used in the same manner as in the synthesis method of Preparation Example 37 to obtain the title compound (4.3 g) as a yellow solid.

LC-MS (ESI): Rt=1.73 min, m/z 492.5 $[M+H]^+$; purity: 100% @ 254 nm, 100% @ 214 nm.

Preparation Example 48: Synthesis of piperidin-3-yl (4-(2-(trifluoromethyl)quinolin-4-yl)piperazin-1-yl) methanone

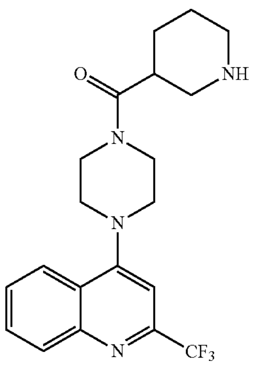 [SMILES: O=C(C1CCCNC1)N1CCN(c2cc(C(F)(F)F)nc3ccccc23)CC1]

Tert-butyl 3-(4-(2-(trifluoromethyl)quinolin-4-yl)piperazine-1-carbonyl)piperidine-1-carboxylate (4.35 g, 8.83 mmol) was used in the same manner as in the synthesis method of Preparation Example 38 to obtain the title compound (3.3 g) as a yellow solid.

LC-MS (ESI): Rt=1.39 min, m/z 393.4 $[M+H]^+$; purity: 100% @ 254 nm, 100% @ 214 nm.

Preparation Example 49: Synthesis of (R)-tert-butyl 3-(4-(2-(trifluoromethyl)quinolin-4-yl)piperazine-1-carbonyl)piperidine-1-carboxylate

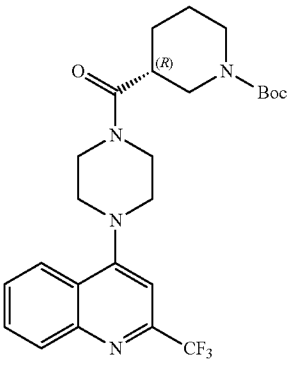

(R)-1-(tert-butoxycarbonyl)piperidine-3-carboxylic acid (134 mg, 0.58 mmol) was used in the same manner as in the synthesis method of Preparation Example 37 to obtain the title compound (250 mg) as a white solid.

LC-MS (ESI): Rt=1.81 min, m/z 493.3 $[M+H]^+$; purity: 100% @ 254 nm, 100% @ 214 nm.

Preparation Example 50: Synthesis of (R)-piperidin-3-yl(4-(2-(trifluoromethyl)quinolin-4-yl)piperazin-1-yl)methanone

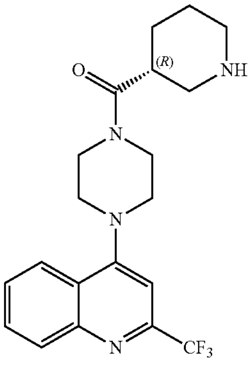

(R)-tert-butyl 3-(4-(2-(trifluoromethyl)quinolin-4-yl)piperazine-1-carbonyl)piperidine-1-carboxylate (260 mg, 0.52 mmol) was used in the same manner as in the synthesis method of Preparation Example 38 to obtain the title compound (200 mg) as a yellow solid.

LC-MS (ESI): Rt=1.55 min, m/z 393.3 $[M+H]^+$; purity: 100% @ 254 nm, 100% @ 214 nm.

Preparation Example 51: Synthesis of (S)-tert-butyl 3-(4-(2-(trifluoromethyl)quinolin-4-yl)piperazine-1-carbonyl) piperidine-1-carboxylate

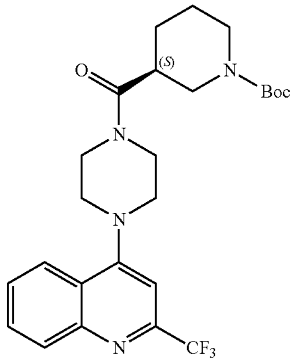

(S)-1-(tert-butoxycarbonyl)piperidine-3-carboxylic acid (134 mg, 0.58 mmol) was used in the same manner as in the synthesis method of Preparation Example 37 to obtain the title compound (250 mg) as a white solid.

LC-MS (ESI): Rt=1.80 min, m/z 493.3 $[M+H]^+$; purity: 100% @ 254 nm, 97.39% @ 214 nm.

Preparation Example 52: Synthesis of (S)-piperidin-3-yl(4-(2-(trifluoromethyl)quinolin-4-yl)piperazin-1-yl)methanone

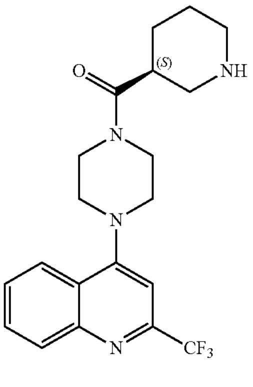

(S)-tert-butyl 3-(4-(2-(trifluoromethyl)quinolin-4-yl)piperazine-1-carbonyl)piperidine-1-carboxylate (260 mg, 0.52 mmol) was used in the same manner as in the synthesis method of Preparation Example 38 to obtain the title compound (170 mg) as a yellow solid.

LC-MS (ESI): Rt=1.56 min, m/z 393.3 $[M+H]^+$; purity: 100% @ 254 nm, 100% @ 214 nm.

Preparation Example 53: Synthesis of 7-methoxy-4-(piperazin-1-yl)quinolone

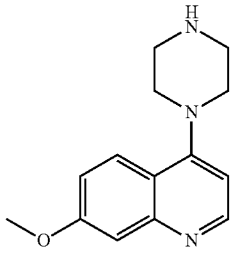 [SMILES: COc1ccc2c(N3CCNCC3)ccnc2c1]

4-Chloro-2-methoxyquinoline (3.00 g, 15.5 mmol) was used in the same manner as in the synthesis method of Preparation Example 36 to obtain the title compound (3.1 g) as a yellow solid.

1H MNR: (400 MHz, $CDCl_3$): δ 8.68 (d, J=6.8 Hz, 1H), 7.94 (d, J=12.4 Hz, 1H), 7.40 (d, J=3.2 Hz, 1H), 7.15 (dd, J=12.0, 3.6 Hz, 1H), 6.76 (d, J=6.8 Hz, 1H), 3.97 (s, 3H), 3.19-3.18 (m, 8H), 1.87 (s, 1H). LC-MS (ESI): Rt=1.213 min, m/z 224.1 $[M+H]^+$; purity: 100% @ 254 nm, 97% @214 nm.

Preparation Example 54: Synthesis of tert-butyl 3-(4-(7-methoxyquinolin-4-yl)piperazine-1-carbonyl)piperidine-1-carboxylate

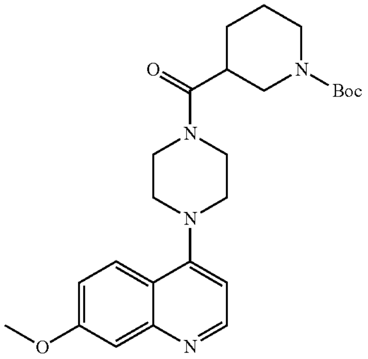 [SMILES: COc1ccc2c(N3CCN(C(=O)C4CCCN(C(=O)OC(C)(C)C)C4)CC3)ccnc2c1]

7-Methoxy-4-(piperazin-1-yl)quinoline (1.50 g, 6.17 mmol) was used in the same manner as in the synthesis method of Preparation Example 3 to obtain the title compound (2.7 g) as a yellow solid.

LC-MS (ESI): Rt=1.61 min, m/z 455.4 $[M+H]^+$; purity: 100% @ 254 nm, 93% @ 214 nm.

Preparation Example 55: Synthesis of (4-(7-methoxyquinolin-4-yl)piperazin-1-yl)(piperidin-3-yl) methanone

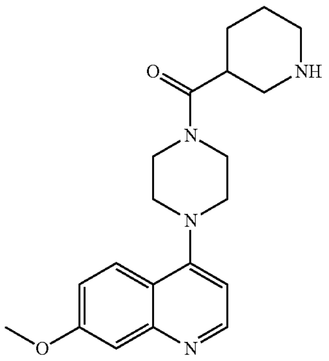 [SMILES: COc1ccc2c(N3CCN(C(=O)C4CCCNC4)CC3)ccnc2c1]

Tert-butyl 3-(4-(7-methoxyquinolin-4-yl)piperazine-1-carbonyl)piperidine-1-carboxylate (2.75 g, 6.04 mmol) was used in the same manner as in the synthesis method of Preparation Example 38 to obtain the title compound (1.8 g) as a yellow solid.

LC-MS (ESI): Rt=1.30 min, m/z 355.4 $[M+H]^+$; purity: 100% @ 254 nm, 100% @214 nm.

Preparation Example 56: Synthesis of 4-(4-((4-(tert-butyl)benzyl)thio)phenyl)pyridine

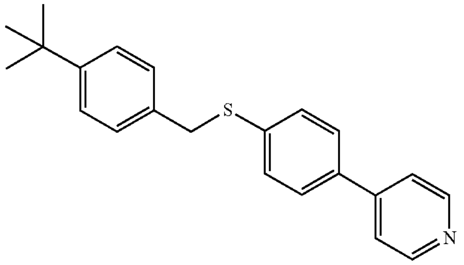 [SMILES: CC(C)(C)c1ccc(CSc2ccc(-c3ccncc3)cc2)cc1]

According to Reaction Scheme 5, 4-(4-bromophenyl) pyridine (500 mg, 2.16 mmol) and (4-(tert-butyl)phenyl) methanethiol (504 mg, 2.80 mmol) were dissolved in 1,4-dioxane (10 mL), and then DIEA (836 mg, 6.48 mmol), Xantphos (249 mg, 0.43 mmol), and $Pd_2(dba)_3$ (198 mg, 0.22 mmol) were added thereto. The reaction solution was reacted at 90° C. for 12 hours under a nitrogen stream, then cooled to room temperature and concentrated under reduced pressure. Water (20 mL) was added to the residue, extraction was carried out with EtOAc (20 mL×3), and the organic layer was washed with brine. The organic layer was concentrated under reduced pressure after removing water with anhydrous $Na_2SO_4$, and the concentrate was purified using a silica gel column (DCM:MeOH=50:1) to obtain the title compound (600 mg, 83% yield) as a light yellow solid.

$^1H$ NMR (400 MHz, $CDCl_3$): δ 8.64 (d, J=6.0 Hz, 2H), 7.55-7.53 (m, 2H), 7.47-7.46 (m, 2H), 7.41-7.39 (m, 2H), 7.35-7.28 (m, 4H), 4.17 (s, 2H), 1.31 (s, 9H).

Preparation Example 57: Synthesis of (4-(pyridin-4-yl)benzene-1-sulfonyl chloride

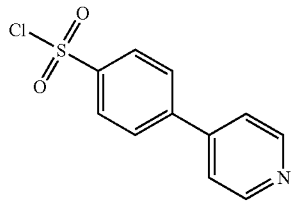 [SMILES: O=S(=O)(Cl)c1ccc(-c2ccncc2)cc1]

4-(4-((4-Tert-butyl)benzyl)thio)phenyl)pyridine (500 mg, 1.50 mmol) was dissolved in acetic acid (3 mL) and purified water (1 mL), and then NCS (604 mg, 4.50 mmol) was added thereto and stirred at 40° C. for 1 hour. Then, the reaction mixture was concentrated under reduced pressure. Water (5 mL) was added to the concentrate, and saturated $Na_2CO_3$ aqueous solution was added to adjust pH to 9. Extraction was carried out using EtOAc (5 mL×3), and the obtained product was washed with brine. The organic layer was dried with anhydrous $Na_2SO_4$ and concentrated to obtain the title compound (320 mg, 84% yield) as a yellow solid.

LC-MS (ESI): Rt=1.46 min, m/z 253.8 $[M+H]^+$; purity: 94% @254 nm, 21% @ 214 nm.

Preparation Example 58: Synthesis of tert-butyl 4-(7-hydroxyquinolin-4-yl)piperazine-1-carboxylate

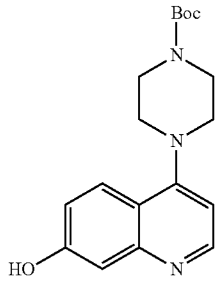 [SMILES: CC(C)(C)OC(=O)N1CCN(c2ccnc3cc(O)ccc23)CC1]

4-Chloroquinolin-7-ol (400 mg, 2.22 mmol) and tert-butyl piperazine-1-carboxylate (413 mg, 4.44 mmol) were added to NMP (4 mL) and DIEA (1 mL), and stirred at 120° C. for 12 hours. The reaction product was cooled to room temperature, the solvent was removed under reduced pressure, and the mixture was extracted three times using a mixed solvent of dichloromethane:methanol=10:1 (20 ml) and water (10 mL×2). The organic layer was washed with brine (20 ml), dried over $Na_2SO_4$, filtered and concentrated under reduced pressure. The concentrate was purified using silica gel column chromatography using a developing solvent of dichloromethane:methanol=20-10:1 to obtain the title compound (610 mg, 83% yield) as a yellow solid.

$^1H$ NMR (400 MHz, $CDCl_3$): δ8.61-8.60 (m, 1H), 7.90-7.87 (m, 1H), 7.52-7.51 (m, 1H), 7.14-7.11 (m, 1H), 6.72-6.70 (m, 1H), 3.72-3.70 (m, 4H), 3.19-3.17 (m, 4H), 1.51 (s, 9H).

Preparation Example 59: Synthesis of 4-(piperazin-1-yl)quinolin-7-ol

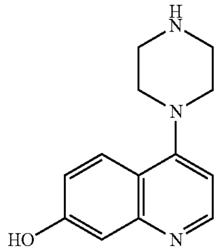 [SMILES: Oc1ccc2c(N3CCNCC3)ccnc2c1]

Tert-butyl 4-(7-hydroxyquironin-4-yl)piperazin-yl-carboxylate (300 mg, 0.91 mmol) was diluted in methanol (2 ml), and 3M in methanol (2 ml) was added thereto. Then, the reaction was carried out at room temperature for 3 hours. The reaction solution was concentrated under reduced pressure and diluted in dichloromethane (10 ml), and saturated aqueous sodium bicarbonate solution was added to adjust the pH to 9. Extraction was carried out three times using a mixed solvent of dichloromethane:methanol=10:1 (20 ml) and water (10 mL×2). The organic layer was washed with brine (20 ml), dried over $Na_2SO_4$, filtered and concentrated under reduced pressure. The concentrate was first purified using silica gel column chromatography using a developing solvent of dichloromethane:methanol=10-5:1, and then crystallized using ethyl acetate (EtOAc) and n-hexane to obtain the title compound. (160 mg, 77% yield) as a yellow solid.

LC-MS (ESI): Rt=0.34 min., m/z 230.1 $[M+H]^+$; purity: 98% @ 254 nm, 90% @ 214 nm.

Preparation Example 60: Synthesis of (S)-tert-butyl 3-(4-(7-hydroxyquinolin-4-yl)piperazine-1-carbonyl) pyrrolidine-1-carboxylate

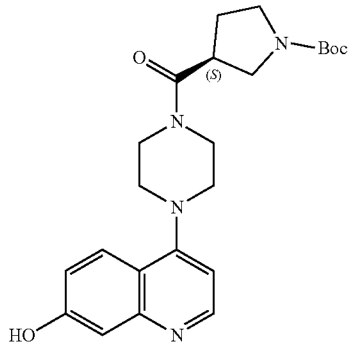

4-(Piperazin-1-yl)quinolin-7-ol (310 mg, 1.35 mmol) and (S)-1-(tert-butoxycarbonyl)pyrrolidine-3-carboxylic acid (323 mg, 1.50 mmol) were used in the same manner as in the synthesis method of Preparation Example 2 to obtain the title compound (100 mg, 38% yield) as a light yellow solid.

LC-MS (ESI): Rt=1.43 min., m/z 427.2 $[M+H]^+$; purity: 80% @ 254 nm, 91% @ 214 nm.

Preparation Example 61: Synthesis of (S)-(4-(7-hydroxyquinolin-4-yl)piperazin-1-yl)(pyrrolidin-3-yl)methanone

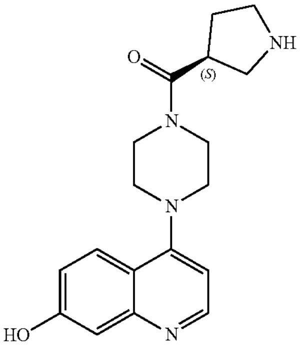

(S)-tert-butyl 3-(4-(7-hydroxyquinolin-4-yl)piperazine-1-carbonyl)pyrrolidine-1-carboxylate (100 mg, 0.23 mmol) was used in the same manner as in the synthesis method of Preparation Example 3 to obtain the title compound (70 mg, 91% yield) as a yellow solid.

LC-MS (ESI): Rt=0.702 min., m/z 327.1 $[M+H]^+$; purity: 93% @ 254 nm.

Preparation Example 62: Synthesis of 6-fluoro-4-(piperazin-1-yl)quinoline

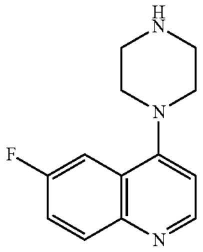 [SMILES: Fc1ccc2nccc(N3CCNCC3)c2c1]

4-Chloro-6-fluoroquinoline (6.0 g, 33.0 mmol) and piperazine (15.0 g, 116 mmol) were used in the same manner as in the synthesis method of Preparation Example 1 to obtain the title compound (5.7 g, 75% yield) as a yellow product.

$^1$HNMR (400 MHz, DMSO-$d_6$): δ 8.72 (d, J=5.3 Hz, 1H), 8.08 (dd, J=9.2, 5.6 Hz, 1H), 7.62 (dd, J=10.0, 2.8 Hz, 1H), 7.46-7.41 (m, 1H), 6.87 (d, J=4.8 Hz, 1H), 4.01-3.88 (m, 4H), 3.61-3.36 (m, 4H). LC-MS (ESI): Rt=1.13 min., m/z 232.0 $[M+H]^+$; purity: 94% @ 254 nm, 97% @214 nm.

Preparation Example 63: Synthesis of tert-butyl (S)-3-(4-(6-fluoroquinolin-4-yl)piperazine-1-carbonyl)pyrrolidine-1-carboxylate

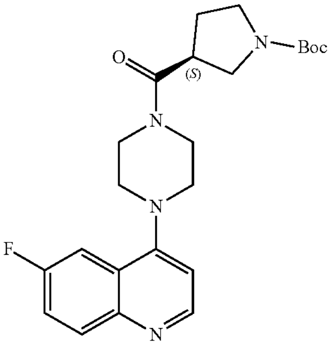

6-Fluoro-4-(piperazin-1-yl)quinoline (200 mg, 0.87 mmol) and (S)-1-(tert-butoxycarbonyl)pyrrolidine-3-carboxylic acid (223 mg, 1.04 mmol)(6.0 g, 33.0 mmol) were used in the same manner as in the synthesis method of Preparation Example 2 to obtain the title compound (320 mg, 86% yield) as a light yellow solid.

$^1$HNMR (400 MHz, $CDCl_3$): δ 8.74 (d, J=5.2 Hz, 1H), 8.09 (dd, J=9.2, 5.6 Hz, 1H), 7.62 (dd, J=10.0, 2.8 Hz, 1H), 7.49-7.44 (m, 1H), 6.89 (d, J=4.8 Hz, 1H), 4.04-3.48 (m, 7H), 3.43-3.34 (m, 1H), 3.31-3.11 (m, 5H), 2.40-2.06 (m, 3H), 1.47 (s, 9H).

Preparation Example 64: Synthesis of (S)-(4-(6-fluoroquinolin-4-yl)piperazin-1-yl)(pyrrolidin-3-yl)methanone

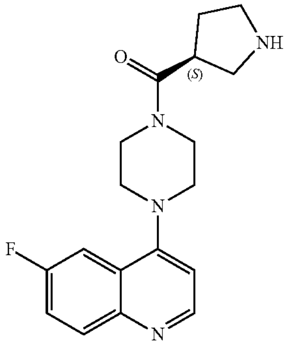

(S)-tert-butyl 3-(4-(6-fluoroquinolin-4-yl)piperazine-1-carbonyl)pyrrolidine-1-carboxylate (320 mg, 0.87 mmol) was used in the same manner as in the synthesis method of Preparation Example 3 to obtain the title compound (220 mg, 90% yield) as a yellow solid.

LC-MS (ESI): Rt=1.19 min., m/z 329.1 $[M+H]^+$; purity: 93% @ 254 nm, 86% @ 214 nm.

Preparation Example 65: Synthesis of 8-fluoro-4-(piperazin-1-yl)quinoline

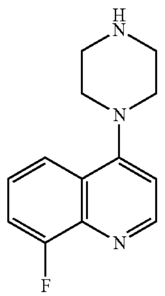 [SMILES: Fc1cccc2c(N3CCNCC3)ccnc12]

4-Chloro-8-fluoroquinoline (5.0 g, 27.5 mmol) and piperazine (13.0 g, 100 mmol) were used in the same manner as in the synthesis method of Preparation Example 1 to obtain the title compound (4.7 g, 74% yield) as a yellow solid.

$^1$H NMR (400 MHz, $CDCl_3$): δ 8.78 (d, J=4.8 Hz, 1H), 7.81-7.79 (m, 1H), 742-7.33 (m, 2H), 6.91 (d, J=4.8 Hz, 1H), 3.24-317 (m, 8H).

Preparation Example 66: Synthesis of tert-butyl (S)-3-(4-(8-fluoroquinolin-4-yl)piperazine-1-carbonyl)pyrrolidine-1-carboxylate

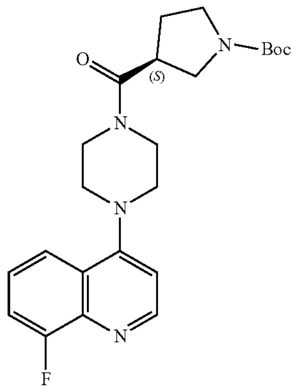

8-Fluoro-4-(piperazin-1-yl)quinoline (500 mg, 2.16 mmol) and (S)-1-(tert-butoxycarbonyl)pyrrolidine-3-carboxylic acid (512 mg, 2.38 mmol) were used in the same manner as in the synthesis method of Preparation Example 2 to obtain the title compound (860 mg, 93% yield) as a light yellow solid.

$^1$H NMR (400 MHz, $CDCl_3$): δ 8.81 (d, J=4.8 Hz, 1H), 7.81-7.78 (m, 1H), 7.49-7.36 (m, 2H), 6.91 (d, J=5.2 Hz, 1H), 4.02-3.76 (m, 4H), 3.67-3.18 (m, 9H), 2.29-2.08 (m, 2H), 1.47 (s, 9H).

Preparation Example 67: Synthesis of (S)-(4-(8-fluoroquinolin-4-yl)piperazin-1-yl)(pyrrolidin-3-yl)methanone

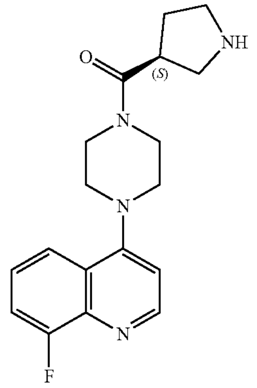

(S)-tert-butyl 3-(4-(8-fluoroquinolin-4-yl)piperazine-1-carbonyl)pyrrolidine-1-carboxylate (850 mg, 1.99 mmol) was used in the same manner as in the synthesis method of Preparation Example 3 to obtain the title compound (610 mg, 94% yield) as a yellow solid.

$^1$H NMR (400 MHz, $CDCl_3$): δ 8.81 (d, J=4.8 Hz, 1H), 7.81-7.79 (m, 1H), 7.50-7.38 (m, 2H), 6.92 (d, J=4.8 Hz, 1H), 4.00-3.78 (m, 4H), 3.30-3.09 (m, 7H), 3.05-2.96 (m, 1H), 2.91-2.85 (m, 1H), 2.13-2.01 (m, 2H).

Preparation Example 68: Synthesis of tert-butyl 4-(7-methylquinolin-4-yl)piperazine-1-carboxylate

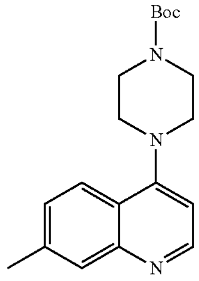 [SMILES: Cc1ccc2c(N3CCN(C(=O)OC(C)(C)C)CC3)ccnc2c1]

4-Chloro-7-methylquinoline (500 mg, 2.81 mmol) and tert-butyl piperazine-1-carboxylate (680 mg, 3.65 mmol) were used in the same manner as in the synthesis method of Preparation Example 58 to obtain the title compound (800 mg, 95% yield) as a yellow solid.

$^1$H NMR (400 MHz, $CDCl_3$): δ 8.70-8.69 (m, 1H), 7.91-7.89 (m, 1H), 7.84 (s, 1H), 7.34-7.32 (m, 1H), 6.78-6.77 (m, 1H), 3.72-3.70 (m, 4H), 3.17-3.15 (m, 4H), 2.54 (s, 3H), 1.51 (s, 9H).

Preparation Example 69: Synthesis of 7-methyl-4-(piperazin-1-yl)quinoline

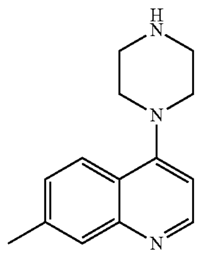 [SMILES: Cc1ccc2c(N3CCNCC3)ccnc2c1]

Tert-butyl 4-(7-methylquinonlin-4-yl)piperazine-1-carboxylate (800 mg, 2.44 mmol) was used in the same manner as in the synthesis method of Preparation Example 59 to obtain the title compound (490 mg, 88% yield) as a yellow solid.

$^1$H NMR (400 MHz, DMSO-$d_6$): δ 8.63-8.62 (m, 1H), 7.93-7.90 (m, 1H), 7.73 (s, 1H), 7.38-7.36 (m, 1H), 6.89-6.88 (m, 1H), 3.12-2.93 (m, 8H), 2.49 (s, 3H).

Preparation Example 70: Synthesis of tert-butyl (S)-3-(4-(7-methylquinolin-4-yl)piperazine-1-carbonyl)pyrrolidine-1-carboxylate

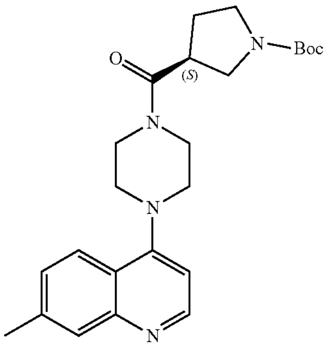

7-Methylquinoneline-4-(piperazin-1-yl)quinoline (200 mg, 0.88 mmol) and (S)-1-(tert-butoxycarbonyl)pyrrolidine-3-carboxylic acid (226 mg, 1.05 mmol) were used in the same manner as in the synthesis method of Preparation Example 2 to obtain the title compound (320 mg, 86% yield) as a light yellow solid.

$^1$HNMR (400 MHz, $CDCl_3$): δ 8.71 (d, J=4.8 Hz, 1H), 7.91-7.89 (m, 1H), 7.86 (s, 1H), 7.36-7.34 (m, 1H), 6.79 (d, J=4.8 Hz, 1H), 4.00-3.94 (m, 2H), 3.88-3.85 (m, 2H), 3.66-3.46 (m, 3H), 3.41-3.22 (m, 7H), 2.55 (s, 1H), 2.13-2.06 (m, 1H), 1.86-1.72 (m, 1H), 1.47 (s, 9H).

Preparation Example 71: Synthesis of (S)-(4-(7-methylquinolin-4-yl)piperazin-1-yl)(pyrrolidin-3-yl) methanone

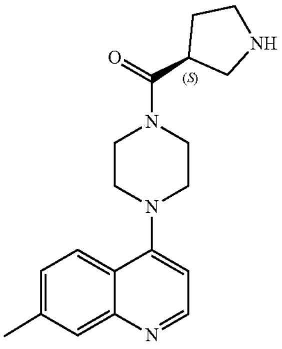

(S)-tert-butyl 3-(4-(7-hydroxyquinolin-4-yl)piperazine-1-carbonyl)pyrrolidine-1-carboxylate (320 mg, 0.76 mmol) was used in the same manner as in the synthesis method of Preparation Example 3 to obtain the title compound (200 mg, 82% yield) as a yellow solid.

LC-MS (ESI): Rt=1.129 min., m/z 325.2 [M+H]$^+$; purity: 94% @ 254 nm.

Preparation Example 72: Synthesis of tert-butyl 4-(7-methoxyquinolin-4-yl)piperazine-1-carboxylate

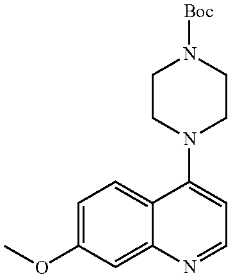 [SMILES: COc1ccc2c(N3CCN(C(=O)OC(C)(C)C)CC3)ccnc2c1]

4-Chloro-7-methoxyquinoline (2.00 g, 10.31 mmol) and tert-butyl piperazine-1-carboxylate (2.49 g, 13.40 mmol) were used in the same manner as in the synthesis method of Preparation Example 58 to obtain the title compound (3.10 g, 88% yield) as a yellow solid.

$^1$H NMR (400 MHz, $CDCl_3$): δ 8.67-8.66 (m, 1H), 7.91-7.89 (m, 1H), 7.40-7.39 (m, 1H), 7.16-7.13 (m, 1H), 6.75-6.73 (m, 1H), 3.95 (s, 3H), 3.72-3.69 (m, 4H), 3.17-3.15 (m, 4H), 1.50 (s, 9H).

Preparation Example 73: Synthesis of 7-methoxy-4-(piperazin-1-yl)quinoline

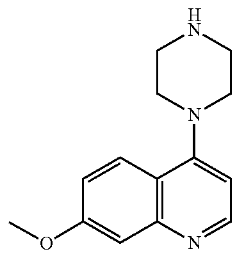 [SMILES: COc1ccc2c(N3CCNCC3)ccnc2c1]

Tert-butyl 4-(7-methoxyquironlin-4-yl)piperazine-1-carboxylate (3.0 g, 8.75 mmol) was used in the same manner as in the synthesis method of Preparation Example 59 to obtain the title compound (2.00 g, 98% yield) as a yellow solid.

$^1$H NMR (400 MHz, $CDCl_3$): δ 8.66-8.64 (m, 1H), 7.93-7.90 (m, 1H), 7.38-7.37 (m, 1H), 7.14-7.11 (m, 1H), 6.74-6.73 (m, 1H), 3.94 (s, 3H), 3.17-3.15 (m, 8H).

Preparation Example 74: Synthesis of (S)-tert-butyl 3-(4-(7-methoxyquinolin-4-yl)piperazine-1-carbonyl)pyrrolidine-1-carboxylate

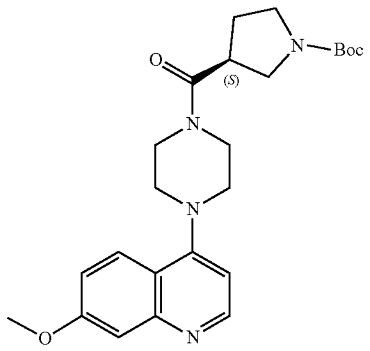

7-Methoxy-4-(piperazin-1-yl)quinoline (1.00 g, 4.12 mmol) and (S)-1-(tert-butoxycarbonyl)pyrrolidine-3-carboxylic acid (970 mg, 4.53 mmol) were used in the same manner as in the synthesis method of Preparation Example 2 to obtain the title compound (100 mg, 38% yield) as a light yellow solid $^1$H NMR (400 MHz, $CDCl_3$): δ 8.68-8.67 (m, 1H), 7.92-7.89 (m, 1H), 7.41-7.40 (m, 1H), 7.19-7.16 (m, 1H), 6.75-6.74 (m, 1H), 3.95 (s, 3H), 3.81-3.49 (m, 5H), 3.44 (s, 2H), 3.37-3.07 (m, 6H), 2.37-2.22 (m, 1H), 2.13-2.04 (m, 1H), 1.47 (s, 9H).

Preparation Example 75: Synthesis of (S)-(4-(7-methoxyquinolin-4-yl)piperazin-1-yl)(pyrrolidin-3-yl)methanone

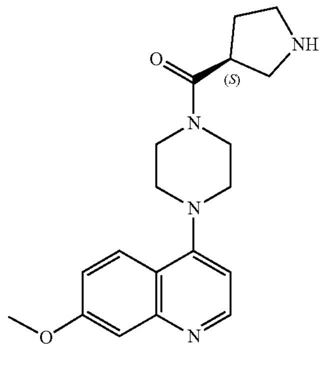

(S)-tert-butyl 3-(4-(7-methoxyquinolin-4-yl)piperazine-1-carbonyl)pyrrolidine-1-carboxylate (1.6 g, 3.64 mmol) was used in the same manner as in the synthesis method of Preparation Example 3 to obtain the title compound (1.1 g, 92% yield) as a yellow solid.

$^1$H NMR (400 MHz, $CDCl_3$): δ 8.69-8.67 (m, 1H), 7.93-7.90 (m, 1H), 7.41-7.40 (m, 1H), 7.18-7.15 (m, 1H), 6.75-6.74 (m, 1H), 3.95 (s, 3H), 3.91-3.82 (m, 4H), 3.28-3.10 (m, 7H), 3.03-2.99 (m, 1H), 2.91-2.85 (m, 1H), 2.08-1.96 (m, 2H).

Preparation Example 76: Synthesis of tert-butyl (S)-3-(4-(2-(trifluoromethyl)quinolin-4-yl)piperazine-1-carbonyl)pyrrolidine-1-carboxylate

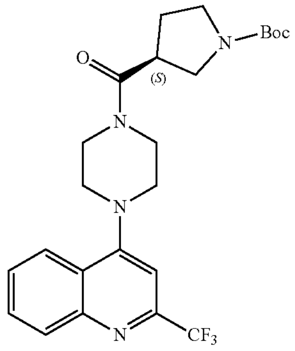

4-(Piperazin-1-yl)-2-(trifluoromethyl)quinoline (770 mg, 2.74 mmol) and (S)-1-(tert-butoxycarbonyl)pyrrolidine-3-carboxylic acid (710 mg, 3.29 mmol) were used in the same manner as in the synthesis method of Preparation Example 2 to obtain the title compound (685 mg, 53% yield) as a light yellow solid.

LC-MS (ESI): Rt=1.73 min. m/z 479.1 $[M+H]^+$; purity: 100% @ 254 nm.

Preparation Example 77: Synthesis of (S)-pyrrolidin-3-yl(4-(2-(trifluoromethyl)quinolin-4-yl)piperazin-1-yl)methanone

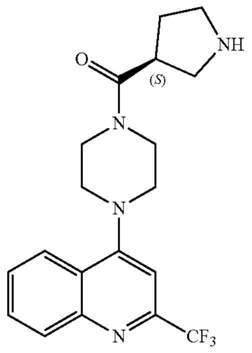

Tert-butyl (S)-3-(4-(2-(trifluoromethyl)quinolin-4-yl)piperazine-1-carbonyl)pyrrolidine-1-carboxylate (685 mg, 1.43 mmol) was used in the same manner as in the synthesis method of Preparation Example 3 to obtain the title compound (670 mg, 96% yield) as a yellow solid.

LC-MS (ESI): Rt=1.96 min. m/z 379.0 $[M+H]^+$; purity: 100% @ 254 nm.

Preparation Example 78: Synthesis of 6,7-difluoro-4-(piperazin-1-yl)quinoline

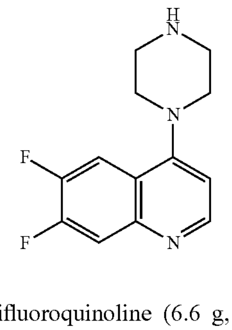

4-Chloro-6,7-difluoroquinoline (6.6 g, 33.0 mmol) and piperazine (15.0 g, 116 mmol) were used in the same manner as in the synthesis method of Preparation Example 1 to obtain the title compound (5.5 g, 66% yield) as a yellow solid.

LC-MS (ESI): Rt=0.183 min., m/z 250.1 $[M+H]^+$; purity: 97% @ 254 nm.

Preparation Example 79: Synthesis of tert-butyl (S)-3-(4-(6,7-difluoroquinolin-4-yl)piperazine-1-carbonyl)pyrrolidine-1-carboxylate

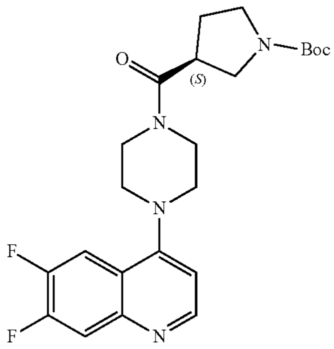

1-(Tert-butoxycarbonyl)pyrrolidine-3-carboxylic acid (717 mg, 3.33 mmol) and 6,7-fluoro-4-(piperazin-1-yl)quinoline (760 mg, 3.05 mmol) were used in the same manner as in the synthesis method of Preparation Example 3 to obtain the title compound (1.1 g, 81% yield) as a yellow solid.

LC-MS (ESI): Rt=1.309 min., m/z 447.2 $[M+H]^+$; purity: 98.2% @ 254 nm.

Preparation Example 80: Synthesis of (S)-(4-(6,7-fluoroquinolin-4-yl)piperazin-1-yl)(pyrrolidin-3-yl)methanone

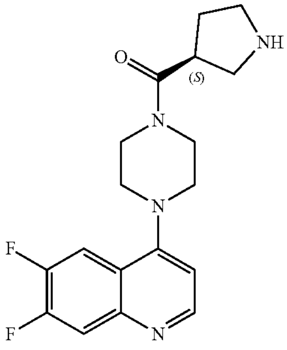

Tert-butyl (S)-3-(4-(6,7-fluoroquinolin-4-yl)piperazine-1-carbonyl)piperidine-1-carboxylate (1.20 g, 2.69 mmol) was used in the same manner as in the synthesis method of Preparation Example 3 to obtain the title compound (670 mg, 80% yield) as a yellow solid.

LC-MS (ESI): Rt=1.243 min., m/z 347.2 $[M+H]^+$; purity: 95% @ 254 nm.

Example 1: Synthesis of N-(4-((3-(4-(7-fluoroquinolin-4-yl)piperazine-1-carbonyl)pyrrolidin-1-yl) sulfonyl)phenyl)acetamide

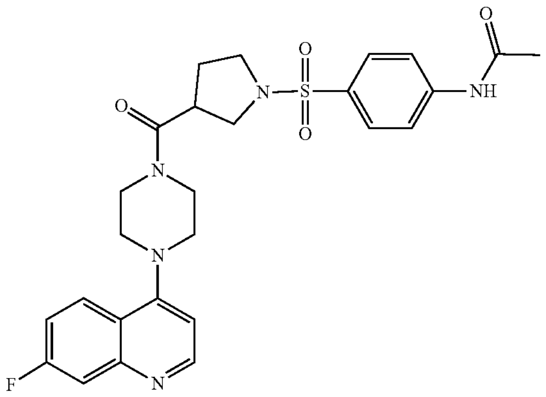 [SMILES: CC(=O)Nc1ccc(S(=O)(=O)N2CCC(C(=O)N3CCN(c4ccnc5cc(F)ccc45)CC3)C2)cc1]

According to Reaction Scheme 1-1, (4-(7-fluoroquinolin-4-yl)piperazin-1-yl)(pyrrolidin-3-yl)methanone (80 mg, 0.24 mmol, Preparation Example 3) and TEA (73 mg, 0.72 mmol) were dissolved in dichloromethane (DCM, 1 mL), and 4-acetamidobenzene-1-sulfonyl chloride (68 mg, 0.29 mmol) diluted in dichloromethane (1 mL) was slowly added thereto and then stirred at room temperature for 2 hours. The reaction solution was concentrated and diluted in dichloromethane (10 mL), and saturated aqueous sodium bicarbonate solution (20 mL) was added thereto.

Extraction was carried out three times using a mixed solvent (20 ml) of dichloromethane:methanol=10:1. The organic layer was dried over $Na_2SO_4$, filtered and concentrated under reduced pressure. The residue was purified using silica gel chromatography (developing solvent, dichloromethane:methanol=15:1) to obtain the title compound (54 mg, 43% yield) as a white solid.

$^1$H NMR (400 MHz, $CDCl_3$): δ 8.75 (d, J=4.8 Hz, 1H), 8.01 (dd, J=9.2, 6.0 Hz 1H), 7.81-7.78 (m, 2H), 7.73-7.69 (m, 3H), 7.59 (s, 1H), 7.33-7.28 (m, 1H), 6.82 (d, J=5.2 Hz, 1H), 3.85 (s, 2H), 3.77-3.68 (m, 2H), 3.66 (dd, J=9.6, 7.6 Hz, 1H), 3.47-3.41 (m, 1H), 3.34-3.15 (m, 7H), 2.22 (s, 3H), 2.11-2.06 (m, 2H). LC-MS (ESI): Rt=3.219 min, m/z 526.2 $[M+H]^+$; purity: 97.72% @ 254 nm, 95.79% @ 214 nm.

Example 2: Synthesis of (R)—N-(4-((3-(4-(7-fluoroquinolin-4-yl)piperazine-1-carbonyl)pyrrolidin-1-yl)sulfonyl)phenyl)acetamide

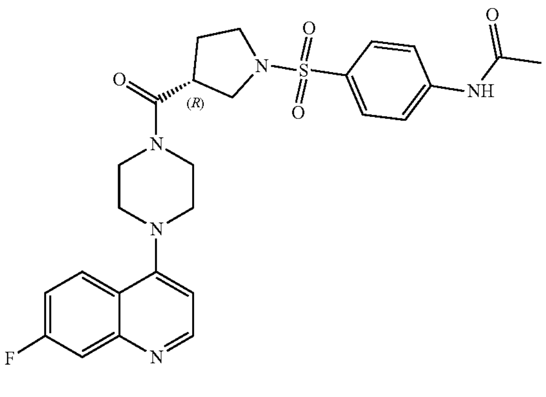

(R)-(4-(7-fluoroquinolin-4-yl)piperazin-1-yl)(pyrrolidin-3-yl)methanone (80 mg, 0.24 mmol, Preparation Example 7) and 4-acetamidobenzene-1-sulfonyl chloride (114 mg, 0.48 mmol) were used in the same manner as in the method of Example 1 to obtain the title compound (54 mg, 42% yield) as a white solid.

$^1$H NMR (400 MHz, $CDCl_3$): δ 8.76-8.75 (m, 1H), 8.03-7.99 (m, 1H), 7.80-7.78 (m, 2H), 7.71-7.69 (m, 3H), 7.64 (s, 1H), 7.33-7.29 (m, 1H), 6.83-6.82 (m, 1H), 3.85 (br s, 2H), 3.74 (br s, 2H), 3.68-3.64 (m, 1H), 3.47-3.41 (m, 1H), 3.34-3.17 (m, 7H), 2.22 (m, 3H), 2.11-2.06 (m, 2H).

LC-MS (ESI): Rt=3.224 min, m/z 526.3 $[M+H]^+$; purity: 99.09% @ 254 nm, 99.82% @ 214 nm. chiral HPLC: Column: Chiralpak IC 5 μm 4.6×250 mm; Mobile Phase: Hex:EtOH=30:70 at 1 mL/min; Temp: 30° C.; Wavelength: 214 nm, Rt=15.671 min, 99.8% ee.

Example 3: Synthesis of (1-((4-(dimethylamino) phenyl)sulfonyl)pyrrolidin-3-yl)(4-(7-fluoroquinolin-4-yl)piperazin-1-yl)methanone

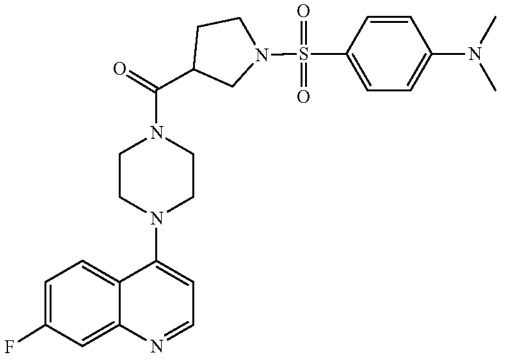 [SMILES: CN(C)c1ccc(S(=O)(=O)N2CCC(C(=O)N3CCN(c4ccnc5cc(F)ccc45)CC3)C2)cc1]

(4-(7-Fluoroquinolin-4-yl)piperazin-1-yl)(pyrrolidin-3-yl)methanone (80 mg, 0.24 mmol) and 4-(dimethylamino) benzene-1-sulfonyl chloride (63 mg, 0.29 mmole) were used in the same manner as in the method of Example 1 to obtain the title compound (54 mg, 44% yield) as a white solid.

$^1$H NMR (400 MHz, $CDCl_3$): δ 8.76 (d, J=5.2 Hz, 1H), 8.01 (dd, J=9.2, 6.0 Hz, 1H), 7.73-7.66 (m, 3H), 7.33-7.28 (m, 1H), 6.82 (d, J=5.2 Hz, 1H), 6.70 (dd, J=7.2, 2.0 Hz, 2H), 3.86 (s, 2H), 3.79-3.72 (m, 2H), 3.69-3.65 (m, 1H), 3.46-3.40 (m, 1H), 3.27-3.16 (m, 7H), 3.05 (s, 6H), 2.12-2.03 (m, 2H). LC-MS (ESI): Rt=3.497 min, m/z 512.2 $[M+H]^+$; purity: 98.07% @ 254 nm, 99.05% @214 nm.

Example 4: Synthesis of (4-(7-fluoroquinolin-4-yl)piperazin-1-yl)(1-((4-hydroxyphenyl)sulfonyl)pyrrolidin-3-yl)methanone

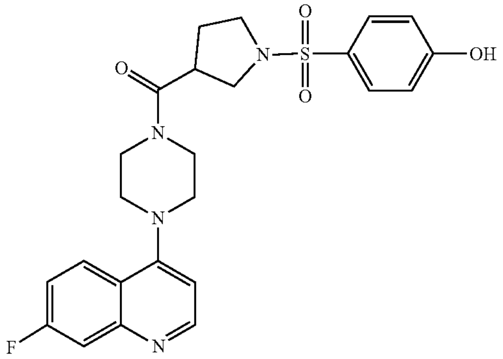 [SMILES: O=C(C1CCN(S(=O)(=O)c2ccc(O)cc2)C1)N1CCN(c2ccnc3cc(F)ccc23)CC1]

(4-(7-Fluoroquinolin-4-yl)piperazin-1-yl)(pyrrolidin-3-yl)methanone (160 mg, 0.48 mmol) and 4-hydroxybenzene-1-sulfonyl chloride (92 mg, 0.48 mmol) were used in the same manner as in the method of Example 1 to obtain the title compound (83 mg, 35% yield) as a white solid.

$^1$H NMR (400 MHz, $CDCl_3$): δ 8.74 (d, J=5.2 Hz, 1H), 8.01 (dd, J=9.2, 6.0 Hz, 1H), 7.73-7.68 (m, 3H), 7.34-7.29 (m, 1H), 6.92 (d, J=8.8 Hz, 2H), 6.83 (d, J=4.8 Hz, 1H), 3.95-3.65 (m, 5H), 3.51-3.45 (m, 1H), 3.31-3.13 (m, 7H), 2.14-2.04 (m, 2H). LC-MS (ESI): Rt=3.233 min, m/z 485.2 $[M+H]^+$; purity: 98.22% @ 254 nm, 98.36% @ 214 nm.

Example 5: Synthesis of (4-(7-fluoroquinolin-4-yl)piperazin-1-yl)(1-((1-methyl-1H-imidazol-2-yl)sulfonyl)pyrrolidin-3-yl)methanone

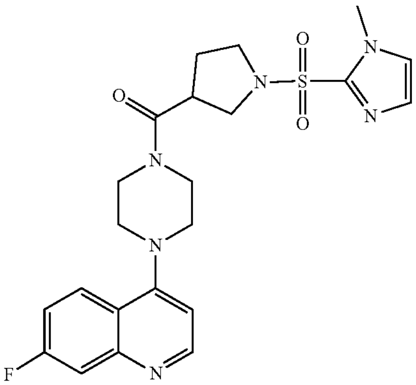 [SMILES: Cn1ccnc1S(=O)(=O)N1CCC(C(=O)N2CCN(c3ccnc4cc(F)ccc34)CC2)C1]

(4-(7-Fluoroquinolin-4-yl)piperazin-1-yl)(pyrrolidin-3-yl)methanone (80 mg, 0.24 mmol) and 1-methyl-1H-imidazole-2-sulfonyl chloride (52 mg, 0.29 mmol) were used in the same manner as in the method of Example 1. The obtained product was purified by C18 chromatography using 20-90% $CH_3CN$ aqueous solution as a developing solvent to obtain the title compound (38 mg, 34% yield) as a white solid.

$^1$H NMR (400 MHz, $CDCl_3$): δ 8.76 (d, J=4.8 Hz, 1H), 8.03 (dd, J=9.2, 6.0 Hz, 1H), 7.72 (dd, J=10.0, 2.4 Hz, 1H), 7.34-7.29 (m, 1H), 7.03 (d, J=1.2 Hz, 1H), 6.97 (d, J=1.2 Hz, 1H), 6.84 (d, J=4.8 Hz, 1H), 3.98-3.88 (m, 6H), 3.85-3.83 (m, 2H), 3.77-3.67 (m, 2H), 3.63-3.55 (m, 2H), 3.26-3.19 (m, 4H), 2.45-2.35 (m, 1H), 2.27-2.18 (m, 1H). LC-MS (ESI): Rt=3.038 min, m/z 473.2 $[M+H]^+$; purity: 97.63% @ 254 nm, 97.73% @ 214 nm.

Example 6: Synthesis of (R)-(4-(7-fluoroquinolin-4-yl)piperazin-1-yl)(1-((1-methyl-1H-imidazol-2-yl)sulfonyl)pyrrolidin-3-yl)methanone

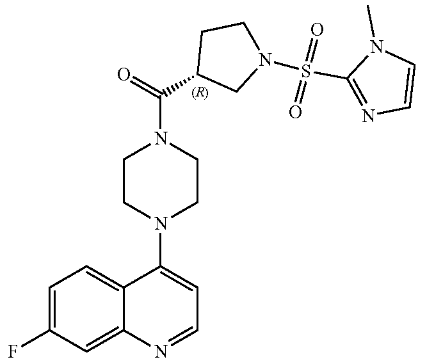

(R)-(4-(7-fluoroquinolin-4-yl)piperazin-1-yl)(pyrrolidin-3-yl)methanone (200 mg, 0.61 mmol) and 1-methyl-1H-imidazole-2-sulfonyl chloride (170 mg, 0.94 mmol) were used in the same manner as in the method of Example 5 to obtain the title compound (120 mg, 42% yield) as a white solid.

$^1$H NMR (400 MHz, $CDCl_3$): δ 8.76 (d, J=4.8 Hz, 1H), 8.05-8.01 (m, 1H), 7.73-7.70 (m, 1H), 7.33-7.29 (m, 1H), 7.03 (s, 1H), 6.97 (s, 1H), 6.84 (d, J=4.8 Hz, 1H), 3.98-3.94 (m, 6H), 3.87-3.79 (m, 2H), 3.76-3.67 (m, 2H), 3.63-3.55 (m, 2H), 3.31-3.14 (m, 4H), 2.43-2.35 (m, 1H), 2.24-2.16 (m, 1H). LC-MS (ESI): Rt=2.692 min, m/z 473.1 $[M+H]^+$; purity: 99.71% @ 254 nm, 99.90% @ 214 nm. chiral HPLC: Column: Chiralpak IA 5 um 4.6×250 mm; Mobile Phase: Hexane:EtOH:DEA=40:60:0.2 at 1 mL/min; Temp: 30° C.; Wavelength: 254 nm, Rt=14.485 min, 100% ee.

Example 7: Synthesis of (S)-(4-(7-fluoroquinolin-4-yl)piperazin-1-yl)(1-((1-methyl-1H-imidazol-2-yl)sulfonyl)pyrrolidin-3-yl)methanone

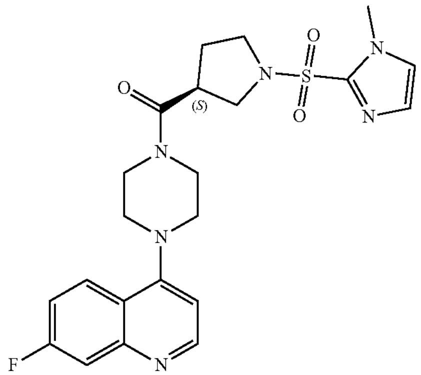

(S)-(4-(7-fluoroquinolin-4-yl)piperazin-1-yl)(pyrrolidin-3-yl)methanone (80 mg, 0.24 mmol, Preparation Example 5)

and 1-methyl-1H-imidazole-2-sulfonyl chloride (52 mg, 0.29 mmol) were used in the same manner as in the method of Example 5 to obtain the title compound (42 mg, 37% yield) as a white solid.

$^1$H NMR (400 MHz, $CDCl_3$): δ 8.76 (d, J=4.8 Hz, 1H), 8.04-8.01 (m, 1H), 7.71 (dd, J=2.4, 10.0 Hz, 1H), 7.34-7.29 (m, 1H), 7.03 (s, 1H), 6.97 (s, 1H), 6.83 (d, J=4.8 Hz, 1H), 3.98-3.88 (m, 6H), 3.87-3.80 (m, 2H), 3.77-3.67 (m, 2H), 3.63-3.57 (m, 2H), 3.23-3.15 (m, 4H), 2.45-2.38 (m, 1H), 2.24-2.17 (m, 1H). LC-MS (ESI): Rt=2.693 min, m/z 473.2 $[M+H]^+$; purity: 98.57% @ 254 nm, 99.71% @ 214 nm. chiral HPLC: Column: Chiralpak IA 5 um 4.6×250 mm; Mobile Phase: Hexane:EtOH:DEA=40:60:0.2 at 1 mL/min; Temp: 30° C.; Wavelength: 254 nm, Rt=11.415 min, 100% ee.

Example 8: Synthesis of (4-(7-fluoroquinolin-4-yl)piperazin-1-yl)(1-((4-nitrophenyl)sulfonyl)pyrrolidin-3-yl)methanone

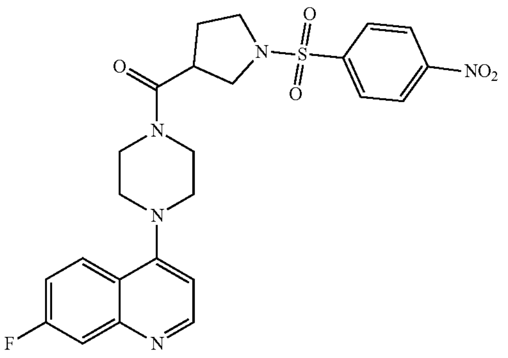 [SMILES: O=C(C1CCN(S(=O)(=O)c2ccc([N+](=O)[O-])cc2)C1)N1CCN(c2ccnc3cc(F)ccc23)CC1]

(4-(7-Fluoroquinolin-4-yl)piperazin-1-yl)(pyrrolidin-3-yl)methanone (100 mg, 0.31 mmol) and 4-nitrobenzene-1-sulfonyl chloride (67 mg, 0.31 mmol) were used in the same manner as in the method of Example 1 to obtain the title compound (55 mg, 35% yield) as a light yellow solid.

$^1$H NMR (400 MHz, $CDCl_3$): δ 8.74 (d, J=4.8 Hz, 1H), 8.40 (d, J=8.8 Hz, 2H), 8.06-7.98 (m, 3H), 7.76 (dd, J=10.0, 2.4 Hz, 1H), 7.34-7.29 (m, 1H), 6.83 (d, J=5.2 Hz, 1H), 3.83-3.70 (m, 5H), 3.58-3.45 (m, 2H), 3.36-3.20 (m, 6H), 2.20-2.03 (m, 2H). LC-MS (ESI): Rt=3.037 min, m/z 514.2 $[M+H]^+$; purity: 97.15% @254 nm, 97.92% @ 214 nm. chiral HPLC: Column: Chiralpak IA 5 μm 4.6×250 mm; Mobile Phase: Hex:EtOH:DEA=30:70:0.2 at 1 mL/min; Temp: 30° C.; Wavelength: 230 nm, Rt=11.415 min, 100% ee.

Example 9: Synthesis of N-(3-((3-(4-(7-fluoroquinolin-4-yl)piperazine-1-carbonyl)pyrrolidin-1-yl)sulfonyl)phenyl)acetamide

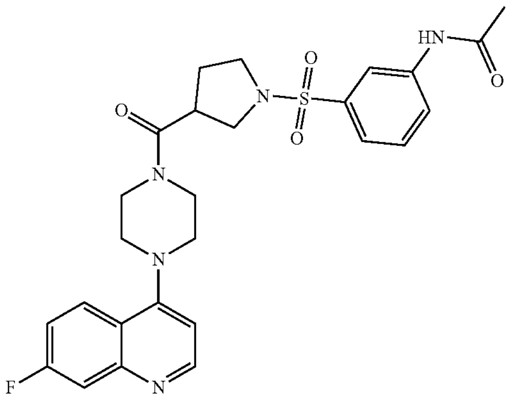 [SMILES: CC(=O)Nc1cccc(S(=O)(=O)N2CCC(C(=O)N3CCN(c4ccnc5cc(F)ccc45)CC3)C2)c1]

(4-(7-Fluoroquinolin-4-yl)piperazin-1-yl)(pyrrolidin-3-yl)methanone (80 mg, 0.24 mmol) and 3-acetylbenzene-1-sulfonyl chloride (68 mg, 0.29 mmol) were used in the same manner as in the method of Example 1 to obtain the title compound (28 mg, 2200 yield) as a white solid.

$^1$HNMR (400 MHz, DMSO-$d_6$): δ 10.30 (s, 1H), 8.71 (d, J=4.8 Hz, 1H), 8.15-8.11 (m, 2H), 7.83 (d, J=8.0 Hz, 1H), 7.68 (dd, J=10.4, 2.8 Hz, 1H), 7.59-7.55 (m, 1H), 7.49-7.45 (m, 2H), 6.98 (d, J=5.2 Hz, 1H), 3.71-3.68 (m, 4H), 3.46-3.40 (m, 2H), 3.28-3.21 (m, 3H), 3.19-3.09 (m, 4H), 2.06 (s, 3H), 2.02-1.94 (m, 1H), 1.85-1.80 (in, 1H). LC-MS (ESI): Rt=3.006 min, m/z 526.2 $[M+H]^+$; purity: 96.65% @ 254 nm, 97.56% @ 214 nm.

Example 10: Synthesis of (1-((1H-1,2,4-triazol-5-yl)sulfonyl)pyrrolidin-3-yl)(4-(7-fluoroquinolin-4-yl)piperazin-1-yl)methanone

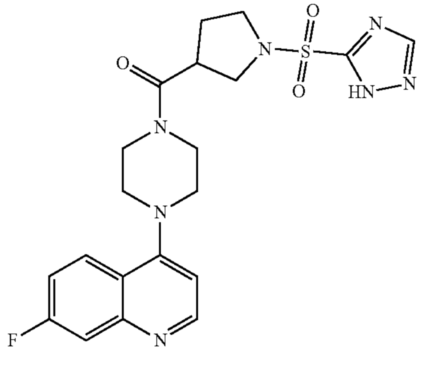 [SMILES: O=C(C1CCN(S(=O)(=O)c2ncn[nH]2)C1)N1CCN(c2ccnc3cc(F)ccc23)CC1]

(4-(7-Fluoroquinolin-4-yl)piperazin-1-yl)(pyrrolidin-3-yl)methanone (80 mg, 0.24 mmol) and 1H-1,2,4-triazole-5-sulfonyl chloride (49 mg, 0.26 mmol) were used in the same manner as in the method of Example 5 to obtain the title compound (18 mg, 16% yield) as a white solid.

$^1$H NMR (400 MHz, $CD_3OD$): δ 8.68 (d, J=5.2 Hz, 1H), 8.65 (s, 1H), 8.25-8.22 (m, 1H), 7.62 (dd, J=2.4, 10.0 Hz, 1H), 7.46-7.41 (m, 1H), 7.06 (d, J=5.2 Hz, 1H), 3.90-3.86 (m, 4H), 3.82-3.77 (m, 1H), 3.65-3.59 (m, 2H), 3.54-3.48 (m, 2H), 3.38-3.34 (m, 2H), 3.30-3.28 (m, 2H), 2.16-2.06

(m, 2H). LC-MS (ESI): Rt=3.290 min., m/z 460.2 $[M+H]^+$; purity: 95.23% @ 254 nm, 97.18% @214 nm.

Example 11: Synthesis of (1-((3,5-dimethyl-1H-pyrazol-4-yl)sulfonyl)pyrrolidin-3-yl)(4-(7-fluoroquinolin-4-yl)piperazin-1-yl)methanone

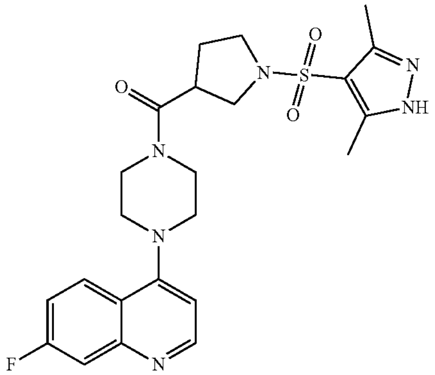 [SMILES: Cc1n[nH]c(C)c1S(=O)(=O)N1CCC(C(=O)N2CCN(c3ccnc4cc(F)ccc34)CC2)C1]

(4-(7-Fluoroquinolin-4-yl)piperazin-1-yl)(pyrrolidin-3-yl)methanone (80 mg, 0.24 mmol) and 3,5-dimethyl-1H-pyrazole-4-sulfonyl chloride (57 mg, 0.26 mmol) were used in the same manner as in the method of Example 5 to obtain the title compound (42 mg, 35% yield) as a white solid.

$^1$H NMR (400 MHz, $CDCl_3$): δ 8.76 (d, J=4.8 Hz, 1H), 8.03-8.00 (m, 1H), 7.73 (dd, J=2.0, 9.6 Hz, 1H), 7.34-7.30 (m, 1H), 6.84 (d, J=4.8 Hz, 1H), 3.89-3.79 (m, 4H), 3.68-3.65 (m, 1H), 3.50-3.46 (m, 1H), 3.39-3.33 (m, 2H), 3.29-3.16 (m, 5H), 2.49 (s, 6H), 2.21-2.14 (m, 2H). LC-MS (ESI): Rt=2.812 min., m/z 487.3 $[M+H]^+$; purity: 95.97% @ 254 nm, 96.88% @ 214 nm.

Example 12: Synthesis of (4-(7-fluoroquinolin-4-yl)piperazin-1-yl)(1-((1,3,5-trimethyl-1H-pyrazol-4-yl)sulfonyl)pyrrolidin-3-yl)methanone

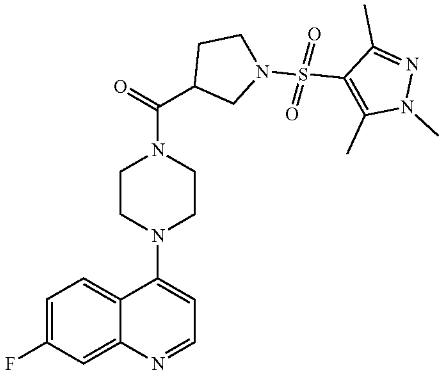 [SMILES: Cc1nn(C)c(C)c1S(=O)(=O)N1CCC(C(=O)N2CCN(c3ccnc4cc(F)ccc34)CC2)C1]

(4-(7-Fluoroquinolin-4-yl)piperazin-1-yl)(pyrrolidin-3-yl)methanone (80 mg, 0.24 mmol) and 1,3,5-trimethyl-1H-pyrazole-4-sulfonyl chloride (46 mg, 0.26 mmol) were used in the same manner as in the method of Example 5 to obtain the title compound (59 mg, 65% yield) as a white solid.

$^1$H NMR (400 MHz, $CDCl_3$): δ 8.76 (d, J=5.2 Hz, 1H), 8.03-8.00 (m, 1H), 7.73 (dd, J=2.0, 10.0 Hz, 1H), 7.34-7.26 (m, 1H), 6.83 (d, J=5.2 Hz, 1H), 3.92-3.85 (m, 2H), 3.80-3.79 (m, 2H), 3.76 (s, 3H), 3.68-3.64 (m, 1H), 3.49-3.43 (m, 1H), 3.37-3.26 (m, 2H), 3.24-3.18 (m, 5H), 2.50 (s, 3H), 2.41 (s, 3H), 2.20-2.15 (m, 2H). LC-MS (ESI): Rt=3.047 min, m/z 501.3 $[M+H]^+$; purity: 96.37% @ 254 nm, 97.22% @ 214 nm.

Example 13: Synthesis of (1-((1H-imidazol-2-yl)sulfonyl)pyrrolidin-3-yl)(4-(7-fluoroquinolin-4-yl)piperazin-1-yl)methanone

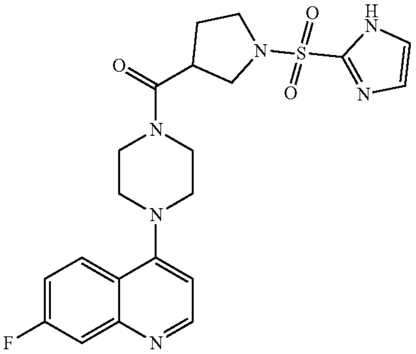 [SMILES: O=C(C1CCN(S(=O)(=O)c2ncc[nH]2)C1)N1CCN(c2ccnc3cc(F)ccc23)CC1]

(4-(7-Fluoroquinolin-4-yl)piperazin-1-yl)(pyrrolidin-3-yl)methanone (100 mg, 0.30 mmol) and 1H-imidazole-2-sulfonyl chloride hydrochloride (65 mg, 0.32 mmol) were used in the same manner as in the method of Example 5 to obtain the title compound (33 mg, 24% yield) as a white solid.

$^1$H NMR (400 MHz, $CDCl_3$): δ 8.76 (d, J=4.8 Hz, 1H), 8.02 (dd, J=6.4, 9.6 Hz, 1H), 7.74 (dd, J=2.8, 10.0 Hz, 1H), 7.35-7.30 (m, 1H), 7.23 (s, 2H), 6.85 (d, J=5.2 Hz, 1H), 3.95-3.78 (m, 5H), 3.73-3.68 (m, 1H), 3.61-3.52 (m, 2H), 3.34-3.22 (m, 5H), 2.22-2.15 (m, 2H). LC-MS (ESI): Rt=3.046 min, m/z 459.2 $[M+H]^+$; purity: 97.38% @ 254 nm, 97.88% @ 214 nm.

Example 14: Synthesis of (4-(7-fluoroquinolin-4-yl)piperazin-1-yl)(1-((1-methyl-1H-imidazol-5-yl)sulfonyl)pyrrolidin-3-yl)methanone

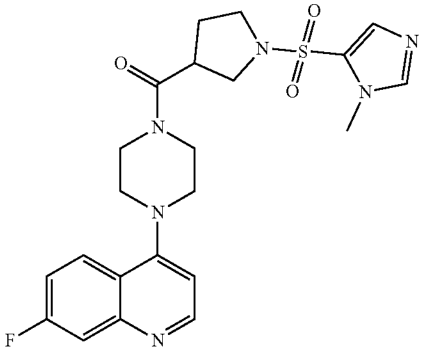 [SMILES: Cn1cncc1S(=O)(=O)N1CCC(C(=O)N2CCN(c3ccnc4cc(F)ccc34)CC2)C1]

(4-(7-Fluoroquinolin-4-yl)piperazin-1-yl)(pyrrolidin-3-yl)methanone (80 mg, 0.24 mmol) and 1-methyl-1H-imidazole-5-sulfonyl chloride (53 mg, 0.26 mmol) were used in the same manner as in the method of Example 5 to obtain the title compound (42 mg, 36% yield) as a white solid.

$^1$H NMR (400 MHz, $CDCl_3$): δ 8.76 (d, J=4.8 Hz, 1H), 8.03-8.00 (m, 1H), 7.72 (dd, J=2.8, 10.4 Hz, 1H), 7.63 (s, 1H), 7.60 (s, 1H), 7.34-7.29 (m, 1H), 6.83 (d, J=4.8 Hz, 1H), 3.90 (s, 3H), 3.88-3.84 (m, 2H), 3.79-3.76 (m, 2H), 3.73-3.69 (m, 1H), 3.59-3.51 (m, 2H), 3.44-3.34 (s, 2H), 3.27-3.14 (s, 4H), 2.27-2.16 (m, 2H). LC-MS (ESI): Rt=3.310 min., m/z 473.3 $[M+H]^+$; purity: 95.52% @ 254 nm, 96.34% @ 214 nm.

Example 15: Synthesis of (4-(7-fluoroquinolin-4-yl)piperazin-1-yl)(1-((4-(oxazol-5-yl)phenyl)sulfonyl)pyrrolidin-3-yl)methanone

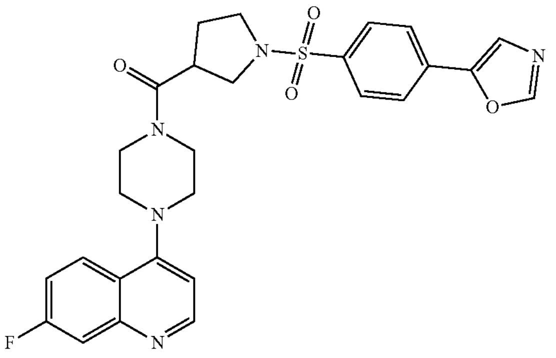 [SMILES: O=C(C1CCN(S(=O)(=O)c2ccc(-c3cnco3)cc2)C1)N1CCN(c2ccnc3cc(F)ccc23)CC1]

(4-(7-Fluoroquinolin-4-yl)piperazin-1-yl)(pyrrolidin-3-yl)methanone (100 mg, 0.3 mmol) and 4-(1,3-oxazol-5-yl)benzene-1-sulfonyl chloride (85 mg, 0.35 mmol) were used in the same manner as in the method of Example 1 to obtain the title compound (45 mg, 28% yield) as a white solid.

$^1$H NMR (400 MHz, $CDCl_3$): δ 8.75 (d, J=4.8 Hz, 1H), 8.02-7.98 (m, 2H), 7.93-7.91 (m, 2H), 7.84-7.82 (m, 2H), 7.72 (dd, J=2.4, 10.0 Hz, 1H), 7.51 (s, 1H), 7.33-7.28 (m, 1H), 6.81 (d, J=5.2 Hz, 1H), 3.89-3.70 (m, 5H), 3.54-3.48 (m, 1H), 3.39-3.27 (m, 3H), 3.22-3.12 (m, 4H), 2.14-2.06 (m, 2H). LC-MS (ESI): Rt=3.416 min, m/z 536.2 $[M+H]^+$; purity: 96.08% @ 254 nm, 96.54% @ 214 nm.

Example 16: Synthesis of (1-((4-bromophenyl)sulfonyl)pyrrolidin-3-yl)(4-(7-fluoroquinolin-4-yl)piperazin-1-yl)methanone

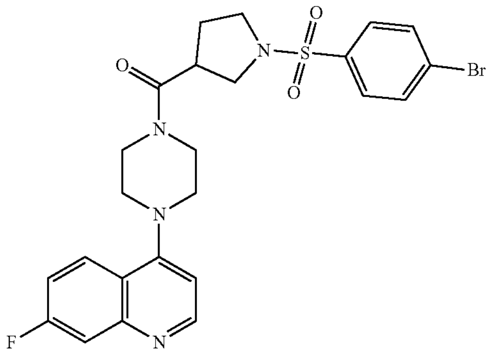 [SMILES: O=C(C1CCN(S(=O)(=O)c2ccc(Br)cc2)C1)N1CCN(c2ccnc3cc(F)ccc23)CC1]

(4-(7-Fluoroquinolin-4-yl)piperazin-1-yl)(pyrrolidin-3-yl)methanone (150 mg, 0.46 mmol) and 4-bromobenzene-1-sulfonyl chloride (140 mg, 0.55 mmol) were used in the same manner as in the method of Example 1 to obtain the title compound (140 mg, 56% yield) as a white solid.

$^1$H NMR (400 MHz, $CDCl_3$): δ 8.75 (d, J=4.8 Hz, 1H), 8.03 (dd, J=9.2, 6.0 Hz, 1H), 7.74-7.963 (m, 5H), 7.35-7.29 (m, 1H), 6.84 (d, J=4.8 Hz, 1H), 3.82-3.70 (m, 5H), 3.57-3.44 (m, 2H), 3.36-3.20 (m, 6H), 2.19-2.01 (m, 2H).

LC-MS (ESI): Rt=1.60 min, m/z 547.0 $[M+H]^+$; purity: 93% @ 254 nm, 94% @ 214 nm.

Example 17: Synthesis of (4-(7-fluoroquinolin-4-yl)piperazin-1-yl)(1-((4-(pyridin-4-yl)phenyl)sulfonyl)pyrrolidin-3-yl)methanone

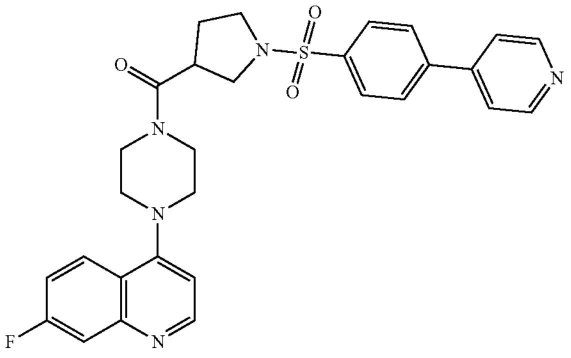 [SMILES: O=C(C1CCN(S(=O)(=O)c2ccc(-c3ccncc3)cc2)C1)N1CCN(c2ccnc3cc(F)ccc23)CC1]

According to Reaction Scheme 1-6, (1-((4-bromophenyl)sulfonyl)pyrrolidin-3-yl)(4-(7-fluoroquinolin-4-yl)piperazin-1-yl)methanone (140 mg, 0.26 mmol) and 4-(4,4,5,5-tetramethyl-1,3,2-dioxaborolan-2-yl)pyridine (63 mg, 0.31 mmol) were dissolved in 1,4-dioxane (3 mL) under nitrogen atmosphere, and then [1,1'-bis(diphenylphosphino)ferrocene] dichloropalladium(II) (57 mg, 0.07 mmol) and potassium carbonate (106 mg, 0.77 mmol) were added thereto at room temperature. After stirring at 100° C. for 20 hours, the mixture was concentrated. Purified water (5 mL) was added to the residue, and extraction was carried out with EtOAc (30 mL×3). The organic layer was washed with water (30 mL×2) and brine (30 mL), dried over $Na_2SO_4$ and concentrated. The residue was first purified by silica gel chromatography using a developing solvent of DCM:MeOH=40:1 to 20:1, and then finally purified by C18 chromatography using 20-90% $CH_3CN$ aqueous solution as a developing solvent to obtain the title compound (25 mg, 18% yield) as a white solid.

$^1$H NMR (400 MHz, $CDCl_3$): δ 8.74-8.70 (m, 3H), 8.03-7.91 (m, 4H), 7.80 (d, J=8.0 Hz, 2H), 7.53 (d, J=6.0 Hz, 2H), 7.37-7.33 (m, 1H), 6.87 (s, 1H), 3.88-3.72 (m, 5H), 3.57-3.51 (m, 1H), 3.40-3.29 (m, 6H), 2.20-2.10 (m, 3H).

LC-MS (ESI): Rt=2.804 min, m/z 546.2 $[M+H]^+$; purity: 96.65% @ 254 nm, 96.12% @ 214 nm.

Example 18: Synthesis of (R)-(4-(7-fluoroquinolin-4-yl)piperazin-1-yl)(1-((4-(pyridin-4-yl)phenyl)sulfonyl)pyrrolidin-3-yl)methanone

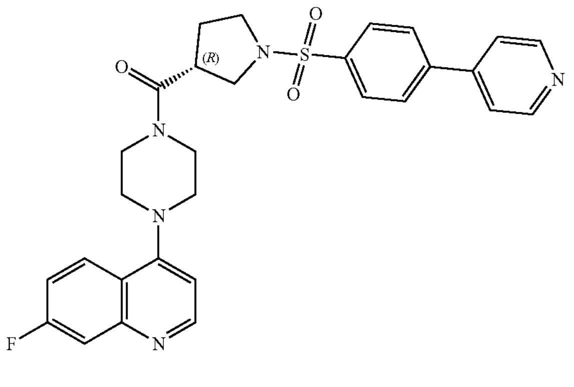

According to Reaction Scheme 6, (R)-(4-(7-fluoroquinolin-4-yl)piperazin-1-yl)(pyrrolidin-3-yl)methanone (300 mg, 0.92 mmol) and 4-(pyridin-4-yl)benzene-1-sulfonyl chloride (279 mg, 1.10 mmol) were used in the same manner as in the method of Example 5 to obtain the title compound (115 mg, 23% yield) as a white solid.

$^1$H NMR (400 MHz, $CDCl_3$): δ 8.76-8.73 (m, 3H), 8.12-7.97 (m, 3H), 7.81-7.79 (m, 2H), 7.70 (dd, J=10.0, 2.4 Hz, 1H), 7.53-7.52 (m, 2H), 7.33-7.28 (m, 1H), 6.81 (d, J=4.8 Hz, 1H), 3.91-3.71 (m, 5H), 3.57-3.51 (m, 1H), 3.39-3.28 (m, 3H), 3.22-3.16 (m, 4H), 2.20-2.07 (m, 2H). LC-MS (ESI): Rt=2.377 min, m/z 546.1 $[M+H]^+$; purity: 98.54% @254 nm, 99.16% @214 nm. Column: Chiralpak IC 5 μm 4.6×250 mm; Mobile Phase: Hexane:EtOH:DEA=30:70 at 1 mL/min; Temp: 30° C.; Wavelength: 254 nm, Rt=11.415 min, 100% ee.

Example 19: Synthesis of (S)-(1-((1H-1,2,4-triazol-5-yl)sulfonyl)pyrrolidin-3-yl)(4-(7-fluoroquinolin-4-yl)piperazin-1-yl)methanone

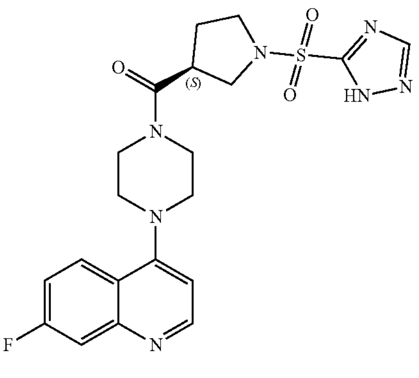

(S)-(4-(7-fluoroquinolin-4-yl)piperazin-1-yl)(pyrrolidin-3-yl)methanone (80 mg, 0.24 mmol, Preparation Example 5) and 1H-1,2,4-triazole-5-sulfonyl chloride (49 mg, 0.26 mmol) were used in the same manner as in the method of Example 5 to obtain the title compound (36 mg, 32% yield) as a white solid.

1H NMR (400 MHz, $CDCl_3$): δ 8.77 (d, J=4.8 Hz, 1H), 8.43 (s, 1H), 8.03-7.99 (m, 1H), 7.21 (dd, J=2.4, 10 Hz, 1H), 7.34-7.26 (m, 1H), 6.83 (d, J=4.8 Hz, 1H), 3.89-3.80 (m, 5H), 3.74-3.67 (m, 2H), 3.62-3.58 (m, 1H), 3.39-3.35 (m, 1H), 3.25-3.19 (m, 4H), 2.24-2.19 (m, 2H). LC-MS (ESI): Rt=3.046 min, m/z 460.2 $[M+H]^+$; purity: 98.03% @254 nm, 98.22% @214 nm. chiral HPLC: Column: Chiralpak IG 5 μm 4.6×250 mm; Mobile Phase: Hexane:EtOH:DEA=50:50:0.2 at 1 mL/min; Temp: 30° C.; Wavelength: 230 nm, Rt=5.863 min, 100% ee.

Example 20: Synthesis of (1-((5-(tert-butyl)-4H-1,2,4-triazol-3-yl)sulfonyl)pyrrolidin-3-yl)(4-(7-fluoroquinolin-4-yl)piperazin-1-yl)methanone

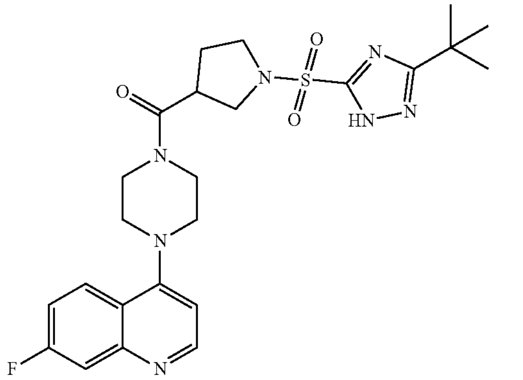 [SMILES: CC(C)(C)c1n[nH]c(S(=O)(=O)N2CCC(C(=O)N3CCN(c4ccnc5cc(F)ccc45)CC3)C2)n1]

According to Reaction Scheme 4, (4-(7-fluoroquinolin-4-yl)piperazin-1-yl)(pyrrolidin-3-yl)methanone (100 mg, 0.23 mmol) was dissolved in DCM (3 mL), and TEA (116 mg, 1.15 mmol) and 5-(tert-butyl)-4H-1,2,4-triazole-3-sulfonyl chloride (78 mg, 0.35 mmol) were added thereto and reacted for 2 hours. After the reaction product was concentrated under reduced pressure, the concentrate was finally purified by C18 chromatography using 20-90% $CH_3CN$ aqueous solution as a developing solvent to obtain the title compound (40 mg, 39% yield) as a white solid.

$^1$H NMR (400 MHz, $CDCl_3$): δ 8.75 (d, J=5.2 Hz, 1H), 8.00 (dd, J=5.6, 8.8 Hz, 1H), 7.71 (dd, J=2.8, 10.0 Hz, 1H), 7.34-7.29 (m, 1H), 6.82 (d, J=4.8 Hz, 1H), 3.92-3.66 (m, 6H), 3.62-3.52 (m, 2H), 3.40-3.22 (m, 1H), 3.24-3.13 (m, 4H), 2.31-2.22 (m, 1H), 2.17-2.09 (m, 1H), 1.44 (s, 9H). LC-MS (ESI): Rt=3.211 min, m/z 516.2 $[M+H]^+$; purity: 97.84% @ 254 nm, 98.12% @ 214 nm.

Example 21: Synthesis of N-(4-((3-(4-(quinolin-4-yl)piperazine-1-carbonyl)pyrrolidin-1-yl)sulfonyl)phenyl)acetamide

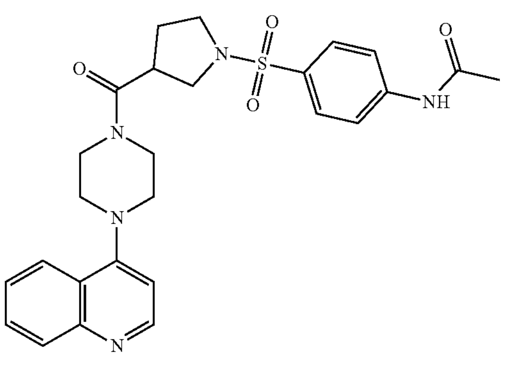 [SMILES: CC(=O)Nc1ccc(S(=O)(=O)N2CCC(C(=O)N3CCN(c4ccnc5ccccc45)CC3)C2)cc1]

Pyrrolidin-3-yl(4-(quinolin-4-yl)piperazin-1-yl)methanol (80 mg, 0.26 mmol) and 4-acetamidobenzene-1-sulfonyl chloride (72 mg, 0.31 mmol) were used in the same manner as in the method of Example 1 to obtain the title compound (45 mg, 34% yield) as a white solid.

$^1$H NMR (400 MHz, $CDCl_3$): δ 8.74 (d, J=4.8 Hz, 1H), 8.10 (d, J=8.4 Hz, 1H), 8.00 (d, J=8.4 Hz, 1H), 7.92 (s, 1H), 7.78-7.76 (m, 2H), 7.72-7.68 (m, 3H), 7.56-7.52 (m, 1H), 6.85 (d, J=4.8 Hz, 1H), 3.86 (s, 2H), 3.75 (s, 2H), 3.65 (dd, J=8.8, 8.0 Hz, 1H), 3.46-3.40 (m, 1H), 3.34-3.20 (m, 7H), 2.22 (s, 3H), 2.11-2.01 (m, 2H).

Example 22: Synthesis of (R)—N-(4-((3-(4-(quinolin-4-yl)piperazine-1-carbonyl)pyrrolidin-1-yl)sulfonyl)phenyl)acetamide

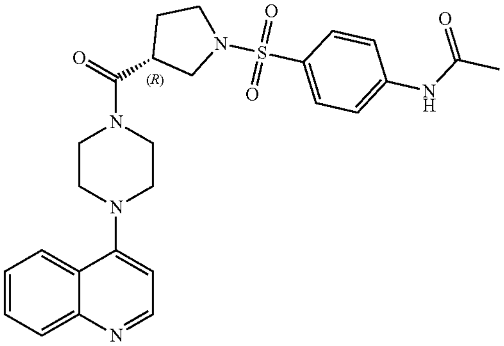

(R)-pyrrolidin-3-yl(4-(quinolin-4-yl)piperazin-1-yl) methanone (80 mg, 0.26 mmol) and 4-acetamidobenzene-1-sulfonyl chloride (72 mg, 0.31 mmol) were used in the same manner as in the method of Example 1 to obtain the title compound (40 mg, 310% yield) as a white solid.

$^1$H NMR (400 MHz, $CDCl_3$): δ 8.73 (d, J=5.2 Hz, 1H), 8.13-8.11 (m, 1H), 8.01-7.99 (m, 1H), 7.79-7.69 (m, 6H), 7.56-7.52 (m, 1H), 6.85 (d, J=5.2 Hz, 1H), 3.92-3.86 (m, 2H), 3.81-3.79 (m, 2H), 3.68-3.63 (m, 1H), 3.46-3.40 (m, 1H), 3.34-3.19 (m, 7H), 2.23 (s, 3H), 2.11-2.06 (m, 2H). LC-MS (ESI): Rt=2.850 min, m/z 508.2 $[M+H]^+$; purity: 99.60% @254 nm, 99.56% @214 nm. chiral HPLC: Column: Chiralpak IC 5 μm 4.6×250 mm; Mobile Phase: ACN:IPA:DEA=90:10:0.2 at 1 mL/min; Temp: 30° C.; Wavelength: 254 nm, Rt=12.312 min, 99.73% ee.

Example 23: Synthesis of (S)—N-(4-((3-(4-(quinolin-4-yl)piperazine-1-carbonyl)pyrrolidin-1-yl)sulfonyl)phenyl)acetamide

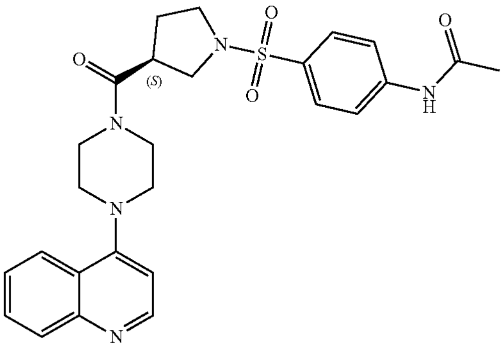

(S)-pyrrolidin-3-yl(4-(quinolin-4-yl)piperazin-1-yl) methanone (80 mg, 0.26 mmol) and 4-acetamidobenzene-1-sulfonyl chloride (72 mg, 0.31 mmol) were used in the same manner as in the method of Example 1 to obtain the title compound (55 mg, 42% yield) as a white solid.

$^1$H NMR (400 MHz, $CDCl_3$): δ 8.74 (d, J=5.2 Hz, 1H), 8.12-8.09 (m, 1H), 8.01-7.99 (m, 1H), 7.88 (s, 1H), 7.78-7.76 (m, 2H), 7.72-7.68 (m, 3H), 7.56-7.52 (m, 1H), 6.85 (d, J=5.2 Hz, 1H), 3.91-3.81 (m, 2H), 3.79-3.71 (m, 2H), 3.67-3.63 (m, 1H), 3.46-3.40 (m, 1H), 3.34-3.17 (m, 7H), 2.22 (s, 3H), 2.11-2.05 (m, 2H). LC-MS (ESI): Rt=2.849 min, m/z 508.2 $[M+H]^+$; purity: 99.36% @ 254 nm, 99.56% @ 214 nm. chiral HPLC: Column: Chiralpak IC 5 μm 4.6×250 mm; Mobile Phase: ACN:IPA:DEA=90:10:0.2 at 1 mL/min; Temp: 30° C.; Wavelength: 254 nm, Rt=14.076 min, 99.63% ee.

Example 24: Synthesis of (1-((6-chloropyridin-3-yl) sulfonyl)pyrrolidin-3-yl)(4-(quinolin-4-yl)piperazin-1-yl)methanone

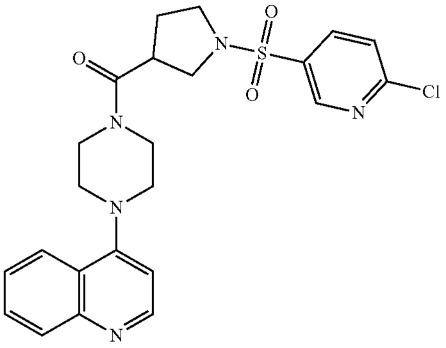 [SMILES: O=C(C1CCN(S(=O)(=O)c2ccc(Cl)nc2)C1)N1CCN(c2ccnc3ccccc23)CC1]

According to Reaction Scheme 1-7, pyrrolidin-3-yl(4-(quinolin-4-yl)piperazin-1-yl)methanone (2.00 g, 6.5 mmol) and TEA (1.30 g, 12.9 mmol) were dissolved in DCM (20 mL), and 6-chloropyridine-3-sulfonyl chloride (1.64 g, 7.7 mmol) diluted in DCM (20 mL) was slowly added thereto at room temperature. The reaction mixture was stirred at room temperature for 1 hour, the solvent was concentrated under reduced pressure, and the residue was purified by silica gel chromatography using a developing solvent of DCM: MeOH=20:1 to obtain the title compound (1.60 g, 52% yield) as a light yellow solid.

$^1$H NMR (400 MHz, $CDCl_3$): δ 8.85 (d, J=2.0 Hz, 1H), 8.77 (d, J=4.8 Hz, 1H), 8.11-8.08 (m, 2H), 8.01-7.99 (m, 1H), 7.72-7.68 (m, 1H), 7.55-7.51 (m, 2H), 6.85 (d, J=4.8 Hz, 1H), 3.88-3.76 (m, 4H), 3.73-3.62 (m, 1H), 3.52-3.44 (m, 2H), 3.35-3.26 (m, 2H), 3.23-3.15 (m, 4H), 2.17-2.11 (m, 2H). LC-MS (ESI): Rt=1.32 min, m/z 486.3 $[M+H]^+$; purity: 99% @ 254 nm, 92% @ 214 nm.

Example 25: Synthesis of (1-((6-phenylpyridin-3-yl)sulfonyl)pyrrolidin-3-yl)(4-(quinolin-4-yl)piperazin-1-yl)methanone

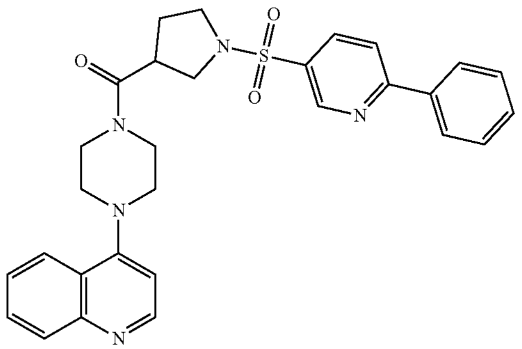 [SMILES: O=C(C1CCN(S(=O)(=O)c2ccc(-c3ccccc3)nc2)C1)N1CCN(c2ccnc3ccccc23)CC1]

(1-((6-Chloropyridin-3-yl)sulfonyl)pyrrolidin-3-yl)(4-(quinolin-4-yl)piperazin-1-yl)methanone (100 mg, 0.21 mmol, Example 24) and phenylboronic acid (30 mg, 0.25 mmol) were dissolved in 1,4-dioxane/water (1.0 ml/0.3 ml), and then [1,1'-bis(diphenylphosphino)ferrocene]dichloropalladium(II) (15 mg, 0.02 mmol) and potassium carbonate (57 mg, 0.42 mmol) were added thereto. The reaction solution was stirred at 80° C. for 20 hours under a nitrogen atmosphere. The reaction product was cooled to room temperature, concentrated under reduced pressure. Purified water (20 mL) was added to the residue, extraction was carried out with EtOAc (30 mL×3), and the organic layer was washed with water (30 mL×2) and brine (30 mL), dried over $Na_2SO_4$ and concentrated. The residue was finally purified by C18 chromatography using 10-60% $CH_3CN$ aqueous solution as a developing solvent to obtain the title compound (83 mg, 76% yield) as a white solid.

$^1$H NMR (400 MHz, $CDCl_3$): δ 9.12 (d, J=1.6 Hz, 1H), 8.76 (d, J=4.8 Hz, 1H), 8.19 (dd, J=2.4, 8.4 Hz, 1H), 8.11-8.04 (m, 3H), 8.00-7.98 (m, 1H), 7.92-7.90 (m, 1H), 7.72-7.68 (m, 1H), 7.57-7.49 (m, 4H), 6.83 (d, J=4.8 Hz, 1H), 3.87-3.83 (m, 2H), 3.79-3.72 (m, 3H), 3.59-3.53 (m, 1H), 3.51-3.48 (m, 1H), 3.46-3.43 (m, 1H), 3.41-3.22 (m, 1H), 3.17-3.12 (m, 4H), 2.17-2.12 (m, 2H). LC-MS (ESI): Rt=3.853 min, m/z 528.2 $[M+H]^+$; purity: 99.83% @ 254 nm, 99.85% @ 214 nm.

Example 26: Synthesis of (1-([2,4'-bipyridin]-5-ylsulfonyl)pyrrolidin-3-yl)(4-(quinolin-4-yl)piperazin-1-yl)methanone

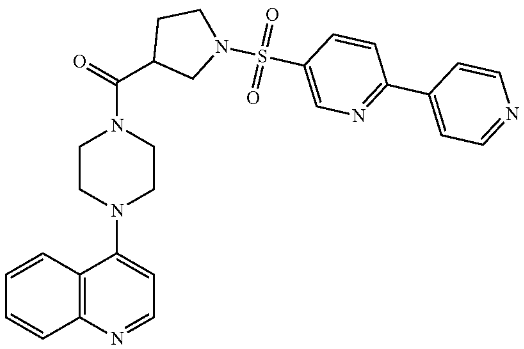 [SMILES: O=C(C1CCN(S(=O)(=O)c2ccc(-c3ccncc3)nc2)C1)N1CCN(c2ccnc3ccccc23)CC1]

(1-((6-Chloropyridin-3-yl)sulfonyl)pyrrolidin-3-yl)(4-(quinolin-4-yl)piperazin-1-yl)methanone (100 mg, 0.21 mmol) and 4-(4,4,5,5-tetramethyl-1,3,2-dioxaborolan-2-yl) pyridine (51 mg, 0.25 mmol) were used in the same manner as in the method of Example 25 to obtain the title compound (83 mg, 76% yield) as a white solid.

$^1$H NMR (400 MHz, DMSO-$d_6$): δ 9.13 (s, 1H), 8.78-8.76 (m, 2H), 8.70 (d, J=4.8 Hz, 1H), 8.39 (s, 2H), 8.15-8.13 (m, 2H), 8.05 (d, J=8.0 Hz, 1H), 7.96 (d, J=8.4 Hz, 1H), 7.72-7.69 (m, 1H), 7.57-7.54 (m, 1H), 6.98 (d, J=5.2 Hz, 1H), 3.73-3.64 (m, 4H), 3.57-3.52 (m, 1H), 3.47-3.42 (m, 2H), 3.36-3.31 (m, 2H), 3.15-3.07 (m, 4H), 2.07-2.02 (m, 1H), 1.89-1.84 (m, 1H). LC-MS (ESI): Rt=2.585 min, m/z 529.2 $[M+H]^+$; purity: 95.58% @ 254 nm, 95.21% @ 214 nm.

Example 27: Synthesis of (1-((6-(3-hydroxyphenyl) pyridin-3-yl)sulfonyl)pyrrolidin-3-yl)(4-(quinolin-4-yl)piperazin-1-yl)methanone

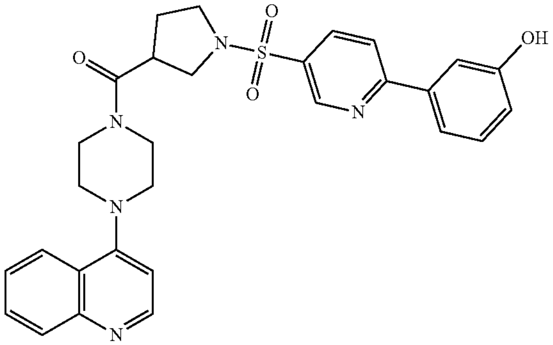 [SMILES: O=C(C1CCN(S(=O)(=O)c2ccc(-c3cccc(O)c3)nc2)C1)N1CCN(c2ccnc3ccccc23)CC1]

(1-((6-Chloropyridin-3-yl)sulfonyl)pyrrolidin-3-yl)(4-(quinolin-4-yl)piperazin-1-yl)methanone (100 mg, 0.21 mmol) and (3-hydroxyphenyl)boronic acid (34 mg, 0.25 mmol) were used in the same manner as in the method of Example 25 to obtain the title compound (68 mg, 61% yield) as a white solid.

$^1$H NMR (400 MHz, DMSO-$d_6$): δ 9.71 (s, 1H), 9.03-9.02 (m, 1H), 8.70 (d, J=4.8 Hz, 1H), 8.28-8.25 (m, 1H), 8.15 (d, J=8.4 Hz, 1H), 8.05 (d, J=8.0 Hz, 1H), 7.96 (d, J=8.4 Hz, 1H), 7.73-7.68 (m, 1H), 7.62-7.54 (m, 3H), 7.36-7.32 (m, 1H), 6.97 (d, J=5.2 Hz, 1H), 6.92 (dd, J=1.6, 8.0 Hz, 1H), 3.78-3.60 (m, 4H), 3.55-3.51 (m, 1H), 3.43-3.39 (m, 2H), 3.38-3.35 (m, 2H), 3.19-3.02 (m, 4H), 2.09-2.00 (m, 1H), 1.90-1.81 (m, 1H). LC-MS (ESI): Rt=3.123 min, m/z 544.1 $[M+H]^+$; purity: 97.60% @ 254 nm, 95.87% @ 214 nm.

Example 28: Synthesis of (1-((6-(4-hydroxyphenyl)pyridin-3-yl)sulfonyl)pyrrolidin-3-yl)(4-(quinolin-4-yl)piperazin-1-yl)methanone

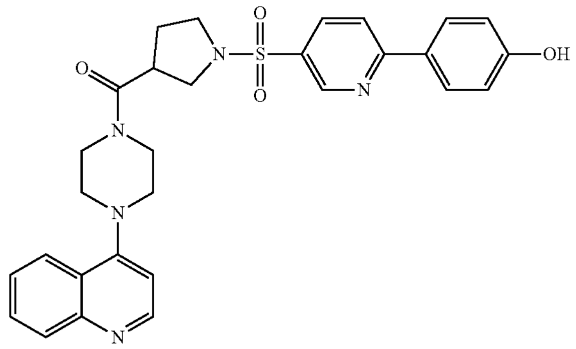 [SMILES: O=C(C1CCN(S(=O)(=O)c2ccc(-c3ccc(O)cc3)nc2)C1)N1CCN(c2ccnc3ccccc23)CC1]

(1-((6-Chloropyridin-3-yl)sulfonyl)pyrrolidin-3-yl)(4-(quinolin-4-yl)piperazin-1-yl)methanone (100 mg, 0.21 mmol) and 4-(4,4,5,5-tetramethyl-1,3,2-dioxabororan-2-yl)phenol (54 mg, 0.25 mmol) were used in the same manner as in the method of Example 25 to obtain the title compound (20 mg, 18% yield) as a white solid.

$^1$H NMR (400 MHz, $CDCl_3$): δ 9.05-9.04 (m, 1H), 8.75 (d, J=4.8 Hz, 1H), 8.14-8.09 (m, 2H), 8.00-7.93 (m, 3H), 7.79-7.77 (m, 1H), 7.71-7.67 (m, 1H), 7.55-7.51 (m, 1H), 6.95-6.92 (m, 2H), 6.82 (d, J=5.2 Hz, 1H), 3.83-3.71 (m, 5H), 3.58-3.52 (m, 1H), 3.45-3.34 (m, 2H), 3.32-3.27 (m, 1H), 3.25-3.13 (m, 4H), 2.17-2.12 (m, 2H). LC-MS (ESI): Rt=2.981 min, m/z 544.1 $[M+H]^+$; purity: 98.33% @ 254 nm, 98.08% @ 214 nm.

Example 29: Synthesis of (1-([2,3'-bipyridin]-5-ylsulfonyl)pyrrolidin-3-yl)(4-(quinolin-4-yl)piperazin-1-yl)methanone

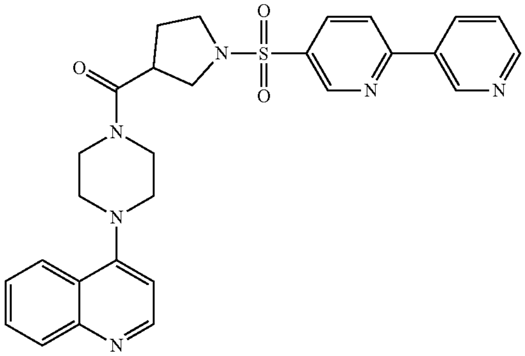 [SMILES: O=C(C1CCN(S(=O)(=O)c2ccc(-c3cccnc3)nc2)C1)N1CCN(c2ccnc3ccccc23)CC1]

(1-((6-Chloropyridin-3-yl)sulfonyl)pyrrolidin-3-yl)(4-(quinolin-4-yl)piperazin-1-yl)methanone (100 mg, 0.21 mmol) and pyridin-3-ylboronic acid (31 mg, 0.25 mmol) were used in the same manner as in the method of Example 25 to obtain the title compound (35 mg, 23% yield) as a light yellow solid.

$^1$H NMR (400 MHz, $CDCl_3$): δ 9.28 (s, 1H), 9.16-9.15 (m, 1H), 8.77-8.73 (m, 2H), 8.42-8.40 (m, 1H), 8.26-8.23 (m, 1H), 8.11-8.09 (m, 1H), 8.00-7.94 (m, 2H), 7.72-7.68 (m, 1H), 7.55-7.51 (m, 1H), 7.48-7.45 (m, 1H), 6.84 (d, J=4.8 Hz, 1H), 3.83-3.73 (m, 5H), 3.60-3.54 (m, 1H), 3.50-3.46 (m, 1H), 3.38-3.33 (m, 2H), 3.24-3.16 (m, 4H), 2.21-2.09 (m, 2H). LC-MS (ESI): Rt=2.801 min, m/z 529.2 $[M+H]^+$; purity: 97.90% @ 254 nm, 97.41% @ 214 nm.

Example 30: Synthesis of N-(5-((3-(4-(quinolin-4-yl)piperazine-1-carbonyl)pyrrolidin-1-yl)sulfonyl)pyridin-2-yl)acetamide

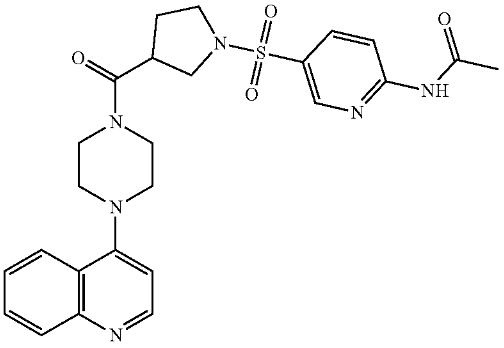 [SMILES: CC(=O)Nc1ccc(S(=O)(=O)N2CCC(C(=O)N3CCN(c4ccnc5ccccc45)CC3)C2)cn1]

As shown in Reaction Scheme 1-7, (1-((6-chloropyridin-3-yl)sulfonyl)pyrrolidin-3-yl)(4-(quinolin-4-yl)piperazin-1-yl)methanone (100 mg, 0.21 mmol) and acetamide (18 mg, 0.32 mmol) were dissolved in 1,4-dioxane (1.0 mL) under a nitrogen atmosphere, and then cesium carbonate (24 mg, 0.42 mmol), tris(dibenzylideneacetone)dipalladium (19 mg, 0.02 mmol) and xantphos (24 mg, 0.04 mmol) were added thereto and stirred at 80° C. for 20 hours. The reaction product was cooled to room temperature and concentrated under reduced pressure. Purified water (20 mL) was added to the residue, extraction was carried out with EtOAc (30 mL×3), and the organic layer was washed with water (30 mL×2) and brine (30 mL), dried over $Na_2SO_4$ and concentrated. The residue was finally purified by C18 chromatography using 50-70% $CH_3CN$ aqueous solution as a developing solvent to obtain the title compound (28 mg, 26% yield) as a white solid.

$^1$H NMR (400 MHz, DMSO-$d_6$): δ 8.77 (d, J=5.2 Hz, 1H), 8.72 (d, J=2.0 Hz, 1H), 8.37 (d, J=8.8 Hz, 1H), 8.13-8.10 (m, 3H), 8.00 (d, J=8.4 Hz, 1H), 7.72-7.69 (m, 1H), 7.55-7.52 (m, 1H), 6.86 (d, J=4.8 Hz, 1H), 3.91-3.76 (m, 4H), 3.73-3.65 (m, 1H), 3.52-3.47 (m, 2H), 3.42-3.37 (m, 1H), 3.33-3.29 (m, 2H), 3.23-3.16 (m, 4H), 2.26 (s, 3H), 2.15-2.11 (m, 2H). LC-MS (ESI): Rt=2.546 min, m/z 544.1 $[M+H]^+$; purity: 96.01% @ 254 nm, 97.48% @ 214 nm.

Example 31: Synthesis of (1-((4-bromophenyl) sulfonyl)pyrrolidin-3-yl)(4-(quinolin-4-yl)piperazin-1-yl)methanone

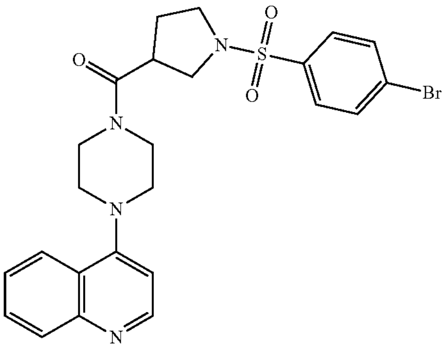 [SMILES: O=C(C1CCN(S(=O)(=O)c2ccc(Br)cc2)C1)N1CCN(c2ccnc3ccccc23)CC1]

Pyrrolidin-3-yl(4-(quinolin-4-yl)piperazin-1-yl)methanone (2 g, 6.5 mmol) and 4-bromobenzene-1-sulfonyl chloride (2 g, 7.7 mmol) were used in the same manner as in the method of Example 1 to obtain the title compound (1.6 mg, 47% yield) as a white solid.

$^1$H NMR (400 MHz, $CDCl_3$): δ 8.77 (d, J=4.4 Hz, 1H), 8.09 (d, J=8.4 Hz, 1H), 8.00 (d, J=8.4 Hz, 1H), 7.74-7.68 (m, 5H), 7.55-7.51 (m, 1H), 6.85 (d, J=5.2 Hz, 1H), 3.86-3.75 (m, 4H), 3.70-3.66 (m, 1H), 3.49-3.45 (m, 1H), 3.37-3.18 (m, 7H), 2.14-2.08 (m, 2H).

Example 32: Synthesis of (1-((4-(pyridin-3-yl)phenyl)sulfonyl)pyrrolidin-3-yl)(4-(quinolin-4-yl)piperazin-1-yl)methanone

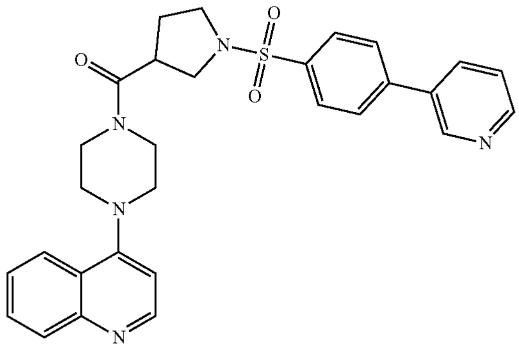 [SMILES: O=C(C1CCN(S(=O)(=O)c2ccc(-c3cccnc3)cc2)C1)N1CCN(c2ccnc3ccccc23)CC1]

According to Reaction Scheme 1-6, (1-((4-bromophenyl) sulfonyl)pyrrolidin-3-yl)(4-(quinolin-4-yl)piperazin-1-yl) methanone (100 mg, 0.19 mmol, Example 31) and pyridin-3-ylboronic acid (28 mg, 0.23 mmol) were used in the same manner as in the method of Example 17 to obtain the title compound (53 mg, 51% yield) as a white solid.

$^1$H NMR (400 MHz, $CDCl_3$): δ 8.89-8.88 (m, 1H), 8.76 (d, J=5.2 Hz, 1H), 8.69-8.67 (m, 1H), 8.12-8.09 (m, 1H), 8.01-7.96 (m, 3H), 7.93-7.90 (m, 1H), 7.77-7.75 (m, 2H), 7.72-7.68 (m, 1H), 7.55-7.51 (m, 1H), 7.45-7.41 (m, 1H), 6.84 (d, J=4.8 Hz, 1H), 3.90-3.87 (m, 2H), 3.82-3.73 (m, 3H), 3.57-3.51 (m, 1H), 3.40-3.29 (m, 3H), 3.24-3.18 (m, 4H), 2.18-2.08 (m, 2H). LC-MS (ESI): Rt=2.826 min, m/z 528.3 [M+H]$^+$; purity: 98.26% @ 254 nm, 98.68% @ 214 nm.

Example 33: Synthesis of (1-((4-(2-methylpyrimidin-5-yl)phenyl)sulfonyl)pyrrolidin-3-yl)(4-(quinolin-4-yl)piperazin-1-yl)methanone

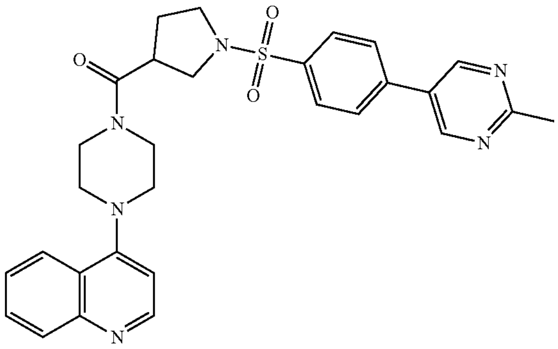 [SMILES: Cc1ncc(-c2ccc(S(=O)(=O)N3CCC(C(=O)N4CCN(c5ccnc6ccccc56)CC4)C3)cc2)cn1]

(1-((4-Bromophenyl)sulfonyl)pyrrolidin-3-yl)(4-(quinolin-4-yl)piperazin-1-yl)methanone (100 mg, 0.19 mmol) and 2-methyl-5-(4,4,5,5-tetramethyl-1,3,2-dioxaborolan-2-yl) pyrimidine (50 mg, 0.23 mmol) were used in the same manner as in the method of Example 17 to obtain the title compound (53 mg, 51% yield) as a white solid.

$^1$H NMR (400 MHz, $CDCl_3$): δ 8.89 (s, 2H), 8.77 (d, J=4.8 Hz, 1H), 8.10 (d, J=8.4 Hz, 1H), 8.00-7.98 (m, 3H), 7.75-7.70 (m, 3H), 7.53 (m, 1H), 6.85 (d, J=4.8 Hz, 1H), 3.87-3.72 (m, 5H), 3.57-3.51 (m, 1H), 3.37-3.19 (m, 7H), 2.83 (s, 3H), 2.20-2.06 (m, 2H). LC-MS (ESI): Rt=2.702 min, m/z 543.1 [M+H]$^+$; purity: 99.10% @ 254 nm, 98.01% @ 214 nm.

Example 34: Synthesis of (1-((4-(6-hydroxypyridin-3-yl)phenyl)sulfonyl)pyrrolidin-3-yl)(4-(quinolin-4-yl)piperazin-1-yl)methanone

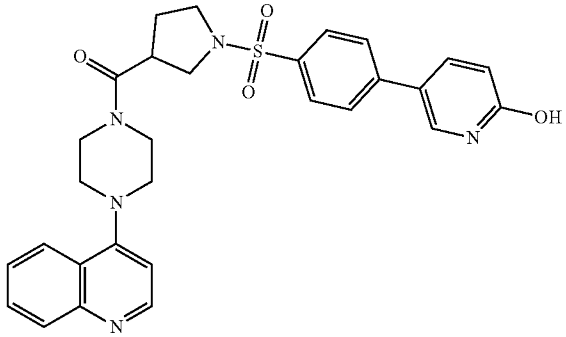 [SMILES: O=C(C1CCN(S(=O)(=O)c2ccc(-c3ccc(O)nc3)cc2)C1)N1CCN(c2ccnc3ccccc23)CC1]

(1-((4-Bromophenyl)sulfonyl)pyrrolidin-3-yl)(4-(quinolin-4-yl)piperazin-1-yl)methanone (100 mg, 0.19 mmol) and 5-(4,4,5,5-tetramethyl-1,3,2-dioxaborolan-2-yl)pyridin-2-ol (50 mg, 0.23 mmol) were used in the same manner as in the method of Example 17 to obtain the title compound (89 mg, 86% yield) as a white solid.

$^1$H NMR (400 MHz, $CDCl_3$): δ 12.13 (br s, 1H), 8.78 (d, J=4.8 Hz, 1H), 8.10 (d, J=8.4 Hz, 1H), 8.00 (d, J=7.6 Hz, 1H), 7.92-7.90 (m, 2H), 7.90-7.77 (m, 1H), 7.72-7.66 (m, 2H), 7.60-7.55 (m, 2H), 7.53-7.51 (m, 1H), 6.85 (d, J=4.8 Hz, 1H), 6.73 (d, J=9.6 Hz, 1H), 3.88-3.69 (m, 5H), 3.56-3.48 (m, 1H), 3.38-3.11 (m, 7H), 2.20-2.04 (m, 2H). LC-MS (ESI): Rt=2.511 min, m/z 544.1 $[M+H]^+$; purity: 99.10% @254 nm, 99.81% @214 nm.

Example 35: Synthesis of (1-((4-morpholinophenyl) sulfonyl)pyrrolidin-3-yl)(4-(quinolin-4-yl)piperazin-1-yl)methanone

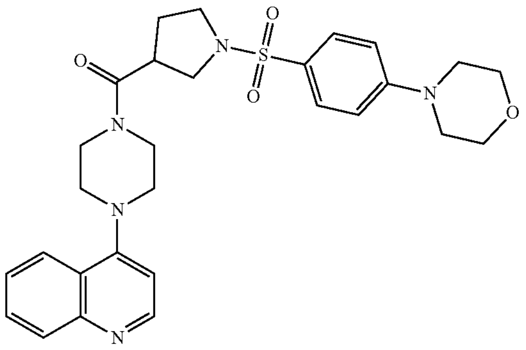 [SMILES: O=C(C1CCN(S(=O)(=O)c2ccc(N3CCOCC3)cc2)C1)N1CCN(c2ccnc3ccccc23)CC1]

According to Reaction Scheme 1-7, morpholin (20 mg, 0.23 mmol) and (1-((4-bromophenyl)sulfonyl)pyrrolidin-3-yl)(4-(quinolin-4-yl)piperazin-1-yl)methanone (80 mg, 0.20 mmol) were dissolved in 1,4-dioxane (1.0 mL), and then cesium carbonate (99 mg, 0.38 mmol), $Pd_2(dba)_3$ (14 mg, 0.02 mmol) and xantphos (18 mg 0.04 mg) mmol) were added thereto and reacted at 80° C. for 20 hours under a nitrogen atmosphere. The reaction solution was cooled to room temperature and concentrated, and the concentrated solution was extracted using water (20 mL) and EtOAc (20 mL×3). Water was removed from the organic layer using anhydrous $Na_2SO_4$, the solvent was removed under reduced pressure, and then C18 column chromatography was carried out using 40-60% $CH_3CN$ aqueous solution as a developing solvent to obtain the title compound (41 mg, 510% yield) as a white solid.

$^1H$ NMR (400 MHz, $CDCl_3$): δ 8.77 (d, J=4.8 Hz, 1H), 8.11 (d, J=8.4 Hz, 1H), 8.01 (d, J=8.4 Hz, 1H), 7.73-7.69 (m, 3H), 7.56-7.52 (m, 1H), 6.93-6.91 (m, 2H), 6.86 (d, J=5.2 Hz, 1H), 3.91-3.84 (m, 6H), 3.80-3.70 (m, 2H), 3.68-3.66 (m, 1H), 3.49-3.42 (m, 1H), 3.33-3.16 (m, 11H), 2.11-2.08 (m, 2H).

LC-MS (ESI): Rt=2.808 min, m/z 536.3 $[M+H]^+$; purity: 97.00% @254 nm, 96.32% @214 nm.

Example 36: Synthesis of (4-(quinolin-4-yl)piperazin-1-yl)(1-(thiophen-2-ylsulfonyl)pyrrolidin-3-yl) methanone

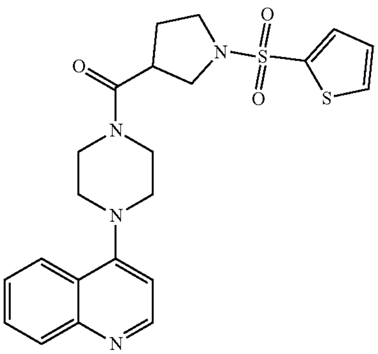 [SMILES: O=C(C1CCN(S(=O)(=O)c2cccs2)C1)N1CCN(c2ccnc3ccccc23)CC1]

Pyrrolidin-3-yl(4-(quinolin-4-yl)piperazin-1-yl)methanone (120 mg, 0.39 mmol) and thiophene-2-sulfonyl chloride (81 mg, 0.44 mmol) were used in the same manner as in the method of Example 1 to obtain the title compound (64 mg, 36% yield) as a white solid.

$^1H$ NMR (400 MHz, $CDCl_3$): δ 8.77 (d, J=4.8 Hz, 1H), 8.09 (d, J=4.8 Hz, 1H), 8.01 (d, J=8.0 Hz, 1H), 7.72-7.70 (m, 1H), 7.64-7.63 (m, 2H), 7.55-7.51 (m, 1H), 7.18-7.16 (m, 1H), 6.85 (d, J=4.8 Hz, 1H), 3.91-3.73 (m, 4H), 3.73-3.69 (m, 1H), 3.52-3.57 (m, 3H), 3.31-3.15 (m, 5H), 2.14-2.08 (m, 2H). LC-MS (ESI): Rt=2.819 min, m/z 457.0 $[M+H]^+$; purity: 99.88% @254 nm, 99.33% @214 nm.

Example 37: Synthesis of (1-((5-methylthiophen-2-yl)sulfonyl)pyrrolidin-3-yl)(4-(quinolin-4-yl)piperazin-1-yl)methanone

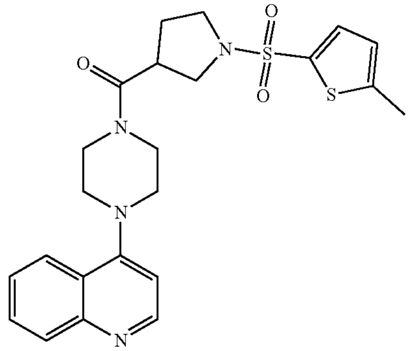 [SMILES: Cc1ccc(S(=O)(=O)N2CCC(C(=O)N3CCN(c4ccnc5ccccc45)CC3)C2)s1]

Pyrrolidin-3-yl(4-(quinolin-4-yl)piperazin-1-yl)methanone (100 mg, 0.32 mmol), TEA (190 mg, 1.88 mmol) and 5-methylthiophene-2-sulfonyl chloride (73 mg, 0.38 mmol) were used in the same manner as in the method of Example 1 to obtain the title compound (51 mg, 34% yield) as a white solid.

$^1H$ NMR (400 MHz, $CDCl_3$): δ 8.77 (d, J=4.8 Hz, 1H), 8.11-8.10 (m, 1H), 8.02-8.00 (m, 1H), 7.73-7.68 (m, 1H), 7.56-7.52 (m, 1H), 7.43 (d, J=3.6 Hz, 1H), 6.86 (d, J=4.8 Hz, 1H), 6.82-6.81 (m, 1H), 3.95-3.89 (m, 2H), 3.85-3.78 (m, 2H), 3.71-3.67 (m, 1H), 3.50-3.43 (m, 1H), 3.40-3.34 (m, 2H), 3.31-3.20 (m, 5H), 2.54 (s, 3H), 2.17-2.07 (m, 2H). LC-MS (ESI): Rt=3.171 min, m/z 471.0 $[M+H]^+$; purity: 99.54% @254 nm, 99.72% @ 214 nm.

Example 38: Synthesis of (4-(quinolin-4-yl)piperazin-1-yl)(1-((1,3,5-trimethyl-1H-pyrazol-4-yl)sulfonyl)pyrrolidin-3-yl)methanone

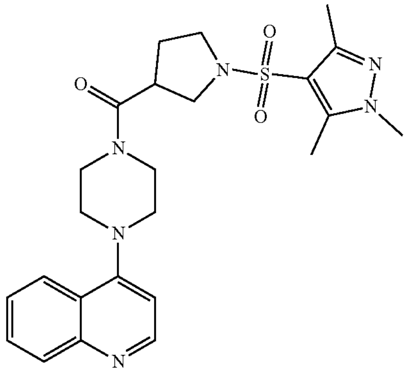 [SMILES: Cc1nn(C)c(C)c1S(=O)(=O)N1CCC(C(=O)N2CCN(c3ccnc4ccccc34)CC2)C1]

Pyrrolidin-3-yl(4-(quinolin-4-yl)piperazin-1-yl)methanone (100 mg, 0.32 mmol) and 1,3,5-trimethyl-1H-pyrazole-4-sulfonyl chloride (77 mg, 0.38 mmol) were used in the same manner as in the method of Example 5 to obtain the title compound (72 mg, 47% yield) as a white solid.

$^1$H NMR (400 MHz, $CDCl_3$): δ 8.77 (d, J=4.8 Hz, 1H), 8.12-8.10 (m, 1H), 8.02-8.00 (m, 1H), 7.73-7.68 (m, 1H), 7.56-7.52 (m, 1H), 6.86 (d, J=4.8 Hz, 1H), 3.93-3.86 (m, 2H), 3.81-3.78 (m, 2H), 3.76 (s, 3H), 3.68-3.64 (m, 1H), 3.49-3.43 (m, 1H), 3.37-3.29 (m, 2H), 3.25-3.18 (m, 5H), 2.50 (s, 3H), 2.41 (s, 3H), 2.20-2.14 (m, 2H). LC-MS (ESI): Rt=3.055 min, m/z 483.2 $[M+H]^+$; purity: 99.12% @ 254 nm, 98.02% @ 214 nm.

Example 39: Synthesis of (1-((3,5-dimethylisoxazol-4-yl)sulfonyl)pyrrolidin-3-yl)(4-(quinolin-4-yl)piperazin-1-yl)methanone

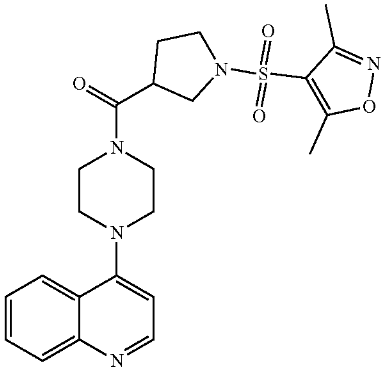 [SMILES: Cc1noc(C)c1S(=O)(=O)N1CCC(C(=O)N2CCN(c3ccnc4ccccc34)CC2)C1]

Pyrrolidin-3-yl(4-(quinolin-4-yl)piperazin-1-yl)methanone (100 mg, 0.32 mmol) and 3,5-dimethylisoxazol-4-sulfonyl chloride (74 mg, 0.38 mmol) in DCM (1 mL) were used in the same manner as in the method of Example 5 to obtain the title compound (66 mg, 44% yield) as a white solid.

$^1$H NMR (400 MHz, $CDCl_3$): δ 8.77 (d, J=4.8 Hz, 1H), 8.12-8.10 (m, 1H), 8.02-8.00 (m, 1H), 7.72-7.68 (m, 1H), 7.56-7.52 (m, 1H), 6.86 (d, J=4.8 Hz, 1H), 3.90-3.86 (m, 2H), 3.81-3.78 (m, 2H), 3.69-3.65 (m, 1H), 3.54-3.48 (m, 2H), 3.41-3.30 (m, 2H), 3.25-3.21 (m, 4H), 2.68 (s, 3H), 2.45 (s, 3H), 2.26-2.15 (m, 2H). LC-MS (ESI): Rt=2.811 min, m/z 470.0 $[M+H]^+$; purity: 99.67% @ 254 nm, 99.08% @ 214 nm.

Example 40: Synthesis of (1-((2,4-dimethylthiazol-5-yl)sulfonyl)pyrrolidin-3-yl)(4-(quinolin-4-yl)piperazin-1-yl)methanone

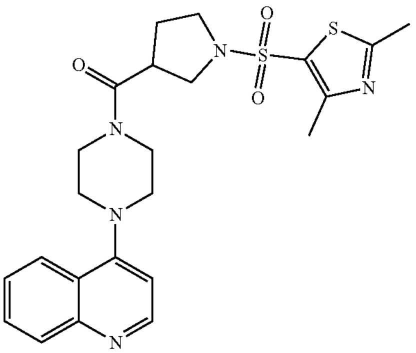 [SMILES: Cc1nc(C)c(S(=O)(=O)N2CCC(C(=O)N3CCN(c4ccnc5ccccc45)CC3)C2)s1]

Pyrrolidin-3-yl(4-(quinolin-4-yl)piperazin-1-yl)methanone (100 mg, 0.32 mmol) and 2,4-dimethylthiazole-5-sulfonyl chloride (79 mg, 0.38 mmol) were used in the same manner as in the method of Example 5 to obtain the title compound (73 mg, 47% yield) as a white solid.

$^1$H NMR (400 MHz, $CDCl_3$): δ 8.77 (d, J=4.8 Hz, 1H), 8.13-8.11 (m, 1H), 8.02-8.00 (m, 1H), 7.73-7.69 (m, 1H), 7.56-7.52 (m, 1H), 6.86 (d, J=4.8 Hz, 1H), 3.94-3.87 (m, 2H), 3.80-3.78 (m, 2H), 3.74-3.70 (m, 1H), 3.55-3.33 (m, 4H), 3.26-3.21 (m, 4H), 2.71 (s, 3H), 2.68 (s, 3H), 2.21-2.17 (m, 2H). LC-MS (ESI): Rt=2.764 min, m/z 486.1 $[M+H]^+$; purity: 98.08% @ 254 nm, 98.49% @214 nm.

Example 41: Synthesis of (4-(quinolin-4-yl)piperazin-1-yl)(1-((5-(trifluoromethyl)pyridin-2-yl)sulfonyl)pyrrolidin-3-yl)methanone

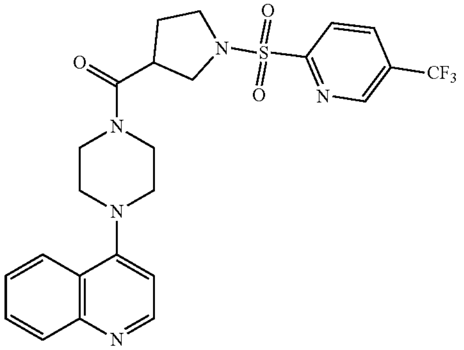 [SMILES: O=C(C1CCN(S(=O)(=O)c2ccc(C(F)(F)F)cn2)C1)N1CCN(c2ccnc3ccccc23)CC1]

Pyrrolidin-3-yl(4-(quinolin-4-yl)piperazin-1-yl)methanone (100 mg, 0.32 mmol) and 5-(trifluoromethyl)pyridine-2-sulfonyl chloride (92 mg, 0.38 mmol) were used in the same manner as in the method of Example 5 to obtain the title compound (50 mg, 30% yield) as a white solid.

$^1$H NMR (400 MHz, $CDCl_3$): δ 8.95 (s, 1H), 8.78-8.77 (m, 1H), 8.19-8.17 (m, 1H), 8.13-8.09 (m, 2H), 8.02-8.00 (m, 1H), 7.72-7.68 (m, 1H), 7.56-7.52 (m, 1H), 6.86 (d,

J=4.8 Hz, 1H), 3.93-3.80 (m, 5H), 3.74-3.66 (m, 2H), 3.63-3.57 (m, 1H), 3.41-3.33 (m, 1H), 3.26-3.21 (m, 4H), 2.31-2.11 (m, 2H). LC-MS (ESI): Rt=3.046 min, m/z 520.0 $[M+H]^+$; purity: 98.64% @ 254 nm, 99.32% @214 nm.

Example 42: Synthesis of (1-((1H-imidazol-2-yl)sulfonyl)pyrrolidin-3-yl)(4-(quinolin-4-yl)piperazin-1-yl)methanone

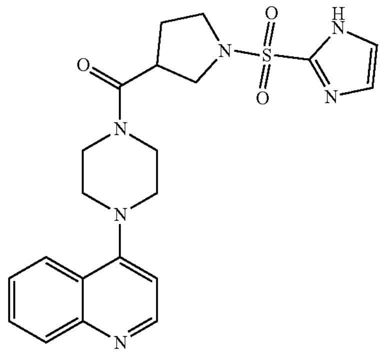 [SMILES: O=C(C1CCN(S(=O)(=O)c2ncc[nH]2)C1)N1CCN(c2ccnc3ccccc23)CC1]

Pyrrolidin-3-yl(4-(quinolin-4-yl)piperazin-1-yl)methanone (120 mg, 0.38 mmol) and 1H-imidazole-2-sulfonyl chloride hydrochloride (90 mg, 0.44 mmol) were used in the same manner as in the method of Example 5 to obtain the title compound (63 mg, 38% yield) as a white solid.

$^1$H NMR (400 MHz, DMSO-$d_6$): δ 13.56 (s, 1H), 8.71 (d, J=5.2 Hz, 1H), 8.08 (d, J=8.4 Hz, 1H), 7.97 (d, J=8.4 Hz, 1H), 7.73-7.70 (m, 1H), 7.59-7.55 (m, 1H), 7.42 (br s, 1H), 7.19 (br s, 1H), 7.01 (d, J=4.8 Hz, 1H), 3.80-3.70 (m, 4H), 3.60-3.56 (m, 1H), 3.46-3.33 (m, 4H), 3.20-3.08 (m, 4H), 2.03-1.94 (m, 1H), 1.90-1.80 (m, 1H). LC-MS (ESI): Rt=2.701 min, m/z 441.2 $[M+H]^+$; purity: 99.44% @ 254 nm, 99.51% @ 214 nm.

Example 43: Synthesis of (1-((1H-1,2,4-triazol-5-yl)sulfonyl)pyrrolidin-3-yl)(4-(quinolin-4-yl)piperazin-1-yl)methanone

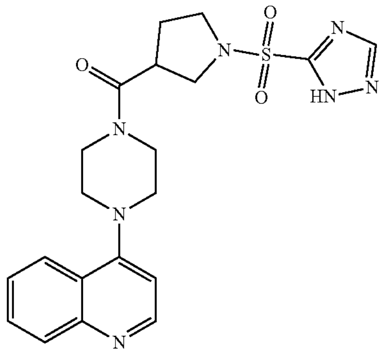 [SMILES: O=C(C1CCN(S(=O)(=O)c2ncn[nH]2)C1)N1CCN(c2ccnc3ccccc23)CC1]

Pyrrolidin-3-yl(4-(quinolin-4-yl)piperazin-1-yl)methanone (100 mg, 0.32 mmol) and 4H-1,2,4-triazole-3-sulfonyl chloride (62 mg, 0.38 mmol) were used in the same manner as in the method of Example 5 to obtain the title compound (72 mg, 51% yield) as a white solid.

$^1$H NMR (400 MHz, $CDCl_3$): δ 8.86 (s, 1H), 8.71 (d, J=5.2 Hz, 1H), 8.10-8.08 (m, 1H), 7.99-7.97 (m, 1H), 7.75-7.72 (m, 1H), 7.60-7.56 (m, 1H), 7.02 (d, J=5.2 Hz, 1H), 3.81-3.69 (m, 4H), 3.64-3.57 (m, 1H), 3.49-3.44 (m, 3H), 3.42-3.35 (m, 1H), 3.23-3.18 (m, 4H), 2.08-2.00 (m, 1H), 1.94-1.86 (m, 1H). LC-MS (ESI): Rt=2.242 min, m/z 442.0 $[M+H]^+$; purity: 99.59% @ 254 nm, 99.59% @ 214 nm.

Example 44: Synthesis of (1-((1-methyl-1H-pyrazol-4-yl)sulfonyl)pyrrolidin-3-yl)(4-(quinolin-4-yl)piperazin-1-yl)methanone

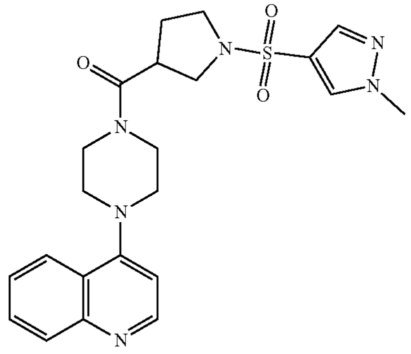 [SMILES: Cn1cc(S(=O)(=O)N2CCC(C(=O)N3CCN(c4ccnc5ccccc45)CC3)C2)cn1]

Pyrrolidin-3-yl(4-(quinolin-4-yl)piperazin-1-yl)methanone (120 mg, 0.39 mmol) and 1-methyl-1H-pyrazole-4-sulfonyl chloride (84 mg, 0.46 mmol) were used in the same manner as in the method of Example 5 to obtain the title compound (78 mg, 44% yield) as a white solid.

$^1$H NMR (400 MHz, $CDCl_3$): δ 8.77 (d, J=5.2 Hz, 1H), 8.11 (d, J=8.0 Hz, 1H), 8.01 (d, J=8.4 Hz, 1H), 7.82 (s, 1H), 7.79 (s, 1H), 7.72-7.68 (m, 1H), 7.56-7.52 (m, 1H), 6.86 (d, J=5.2 Hz, 1H), 3.98 (s, 3H), 3.92-3.84 (m, 2H), 3.82-3.74 (m, 2H), 3.68-3.62 (m, 1H), 3.48-3.42 (m, 1H), 3.33-3.18 (m, 7H), 2.16-2.09 (m, 2H). LC-MS (ESI): Rt=2.524 min., m/z 455.0 $[M+H]^+$; purity: 98.91% @254 nm, 98.31% @ 214 nm.

Example 45: Synthesis of (1-((3,5-dimethyl-1H-pyrazol-4-yl)sulfonyl)pyrrolidin-3-yl)(4-(quinolin-4-yl)piperazin-1-yl)methanone

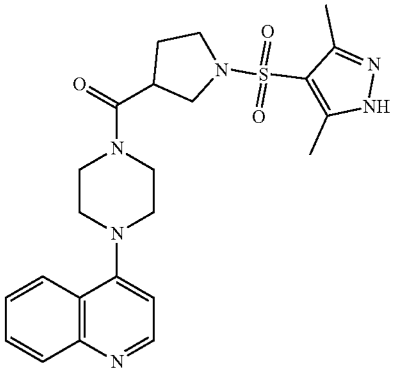 [SMILES: Cc1n[nH]c(C)c1S(=O)(=O)N1CCC(C(=O)N2CCN(c3ccnc4ccccc34)CC2)C1]

Pyrrolidin-3-yl(4-(quinolin-4-yl)piperazin-1-yl)methanone (120 mg, 0.39 mmol) and 1-methyl-1H-pyrazole-4-sulfonyl chloride (91 mg, 0.46 mmol) were used in the same manner as in the method of Example 5 to obtain the title compound (76 mg, 42% yield) as a white solid.

$^1$H NMR (400 MHz, DMSO-$d_6$): δ 13.04 (s, 1H), 8.71 (d, J=5.2 Hz, 1H), 8.08 (d, J=8.4 Hz, 1H), 7.97 (d, J=8.0 Hz, 1H), 7.74-7.70 (m, 1H), 7.59-7.55 (m, 1H), 7.00 (d, J=5.2 Hz, 1H), 3.77-3.73 (m, 4H), 3.48-3.44 (m, 1H), 3.37-3.33 (m, 1H), 3.27-3.24 (m, 1H), 3.16-3.13 (m, 6H), 2.39 (s, 3H), 2.32 (s, 3H), 2.10-2.07 (m, 1H), 1.90-1.86 (m, 1H). LC-MS (ESI): Rt=2.928 min., m/z 469.3 [M+H]$^+$; purity: 95.14% @ 254 nm, 96.51% @ 214 nm.

Example 46: Synthesis of (1-((1-methyl-1H-imidazol-4-yl)sulfonyl)pyrrolidin-3-yl)(4-(quinolin-4-yl)piperazin-1-yl)methanone

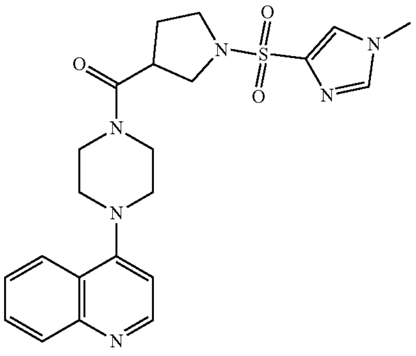 [SMILES: Cn1cnc(S(=O)(=O)N2CCC(C(=O)N3CCN(c4ccnc5ccccc45)CC3)C2)c1]

Pyrrolidin-3-yl(4-(quinolin-4-yl)piperazin-1-yl)methanone (120 mg, 0.39 mmol) and 1-methyl-1H-imidazole-4-sulfonyl chloride (84 mg, 0.46 mmol) were used in the same manner as in the method of Example 5 to obtain the title compound (56 mg, 32% yield) as a white solid.

$^1$H NMR (400 MHz, $CDCl_3$): δ 8.77 (d, J=4.8 Hz, 1H), 8.11 (d, J=8.4 Hz, 1H), 8.02 (d, J=8.4 Hz, 1H), 7.72-7.68 (m, 1H), 7.56-7.52 (m, 1H), 7.48 (s, 2H), 6.86 (d, J=5.2 Hz, 1H), 3.94-3.80 (m, 5H), 3.77 (s, 3H), 3.63-3.57 (m, 1H), 3.49-3.41 (m, 2H), 3.33-3.17 (m, 5H), 2.27-2.17 (m, 1H), 2.10-2.02 (m, 1H). LC-MS (ESI): Rt=2.265 min., m/z 455.1 [M+H]$^+$; purity: 99.12% @ 254 nm, 99.70% @ 214 nm.

Example 47: Synthesis of N-(4-methyl-5-((3-(4-(quinolin-4-yl)piperazine-1-carbonyl)pyrrolidin-1-yl)sulfonyl)thiazol-2-yl)acetamide

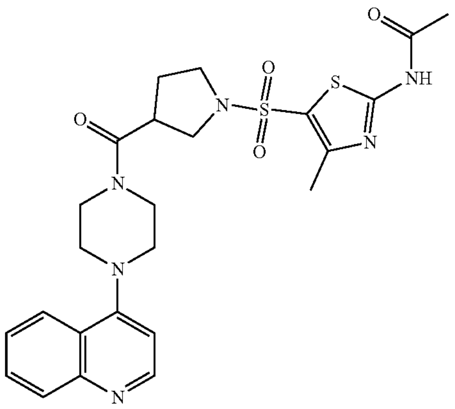 [SMILES: CC(=O)Nc1nc(C)c(S(=O)(=O)N2CCC(C(=O)N3CCN(c4ccnc5ccccc45)CC3)C2)s1]

Pyrrolidin-3-yl(4-(quinolin-4-yl)piperazin-1-yl)methanone (120 mg, 0.39 mmol) and 2-acetamido-4-methylthiazole-5-sulfonyl chloride (118 mg, 0.46 mmol) were used in the same manner as in the method of Example 5 to obtain the title compound (63 mg, 31% yield) as a white solid.

$^1$H NMR (400 MHz, $CDCl_3$): δ 9.51 (br s, 1H), 8.77 (d, J=4.8 Hz, 1H), 8.10 (d, J=8.4 Hz, 1H), 8.02 (d, J=8.4 Hz, 1H), 7.72-7.68 (m, 1H), 7.56-7.52 (m, 1H), 6.86 (d, J=4.8 Hz, 1H), 3.89-3.73 (m, 5H), 3.53-3.34 (m, 4H), 3.26-3.20 (m, 4H), 2.57 (s, 3H), 2.29 (s, 3H), 2.26-2.15 (m, 2H). LC-MS (ESI): Rt=2.954 min., m/z 529.1 [M+H]$^+$; purity: 97.28% @ 254 nm, 95.87% @ 214 nm.

Example 48: Synthesis of (R)—N-(4-methyl-5-((3-(4-(quinolin-4-yl)piperazine-1-carbonyl)pyrrolidin-1-yl)sulfonyl)thiazol-2-yl)acetamide

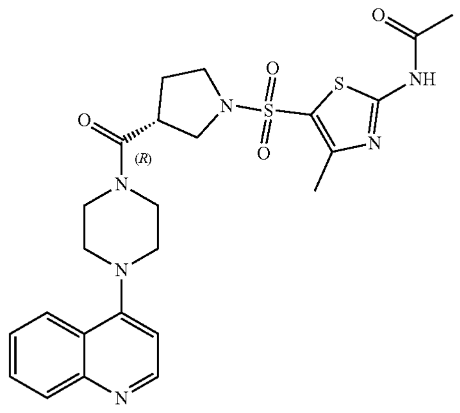

(R)-pyrrolidin-3-yl(4-(quinolin-4-yl)piperazin-1-yl)methanone (80 mg, 0.26 mmol) and 2-acetamido-4-methylthiazole-5-sulfonyl chloride (79 mg, 0.31 mmol) were used in the same manner as in the method of Example 5 to obtain the title compound (33 mg, 24% yield) as a white solid.

$^1$H NMR (400 MHz, $CDCl_3$): δ 9.90 (br s, 1H), 8.78 (d, J=4.8 Hz, 1H), 8.11-8.09 (m, 1H), 8.02-8.00 (m, 1H), 7.72-7.68 (m, 1H), 7.55-7.51 (m, 1H), 6.86 (d, J=4.8 Hz, 1H), 3.94-3.90 (m, 2H), 3.86-3.81 (m, 2H), 3.78-3.73 (m, 1H), 3.55-3.34 (m, 4H), 3.29-3.20 (m, 4H), 2.56 (s, 3H), 2.29 (s, 3H), 2.27-2.24 (m, 1H), 2.22-2.13 (m, 1H). LC-MS (ESI): Rt=3.102 min, m/z 529.3 [M+H]$^+$; purity: 95.15% @ 254 nm, 98.56% @ 214 nm. Chiral HPLC: Column: Chiralpak IB 5 μm 4.6×250 mm; Mobile Phase: HAX: EtOH=40:60 at 1 mL/min; Temp: 30° C.; Wavelength: 230 nm, Rt=7.893 min, 99.66% ee.

Example 49: Synthesis of (S)—N-(4-methyl-5-((3-(4-(quinolin-4-yl)piperazine-1-carbonyl)pyrrolidin-1-yl)sulfonyl)thiazol-2-yl)acetamide

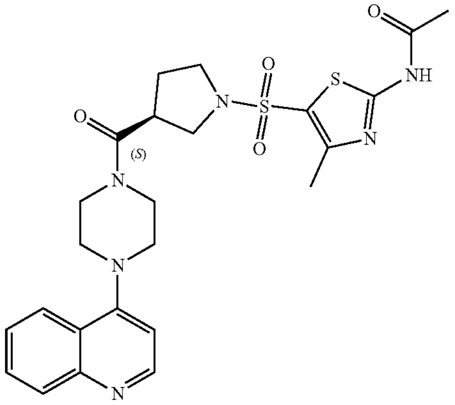

(S)-pyrrolidin-3-yl(4-(quinolin-4-yl)piperazin-1-yl)methanone (80 mg, 0.26 mmol) and 2-acetamido-4-methylthiazole-5-sulfonyl chloride (79 mg, 0.31 mmol) were used in the same manner as in the method of Example 5 to obtain the title compound (44 mg, 32% yield) as a white solid.

$^1$H NMR (400 MHz, $CDCl_3$): δ 9.47 (br s, 1H), 8.78 (d, J=4.8 Hz, 1H), 8.11 (d, J=8.4 Hz, 1H), 8.02 (d, J=8.0 Hz, 1H), 7.70 (m, 1H), 7.56-7.52 (m, 1H), 6.86 (d, J=5.2 Hz, 1H), 3.92-3.79 (m, 4H), 3.77-3.72 (m, 1H), 3.53-3.45 (m, 3H), 3.41-3.34 (m, 1H), 3.30-3.18 (m, 4H), 2.57 (s, 3H), 2.29 (s, 3H), 2.21-2.16 (m, 2H). LC-MS (ESI): Rt=3.100 min., m/z 529.2 $[M+H]^+$; purity: 97.74% @ 254 nm, 99.09% @214 nm. Chiral HPLC: Column: Chiralpak IB 5 μm 4.6×250 mm; Mobile Phase: HAX:EtOH=40:60 at 1 mL/min; Temp: 30° C.; Wavelength: 230 nm, Rt=10.478 min, 99.19% ee.

Example 50: Synthesis of methyl 3-((3-(4-(quinolin-4-yl)piperazine-1-carbonyl)pyrrolidin-1-yl)sulfonyl)thiophene-2-carboxylate

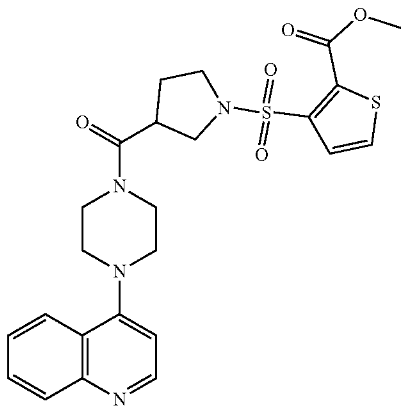 [SMILES: COC(=O)c1sccc1S(=O)(=O)N1CCC(C(=O)N2CCN(c3ccnc4ccccc34)CC2)C1]

Pyrrolidin-3-yl(4-(quinolin-4-yl)piperazin-1-yl)methanone (120 mg, 0.39 mmol) and methyl 3-(chlorosulfonyl)thiophene-2-carboxylate (112 mg, 0.46 mmol) were used in the same manner as in the method of Example 1 to obtain the title compound (75 mg, 38% yield) as a white solid.

$^1$H NMR (400 MHz, $CDCl_3$): δ 8.77 (d, J=5.2 Hz, 1H), 8.10 (d, J=8.4 Hz, 1H), 8.02 (d, J=8.4 Hz, 1H), 7.72-7.68 (m, 1H), 7.55-7.49 (m, 3H), 6.87 (d, J=5.2 Hz, 1H), 3.40-3.97 (m, 1H), 3.95-3.92 (m, 5H), 3.83-3.82 (m, 2H), 3.65-3.57 (m, 3H), 3.36-3.20 (m, 5H), 2.29-2.22 (m, 1H), 2.19-2.12 (m, 1H). LC-MS (ESI): Rt=3.259 min., m/z 515.2 $[M+H]^+$; purity: 97.10% @254 nm, 98.72% @214 nm.

Example 51: Synthesis of (1-((6-methoxypyridin-3-yl)sulfonyl)pyrrolidin-3-yl)(4-(quinolin-4-yl)piperazin-1-yl)methanone

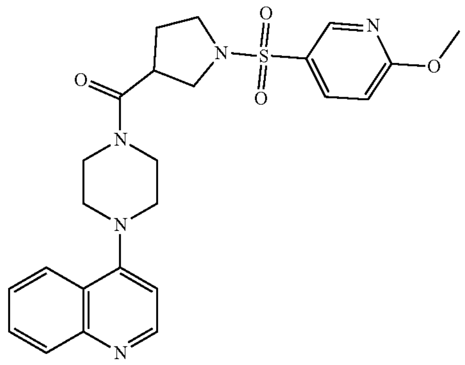 [SMILES: COc1ccc(S(=O)(=O)N2CCC(C(=O)N3CCN(c4ccnc5ccccc45)CC3)C2)cn1]

Pyrrolidin-3-yl(4-(quinolin-4-yl)piperazin-1-yl)methanone (120 mg, 0.39 mmol) and 6-methoxypyridin-3-sulfonyl chloride (97 mg, 0.46 mmol) were used in the same manner as in the method of Example 5 to obtain the title compound (76 mg, 41% yield) as a yellow solid.

$^1$H NMR (400 MHz, $CDCl_3$): δ 8.77 (d, J=4.8 Hz, 1H), 8.66-8.65 (m, 1H), 8.11 (d, J=8.4 Hz, 1H), 8.02-7.96 (m, 2H), 7.72-7.68 (m, 1H), 7.55-7.51 (m, 1H), 6.87-6.85 (m, 2H), 4.02 (s, 3H), 3.90-3.86 (m, 2H), 3.77-3.71 (m, 2H), 3.69-3.66 (m, 1H), 3.52-3.46 (m, 1H), 3.37-3.16 (m, 7H), 2.17-2.09 (m, 2H). LC-MS (ESI): Rt=2.810 min., m/z 482.1 $[M+H]^+$; purity: 99.74% @ 254 nm, 99.91% @ 214 nm.

Example 52: Synthesis of (1-((6-fluoropyridin-2-yl)sulfonyl)pyrrolidin-3-yl)(4-(quinolin-4-yl)piperazin-1-yl)methanone

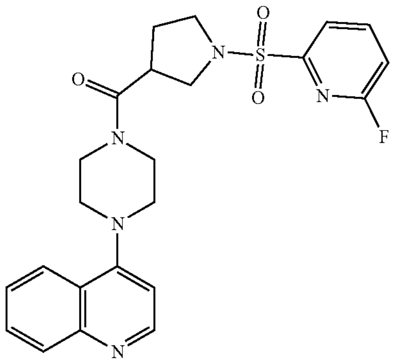 [SMILES: O=C(C1CCN(S(=O)(=O)c2cccc(F)n2)C1)N1CCN(c2ccnc3ccccc23)CC1]

Pyrrolidin-3-yl(4-(quinolin-4-yl)piperazin-1-yl)methanone (120 mg, 0.39 mmol) and 6-fluoropyridin-2-sulfonyl chloride (91 mg, 0.46 mmol) were used in the same manner as in the method of Example 5 to obtain the title compound (80 mg, 44% yield) as a yellow solid.

$^1$H NMR (400 MHz, $CDCl_3$): δ 8.78 (d, J=4.8 Hz, 1H), 8.12-8.01 (m, 3H), 7.91-7.88 (m, 1H), 7.73-7.68 (m, 1H), 7.56-7.52 (m, 1H), 7.16 (dd, J=2.4, 8.4 Hz, 1H), 6.87 (d, J=4.8 Hz, 1H), 4.03-3.99 (m, 1H), 3.90-3.83 (m, 4H), 3.72-3.62 (m, 2H), 3.50-3.34 (m, 2H), 3.31-3.20 (m, 4H), 2.35-2.28 (m, 1H), 2.17-2.11 (m, 1H). LC-MS (ESI): Rt=2.985 min., m/z 470.1 $[M+H]^+$; purity: 98.92% @254 nm, 98.95% @214 nm.

Example 53: Synthesis of (4-(7-fluoroquinolin-4-yl) piperazin-1-yl)(1-(4-nitrobenzyl)pyrrolidin-3-yl) methanone

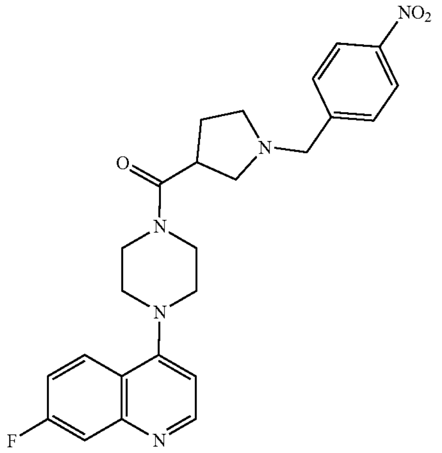 [SMILES: O=C(C1CCN(Cc2ccc([N+](=O)[O-])cc2)C1)N1CCN(c2ccnc3cc(F)ccc23)CC1]

According to Reaction Scheme 1-8, (4-(7-fluoroquinolin-4-yl)piperazin-1-yl)(pyrrolidin-3-yl)methanone (80 mg, 0.24 mmol) and TEA (123 mg, 1.21 mmol) were dissolved in DCM (1 mL), and then 1-(bromomethyl)-4-nitrobenzene (63 mg, 0.29 mmol) diluted in DCM (1 mL) was slowly added thereto. After reacting at room temperature for 4 hours, the reaction product was concentrated under reduced pressure. The residue was finally purified by C18 chromatography using 10-60% $CH_3CN$ aqueous solution as a developing solvent to obtain the title compound (50 mg, 44% yield) as a white solid.

$^1$H NMR (400 MHz, $CDCl_3$): δ 8.75 (d, J=5.2 Hz, 1H), 8.20-8.18 (m, 2H), 8.04-8.00 (m, 1H), 7.72-7.69 (m, 1H), 7.57-7.55 (m, 2H), 7.32-7.26 (m, 1H), 6.82 (d, J=5.2 Hz, 1H), 3.94-3.89 (m, 2H), 3.84-3.78 (m, 4H), 3.34-3.28 (m, 1H), 3.21-3.20 (m, 4H), 2.96-2.84 (m, 3H), 2.64-2.58 (m, 1H), 2.20-2.14 (m, 2H). LC-MS (ESI): Rt=2.539 min., m/z 464.1 $[M+H]^+$; purity: 99.66% @254 nm, 99.59% @214 nm.

Example 54: Synthesis of (4-(7-fluoroquinolin-4-yl) piperazin-1-yl)(1-((4-nitrophenyl)sulfonyl)piperidin-4-yl)methanone

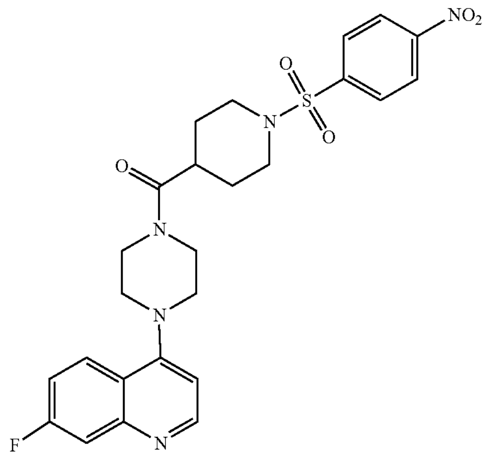 [SMILES: O=C(C1CCN(S(=O)(=O)c2ccc([N+](=O)[O-])cc2)CC1)N1CCN(c2ccnc3cc(F)ccc23)CC1]

According to Reaction Scheme 1-2, (4-(7-fluoroquinolin-4-yl)piperazin-1-yl)(piperidin-4-yl)methanone (125 mg, 0.31 mmol, Preparation Example 9) and TEA (94 mg, 0.93 mmol) were dissolved in dichloromethane (1 mL), and 4-nitrobenzene-1-sulfonyl chloride (69 mg, 0.31 mmol) diluted in dichloromethane (1 mL) was slowly added thereto and stirred at room temperature for 2 hours. The reaction solution was concentrated and diluted in dichloromethane (10 mL), saturated aqueous sodium bicarbonate solution (20 mL) was added, and extraction was carried out three times using a mixed solvent of dichloromethane:methanol=10:1 (20 mL). The organic layer was dried over $Na_2SO_4$, filtered and concentrated under reduced pressure. The residue was purified using silica gel chromatography (developing solvent, dichloromethane:methanol=15:1) to obtain the title compound (35 mg, 21% yield) as a white solid.

$^1$H NMR (400 MHz, $CDCl_3$): δ 8.67 (d, J=5.2 Hz, 1H), 8.39 (d, J=8.4 Hz, 2H), 8.02-7.96 (m, 3H), 7.91-7.89 (m, 1H), 7.35-7.30 (m, 1H), 6.85 (d, J=5.2 Hz, 1H), 3.89-3.75 (m, 6H), 3.36 (s, 4H), 2.68-2.56 (m, 3H), 1.97-1.92 (m, 2H), 1.88-1.83 (m, 2H). LC-MS (ESI): Rt=3.534 min, m/z 528.2 $[M+H]^+$; purity: 97.26% @ 254 nm, 97.31% @ 214 nm.

Example 55: Synthesis of N-(3-((4-(4-(7-fluoroquinolin-4-yl)piperazine-1-carbonyl)piperidin-1-yl)sulfonyl)phenyl)acetamide

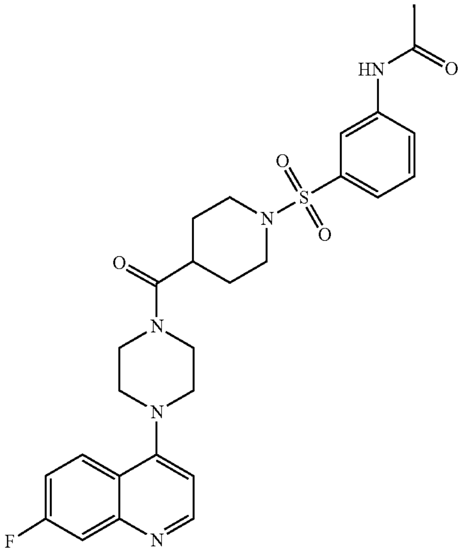 [SMILES: CC(=O)Nc1cccc(S(=O)(=O)N2CCC(C(=O)N3CCN(c4ccnc5cc(F)ccc45)CC3)CC2)c1]

4-(7-Fluoroquinolin-4-yl)piperazin-1-yl)(piperidin-4-yl)methanone (80 mg, 0.23 mmol) and 3-acetamidobenzene-1-sulfonyl chloride (65 mg, 0.28 mmol) were used in the same manner as in the method of Example 54 to obtain the title compound (61 mg, 50% yield) as a white solid.

$^1$H NMR (400 MHz, $CDCl_3$): δ 8.73 (d, J=5.2 Hz, 1H), 8.00 (dd, J=9.2, 6.0 Hz, 1H), 7.85 (s, 2H), 7.72-7.69 (m, 2H), 7.52-7.46 (m, 2H), 7.32-7.28 (m, 1H), 6.80 (d, J=4.8 Hz, 1H), 3.88-3.71 (m, 6H), 3.19-3.17 (m, 4H), 2.53-2.47 (m, 3H), 2.21 (s, 3H), 2.00-1.91 (m, 2H), 1.84-1.80 (m, 2H). LC-MS (ESI): Rt=3.395 min, m/z 540.3 $[M+H]^+$; purity: 98.56% @ 254 nm, 98.67% @ 214 nm.

Example 56: Synthesis of (1-((4-bromophenyl)sulfonyl)piperidin-4-yl)(4-(7-fluoroquinolin-4-yl)piperazin-1-yl)methanone

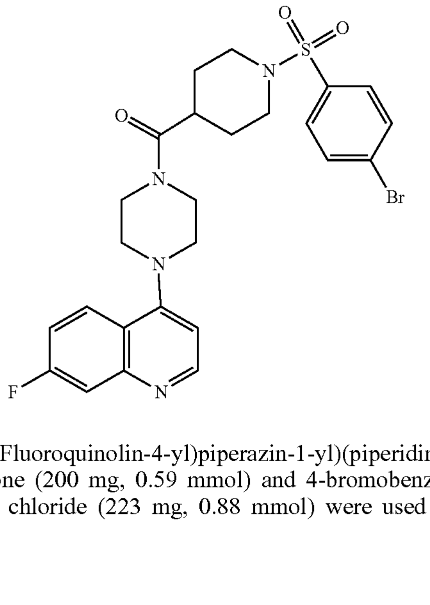

(4-(7-Fluoroquinolin-4-yl)piperazin-1-yl)(piperidin-4-yl)methanone (200 mg, 0.59 mmol) and 4-bromobenzene-1-sulfonyl chloride (223 mg, 0.88 mmol) were used in the same manner as in the method of Example 54 to obtain the title compound (120 mg, 24% yield) as a white solid. LC-MS (ESI): Rt=1.183 min, m/z 561.0 $[M+H]^+$; purity: 58.06% @ 214 nm.

Example 57: Synthesis of (4-(7-fluoroquinolin-4-yl)piperazin-1-yl)(1-((4-(pyridin-4-yl)phenyl)sulfonyl)piperidin-4-yl)methanone

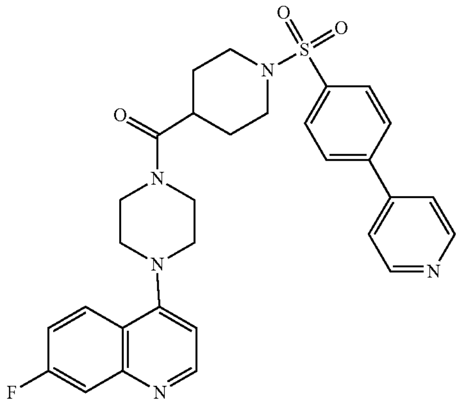 [SMILES: O=C(C1CCN(S(=O)(=O)c2ccc(-c3ccncc3)cc2)CC1)N1CCN(c2ccnc3cc(F)ccc23)CC1]

(1-((4-Bromophenyl)sulfonyl)piperidin-4-yl)(4-(7-fluoroquinolin-4-yl)piperazin-1-yl)methanone (120 mg, 0.21 mmol, Example 56) and 4-(4,4,5,5-tetramethyl-1,3,2-dioxaborolan-2-yl)pyridine (66 mg, 0.32 mmol) were used in the same manner as in the method of Example 17 to obtain the title compound (28 mg, 24% yield) as a white solid.

$^1$H NMR (400 MHz, $CDCl_3$): δ 8.74-8.71 (m, 3H), 8.00 (dd, J=9.2, 6.0 Hz, 1H), 7.91-7.89 (m, 2H), 7.80-7.76 (m, 3H), 7.53-7.51 (m, 2H), 7.32-7.28 (m, 1H), 6.81 (d, J=4.8 Hz, 1H), 3.91-3.73 (m, 6H), 3.23 (s, 4H), 2.63-2.53 (m, 3H), 2.02-1.94 (m, 2H), 1.87-1.83 (m, 2H). LC-MS (ESI): Rt=2.900 min, m/z 560.3 $[M+H]^+$; purity: 98.16% @ 254 nm, 98.46% @ 214 nm.

Example 58: Synthesis of (4-(7-fluoroquinolin-4-yl)piperazin-1-yl)(1-((4-(pyridin-3-yl)phenyl)sulfonyl)piperidin-4-yl)methanone

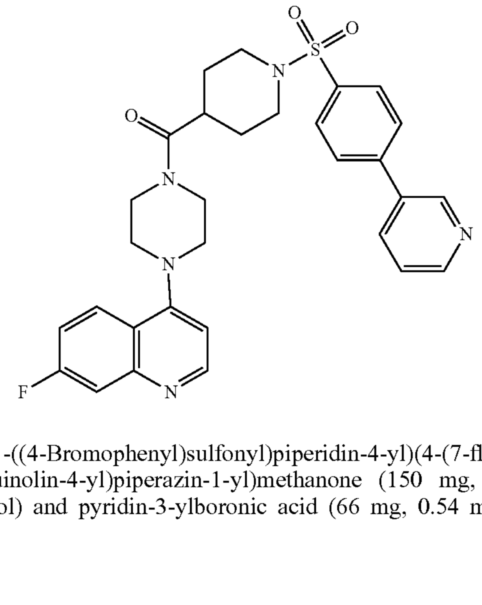

(1-((4-Bromophenyl)sulfonyl)piperidin-4-yl)(4-(7-fluoroquinolin-4-yl)piperazin-1-yl)methanone (150 mg, 0.27 mmol) and pyridin-3-ylboronic acid (66 mg, 0.54 mmol)

were used in the same manner as in the method of Example 17 to obtain the title compound (33 mg, 22% yield) as a white solid.

$^1H$ NMR (400 MHz, $CDCl_3$): δ 8.88 (s, 1H), 8.74 (m, J=4.8 Hz, 1H), 8.69 (m, J=3.6 Hz, 1H), 7.99 (dd, J=9.2, 6.0 Hz, 1H), 7.93-7.88 (m, 3H), 7.75-7.69 (m, 3H), 7.44 (dd, J=8.0, 5.2 Hz, 1H), 7.31-7.29 (m, 1H), 6.80 (d, J=4.8 Hz, 1H), 3.95-3.79 (m, 4H), 3.72 (s, 2H), 3.18-3.16 (m, 4H), 2.61-2.52 (m, 3H), 2.04-1.94 (m, 2H), 1.87-1.83 (m, 2H). LC-MS (ESI): Rt=2.752 min, m/z 560.3 $[M+H]^+$; purity: 98.65% @ 254 nm, 95.49% @ 214 nm.

Example 59: Synthesis of (1-((6-chloropyridin-3-yl)sulfonyl)piperidin-3-yl)(4-(7-fluoroquinolin-4-yl)piperazin-1-yl)methanone

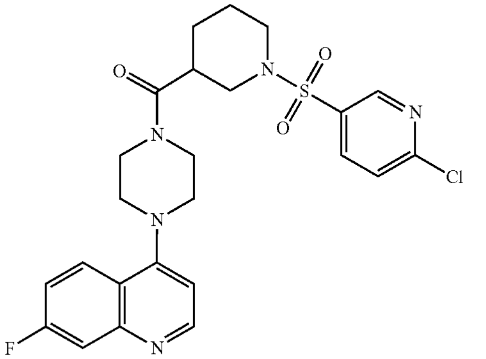 [SMILES: O=C(C1CCCN(S(=O)(=O)c2ccc(Cl)nc2)C1)N1CCN(c2ccnc3cc(F)ccc23)CC1]

(4-(7-Fluoroquinolin-4-yl)piperazin-1-yl)(piperidin-3-yl)methanone (200 mg, 0.58 mmol) and 6-chloropyridin-3-sulfonyl chloride (248 mg, 1.17 mmol) were used in the same manner as in the method of Example 5 to obtain the title compound (188 mg, 62% yield) as a white solid. LC-MS (ESI): Rt=1.373 min, m/z 518.1 $[M+H]^+$; purity: 97.99% @ 254 nm.

Example 60: Synthesis of N-(5-((3-(4-(7-fluoroquinolin-4-yl)piperazine-1-carbonyl)piperidin-1-yl)sulfonyl)pyridin-2-yl)acetamide

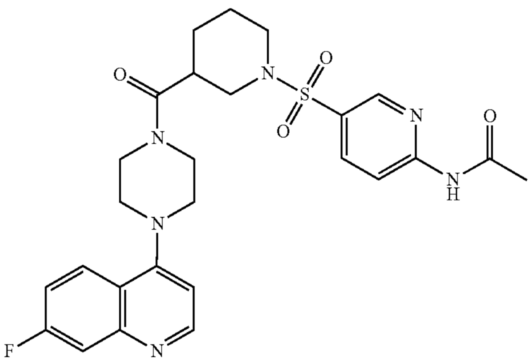 [SMILES: CC(=O)Nc1ccc(S(=O)(=O)N2CCCC(C(=O)N3CCN(c4ccnc5cc(F)ccc45)CC3)C2)cn1]

According to Reaction Scheme 1-7, (1-((6-chloropyridin-3-yl)sulfonyl)piperidin-3-yl)(4-(7-fluoroquinolin-4-yl)piperazin-1-yl)methanone (50 mg, 0.10 mmol, Example 59) and acetamide (9 mg, 0.16 mmol) were dissolved in 1,4-dioxane (0.5 mL), and tris[dibenzylideneacetone]dipalladium (9 mg, 0.001 mmol), xantphos (11 mg, 0.002 mmol) and $Cs_2CO_3$ (63 mg, 0.19 mmol) were added thereto at room temperature. The reaction solution was stirred at 100° C. for 4 hours under a nitrogen atmosphere. The reaction solution was cooled to room temperature, diluted with EtOAc (30 mL) and washed with water (10 mL×2) and brine (10 mL). After removing water from the organic layer using anhydrous $Na_2SO_4$, and the obtained product was concentrated under reduced pressure. The concentrate was purified by C18 chromatography using 20-80% $CH_3CN$ aqueous solution as a developing solvent to obtain the title compound (31 mg, 60% yield) as a white solid.

$^1H$ NMR (400 MHz, $CDCl_3$): δ 8.77 (d, J=5.2 Hz, 1H), 8.64-8.63 (m, 1H), 8.37 (d, J=8.8 Hz, 1H), 8.11 (br s, 1H), 8.05-8.01 (m, 2H), 7.75-7.71 (m, 1H), 7.35-7.30 (m, 1H), 6.85 (d, J=4.8 Hz, 1H), 3.94-3.77 (m, 6H), 3.30-3.17 (m, 4H), 2.97-2.90 (m, 1H), 2.57 (t, J=12.0 Hz, 1H), 2.34-2.29 (m, 1H), 2.27 (m, 3H), 1.93-1.86 (m, 2H), 1.78-1.73 (m, 1H), 1.57-1.49 (m, 1H).

LC-MS (ESI): Rt=2.565 min, m/z 541.2 $[M+H]^+$; purity: 99.73% @ 254 nm, 99.58% @ 214 nm.

Example 61: Synthesis of (4-(7-fluoroquinolin-4-yl)piperazin-1-yl)(1-((6-morpholinopyridin-3-yl)sulfonyl)piperidin-3-yl)methanone

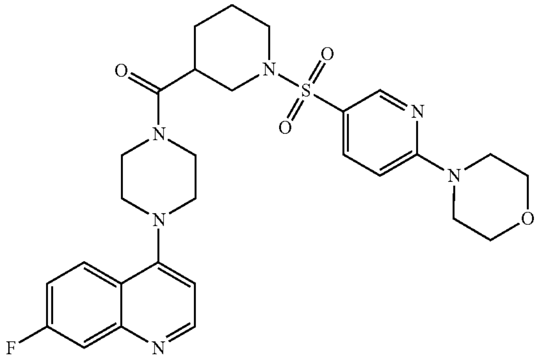 [SMILES: O=C(C1CCCN(S(=O)(=O)c2ccc(N3CCOCC3)nc2)C1)N1CCN(c2ccnc3cc(F)ccc23)CC1]

(1-((6-Chloropyridin-3-yl)sulfonyl)piperidin-3-yl)(4-(7-fluoroquinolin-4-yl)piperazin-1-yl)methanone (50 mg, 0.10 mmol) and morpholin (13 mg, 0.16 mmol) were used in the same manner as in the method of Example 60 to obtain the title compound (36 mg, 65% yield) as a white solid.

$^1H$ NMR (400 MHz, $CDCl_3$): δ 8.76 (d, J=4.8 Hz, 1H), 8.52-8.51 (m, 1H), 8.05-8.01 (m, 1H), 7.77-7.74 (m, 2H), 7.36-7.29 (m, 1H), 6.85 (d, J=5.2 Hz, 1H), 6.62 (d, J=9.2 Hz, 1H), 3.89-3.81 (m, 10H), 3.68-3.66 (m, 4H), 3.28-3.21 (m, 4H), 2.98-2.90 (m, 1H), 2.50 (t, J=14.4 Hz, 1H), 2.28-2.24 (m, 1H), 1.91-1.82 (m, 2H), 1.78-1.70 (m, 1H), 1.52-1.48 (m, 1H). LC-MS (ESI): Rt=3.282 min, m/z 569.3 $[M+H]^+$; purity: 99.65% @ 254 nm, 99.87% @ 214 nm.

Example 62: Synthesis of (4-(7-fluoroquinolin-4-yl)piperazin-1-yl)(1-((6-(4-methylpiperazin-1-yl)pyridin-3-yl)sulfonyl)piperidin-3-yl)methanone

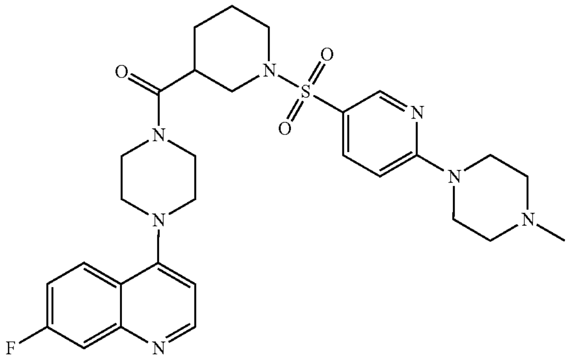 [SMILES: CN1CCN(c2ccc(S(=O)(=O)N3CCCC(C(=O)N4CCN(c5ccnc6cc(F)ccc56)CC4)C3)cn2)CC1]

(1-((6-Chloropyridin-3-yl)sulfonyl)piperidin-3-yl)(4-(7-fluoroquinolin-4-yl)piperazin-1-yl)methanone (50 mg, 0.10 mmol) and 1-methylpiperazine (15 mg, 0.16 mmol) were used in the same manner as in the method of Example 60 to obtain the title compound (49 mg, 88% yield) as a white solid.

$^1$H NMR (400 MHz, $CDCl_3$): 8.77-8.76 (m, 1H), 8.50-8.49 (m, 1H), 8.05-8.01 (m, 1H), 7.74-7.70 (m, 2H), 7.34-7.27 (m, 1H), 6.85-6.84 (m, 1H), 6.63 (d, J=9.2 Hz, 1H), 3.88-3.77 (m, 10H), 3.25-3.19 (m, 4H), 2.96-2.90 (m, 1H), 2.60 (m, 4H), 2.50 (t, J=12.0 Hz, 1H), 2.42 (m, 3H), 2.28-2.27 (m, 1H), 1.90-1.84 (m, 2H), 1.78-1.72 (m, 1H), 1.55-1.49 (m, 1H).

LC-MS (ESI): Rt=3.699 min, m/z 582.2 $[M+H]^+$; purity: 95.15% @ 254 nm, 96.05% @ 214 nm.

Example 63: Synthesis of (1-((4-bromophenyl)sulfonyl)piperidin-4-yl)(4-(quinolin-4-yl)piperazin-1-yl)methanone

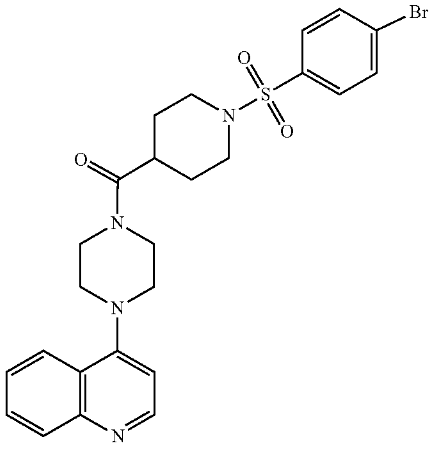 [SMILES: O=C(C1CCN(S(=O)(=O)c2ccc(Br)cc2)CC1)N1CCN(c2ccnc3ccccc23)CC1]

Piperidin-4-yl(4-(quinolin-4-yl)piperazin-1-yl)methanone (150 mg, 0.46 mmol) and 4-bromobenzene-1-sulfonyl chloride (176 mg, 0.69 mmol) were used in the same manner as in the method of Example 54 to obtain the title compound (160 mg, 64% yield) as a white solid.

$^1$H NMR (400 MHz, $CDCl_3$): δ 8.79 (d, J=6.4 Hz, 1H), 8.16-8.14 (m, 1H), 8.05-8.02 (m, 1H), 7.76-7.66 (m, 5H), 7.59-7.54 (m, 1H), 6.88 (d, J=6.4 Hz, 1H), 3.93 (br s, 2H), 3.84-3.72 (m, 4H), 3.26-3.24 (m, 4H), 2.61-2.50 (m, 3H), 2.02-1.95 (m, 2H), 1.89-1.86 (m, 2H).

Example 64: Synthesis of (1-((4-(pyridin-4-yl)phenyl)sulfonyl)piperidin-4-yl)(4-(quinolin-4-yl)piperazin-1-yl)methanone

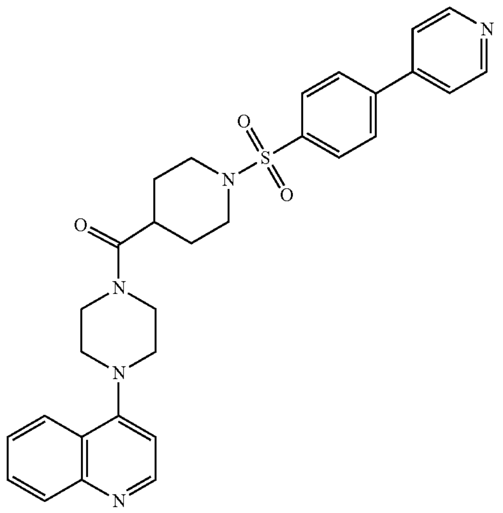 [SMILES: O=C(C1CCN(S(=O)(=O)c2ccc(-c3ccncc3)cc2)CC1)N1CCN(c2ccnc3ccccc23)CC1]

According to Reaction Scheme 1-6, (1-((4-bromophenyl)sulfonyl)piperidin-4-yl)(4-(quinolin-4-yl)piperazin-1-yl)methanone (150 mg, 0.28 mmol, Example 63) and 4-(4,4,5,5-tetramethyl-1,3,2-dioxabororan-2-yl)pyridine (68 mg, 0.33 mmol) were used in the same manner as in the method of Example 17 to obtain the title compound (25 mg, 17% yield) as a white solid.

$^1$H NMR (400 MHz, $CDCl_3$): δ 8.76-8.73 (m, 3H), 8.08 (d, J=8.4 Hz, 1H), 7.98 (d, J=8.0 Hz, 1H), 7.91-7.89 (m, 2H), 7.80-7.77 (m, 2H), 7.71-7.67 (m, 1H), 7.53-7.49 (m, 3H), 6.82 (d, J=4.8 Hz, 1H), 3.89-3.82 (m, 4H), 3.72 (s, 2H), 3.20-3.18 (m, 4H), 2.64-2.53 (m, 3H), 2.03-1.93 (m, 2H), 1.88-1.83 (m, 2H).

LC-MS (ESI): Rt=3.337 min, m/z 542.3 $[M+H]^+$; purity: 98.53% @254 nm, 97.89% @214 nm.

Example 65: Synthesis of N-(4-((3-(4-(7-fluoroquinolin-4-yl)piperazine-1-carbonyl)azetidin-1-yl)sulfonyl)phenyl)acetamide

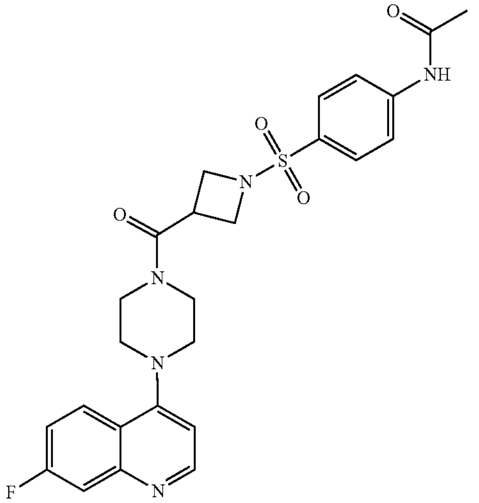 [SMILES: CC(=O)Nc1ccc(S(=O)(=O)N2CC(C(=O)N3CCN(c4ccnc5cc(F)ccc45)CC3)C2)cc1]

According to Reaction Scheme 1-3, (azetidin-3-yl(4-(7-fluoroquinolin-4-yl)piperazin-1-yl)methanone (80 mg, 0.24 mmol, Preparation Example 11) and TEA (77 mg, 0.77 mmol) were dissolved in dichloromethane (1 mL), and 4-acetamidobenzene-1-sulfonyl chloride (71 mg, 0.31 mmol) diluted in dichloromethane (1 mL) was slowly added thereto and stirred at room temperature for 2 hours. The reaction solution was concentrated, diluted in dichloromethane (10 mL), saturated aqueous sodium bicarbonate solution (20 mL) was added, and extraction was carried out three times using a mixed solvent (20 ml) of dichloromethane: methanol=10:1. The organic layer was dried over $Na_2SO_4$, filtered and concentrated under reduced pressure. The residue was purified using silica gel chromatography (developing solvent, dichloromethane methanol=15:1) to obtain the title compound (32 mg, 25% yield) as a white solid.

$^1$H NMR (400 MHz, $CDCl_3$): δ 8.74 (d, J=5.2 Hz, 1H), 8.00-7.96 (m, 1H), 7.82-7.71 (m, 5H), 7.58 (s, 1H), 7.32-7.30 (m, 1H), 6.81 (d, J=4.8 Hz, 1H), 4.01-3.99 (m, 4H), 3.87 (s, 2H), 3.50 (s, 3H), 3.16 (s, 4H), 2.24 (s, 3H).

LC-MS (ESI): Rt=2.804 min, m/z 546.2 [M+H]$^+$; purity: 96.65% @ 254 nm, 96.12% @ 214 nm.

Example 66: Synthesis of (4-(7-fluoroquinolin-4-yl)piperazin-1-yl)(1-((4-hydroxyphenyl)sulfonyl)azetidin-3-yl)methanone

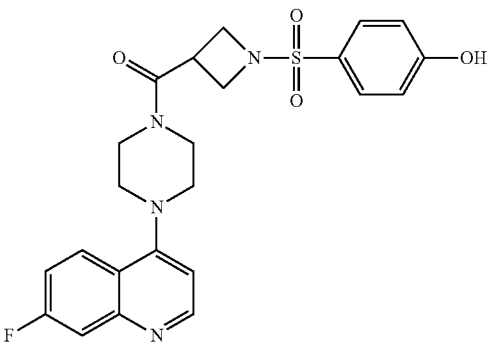 [SMILES: O=C(C1CN(S(=O)(=O)c2ccc(O)cc2)C1)N1CCN(c2ccnc3cc(F)ccc23)CC1]

Azetidin-3-yl(4-(7-fluoroquinolin-4-yl)piperazin-1-yl)methanone (150 mg, 0.48 mmol) and 4-hydroxybenzene-1-sulfonyl chloride (92 mg, 0.48 mmol) were used in the same manner as in the method of Example 65 to obtain the title compound (70 mg, 31% yield) as a white solid.

$^1$H NMR (400 MHz, DMSO-$d_6$): δ 10.60 (br s, 1H), 8.71 (d, J=5.2 Hz, 1H), 8.11 (dd, J=9.2, 6.4 Hz, 1H), 7.69-7.64 (m, 3H), 7.49-7.44 (m, 1H), 7.01-6.96 (m, 3H), 3.88-3.83 (m, 2H), 3.77 (t, J=6.8 Hz, 2H), 3.67-3.59 (m, 3H), 3.53-3.43 (m, 2H), 3.09 (s, 4H). LC-MS (ESI): Rt=3.539 min, m/z 471.1 [M+H]$^+$; purity: 98.55% @ 254 nm, 97.76% @ 214 nm.

Example 67: Synthesis of (4-(7-fluoroquinolin-4-yl)piperazin-1-yl)(1-((4-nitrophenyl)sulfonyl)azetidin-3-yl)methanone

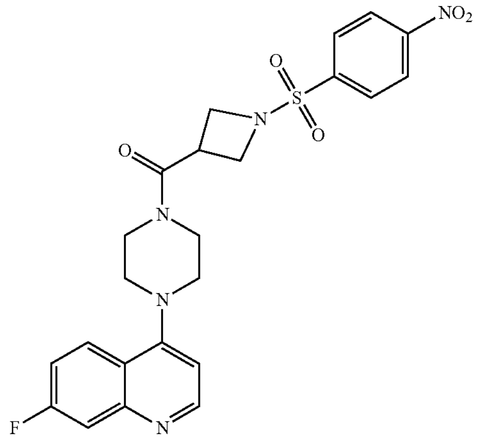 [SMILES: O=C(C1CN(S(=O)(=O)c2ccc([N+](=O)[O-])cc2)C1)N1CCN(c2ccnc3cc(F)ccc23)CC1]

Azetidin-3-yl(4-(7-fluoroquinolin-4-yl)piperazin-1-yl)methanone (100 mg, 0.32 mmol) and 4-nitrobenzene-1-sulfonyl chloride (70 mg, 0.32 mmol) were used in the same manner as in the method of Example 65 to obtain the title compound (43 mg, 27% yield) as a white solid.

$^1$H NMR (400 MHz, DMSO-$d_6$): δ 8.71 (d, J=5.2 Hz, 1H), 8.49 (d, J=8.8 Hz, 2H), 8.13-8.08 (m, 3H), 7.67 (dd, J=10.4, 2.8 Hz, 1H), 7.49-7.44 (m, 1H), 6.97 (d, J=4.8 Hz, 1H), 4.05-4.01 (m, 2H), 3.95-3.91 (m, 2H), 3.70-3.63 (m, 3H), 3.49-3.47 (m, 2H), 3.13-3.08 (m, 4H). LC-MS (ESI): Rt=2.800 min, m/z 500.1 $[M+H]^+$; purity: 97.04% @254 nm, 98.41% @214 nm.

Example 68: Synthesis of (1-((4-bromophenyl) sulfonyl)azetidin-3-yl)(4-(7-fluoroquinolin-4-yl) piperazin-1-yl)methanone

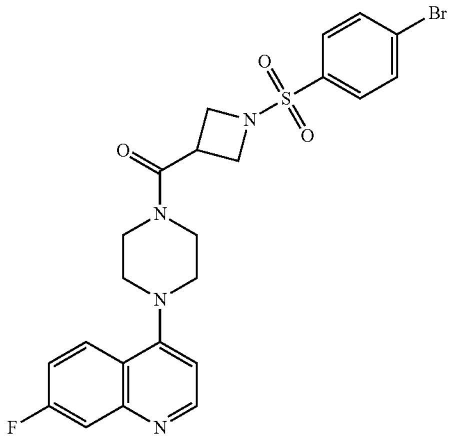 [SMILES: O=C(C1CN(S(=O)(=O)c2ccc(Br)cc2)C1)N1CCN(c2ccnc3cc(F)ccc23)CC1]

Azetidin-3-yl(4-(7-fluoroquinolin-4-yl)piperazin-1-yl) methanone (150 mg, 0.48 mmol) and 4-bromobenzene-1-sulfonyl chloride (146 mg, 0.57 mmol) were used in the same manner as in the method of Example 65 to obtain the title compound (130 mg, 51% yield) as a white solid.

$^1$H NMR (400 MHz, $CDCl_3$): δ 8.73 (d, J=4.8 Hz, 1H), 7.98 (dd, J=9.6, 6.0 Hz, 1H), 7.81-7.79 (m, 1H), 7.75-7.71 (m, 4H), 7.34-7.29 (m, 1H), 6.83 (d, J=4.8 Hz, 1H), 4.07-4.01 (m, 4H), 3.89-3.81 (m, 2H), 3.58-3.48 (m, 3H), 3.28-3.19 (m, 4H).

Example 69: Synthesis of (4-(7-fluoroquinolin-4-yl) piperazin-1-yl)(1-((4-(pyridin-4-yl)phenyl)sulfonyl) azetidin-3-yl)methanone

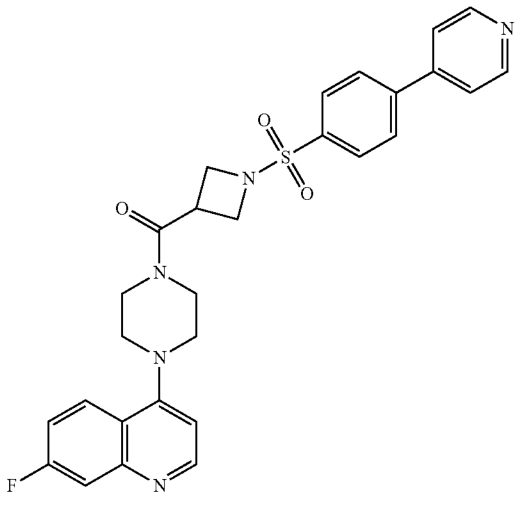 [SMILES: O=C(C1CN(S(=O)(=O)c2ccc(-c3ccncc3)cc2)C1)N1CCN(c2ccnc3cc(F)ccc23)CC1]

(1-((4-Bromophenyl)sulfonyl)azetidin-3-yl)(4-(7-fluoroquinolin-4-yl)piperazin-1-yl)methanone (120 mg, 0.23 mmol, Example 68) and 4-(4,4,5,5-tetramethyl-1,3,2-dioxaborolan-2-yl)pyridine (66 mg, 0.32 mmol) were used in the same manner as in the method of Example 17 to obtain the title compound (45 mg, 38% yield) as a white solid.

$^1$H NMR (400 MHz, $CDCl_3$): δ 8.76-8.73 (m, 3H), 8.00-7.95 (m, 3H), 7.91-7.89 (m, 2H), 7.85-7.83 (m, 2H), 7.76 (dd, J=10.4, 2.0 Hz, 1H), 7.56-7.54 (m, 2H), 7.33-7.28 (m, 1H), 6.81 (d, J=5.2 Hz, 1H), 4.10-4.08 (m, 4H), 3.84 (s, 2H), 3.61-3.52 (m, 3H), 3.21-3.20 (m, 4H). LC-MS (ESI): Rt=3.251 min, m/z 532.2 $[M+H]^+$; purity: 97.57% @ 254 nm, 97.48% @ 214 nm.

Example 70: Synthesis of N-(4-((3-(4-(quinolin-4-yl)piperazine-1-carbonyl)azetidin-1-yl)sulfonyl)phenyl)acetamide

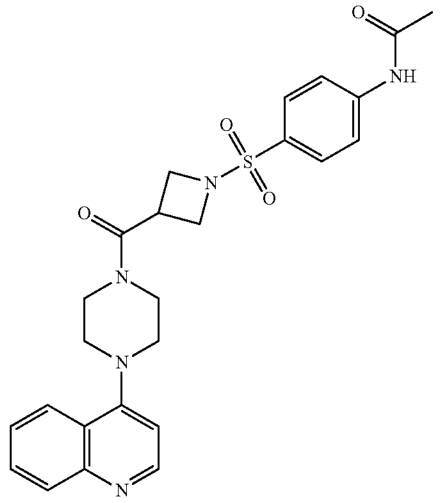 [SMILES: CC(=O)Nc1ccc(S(=O)(=O)N2CC(C(=O)N3CCN(c4ccnc5ccccc45)CC3)C2)cc1]

Azetidin-3-yl(4-(quinolin-4-yl)piperazin-1-yl)methanone (130 mg, 0.44 mmol) and 4-acetamidobenzene-1-sulfonyl chloride (123 mg, 0.53 mmol) were used in the same manner as in the method of Example 65 to obtain the title compound (130 mg, 60% yield) as a white solid.

$^1$H NMR (400 MHz, $CDCl_3$): δ 8.75 (d, J=5.2 Hz, 1H), 8.08 (d, J=8.4 Hz, 1H), 7.97 (d, J=8.0 Hz, 1H), 7.81-7.73 (m, 5H), 7.71-7.67 (m, 1H), 7.54-7.50 (m, 1H), 6.83 (d, J=5.2 Hz, 1H), 4.04-3.97 (m, 4H), 3.88-3.78 (m, 2H), 3.53-3.49 (m, 3H), 3.20-3.12 (m, 4H), 2.23 (s, 3H). LC-MS (ESI): Rt=3.009 min, m/z 494.3 $[M+H]^+$; purity: 99.47% @254 nm, 99.13% @214 nm.

Example 71: Synthesis of (4-(7-fluoroquinolin-4-yl)piperazin-1-yl)(1-((3-nitrophenyl)sulfonyl)azetidin-3-yl)methanone

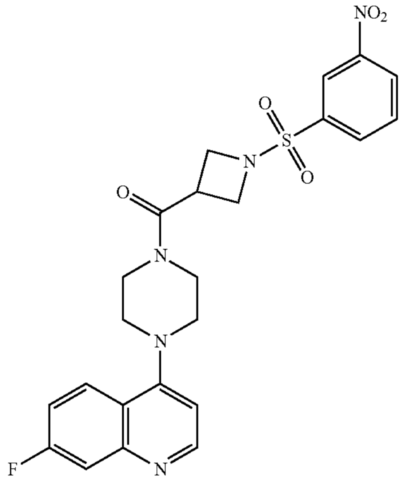 [SMILES: O=C(C1CN(S(=O)(=O)c2cccc([N+](=O)[O-])c2)C1)N1CCN(c2ccnc3cc(F)ccc23)CC1]

Azetidin-3-yl(4-(quinolin-4-yl)piperazin-1-yl)methanone (500 mg, 1.59 mmol) and 3-nitrobenzene-1-sulfonyl chloride (420 mg, 1.91 mmol) were used in the same manner as in the method of Example 65 to obtain the title compound (280 mg, 35% yield) as a light yellow solid.

$^1$H NMR (400 MHz, $CDCl_3$): δ 8.75 (d, J=5.2 Hz, 1H), 8.70-8.69 (m, 1H), 8.53-8.50 (m, 1H), 8.21-8.19 (m, 1H), 7.97 (dd, J=9.2, 6.0 Hz, 1H), 7.83 (t, J=8.0 Hz, 1H), 7.73 (dd, J=10.0, 2.4 Hz, 1H), 7.33-7.28 (m, 1H), 6.81 (d, J=4.8 Hz, 1H), 4.17-4.07 (m, 4H), 3.83-3.81 (m, 2H), 3.63-3.57 (m, 1H), 3.55-3.50 (m, 2H), 3.19-3.15 (m, 4H).

LC-MS (ESI): Rt=2.741 min, m/z 500.0 $[M+H]^+$; purity: 98.11% @254 nm, 97.91% @214 nm.

Example 72: Synthesis of (1-((3-aminophenyl)sulfonyl)azetidin-3-yl)(4-(7-fluoroquinolin-4-yl)piperazin-1-yl)methanone

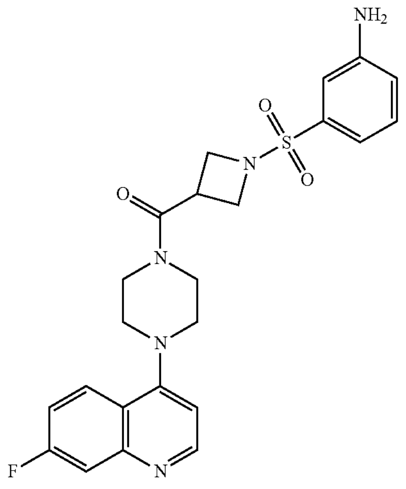 [SMILES: Nc1cccc(S(=O)(=O)N2CC(C(=O)N3CCN(c4ccnc5cc(F)ccc45)CC3)C2)c1]

(4-(7-Fluoroquinolin-4-yl)piperazin-1-yl)(1-((3-nitrophenyl)sulfonyl)azetidin-3-yl)methanone (40 mg, 0.08 mmol, Example 71) was dissolved in a solvent of ethanol (1 mL) and water (1 mL), and iron powder (45 mg, 0.80 mmol) and $NH_4Cl$ (86 mg, 1.60 mmol) were added thereto and stirred at 40° C. for 3 hours. The reaction product was filtered, the obtained solution was depressurized to remove the solvent, and the compound was purified by silica gel column using a developing solvent of DCM:MeOH=15:1 to obtain the title compound (25 mg, 66% yield).

$^1$H NMR (400 MHz, $CDCl_3$): δ 8.75 (d, J=4.8 Hz, 1H), 7.98 (dd, J=9.2, 6.0 Hz, 1H), 7.72 (dd, J=10.0, 2.8 Hz, 1H), 7.36-7.27 (m, 2H), 7.22-7.20 (m, 1H), 7.13-7.12 (m, 1H), 6.93-6.90 (m, 1H), 6.81 (d, J=5.2 Hz, 1H), 4.08-4.00 (m, 4H), 3.96 (s, 2H), 3.84-3.83 (m, 2H), 3.52-3.44 (m, 3H), 3.20-3.13 (m, 4H). LC-MS (ESI): Rt=2.633 min, m/z 470.1 $[M+H]^+$; purity: 97.59% @ 254 nm, 98.36% @ 214 nm.

Example 73: Synthesis of N-(3-((3-(4-(7-fluoroquinolin-4-yl)piperazine-1-carbonyl)azetidin-1-yl)sulfonyl)phenyl)acetamide

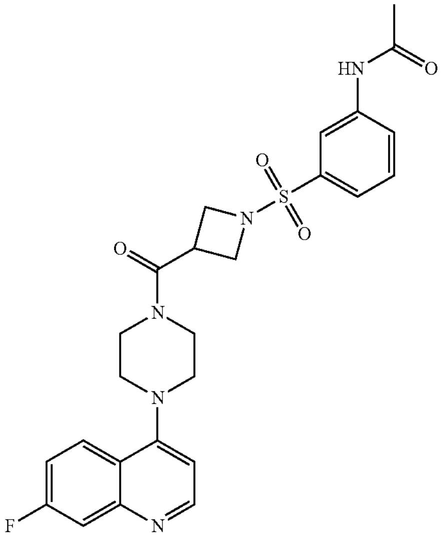 [SMILES: CC(=O)Nc1cccc(S(=O)(=O)N2CC(C(=O)N3CCN(c4ccnc5cc(F)ccc45)CC3)C2)c1]

Azetidin-3-yl(4-(quinolin-4-yl)piperazin-1-yl)methanone (130 mg, 0.44 mmol) and 3-acetamidobenzene-1-sulfonyl chloride (123 mg, 0.53 mmol) were used in the same manner as in the method of Example 65 to obtain the title compound (110 mg, 51% yield) as a white solid.

$^1$H NMR (400 MHz, $CDCl_3$): δ 8.73 (d, J=5.2 Hz, 1H), 7.99-7.92 (m, 3H), 7.85 (s, 1H), 7.71 (dd, J=10.4, 2.8 Hz, 1H), 7.59-7.52 (m, 2H), 7.32-7.28 (m, 1H), 6.81 (d, J=4.8 Hz, 1H), 4.10-4.02 (m, 4H), 3.81 (s, 2H), 3.53-3.45 (m, 3H), 3.19-3.14 (m, 4H), 2.20 (s, 3H). LC-MS (ESI): Rt=3.118 min, m/z 512.2 $[M+H]^+$; purity: 97.43% @254 nm, 98.15% @214 nm.

Example 74: Synthesis of N-(4-((3-(4-(quinazolin-4-yl)piperazine-1-carbonyl)piperidin-1-yl)sulfonyl)phenyl)acetamide

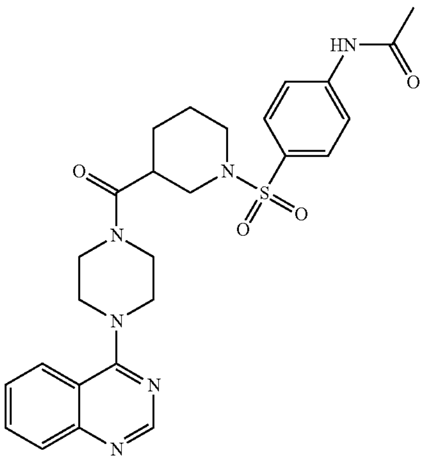 [SMILES: CC(=O)Nc1ccc(S(=O)(=O)N2CCCC(C(=O)N3CCN(c4ncnc5ccccc45)CC3)C2)cc1]

According to Reaction Scheme 2, piperidin-3-yl(4-(quinazolin-4-yl)piperazin-1-yl) methanone (60 mg, 0.18 mmol, Preparation Example 19) and TEA (56 mg, 0.54 mmol) were dissolved in dichloromethane (2 mL), and 4-acetamidobenzene-1-sulfonyl chloride (43 mg, 0.18 mmol) diluted in dichloromethane (1 mL) was added thereto and stirred at room temperature for 2 hours. After concentrating the reaction product, the concentrate was purified by C18 chromatography using 30-80% $CH_3CN$ (acetonitrile) aqueous solution as a developing solvent to obtain the title compound (60 mg, 63% yield) as a white solid.

$^1$H NMR (400 MHz, $CDCl_3$): δ 8.78 (s, 1H), 7.94 (d, J=8.4 Hz, 1H), 7.89 (d, J=8.4 Hz, 1H), 7.78 (t, J=8.0 Hz, 1H), 7.73 (s, 1H), 7.70 (s, 4H), 7.51 (t, J=7.2 Hz, 1H), 3.86-3.77 (m, 10H), 2.92-2.86 (m, 1H), 2.49 (t, J=11.2 Hz, 1H), 2.28-2.24 (m, 1H), 2.21 (s, 3H), 1.89-1.82 (m, 2H), 1.77-1.73 (m, 1H), 1.50-1.42 (m, 1H). LC-MS (ESI): Rt=3.212 min, m/z 523.2 $[M+H]^+$; purity: 99.20% @254 nm, 99.57% @214 nm.

Example 75: Synthesis of (4-(quinazolin-4-yl)piperazin-1-yl)(1-tosylpiperidin-3-yl)methanone

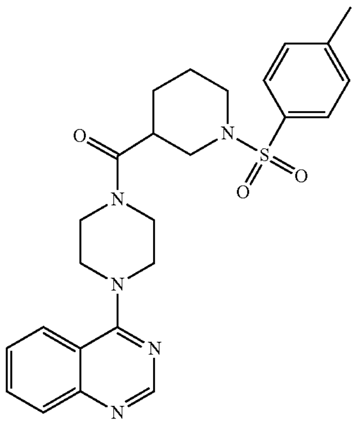 [SMILES: Cc1ccc(S(=O)(=O)N2CCCC(C(=O)N3CCN(c4ncnc5ccccc45)CC3)C2)cc1]

Piperidin-3-yl(4-(quinazolin-4-yl)piperazin-1-yl)methanone (60 mg, 0.18 mmol) and 4-methylbenzene-1-sulfonyl chloride (35 mg, 0.18 mmol) were used in the same manner as in the method of Example 74 to obtain the title compound the title compound (55 mg, 63% yield) as a white solid.

$^1$H NMR (400 MHz, $CDCl_3$): δ 8.78 (s, 1H), 7.94 (d, J=8.4 Hz, 1H), 7.89 (d, J=8.4 Hz, 1H), 7.78 (t, J=8.0 Hz, 1H), 7.64 (t, J=8.4 Hz, 2H), 7.51 (t, J=7.6 Hz, 1H), 7.32 (d, J=8.0 Hz, 2H), 3.87-3.77 (m, 10H), 2.93-2.87 (m, 1H), 2.50-2.47 (m, 1H), 2.43 (s, 3H), 2.22 (td, J=12.0, 2.8 Hz, 1H), 1.88-1.81 (m, 2H), 1.75-1.70 (m, 1H), 1.52-1.41 (m, 1H). LC-MS (ESI): Rt=3.758 min, m/z 480.2 $[M+H]^+$; purity: 99.14% @ 254 nm, 99.48% @ 214 nm.

Example 76: Synthesis of (1-((4-fluorophenyl)sulfonyl)piperidin-3-yl)(4-(quinazolin-4-yl)piperazin-1-yl)methanone

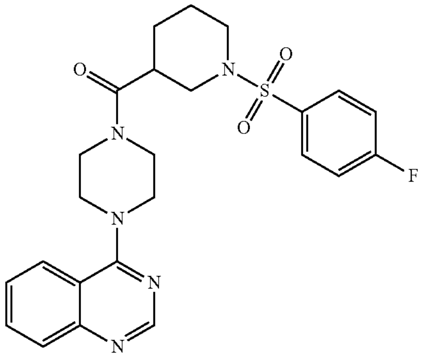 [SMILES: O=C(C1CCCN(S(=O)(=O)c2ccc(F)cc2)C1)N1CCN(c2ncnc3ccccc23)CC1]

Piperidin-3-yl(4-(quinazolin-4-yl)piperazin-1-yl)methanone (60 mg, 0.18 mmol) and 4-fluorobenzene-1-sulfonyl chloride (36 mg, 0.18 mmol) were used in the same manner as in the method of Example 74 to obtain the title compound (45 mg, 51% yield) as a white solid.

$^1$H NMR (400 MHz, $CDCl_3$): δ 8.78 (s, 1H), 7.95 (d, J=8.4 Hz, 1H), 7.89 (d, J=8.4 Hz, 1H), 7.80-7.76 (m, 3H), 7.51 (t, J=8.0 Hz, 1H), 7.22 (t, J=8.8 Hz, 2H), 3.88-3.77 (m, 10H), 2.94-2.88 (m, 1H), 2.51 (t, J=11.6 Hz, 1H), 2.24 (td, J=12.0, 2.8 Hz, 1H), 1.91-1.83 (m, 2H), 1.76-1.72 (m, 1H), 1.52-1.43 (m, 1H). LC-MS (ESI): Rt=3.676 min, m/z 484.2 $[M+H]^+$; purity: 99.18% @254 nm, 99.36% @ 214 nm.

Example 77: Synthesis of 1-((4-(dimethylamino)phenyl)sulfonyl)piperidin-3-yl)(4-(quinazolin-4-yl)piperazin-1-yl)methanone

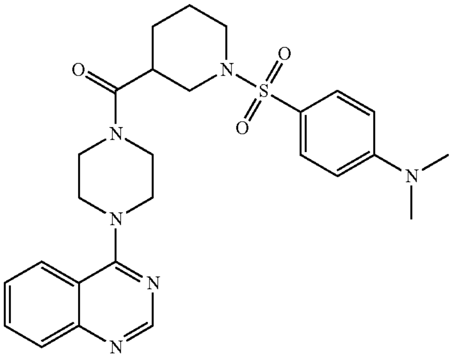 [SMILES: CN(C)c1ccc(S(=O)(=O)N2CCCC(C(=O)N3CCN(c4ncnc5ccccc45)CC3)C2)cc1]

Piperidin-3-yl(4-(quinazolin-4-yl)piperazin-1-yl)methanone (60 mg, 0.18 mmol) and 4-4-(dimethylamino)benzene-1-sulfonyl chloride (41 mg, 0.18 mmol) were used in the same manner as in the method of Example 74 to obtain the title compound (55 mg, 59% yield) as a white solid.

$^1$H NMR (400 MHz, $CDCl_3$): δ 8.78 (s, 1H), 7.95 (d, J=8.4 Hz, 1H), 7.89 (d, J=8.4 Hz, 1H), 7.78 (t, J=8.0 Hz, 1H), 7.58 (d, J=9.2 Hz, 2H), 7.51 (t, J=8.0 Hz, 1H), 6.68 (d, J=9.2 Hz, 2H), 3.81-3.77 (m, 10H), 3.05 (s, 6H), 2.92-2.87 (m, 1H), 2.44 (t, J=11.2 Hz, 1H), 2.21 (t, J=12.0 Hz, 1H), 1.86-1.79 (m, 2H), 1.75-1.70 (m, 1H), 1.51-1.42 (m, 1H). LC-MS (ESI): Rt=3.709 min, m/z 509.3 $[M+H]^+$; purity: 98.57% @ 254 nm, 98.98% @ 214 nm.

Example 78: Synthesis of (1-((4-hydroxyphenyl)sulfonyl)piperidin-3-yl)(4-(quinazolin-4-yl)piperazin-1-yl)methanone

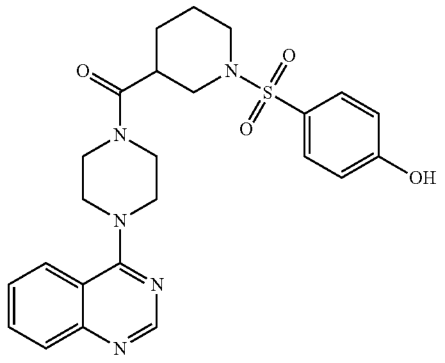 [SMILES: O=C(C1CCCN(S(=O)(=O)c2ccc(O)cc2)C1)N1CCN(c2ncnc3ccccc23)CC1]

Piperidin-3-yl(4-(quinazolin-4-yl)piperazin-1-yl)methanone (120 mg, 0.34 mmol) and 4-hydroxybenzene-1-sulfonyl chloride (65 mg, 0.34 mmol) were used in the same manner as in the method of Example 74 to obtain the title compound (20 mg, 17% yield) as a white solid.

$^1$H NMR (400 MHz, DMSO-$d_6$): δ 10.54 (s, 1H), 8.65 (s, 1H), 8.05 (d, J=8.0 Hz, 1H), 7.84-7.83 (m, 2H), 7.59-7.54 (m, 3H), 6.97 (d, J=8.4 Hz, 1H), 3.78-3.71 (m, 6H), 3.67-3.58 (m, 4H), 2.94-2.88 (m, 1H), 2.25 (t, J=11.2 Hz, 1H), 2.12 (t, J=12.0 Hz, 1H), 1.79-1.71 (m, 2H), 1.64-1.57 (m, 1H), 1.25-1.15 (m, 1H). LC-MS (ESI): Rt=3.739 min, m/z 484.2 $[M+H]^+$; purity: 98.34% @ 254 nm, 99.10% @ 214 nm.

Example 79: Synthesis of N-(4-(3-(1-(2-methylquinazolin-4-yl)piperazine-4-carbonyl)piperidin-1-ylsulfonyl)phenyl)acetamide

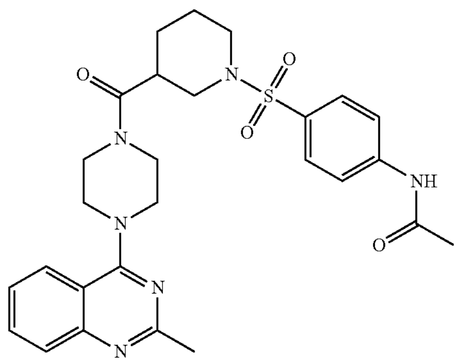 [SMILES: CC(=O)Nc1ccc(S(=O)(=O)N2CCCC(C(=O)N3CCN(c4nc(C)nc5ccccc45)CC3)C2)cc1]

(4-(2-Methylquinazolin-4-yl)piperazin-1-yl)(piperidin-3-yl)methanone (80 mg, 0.23 mmol, Preparation Example 21) and 4-acetamidobenzene-1-sulfonyl chloride (61 mg, 0.26 mmol) were used in the same manner as in the method of Example 74 to obtain the title compound (55 mg, 44% yield) as a white solid.

$^1$H NMR (400 MHz, $CDCl_3$): δ 7.85 (dd, J=8.0, 3.2 Hz, 2H), 7.74 (d, J=7.2 Hz, 1H), 7.71-7.68 (m, 5H), 7.43 (t, J=7.2 Hz, 1H), 3.86-3.73 (m, 10H), 2.93-2.85 (m, 1H), 2.69 (s, 3H), 2.49 (t, J=11.2 Hz, 1H), 2.27-2.23 (m, 1H), 2.22 (s, 3H), 1.89-1.82 (m, 2H), 1.77-1.70 (m, 1H), 1.51-1.40 (m, 1H). LC-MS (ESI): Rt=3.696 min, m/z 537.3 $[M+H]^+$; purity: 95.06% @ 254 nm, 97.69% @214 nm.

Example 80: Synthesis of (4-(2-methylquinazolin-4-yl)piperazin-1-yl)(1-tosylpiperidin-3-yl)methanone

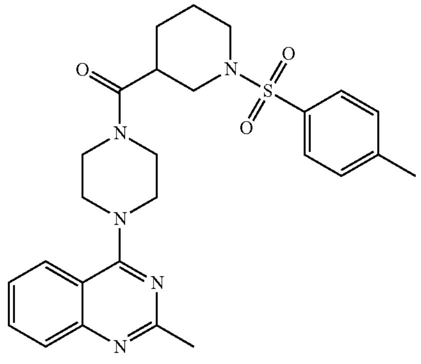 [SMILES: Cc1ccc(S(=O)(=O)N2CCCC(C(=O)N3CCN(c4nc(C)nc5ccccc45)CC3)C2)cc1]

(4-(2-Methylquinazolin-4-yl)piperazin-1-yl)(piperidin-3-yl)methanone (80 mg, 0.23 mmol) and 4-methylbenzene-1-sulfonyl chloride (49 mg, 0.26 mmol) were used in the same manner as in the method of Example 74 to obtain the title compound (70 mg, 60% yield) as a white solid.

$^1$H NMR (400 MHz, $CDCl_3$): δ 7.88 (dd, J=8.8, 3.2 Hz, 2H), 7.73 (t, J=7.2 Hz, 1H), 7.64 (d, J=8.4 Hz, 2H), 7.43 (t, J=6.8 Hz, 1H), 7.32 (d, J=8.0 Hz, 2H), 3.87-3.74 (m, 10H), 2.94-2.88 (m, 1H), 2.69 (s, 3H), 2.50-2.44 (m, 1H), 2.42 (s, 3H), 2.22 (td, J=12.0, 2.8 Hz, 1H), 1.89-1.81 (m, 2H), 1.77-1.69 (m, 1H), 1.52-1.40 (m, 1H). LC-MS (ESI): Rt=3.481 min, m/z 494.2 $[M+H]^+$; purity: 95.98% @ 254 nm, 95.27% @ 214 nm.

Example 81: Synthesis of (1-(4-fluorophenylsulfonyl)piperidin-3-yl)(4-(2-methylquinazolin-4-yl)piperazin-1-yl)methanone

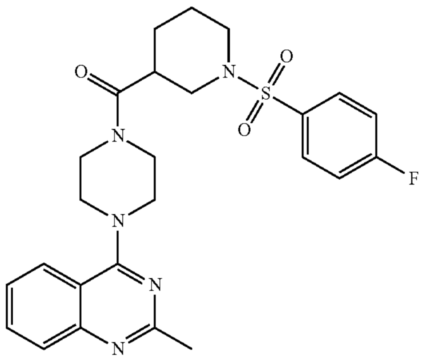 [SMILES: Cc1nc(N2CCN(C(=O)C3CCCN(S(=O)(=O)c4ccc(F)cc4)C3)CC2)c2ccccc2n1]

(4-(2-Methylquinazolin-4-yl)piperazin-1-yl)(piperidin-3-yl)methanone (80 mg, 0.23 mmol) and 4-methylbenzene-1-sulfonyl chloride (51 mg, 0.26 mmol) were used in the same manner as in the method of Example 74 to obtain the title compound (62 mg, 53% yield) as a white solid.

$^1$H NMR (400 MHz, $CDCl_3$): δ 7.86 (t, J=6.0 Hz, 2H), 7.80-7.71 (m, 3H), 7.43 (t, J=7.2 Hz, 1H), 7.22 (t, J=8.8 Hz, 2H), 3.88-3.73 (m, 10H), 2.95-2.88 (m, 1H), 2.69 (s, 3H), 2.51 (t, J=11.2 Hz, 1H), 2.24 (td, J=12.0, 2.8 Hz, 1H), 1.91-1.83 (m, 2H), 1.79-1.71 (m, 1H), 1.53-1.44 (m, 1H). LC-MS (ESI): Rt=3.175 min, m/z 498.2 $[M+H]^+$; purity: 96.08% @ 254 nm, 97.38% @ 214 nm.

Example 82: Synthesis of (1-(4-(dimethylamino)phenylsulfonyl)piperidin-3-yl)(4-(2-methylquinazolin-4-yl)piperazin-1-yl)methanone

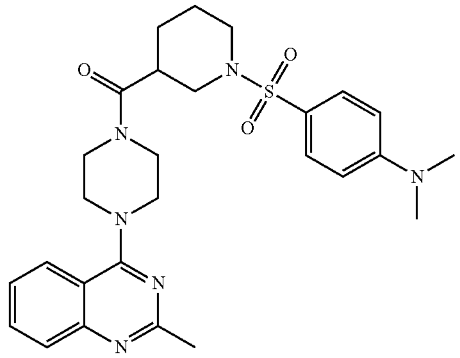 [SMILES: Cc1nc(N2CCN(C(=O)C3CCCN(S(=O)(=O)c4ccc(N(C)C)cc4)C3)CC2)c2ccccc2n1]

(4-(2-Methylquinazolin-4-yl)piperazin-1-yl)(piperidin-3-yl)methanone (80 mg, 0.23 mmol) and 4-(dimedilamino)benzene-1-sulfonyl chloride (57 mg, 0.26 mmol) were used in the same manner as in the method of Example 74 to obtain the title compound (50 mg, 41% yield) as a white solid.

Example 83: Synthesis of N-(4-(3-(1-(7-chloroquinolin-4-yl)piperazine-4-carbonyl)piperidine-1-carbonyl)phenyl)acetamide

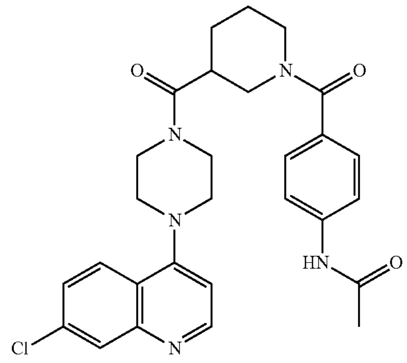 [SMILES: CC(=O)Nc1ccc(C(=O)N2CCCC(C(=O)N3CCN(c4ccnc5cc(Cl)ccc45)CC3)C2)cc1]

According to Reaction Scheme 3, 4-acetamidobenzoic acid (44 mg, 0.24 mmol), N,N-diisopropylethylamine (86 mg, 0.66 mmol) and HATU (102 mg, 0.24 mmol) were added to dimethylformamide (DMF, 5 mL) and stirred at room temperature for 5 minutes. Then, (4-(7-chloroquinolin-4-yl)piperazin-1-yl)(piperidin-3-yl)methanone (80 mg, 0.22 mmol, Preparation Example 38) dissolved in DMF (1 ml) was added thereto, and the reaction solution was stirred at room temperature for 1 hour. After adding water (300 mL) to the reaction solution, extraction was carried out using ethyl acetate (EtOAc) (30 ml×3) to separate the organic layer. Water was removed from the organic layer using $Na_2SO_4$, and the obtained product was filtered and concentrated under reduced pressure. The concentrate was purified by C18 chromatography using 30-80% $CH_3CN$ (acetonitrile) aqueous solution as a developing solvent to obtain the title compound (65 mg, 56% yield) as a white solid.

$^1$H NMR (400 MHz, $CDCl_3$): δ 8.74 (d, J=4.8 Hz, 1H), 8.07 (d, J=1.6 Hz, 1H), 7.96-7.94 (m, 1H), 7.53 (d, J=8.4 Hz, 3H), 7.47 (dd, J=9.2, 2.0 Hz, 1H), 7.40 (d, J=3.6 Hz, 2H), 6.84 (s, 1H), 4.72-4.70 (m, 1H), 3.96-3.59 (m, 5H), 3.28-3.12 (m, 5H), 2.97-2.85 (m, 2H), 2.18 (s, 3H), 1.97-1.86 (m, 3H), 1.51-1.45 (m, 1H). LC-MS (ESI): Rt=3.424 min, m/z 520.1 $[M+H]^+$; purity: 99.35% @ 254 nm, 98.98% @214 nm.

Example 84: Synthesis of (4-(7-chloroquinolin-4-yl)piperazin-1-yl)(1-(4-fluorophenylcarbonyl)piperidin-3-yl)methanone

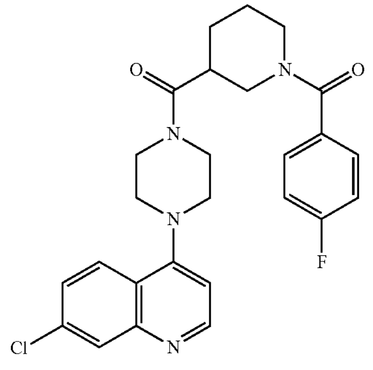 [SMILES: O=C(c1ccc(F)cc1)N1CCCC(C(=O)N2CCN(c3ccnc4cc(Cl)ccc34)CC2)C1]

4-Fluorobenzoic acid (34 mg, 0.24 mmol) and (4-(7-chloroquinolin-4-yl)piperazin-1-yl)(piperidin-3-yl)methanone (80 mg, 0.22 mmol) were used in the same manner as in the method of Example 83 to obtain the title compound (80 mg, 75% yield) as a white solid.

$^1$H NMR (400 MHz, $CDCl_3$): δ 8.76 (d, J=5.2 Hz, 1H), 8.07 (d, J=1.6 Hz, 1H), 7.95-7.94 (m, 1H), 7.48-7.43 (m, 3H), 7.11 (t, J=8.8 Hz, 2H), 6.85-6.81 (m, 1H), 4.70-4.68 (m, 1H), 4.00-3.80 (m, 5H), 3.28-2.99 (m, 5H), 2.88-2.82 (m, 2H), 1.88-1.87 (m, 2H), 1.79-1.72 (m, 1H), 1.49-1.41 (m, 1H). LC-MS (ESI): Rt=3.725 min, m/z 481.2 $[M+H]^+$; purity: 97.60% @254 nm, 98.38% @214 nm.

Example 85: Synthesis of (4-(7-chloroquinolin-4-yl)piperazin-1-yl)(1-(phenylcarbonyl)piperidin-3-yl)methanone

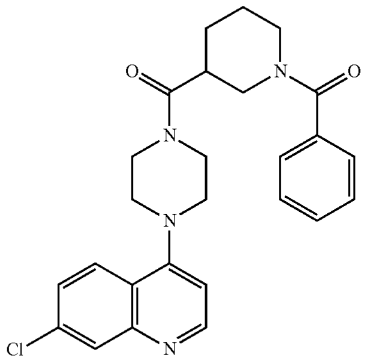 [SMILES: O=C(c1ccccc1)N1CCCC(C(=O)N2CCN(c3ccnc4cc(Cl)ccc34)CC2)C1]

According to Reaction Scheme 3, (4-(7-chloroquinolin-4-yl)piperazin-1-yl)(piperidin-3-yl)methanone (80 mg, 0.22 mmol) and TEA (56 mg, 0.54 mmol) were dissolved in dichloromethane (2 mL), and benzoyl chloride (35 mg, 0.24 mmol) diluted in dichloromethane (1 mL) was added thereto and stirred at room temperature for 2 hours. After concentrating the reaction product, the concentrate was purified by C18 chromatography using 30-80% $CH_3CN$ (acetonitrile) aqueous solution as a developing solvent to obtain the title compound (65 mg, 63% yield) as a white solid.

$^1$H NMR (400 MHz, $CDCl_3$): δ 8.75 (d, J=4.8 Hz, 1H), 8.07 (d, J=2.0 Hz, 1H), 7.97-7.88 (m, 1H), 7.48-7.47 (m, 1H), 7.45-7.42 (m, 5H), 6.85-6.76 (m, 1H), 4.75-4.72 (m, 1H), 4.01-3.78 (m, 4H), 3.60-3.52 (m, 1H), 3.29-3.08 (m, 5H), 2.97-2.84 (m, 2H), 1.97-1.92 (m, 2H), 1.76-1.74 (m, 1H), 1.48-1.47 (m, 1H). LC-MS (ESI): Rt=3.574 min, m/z 463.2 $[M+H]^+$; purity: 99.72% @ 254 nm, 99.60% @ 214 nm.

Example 86: Synthesis of (4-(7-chloroquinolin-4-yl)piperazin-1-yl)(1-(cyclohexylcarbonyl)piperidin-3-yl)methanone

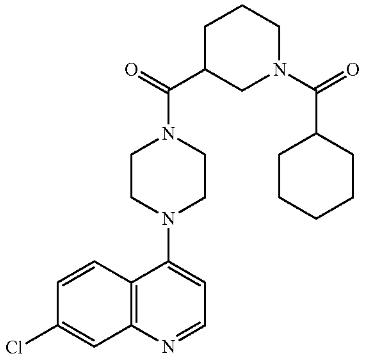 [SMILES: O=C(C1CCCN(C(=O)C2CCCCC2)C1)N1CCN(c2ccnc3cc(Cl)ccc23)CC1]

(4-(7-chloroquinolin-4-yl)piperazin-1-yl)(piperidin-3-yl)methanone (80 mg, 0.22 mmol) and cyclohexanecarbonyl chloride (36 mg, 0.25 mmol) were used in the same manner as in the method of Example 85 to obtain the title compound (70 mg, 67% yield) as a white solid.

$^1$H NMR (400 MHz, $CDCl_3$): δ 8.74 (d, J=4.8 Hz, 1H), 8.06 (d, J=2.0 Hz, 1H), 7.94 (d, J=9.2 Hz, 1H), 7.45 (dd, J=8.8, 2.0 Hz, 1H), 6.84 (d, J=4.8 Hz, 1H), 4.72-4.70 (m, 1H), 3.95-3.91 (m, 3H), 3.82-3.80 (m, 2H), 3.26-3.23 (m, 3H), 3.14-3.08 (m, 2H), 2.66-2.63 (m, 2H), 2.52-2.47 (m, 1H), 1.94-1.87 (m, 5H), 1.80-1.71 (m, 4H), 1.57-1.46 (m, 2H), 1.26-1.25 (m, 3H). LC-MS (ESI): Rt=3.393 min, m/z 469.2 $[M+H]^+$; purity: 99.66% @ 254 nm, 99.35% @ 214 nm.

Example 87: Synthesis of (4-(7-chloroquinolin-4-yl)piperazin-1-yl)(1-(pyridine-4-ylcarbonyl)piperidin-3-yl)methanone

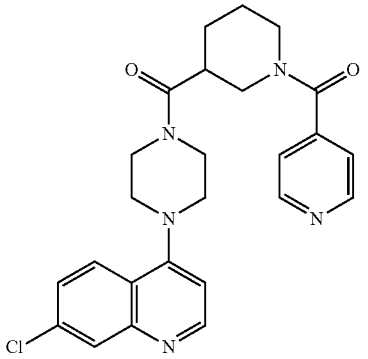 [SMILES: O=C(c1ccncc1)N1CCCC(C(=O)N2CCN(c3ccnc4cc(Cl)ccc34)CC2)C1]

Isonicotinic acid (30 mg, 0.24 mmol) and (4-(7-chloroquinolin-4-yl)piperazin-1-yl)(piperidin-3-yl)methanone (80 mg, 0.22 mmol) were used in the same manner as in the method of Example 83 to obtain the title compound (75 mg, 73% yield) as a white solid.

$^1$H NMR (400 MHz, $CDCl_3$): δ 8.76 (d, J=4.8 Hz, 1H), 8.71 (d, J=4.8 Hz, 2H), 8.08 (d, J=1.6 Hz, 1H), 7.93 (d, J=9.2 Hz, 1H), 7.47 (d, J=7.2 Hz, 1H), 7.30 (d, J=5.2 Hz, 2H), 6.83 (d, J=4.8 Hz, 1H), 4.72-4.65 (m, 1H), 3.96-3.79 (m, 3H), 3.65-3.61 (m, 2H), 3.30-3.02 (m, 6H), 2.88-2.83 (m, 1H), 2.03-1.93 (m, 2H), 1.83-1.80 (m, 1H), 1.50-1.44 (m, 1H). LC-MS (ESI): Rt=2.679 min, m/z 464.1 $[M+H]^+$; purity: 98.66% @ 254 nm, 96.42% @ 214 nm.

Example 88: Synthesis of (4-(7-chloroquinolin-4-yl) piperazin-1-yl)(1-(4-methoxyphenylcarbonyl)piperidin-3-yl)methanone

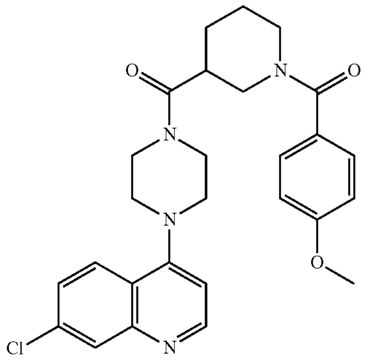 [SMILES: COc1ccc(C(=O)N2CCCC(C(=O)N3CCN(c4ccnc5cc(Cl)ccc45)CC3)C2)cc1]

(4-(7-Chloroquinolin-4-yl)piperazin-1-yl)(piperidin-3-yl) methanone (80 mg, 0.22 mmol) and 4-methoxybenzoyl chloride (42 mg, 0.24 mmol) were used in the same manner as in the method of Example 85 to obtain the title compound (70 mg, 73% yield) as a white solid.

$^1$H NMR (400 MHz, $CDCl_3$): δ 8.75 (d, J=4.8 Hz, 1H), 8.07 (d, J=2.0 Hz, 1H), 7.94 (d, J=7.2 Hz, 1H), 7.46 (dd, J=9.2, 2.0 Hz, 1H), 7.41 (d, J=8.4 Hz, 2H), 6.92 (d, J=8.8 Hz, 2H), 6.84 (s, 1H), 4.69-4.65 (m, 1H), 4.00-3.83 (m, 5H), 3.82 (s, 3H), 3.36-3.14 (m, 5H), 3.03-2.77 (m, 2H), 1.96-1.90 (m, 2H), 1.79-1.71 (m, 1H), 1.50-1.41 (m, 1H). LC-MS (ESI): Rt=3.585 min, m/z 493.1 $[M+H]^+$; purity: 99.70% @ 254 nm, 99.61% @ 214 nm.

Example 89: Synthesis of N-(4-(3-(4-(7-methoxyquinolin-4-yl)piperazine-1-carbonyl)piperidine-1-carbonyl)phenyl)acetamide

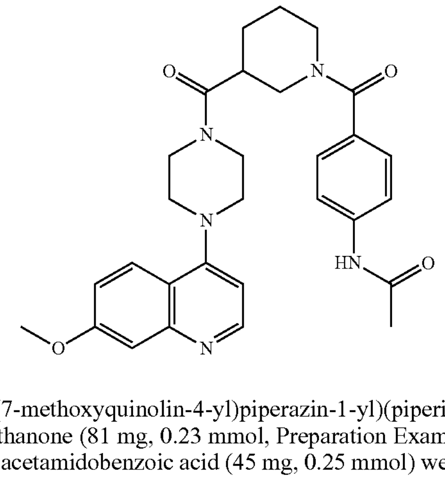

(4-(7-methoxyquinolin-4-yl)piperazin-1-yl)(piperidin-3-yl)methanone (81 mg, 0.23 mmol, Preparation Example 55) and 4-acetamidobenzoic acid (45 mg, 0.25 mmol) were used in the same manner as in the method of Example 83 to obtain the title compound (60 mg, 52% yield) as a white solid.

$^1$H NMR (400 MHz, $CDCl_3$): δ 8.67 (d, J=5.2 Hz, 1H), 7.90 (d, J=1.6 Hz, 1H), 7.54 (d, J=8.4 Hz, 3H), 7.40-7.38 (m, 3H), 7.16 (dd, J=9.2, 3.0 Hz, 1H), 6.73 (s, 1H), 4.72-4.68 (m, 1H), 4.01-3.95 (m, 1H), 3.94 (s, 3H), 3.87-3.79 (m, 4H), 3.25-3.08 (m, 5H), 2.96-2.62 (m, 2H), 2.18 (s, 3H), 2.00-1.89 (m, 2H), 1.76-1.71 (m, 1H), 1.48-1.25 (m, 1H). LC-MS (ESI): Rt=3.961 min, m/z 516.3 $[M+H]^+$; purity: 99.70% @ 254 nm, 99.65% @ 214 nm.

Example 90: Synthesis of (1-(4-fluorobenzoyl)piperidin-3-yl)(4-(7-methoxyquinolin-4-yl)piperazin-1-yl)methanone

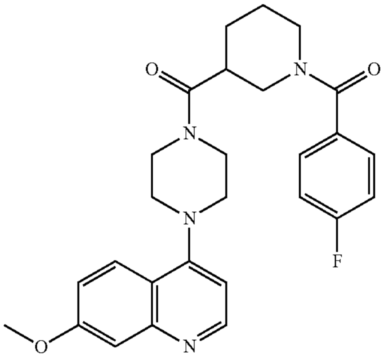 [SMILES: COc1ccc2c(N3CCN(C(=O)C4CCCN(C(=O)c5ccc(F)cc5)C4)CC3)ccnc2c1]

(4-(7-Methoxyquinolin-4-yl)piperazin-1-yl)(piperidin-3-yl)methanone (81 mg, 0.23 mmol) and 4-fluorobenzoic acid (34 mg, 0.25 mmol) were used in the same manner as in the method of Example 83 to obtain the title compound (55 mg, 52% yield) as a white solid.

$^1$H NMR (400 MHz, $CDCl_3$): δ 8.58 (d, J=5.2 Hz, 1H), 7.83-7.82 (m, 1H), 7.39-7.33 (m, 3H), 7.10 (dd, J=9.6, 2.0 Hz, 1H), 7.04 (t, J=8.8 Hz, 2H), 6.68 (s, 1H), 4.62-4.61 (m, 1H), 3.88 (s, 3H), 3.85-3.70 (m, 5H), 3.27-3.07 (m, 5H), 2.92-2.78 (m, 2H), 1.93-1.78 (m, 3H), 1.50-1.18 (m, 1H). LC-MS (ESI): Rt=3.518 min, m/z 477.1 $[M+H]^+$; purity: 98.94% @ 254 nm, 97.05% @ 214 nm.

Example 91: Synthesis of (1-benzoylpiperidin-3-yl) (4-(7-methoxyquinolin-4-yl)piperazin-1-yl)methanone

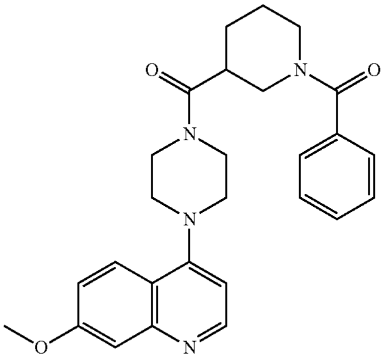 [SMILES: COc1ccc2c(N3CCN(C(=O)C4CCCN(C(=O)c5ccccc5)C4)CC3)ccnc2c1]

(4-(7-Methoxyquinolin-4-yl)piperazin-1-yl)(piperidin-3-yl)methanone (81 mg, 0.23 mmol) and benzoyl chloride (34 mg, 0.25 mmol) were used in the same manner as in the method of Example 85 to obtain the title compound (60 mg, 59% yield) as a white solid.

$^1$H NMR (400 MHz, $CDCl_3$): δ 8.67 (d, J=4.8 Hz, 1H), 7.92-7.83 (m, 1H), 7.42 (s, 6H), 7.17 (dd, J=9.2, 2.0 Hz, 1H), 6.76-6.66 (m, 1H), 4.76-4.73 (m, 1H), 4.05-3.98 (m, 1H), 3.95 (s, 3H), 3.88-3.59 (m, 4H), 3.33-3.07 (m, 5H), 3.00-2.59 (m, 2H), 2.00-1.83 (m, 3H), 1.50-1.40 (m, 1H). LC-MS (ESI): Rt=3.521 min, m/z 459.2 $[M+H]^+$; purity: 99.47% @ 254 nm, 99.21% @ 214 nm.

Example 92: Synthesis of (4-(7-methoxyquinolin-4-yl)piperazin-1-yl)(1-(cyclohexylcarbonyl)piperidin-3-yl)methanone

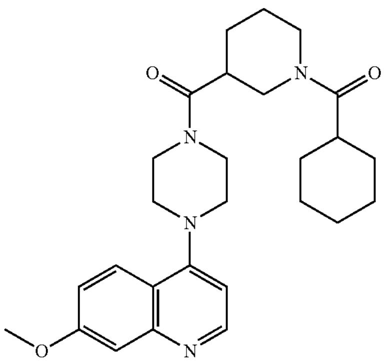 [SMILES: COc1ccc2c(N3CCN(C(=O)C4CCCN(C(=O)C5CCCCC5)C4)CC3)ccnc2c1]

(4-(7-Methoxyquinolin-4-yl)piperazin-1-yl)(piperidin-3-yl)methanone (81 mg, 0.23 mmol) and cyclohexanecarbonyl chloride (35 mg, 0.24 mmol) were used in the same manner as in the method of Example 85 to obtain the title compound (62 mg, 61% yield) as a white solid.

$^1$H NMR (400 MHz, $CDCl_3$): δ 8.69-8.66 (m, 1H), 7.89 (d, J=5.2 Hz, 1H), 7.40 (d, J=2.4 Hz, 1H), 7.16 (dd, J=9.2, 2.4 Hz, 1H), 6.74 (d, J=4.8 Hz, 1H), 4.72-4.70 (m, 1H), 3.95 (s, 3H), 3.94-3.79 (m, 5H), 3.25-3.04 (m, 5H), 2.65-2.60 (m, 2H), 2.49-2.46 (m, 1H), 1.94-1.87 (m, 3H), 1.74-1.59 (m, 5H), 1.50-1.45 (m, 3H), 1.26-1.22 (m, 3H). LC-MS (ESI): Rt=3.532 min, m/z 465.2 $[M+H]^+$; purity: 99.51% @ 254 nm, 99.16% @ 214 nm.

Example 93: Synthesis of (4-(7-methoxyquinolin-4-yl)piperazin-1-yl)(1-(pyridine-4-ylcarbonyl)piperidin-3-yl)methanone

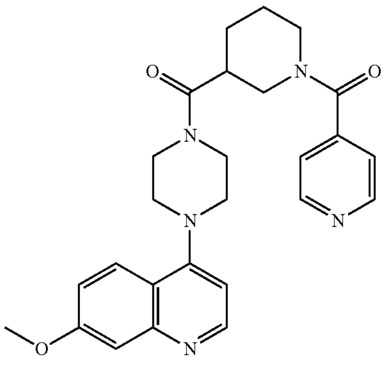 [SMILES: COc1ccc2c(N3CCN(C(=O)C4CCCN(C(=O)c5ccncc5)C4)CC3)ccnc2c1]

(4-(7-Methoxyquinolin-4-yl)piperazin-1-yl)(piperidin-3-yl)methanone (81 mg, 0.23 mmol) and isonicotinic acid (31 mg, 0.25 mmol) were used in the same manner as in the method of Example 83 to obtain the title compound (79 mg, 69% yield) as a white solid.

$^1$H NMR (400 MHz, $CDCl_3$): δ 8.71 (d, J=5.6 Hz, 2H), 8.68 (d, J=4.8 Hz, 1H), 7.93-7.84 (m, 1H), 7.41-7.40 (m, 1H), 7.30 (d, J=9.6 Hz, 2H), 7.17 (dd, J=9.2, 2.4 Hz, 1H), 6.77-6.69 (m, 1H), 4.73-4.66 (m, 1H), 4.05-3.98 (m, 1H), 3.95 (s, 3H), 3.86-3.78 (m, 2H), 3.46-3.40 (m, 2H), 3.26-3.13 (m, 5H), 3.10-3.05 (m, 1H), 2.88-2.86 (m, 1H), 2.00-1.92 (m, 2H), 1.83-1.79 (m, 1H), 1.48-1.30 (m, 1H). LC-MS (ESI): Rt=6.835 min, m/z 460.2 $[M+H]^+$; purity: 96.13% @ 254 nm, 97.19% @214 nm.

Example 94: Synthesis of (4-(7-methoxyquinolin-4-yl)piperazin-1-yl)(1-(4-methoxyphenylcarbonyl)piperidin-3-yl)methanone

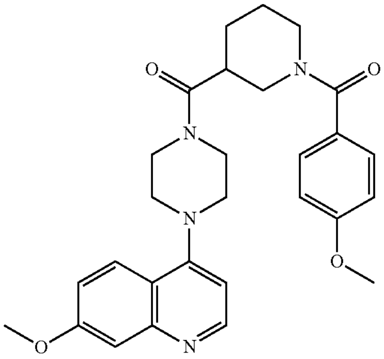

(4-(7-Methoxyquinolin-4-yl)piperazin-1-yl)(piperidin-3-yl)methanone (81 mg, 0.23 mmol) and cyclohexanecarbonyl chloride (41 mg, 0.24 mmol) were used in the same manner as in the method of Example 85 to obtain the title compound (75 mg, 70% yield) as a white solid.

$^1$H NMR (400 MHz, $CDCl_3$): δ 8.67 (d, J=5.2 Hz, 1H), 7.89 (d, J=6.4 Hz, 1H), 7.42-7.40 (m, 3H), 7.16 (dd, J=8.8, 2.4 Hz, 1H), 6.92 (d, J=8.8 Hz, 1H), 6.73 (s, 1H), 4.70-4.68 (m, 1H), 3.95-3.77 (m, 11H), 3.21-3.09 (m, 5H), 2.94-2.83 (m, 2H), 1.96-1.90 (m, 3H), 1.48-1.44 (m, 1H). LC-MS (ESI): Rt=3.186 min, m/z 489.2 $[M+H]^+$; purity: 98.34% @ 254 nm, 98.79% @ 214 nm.

Example 95: Synthesis of N-(4-(3-(1-(2-(trifluoromethyl)quinolin-4-yl)piperazine-4-carbonyl)piperidine-1-carbonyl)phenyl)acetamide

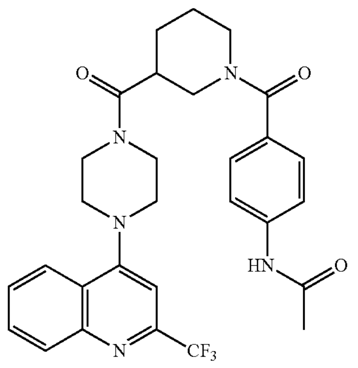 [SMILES: CC(=O)Nc1ccc(C(=O)N2CCCC(C(=O)N3CCN(c4cc(C(F)(F)F)nc5ccccc45)CC3)C2)cc1]

Piperidin-3-yl(4-(2-(trifluoromethyl)quinolin-4-yl)piperazin-1-yl)methanone (81 mg, 0.20 mmol, Preparation Example 48) and 4-acetamidobenzoic acid (45 mg, 0.25 mmol) were used in the same manner as in the method of Example 83 to obtain the title compound (66 mg, 58% yield) as a white solid.

$^1$H NMR (400 MHz, $CDCl_3$): δ 8.19 (d, J=8.4 Hz, 1H), 8.06-8.04 (m, 1H), 7.77 (t, J=6.8 Hz, 1H), 7.62 (t, J=7.6 Hz, 1H), 7.54-7.52 (m, 3H), 7.39 (d, J=7.6 Hz, 2H), 7.15-7.10 (m, 1H), 4.70-4.66 (m, 1H), 4.03-3.63 (m, 5H), 3.29-3.12 (m, 5H), 2.85-2.81 (m, 2H), 2.18 (s, 3H), 1.98-1.72 (m, 3H), 1.46-1.44 (m, 1H). LC-MS (ESI): Rt=3.338 min, m/z 554.2 $[M+H]^+$; purity: 99.84% @254 nm, 99.40% @ 214 nm.

Example 96: Synthesis of (1-(4-fluorobenzoyl)piperidin-3-yl)(4-(2-(trifluoromethyl)quinolin-4-yl)piperazin-1-yl)methanone

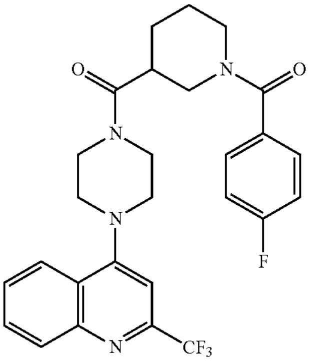 [SMILES: O=C(c1ccc(F)cc1)N1CCCC(C(=O)N2CCN(c3cc(C(F)(F)F)nc4ccccc34)CC2)C1]

Piperidin-3-yl(4-(2-(trifluoromethyl)quinolin-4-yl)piperazin-1-yl)methanone (80 mg, 0.20 mmol) and 4-fluorobenzoic acid (31 mg, 0.22 mmol) were used in the same manner as in the method of Example 83 to obtain the title compound (68 mg, 66% yield) as a white solid.

$^1$H NMR (400 MHz, $CDCl_3$): δ 8.19 (d, J=8.0 Hz, 1H), 8.06-8.04 (m, 1H), 7.77 (t, J=8.4 Hz, 1H), 7.63 (t, J=8.0 Hz, 1H), 7.47-7.49 (m, 2H), 7.15-7.09 (m, 3H), 4.70-4.68 (m, 1H), 4.04-3.94 (m, 5H), 3.37-3.11 (m, 5H), 2.99-2.86 (m, 2H), 1.99-1.70 (m, 3H), 1.46-1.45 (m, 1H). LC-MS (ESI): Rt=3.676 min, m/z 515.2 $[M+H]^+$; purity: 99.62% @ 254 nm, 99.76% @ 214 nm.

Example 97: Synthesis of (1-(cyclohexylcarbonyl)piperidin-3-yl)(4-(2-(trifluoromethyl)quinolin-4-yl)piperazin-1-yl)methanone

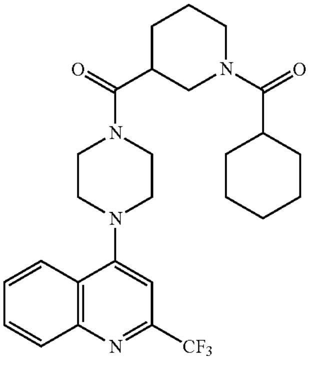 [SMILES: O=C(C1CCCN(C(=O)C2CCCCC2)C1)N1CCN(c2cc(C(F)(F)F)nc3ccccc23)CC1]

Piperidin-3-yl(4-(2-(trifluoromethyl)quinolin-4-yl)piperazin-1-yl)methanone (80 mg, 0.20 mmol) and cyclohexanecarbonyl chloride (32 mg, 0.22 mmol) were used in the same manner as in the method of Example 85 to obtain the title compound (55 mg, 55% yield) as a white solid.

$^1$H NMR (400 MHz, $CDCl_3$): δ 8.18 (d, J=8.0 Hz, 1H), 8.04 (d, J=8.4 Hz, 1H), 7.77 (t, J=7.2 Hz, 1H), 7.61 (t, J=7.2 Hz, 1H), 7.16-4.14 (m, 1H), 4.72-4.70 (m, 1H), 3.98-3.84 (m, 5H), 3.36-3.22 (m, 4H), 3.10-3.06 (m, 1H), 2.65-2.63 (m, 2H), 2.53-2.47 (m, 1H), 1.95-1.88 (m, 3H), 1.80-1.62 (m, 5H), 1.57-1.45 (m, 3H), 1.29-1.25 (m, 3H). LC-MS (ESI): Rt=3.444 min, m/z 503.2 $[M+H]^+$; purity: 97.34% @ 254 nm, 99.39% @ 214 nm.

Example 98: Synthesis of (1-isonicotinoylpiperidin-3-yl)(4-(2-(trifluoromethyl)quinolin-4-yl)piperazin-1-yl)methanone

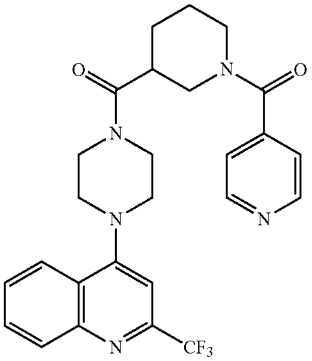 [SMILES: O=C(c1ccncc1)N1CCCC(C(=O)N2CCN(c3cc(C(F)(F)F)nc4ccccc34)CC2)C1]

Piperidin-3-yl(4-(2-(trifluoromethyl)quinolin-4-yl)piperazin-1-yl)methanone (80 mg, 0.20 mmol) and isonicotinic acid (27 mg, 0.22 mmol) were used in the same manner as in the method of Example 83 to obtain the title compound (45 mg, 45% yield) as a white solid.

$^1$H NMR (400 MHz, $CDCl_3$): δ 8.71 (d, J=5.6 Hz, 2H), 8.20 (d, J=8.8 Hz, 1H), 8.07-7.99 (m, 1H), 7.78 (t, J=7.6 Hz, 1H), 7.63 (d, J=7.6 Hz, 1H), 7.30 (d, J=6.0 Hz, 2H), 7.16-7.11 (m, 1H), 4.73-4.65 (m, 1H), 4.00-3.92 (m, 3H), 3.75-3.62 (m, 2H), 3.44-3.15 (m, 5H), 3.09-3.03 (m, 1H), 2.89-2.86 (m, 1H), 2.02-1.94 (m, 2H), 1.84-1.80 (m, 1H), 1.51-1.44 (m, 1H). LC-MS (ESI): Rt=3.393 min, m/z 498.2 $[M+H]^+$; purity: 98.24% @ 254 nm, 97.81% @ 214 nm.

Example 99: Synthesis of (1-(4-methoxybenzoyl)piperidin-3-yl)(4-(2-(trifluoromethyl)quinolin-4-yl)piperazin-1-yl)methanone

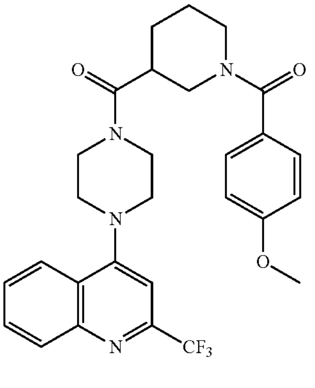 [SMILES: COc1ccc(C(=O)N2CCCC(C(=O)N3CCN(c4cc(C(F)(F)F)nc5ccccc45)CC3)C2)cc1]

Piperidin-3-yl(4-(2-(trifluoromethyl)quinolin-4-yl)piperazin-1-yl)methanone (80 mg, 0.20 mmol) and 4-methoxybenzoyl chloride (38 mg, 0.22 mmol) were used in the same manner as in the method of Example 85 to obtain the title compound (68 mg, 65% yield) as a white solid.

$^1$H NMR (400 MHz, $CDCl_3$): δ 8.19 (d, J=8.4 Hz, 1H), 8.04 (d, J=7.6 Hz, 1H), 7.77 (td, J=8.0, 1.2 Hz, 1H), 7.62 (t, J=7.2 Hz, 1H), 7.42 (d, J=8.8 Hz, 2H), 7.14 (s, 1H), 6.92 (d, J=8.8 Hz, 2H), 4.74-4.63 (m, 1H), 4.09-3.86 (m, 5H), 3.82 (s, 3H), 3.41-3.14 (m, 5H), 2.95-2.83 (m, 2H), 2.00-1.97 (m, 2H), 1.80-1.75 (m, 1H), 1.49-1.42 (m, 1H). LC-MS (ESI): Rt=3.460 min, m/z 527.2 $[M+H]^+$; purity: 99.11% @ 254 nm, 99.42% @ 214 nm.

Example 100: Synthesis of N-(4-(3-(1-(2-methylquinolin-4-yl)piperazine-4-carbonyl)piperidine-1-carbonyl)phenyl)acetamide

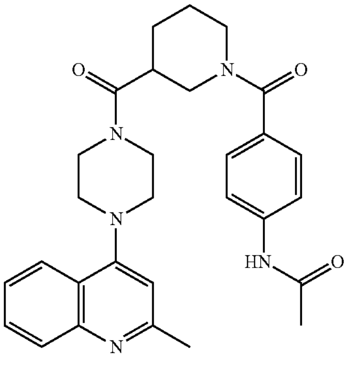 [SMILES: CC(=O)Nc1ccc(C(=O)N2CCCC(C(=O)N3CCN(c4cc(C)nc5ccccc45)CC3)C2)cc1]

(4-(2-Methylquinolin-4-yl)piperazin-1-yl)(piperidin-3-yl)methanone (80 mg, 0.23 mmol) and 4-acetamidobenzoic acid (47 mg, 0.26 mmol) were used in the same manner as in the method of Example 83 to obtain the title compound (70 mg, 59% yield) as a white solid.

$^1$H NMR (400 MHz, $CDCl_3$): δ 7.99 (d, J=8.4 Hz, 1H), 7.95 (s, 1H), 7.64 (t, J=7.6 Hz, 2H), 7.53 (t, J=7.6 Hz, 2H), 7.45 (t, J=7.6 Hz, 1H), 7.39 (d, J=6.8 Hz, 2H), 6.74 (s, 1H), 4.72-4.70 (m, 1H), 3.99-3.60 (m, 5H), 3.26-3.14 (m, 5H), 3.04-2.81 (m, 2H), 2.68 (s, 3H), 2.17 (s, 3H), 1.97-1.83 (m, 3H), 1.48-1.40 (m, 1H). LC-MS (ESI): Rt=3.137 min, m/z 500.3 $[M+H]^+$; purity: 99.55% @ 254 nm, 99.85% @ 214 nm.

Example 101: Synthesis of (1-(4-fluorobenzoyl)piperidin-3-yl)(4-(2-methylquinolin-4-yl)piperazin-1-yl)methanone

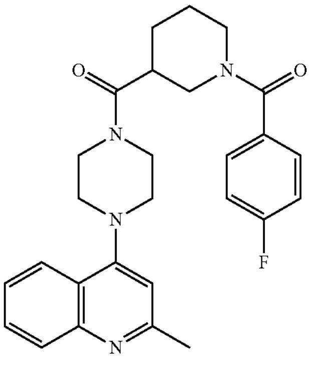

(4-(2-Methylquinolin-4-yl)piperazin-1-yl)(piperidin-3-yl)methanone (80 mg, 0.23 mmol, Preparation Example 41) and 4-fluorobenzoic acid (36 mg, 0.26 mmol) were used in the same manner as in the method of Example 83 to obtain the title compound (65 mg, 60% yield) as a white solid.

$^1$H NMR (400 MHz, $CDCl_3$): δ 8.00 (d, J=8.4 Hz, 1H), 7.95 (s, 1H), 7.65 (t, J=8.0 Hz, 1H), 7.47-7.43 (m, 3H), 7.11 (t, J=8.8 Hz, 2H), 6.74 (s, 1H), 4.72-4.69 (m, 1H), 4.00-3.76 (m, 5H), 3.27-3.03 (m, 5H), 2.97-2.84 (m, 2H), 2.69 (s, 3H), 2.01-1.92 (m, 2H), 1.78-1.76 (m, 1H), 1.50-1.44 (m, 1H). LC-MS (ESI): Rt=3.605 min, m/z 461.3 $[M+H]^+$; purity: 99.81% @ 254 nm, 99.91% @214 nm.

Example 102: Synthesis of (1-benzoylpiperidin-3-yl)(4-(2-methylquinolin-4-yl)piperazin-1-yl)methanone

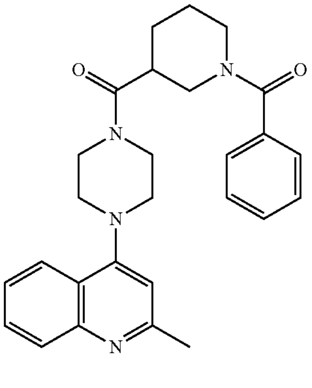

(4-(2-Methylquinolin-4-yl)piperazin-1-yl)(piperidin-3-yl)methanone (80 mg, 0.23 mmol) and benzoyl chloride (37 mg, 0.26 mmol) were used in the same manner as in the method of Example 85 to obtain the title compound (72 mg, 69% yield) as a white solid.

$^1$H NMR (400 MHz, $CDCl_3$): δ 7.99 (d, J=8.4 Hz, 1H), 7.96-7.91 (m, 1H), 7.64 (td, J=8.0, 0.8 Hz, 1H), 7.47-7.45 (m, 1H), 7.42 (s, 5H), 6.76-6.67 (m, 1H), 4.77-4.73 (m, 1H), 4.02-3.81 (m, 4H), 3.60-3.50 (m, 1H), 3.28-3.08 (m, 5H), 2.98-2.87 (m, 2H), 2.69 (s, 3H), 2.00-1.89 (m, 2H), 1.76-1.72 (m, 1H), 1.48-1.40 (m, 1H). LC-MS (ESI): Rt=3.585 min, m/z 443.2 $[M+H]^+$; purity: 99.39% @ 254 nm, 99.62% @ 214 nm.

Example 103: Synthesis of (1-(cyclohexylcarbonyl)piperidin-3-yl)(4-(2-methylquinolin-4-yl)piperazin-1-yl)methanone

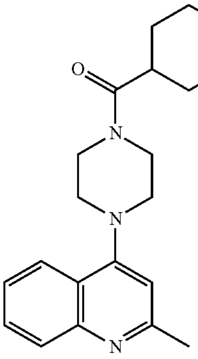

(4-(2-Methylquinolin-4-yl)piperazin-1-yl)(piperidin-3-yl)methanone (80 mg, 0.23 mmol) and cyclohexanecarbonyl chloride (38 mg, 0.26 mmol) were used in the same manner as in the method of Example 85 to obtain the title compound (75 mg, 71% yield) as a white solid.

$^1$H NMR (400 MHz, $CDCl_3$): δ 7.99 (d, J=8.4 Hz, 1H), 7.95 (d, J=8.4 Hz, 1H), 7.64 (t, J=7.2 Hz, 1H), 7.44 (t, J=7.2 Hz, 1H), 6.74 (s, 1H), 4.73-4.67 (m, 1H), 3.98-3.92 (m, 3H), 3.81-3.80 (m, 2H), 3.27-3.25 (m, 3H), 3.11-3.04 (m, 2H), 2.68 (s, 3H), 2.65-2.60 (m, 2H), 2.53-2.46 (m, 1H), 1.95-1.87 (m, 2H), 1.80-1.69 (m, 6H), 1.57-1.45 (m, 3H), 1.31-1.24 (m, 3H). LC-MS (ESI): Rt=3.544 min, m/z 449.3 $[M+H]^+$; purity: 99.39% @ 254 nm, 99.65% @ 214 nm.

Example 104: Synthesis of (1-isonicotinoylpiperidin-3-yl)(4-(2-methylquinolin-4-yl)piperazin-1-yl)methanone

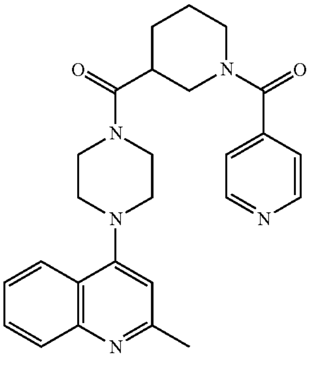 [SMILES: Cc1cc(N2CCN(C(=O)C3CCCN(C(=O)c4ccncc4)C3)CC2)c2ccccc2n1]

(4-(2-Methylquinolin-4-yl)piperazin-1-yl)(piperidin-3-yl)methanone (100 mg, 0.30 mmol) and isonicotinic acid (40 mg, 0.33 mmol) were used in the same manner as in the method of Example 83 to obtain the title compound (75 mg, 71% yield) as a white solid.

$^1$H NMR (400 MHz, $CDCl_3$): δ 8.71 (d, J=5.6 Hz, 2H), 8.02-7.96 (m, 2H), 7.65 (t, J=7.6 Hz, 1H), 7.46 (d, J=7.2 Hz, 1H), 7.30 (d, J=5.6 Hz, 2H), 6.76-6.70 (m, 1H), 4.73-4.65 (m, 1H), 3.97-3.88 (m, 3H), 3.65-3.62 (m, 2H), 3.47-3.06 (m, 6H), 2.89-2.84 (m, 1H), 2.69 (s, 3H), 2.05-1.93 (m, 2H), 1.83-1.79 (m, 1H), 1.48-1.44 (m, 1H). LC-MS (ESI): Rt=3.180 min, m/z 444.2 $[M+H]^+$; purity: 99.63% @ 254 nm, 99.71% @ 214 nm.

Example 105: Synthesis of N-(4-(3-(4-(7-fluoroquinolin-4-yl)piperazine-1-carbonyl)piperidine-1-carbonyl)phenyl)acetamide

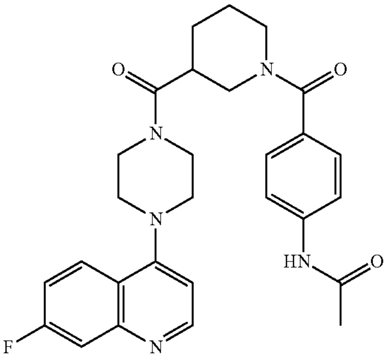 [SMILES: CC(=O)Nc1ccc(C(=O)N2CCCC(C(=O)N3CCN(c4ccnc5cc(F)ccc45)CC3)C2)cc1]

(4-(7-Fluoroquinolin-4-yl)piperazin-1-yl)(piperidin-3-yl)methanone (80 mg, 0.22 mmol, Preparation Example 25) and 4-acetamidobenzoic acid (52 mg, 0.29 mmol) were used in the same manner as in the method of Example 83 to obtain the title compound (70 mg, 48% yield) as a white solid.

$^1$H NMR (400 MHz, $CDCl_3$): δ 8.74 (d, J=4.4 Hz, 1H), 8.02 (s, 1H), 7.70 (dd, J=10.0, 2.4 Hz, 1H), 7.55-7.47 (m, 3H), 7.39 (d, J=8.0 Hz, 2H), 7.30 (td, J=10.2, 2.4 Hz, 1H), 6.82 (s, 1H), 4.73-4.67 (m, 1H), 3.95-3.60 (m, 5H), 3.28-3.09 (m, 5H), 2.96-2.86 (m, 2H), 2.18 (s, 3H), 2.02-1.90 (m, 2H), 1.80-1.74 (m, 1H), 1.49-1.26 (m, 1H). LC-MS (ESI): Rt=2.784 min, m/z 504.2 $[M+H]^+$; purity: 99.15% @ 254 nm, 99.64% @ 214 nm.

Example 106: Synthesis of (1-(4-fluorobenzoyl)piperidin-3-yl)(4-(7-fluoroquinolin-4-yl)piperazin-1-yl)methanone

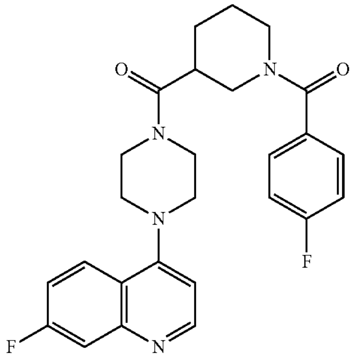 [SMILES: O=C(c1ccc(F)cc1)N1CCCC(C(=O)N2CCN(c3ccnc4cc(F)ccc34)CC2)C1]

(4-(7-Fluoroquinolin-4-yl)piperazin-1-yl)(piperidin-3-yl)methanone (100 mg, 0.29 mmol) and 4-fluorobenzoic acid (41 mg, 0.29 mmol) were used in the same manner as in the method of Example 83 to obtain the title compound (60 mg, 44% yield) as a white solid.

$^1$H NMR (400 MHz, $CDCl_3$): δ 8.75 (d, J=4.8 Hz, 1H), 8.02 (s, 1H), 7.70 (dd, J=10.0, 2.4 Hz, 1H), 7.46-7.43 (m, 2H), 7.30 (td, J=8.8, 2.0 Hz, 1H), 7.11 (t, J=8.8 Hz, 2H), 6.83 (s, 1H), 4.71-4.67 (m, 1H), 3.99-3.60 (m, 5H), 3.29-3.15 (m, 5H), 2.99-2.86 (m, 2H), 2.01-1.89 (m, 2H), 1.80-1.76 (m, 1H), 1.50-1.42 (m, 1H). LC-MS (ESI): Rt=3.116 min, m/z 465.2 $[M+H]^+$; purity: 97.61% @ 254 nm, 98.05% @ 214 nm.

Example 107: Synthesis of (1-benzoylpiperidin-3-yl)(4-(7-fluoroquinolin-4-yl)piperazin-1-yl)methanone

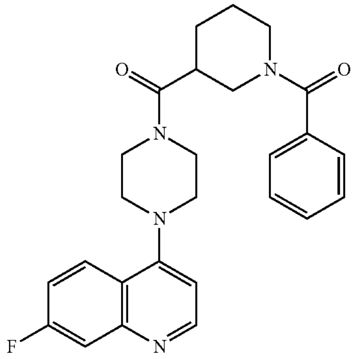 [SMILES: O=C(c1ccccc1)N1CCCC(C(=O)N2CCN(c3ccnc4cc(F)ccc34)CC2)C1]

(4-(7-Fluoroquinolin-4-yl)piperazin-1-yl)(piperidin-3-yl) methanone (80 mg, 0.23 mmol) and benzoyl chloride (36 mg, 0.25 mmol) were used in the same manner as in the method of Example 85 to obtain the title compound (55 mg, 53% yield) as a white solid.

$^1$H NMR (400 MHz, $CDCl_3$): δ 8.75 (d, J=4.8 Hz, 1H), 8.03-8.02 (m, 1H), 7.70 (dd, J=10.0, 2.4 Hz, 1H), 7.42 (s, 5H), 7.30 (td, J=9.2, 2.4 Hz, 1H), 6.84-6.75 (m, 1H), 4.76-4.73 (m, 1H), 4.01-3.81 (m, 5H), 3.31-3.06 (m, 5H), 3.00-2.87 (m, 2H), 2.01-1.89 (m, 2H), 1.76-1.67 (m, 1H), 1.45-1.39 (m, 1H). LC-MS (ESI): Rt=2.957 min, m/z 447.2 $[M+H]^+$; purity: 95.71% @ 254 nm, 96.32% @214 nm.

Example 108: Synthesis of (1-(cyclohexylcarbonyl) piperidin-3-yl)(4-(7-fluoroquinolin-4-yl)piperazin-1-yl)methanone

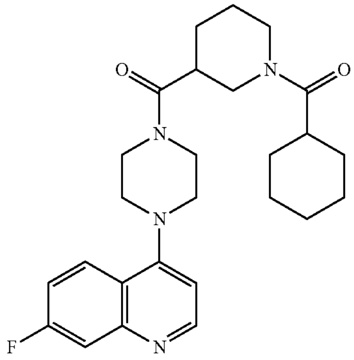 [SMILES: O=C(C1CCCN(C(=O)C2CCCCC2)C1)N1CCN(c2ccnc3cc(F)ccc23)CC1]

(4-(7-Fluoroquinolin-4-yl)piperazin-1-yl)(piperidin-3-yl) methanone (80 mg, 0.23 mmol) and cyclohexanecarbonyl chloride (38 mg, 0.25 mmol) were used in the same manner as in the method of Example 85 to obtain the title compound (60 mg, 57% yield) as a white solid.

$^1$H NMR (400 MHz, $CDCl_3$): δ 8.74 (d, J=4.8 Hz, 1H), 8.03-8.00 (m, 1H), 7.69 (dd, J=10.0, 2.4 Hz, 1H), 7.29-7.26 (m, 1H), 6.83-6.81 (m, 1H), 4.72-4.67 (m, 1H), 3.99-3.80 (m, 5H), 3.26-3.04 (m, 5H), 2.65-2.63 (m, 2H), 2.52-2.47 (m, 1H), 1.96-1.92 (m, 2H), 1.87-1.80 (m, 3H), 1.75-1.74 (m, 1H), 1.71-1.66 (m, 2H), 1.53-1.47 (m, 3H), 1.26-1.24 (m, 3H). LC-MS (ESI): Rt=2.665 min, m/z 453.3 $[M+H]^+$; purity: 96.01% @ 254 nm, 96.85% @ 214 nm.

Example 109: Synthesis of (4-(7-fluoroquinolin-4-yl)piperazin-1-yl)(1-isonicotinoylpiperidin-3-yl) methanone

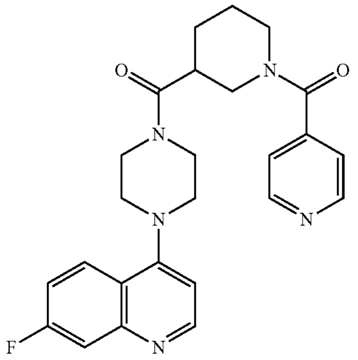 [SMILES: O=C(c1ccncc1)N1CCCC(C(=O)N2CCN(c3ccnc4cc(F)ccc34)CC2)C1]

(4-(7-Fluoroquinolin-4-yl)piperazin-1-yl)(piperidin-3-yl) methanone (120 mg, 0.35 mmol) and 4-isonicotinic acid (43 mg, 0.35 mmol) were used in the same manner as in the method of Example 83 to obtain the title compound (38 mg, 37% yield) as a white solid.

$^1$H NMR (400 MHz, $CDCl_3$): δ 8.76 (d, J=4.8 Hz, 1H), 8.71 (d, J=5.6 Hz, 2H), 8.08-7.95 (m, 1H), 7.70 (dd, J=10.0, 2.4 Hz, 1H), 7.32-7.28 (m, 3H), 6.85-6.78 (m, 1H), 4.72-4.64 (m, 1H), 3.96-3.62 (m, 5H), 3.43-3.08 (m, 5H), 3.06-3.02 (m, 1H), 2.93-2.82 (m, 1H), 2.02-1.92 (m, 2H), 1.83-1.80 (m, 1H), 1.47-1.28 (m, 1H). LC-MS (ESI): Rt=2.248 min, m/z 448.1 $[M+H]^+$; purity: 97.03% @ 254 nm, 97.41% @ 214 nm.

Example 110: Synthesis of (4-(7-fluoroquinolin-4-yl)piperazin-1-yl)(1-(4-methoxybenzoyl)piperidin-3-yl)methanone

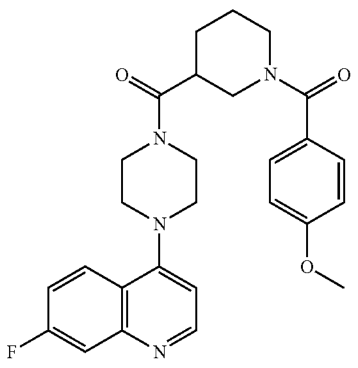 [SMILES: COc1ccc(C(=O)N2CCCC(C(=O)N3CCN(c4ccnc5cc(F)ccc45)CC3)C2)cc1]

(4-(7-Fluoroquinolin-4-yl)piperazin-1-yl)(piperidin-3-yl) methanone (80 mg, 0.23 mmol) and 4-methoxybenzoyl chloride (44 mg, 0.25 mmol) were used in the same manner as in the method of Example 85 to obtain the title compound (65 mg, 58% yield) as a white solid.

$^1$H NMR (400 MHz, $CDCl_3$): δ 8.75 (d, J=4.8 Hz, 1H), 8.01 (brs, 1H), 7.70 (dd, J=10.0, 2.4 Hz, 1H), 7.41 (d, J=8.8 Hz, 1H), 7.32-7.27 (m, 1H), 6.92 (d, J=8.8 Hz, 2H), 6.81 (s, 1H), 4.73-4.65 (m, 1H), 4.02-3.90 (m, 5H), 3.82 (s, 3H), 3.29-3.15 (m, 5H), 2.98-2.64 (m, 2H), 2.01-1.91 (m, 2H), 1.79-1.75 (m, 1H), 1.49-1.43 (m, 1H). LC-MS (ESI): Rt=2.999 min, m/z 477.3 [M+H]$^+$; purity: 95.50% @ 254 nm, 96.88% @ 214 nm.

Example 111: Synthesis of N-(4-(3-(1-(quinolin-4-yl)piperazine-4-carbonyl)piperidine-1-carbonyl)phenyl)acetamide

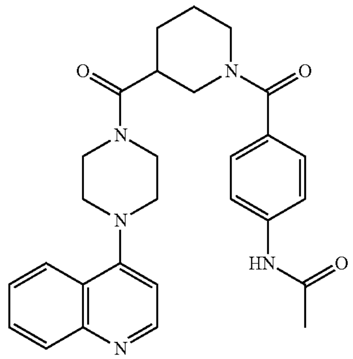

Piperidin-3-yl(4-(quinolin-4-yl)piperazin-1-yl)methanone (100 mg, 0.31 mmol, Preparation Example 31) and 4-acetamidobenzoic acid (55 mg, 0.31 mmol) were used in the same manner as in the method of Example 83 to obtain the title compound (85 mg, 37% yield) as a white solid.

$^1$H NMR (400 MHz, $CDCl_3$): δ 8.74 (d, J=5.2 Hz, 1H), 8.08 (d, J=8.4 Hz, 1H), 8.03-8.01 (m, 1H), 7.68 (t, J=7.2 Hz, 1H), 7.63-7.60 (m, 1H), 7.54-7.50 (m, 3H), 7.39 (d, J=7.2 Hz, 1H), 6.85 (s, 1H), 4.75-4.68 (m, 1H), 3.95-3.61 (m, 5H), 3.32-3.12 (m, 5H), 2.97-2.63 (m, 2H), 2.17 (s, 3H), 2.00-1.91 (m, 2H), 1.80-1.73 (m, 1H), 1.52-1.41 (m, 1H). LC-MS (ESI): Rt=3.749 min, m/z 486.3 [M+H]$^+$; purity: 98.16% @ 254 nm, 98.75% @ 214 nm.

Example 112: Synthesis of (1-(4-fluorophenylcarbonyl)piperidin-3-yl)(4-(quinolin-4-yl)piperazin-1-yl)methanone

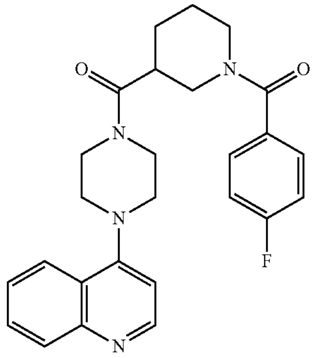 [SMILES: O=C(c1ccc(F)cc1)N1CCCC(C(=O)N2CCN(c3ccnc4ccccc34)CC2)C1]

Piperidin-3-yl(4-(quinolin-4-yl)piperazin-1-yl)methanone (100 mg, 0.31 mmol) and 4-fluorobenzoic acid (43 mg, 0.31 mmol) were used in the same manner as in the method of Example 83 to obtain the title compound (75 mg, 55% yield) as a white solid.

$^1$H NMR (400 MHz, $CDCl_3$): δ 8.76 (d, J=4.8 Hz, 1H), 8.08 (d, J=8.4 Hz, 1H), 8.03-8.02 (m, 1H), 7.69 (td, J=8.0, 1.2 Hz, 1H), 7.52 (t, J=7.6 Hz, 1H), 7.46-7.43 (m, 2H), 7.11 (t, J=8.8 Hz, 2H), 6.85 (s, 1H), 4.72-4.69 (m, 1H), 3.99-3.58 (m, 5H), 3.36-3.18 (m, 5H), 2.98-2.87 (m, 2H), 2.01-1.91 (m, 2H), 1.79-1.76 (m, 1H), 1.49-1.41 (m, 1H). LC-MS (ESI): Rt=3.867 min, m/z 447.2 [M+H]$^+$; purity: 99.21% @ 254 nm, 99.47% @ 214 nm.

Example 113: Synthesis of (1-benzoylpiperidin-3-yl)(4-(quinolin-4-yl)piperazin-1-yl)methanone

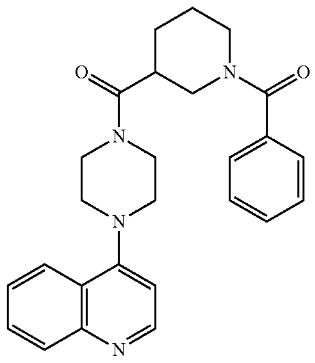 [SMILES: O=C(c1ccccc1)N1CCCC(C(=O)N2CCN(c3ccnc4ccccc34)CC2)C1]

Piperidin-3-yl(4-(quinolin-4-yl)piperazin-1-yl)methanone (80 mg, 0.25 mmol) and benzoyl chloride (38 mg, 0.28 mmol) were used in the same manner as in the method of Example 85 to obtain the title compound (70 mg, 62% yield) as a white solid.

$^1$H NMR (400 MHz, $CDCl_3$): δ 8.76 (d, J=5.2 Hz, 1H), 8.09 (d, J=8.4 Hz, 1H), 8.04-7.97 (m, 1H), 7.69 (td, J=8.4, 1.2 Hz, 1H), 7.52 (t, J=7.6 Hz, 1H), 7.42 (s, 5H), 6.86-6.78

(m, 1H), 4.77-4.74 (m, 1H), 4.01-3.50 (m, 5H), 3.33-3.04 (m, 5H), 2.97-2.59 (m, 2H), 2.01-1.92 (m, 2H), 1.76-1.73 (m, 1H), 1.50-1.40 (m, 1H). LC-MS (ESI): Rt=3.718 min, m/z 429.2 $[M+H]^+$; purity: 99.53% @ 254 nm, 99.37% @ 214 nm.

Example 114: Synthesis of (1-(cyclohexylcarbonyl) piperidin-3-yl)(4-(quinolin-4-yl)piperazin-1-yl) methanone

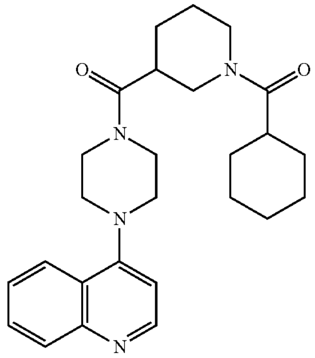 [SMILES: O=C(C1CCCN(C(=O)C2CCCCC2)C1)N1CCN(c2ccnc3ccccc23)CC1]

Piperidin-3-yl(4-(quinolin-4-yl)piperazin-1-yl)methanone (80 mg, 0.25 mmol) and cyclohexanecarbonyl chloride (40 mg, 0.28 mmol) were used in the same manner as in the method of Example 85 to obtain the title compound (65 mg, 61% yield) as a white solid.

$^1H$ NMR (400 MHz, $CDCl_3$): δ 8.75 (d, J=4.8 Hz, 1H), 8.07 (d, J=8.0 Hz, 1H), 8.01 (d, J=8.0 Hz, 1H), 7.68 (d, J=7.2 Hz, 1H), 7.51 (t, J=7.6 Hz, 1H), 6.85 (d, J=5.2 Hz, 1H), 4.73-4.67 (m, 1H), 3.99-3.81 (m, 5H), 3.28-3.04 (m, 5H), 2.66-2.63 (m, 2H), 2.52-2.47 (m, 1H), 1.94-1.87 (m, 2H), 1.80-1.71 (m, 5H), 1.54-1.47 (m, 3H), 1.31-1.24 (m, 3H). LC-MS (ESI): Rt=2.635 min, m/z 435.3 $[M+H]^+$; purity: 99.29% @ 254 nm, 99.18% @ 214 nm.

Example 115: Synthesis of (1-isonicotinoylpiperidin-3-yl)(4-(quinolin-4-yl)piperazin-1-yl)methanone

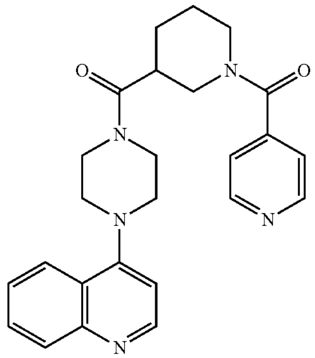 [SMILES: O=C(c1ccncc1)N1CCCC(C(=O)N2CCN(c3ccnc4ccccc34)CC2)C1]

Piperidin-3-yl(4-(quinolin-4-yl)piperazin-1-yl)methanone (120 mg, 0.37 mmol) and isonicotinic acid (46 mg, 0.37 mmol) were used in the same manner as in the method of Example 83 to obtain the title compound (62 mg, 39% yield) as a white solid.

$^1H$ NMR (400 MHz, $CDCl_3$): δ 8.77 (d, J=4.8 Hz, 1H), 8.71 (d, J=5.2 Hz, 2H), 8.09 (d, J=8.8 Hz, 1H), 8.05-7.96 (m,

1H), 7.69 (t, J=7.6 Hz, 1H), 7.53 (t, J=8.0 Hz, 1H), 7.31 (d, J=5.6 Hz, 2H), 6.88-4.80 (m, 1H), 4.73-4.65 (m, 1H), 4.01-3.90 (m, 3H), 3.78-3.62 (m, 2H), 3.45-3.16 (m, 5H), 3.06 (t, J=12.8 Hz, 1H), 2.89-2.84 (m, 1H), 2.03-1.93 (m, 2H), 1.83-1.80 (m, 1H), 1.50-1.43 (m, 1H). LC-MS (ESI): Rt=3.674 min, m/z 430.2 $[M+H]^+$; purity: 99.52% @ 254 nm, 98.95% @214 nm.

Example 116: Synthesis of (1-(4-methoxyphenylcarbonyl)piperidin-3-yl)(4-(quinolin-4-yl)piperazin-1-yl)methanone

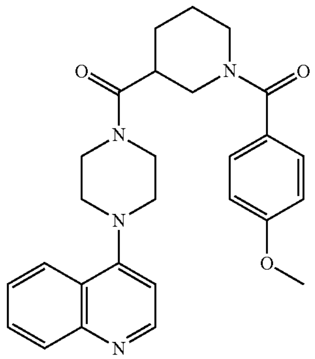 [SMILES: COc1ccc(C(=O)N2CCCC(C(=O)N3CCN(c4ccnc5ccccc45)CC3)C2)cc1]

Piperidin-3-yl(4-(quinolin-4-yl)piperazin-1-yl)methanone (80 mg, 0.25 mmol) and 4-methoxybenzoyl chloride (38 mg, 0.28 mmol) were used in the same manner as in the method of Example 85 to obtain the title compound (65 mg, 57% yield) as a white solid.

$^1H$ NMR (400 MHz, $CDCl_3$): δ 8.76 (d, J=5.2 Hz, 1H), 8.09 (d, J=8.0 Hz, 1H), 8.02 (d, J=7.2 Hz, 1H), 7.69 (d, J=8.0 Hz, 1H), 7.52 (d, J=7.6 Hz, 1H), 7.41 (d, J=8.4 Hz, 2H), 6.92 (d, J=8.8 Hz, 2H), 6.84 (s, 1H), 4.75-4.66 (m, 1H), 4.09-3.86 (m, 5H), 3.82 (s, 3H), 3.48-3.09 (m, 5H), 2.96-2.64 (m, 2H), 2.00-1.89 (m, 2H), 1.81-1.75 (m, 1H), 1.53-1.45 (m, 1H). LC-MS (ESI): Rt=3.748 min, m/z 459.3 $[M+H]^+$; purity: 99.38% @ 254 nm, 99.37% @ 214 nm.

Example 117: Synthesis of (1-(cyclohexylsulfonyl) piperidin-3-yl)(4-(7-fluoroquinolin-4-yl)piperazin-1-yl)methanone

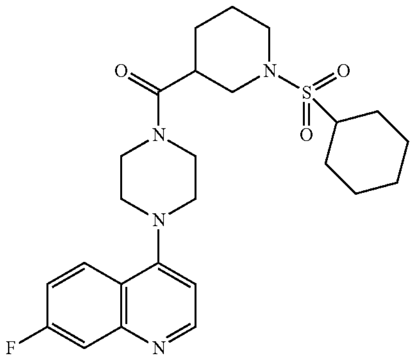 [SMILES: O=C(C1CCCN(S(=O)(=O)C2CCCCC2)C1)N1CCN(c2ccnc3cc(F)ccc23)CC1]

According to Reaction Scheme 1-4, (4-(7-fluoroquinolin-4-yl)piperazin-1-yl)(piperidin-3-yl)methanone (180 mg, 0.53 mmol) and TEA (89 mg, 0.88 mmol) were dissolved in dichloromethane (3 mL), and cyclohexanesulfonyl chloride (144 mg, 0.79 mmol) diluted in dichloromethane (1 mL) was slowly added thereto and stirred at room temperature for 2 hours. The mixture was concentrated under reduced pressure, and the residue was purified by C18 chromatography using 30-90% $CH_3CN$ (acetonitrile) aqueous solution as a developing solvent to obtain the title compound (55 mg, 21% yield) as a white solid.

$^1$HNMR (400 MHz, $CDCl_3$): δ 8.76 (d, J=4.8 Hz, 1H), 8.02 (dd, J=9.2, 6.0 Hz, 1H), 7.70 (dd, J=10.0, 2.8 Hz, 1H), 7.30 (td, J=9.6, 2.8 Hz, 1H), 6.83 (d, J=4.2 Hz, 1H), 3.89-3.82 (m, 6H), 3.24-3.18 (m, 4H), 3.08 (t, J=12.8 Hz, 1H), 2.91-2.84 (m, 3H), 2.11 (d, J=11.2 Hz, 2H), 2.00-1.97 (m, 1H), 1.89-1.86 (m, 2H), 1.81-1.68 (m, 4H), 1.50-1.47 (m, 2H), 1.28-1.19 (m, 3H).

MS (ESI): Rt=4.162 min, m/z 489.2 $[M+H]^+$; purity: 97.70% @254 nm, 97.95% @214 nm.

Example 118: Synthesis of (4-(7-fluoroquinolin-4-yl)piperazin-1-yl)(1-(1-methyl-1H-imidazol-2-ylsulfonyl)piperidin-3-yl)methanone

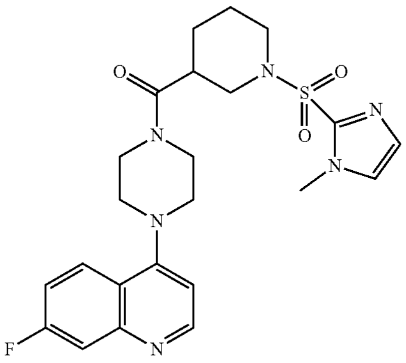 [SMILES: Cn1ccnc1S(=O)(=O)N1CCCC(C(=O)N2CCN(c3ccnc4cc(F)ccc34)CC2)C1]

(4-(7-Fluoroquinolin-4-yl)piperazin-1-yl)(piperidin-3-yl) methanone (80 mg, 0.23 mmol) and 1-methyl-1H-imidazole-2-sulfonyl chloride (47 mg, 0.26 mmol) were used in the same manner as in the method of Example 117 to obtain the title compound (60 mg, 53% yield) as a white solid.

$^1$HNMR (400 MHz, $CDCl_3$): δ 8.75 (d, J=4.8 Hz, 1H), 8.04-8.00 (m, 1H), 7.70 (dd, J=12.4, 2.8 Hz, 1H), 7.33-7.28 (m, 1H), 7.06 (s, 1H), 6.95 (s, 1H), 6.83 (d, J=5.2 Hz, 1H), 4.00-3.96 (m, 2H), 3.92 (s, 3H), 3.88-3.85 (m, 4H), 3.23-3.17 (m, 5H), 3.07-3.02 (m, 2H), 1.98-1.95 (m, 1H), 1.88-1.85 (m, 1H), 1.77-1.72 (m, 2H). LCMS (ESI): Rt=2.524 min, m/z 487.2 $[M+H]^+$; purity: 96.38% @ 254 nm, 97.04% @ 214 nm.

Example 119: Synthesis of (1-(cyclopropylsulfonyl) piperidin-3-yl)(4-(7-fluoroquinolin-4-yl)piperazin-1-yl)methanone

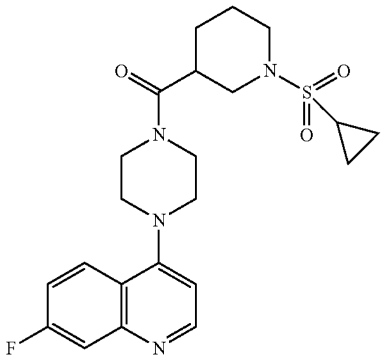 [SMILES: O=C(C1CCCN(S(=O)(=O)C2CC2)C1)N1CCN(c2ccnc3cc(F)ccc23)CC1]

(4-(7-Fluoroquinolin-4-yl)piperazin-1-yl)(piperidin-3-yl) methanone (80 mg, 0.23 mmol) and cyclopropanesulfonyl chloride (36 mg, 0.26 mmol) were used in the same manner as in the method of Example 117 to obtain the title compound (50 mg, 48% yield) as a light yellow solid.

$^1$HNMR (400 MHz, $CDCl_3$): δ 8.76 (d, J=4.2 Hz, 1H), 8.02 (dd, J=9.2, 6.0 Hz, 1H), 7.70 (dd, J=9.6, 2.4 Hz, 1H), 7.33-7.30 (m, 1H), 6.84 (d, J=5.2 Hz, 1H), 3.89-3.83 (m, 6H), 3.25-3.22 (m, 4H), 3.04 (d, J=12.0 Hz, 1H), 2.90-2.89 (m, 1H), 2.83-2.80 (m, 1H), 2.31-2.27 (m, 1H), 1.97-1.95 (m, 1H), 1.89-1.86 (m, 1H), 1.71-1.60 (m, 2H), 1.18-1.15 (m, 2H), 1.02-0.98 (m, 2H).

MS (ESI): Rt=3.710 min, m/z 447.2 $[M+H]^+$; purity: 97.05% @ 254 nm, 97.79% @ 214 nm.

Example 120: Synthesis of (1-(1-methyl-1H-imidazol-2-ylsulfonyl)piperidin-3-yl)(4-(quinolin-4-yl) piperazin-1-yl)methanone

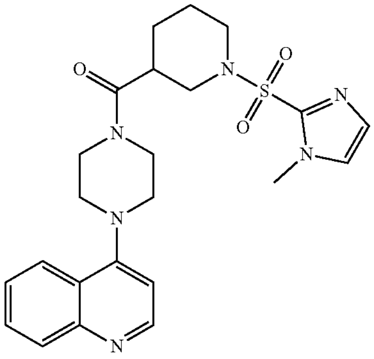 [SMILES: Cn1ccnc1S(=O)(=O)N1CCCC(C(=O)N2CCN(c3ccnc4ccccc34)CC2)C1]

Piperidin-3-yl(4-(quinolin-4-yl)piperazin-1-yl)methanone (80 mg, 0.25 mmol) and 1-methyl-1H-imidazole-2-sulfonyl chloride (49 mg, 0.27 mmol) were used in the same manner as in the method of Example 117 to obtain the title compound (60 mg, 52% yield) as a white solid.

$^1$HNMR (400 MHz, $CDCl_3$): δ 8.76 (d, J=5.2 Hz, 1H), 8.08 (d, J=8.4 Hz, 1H), 8.02 (d, J=8.4 Hz, 1H), 7.69 (t, J=7.2 Hz, 1H), 7.52 (t, J=7.2 Hz, 1H), 7.06 (s, 1H), 6.95 (s, 1H), 6.86 (d, J=4.8 Hz, 1H), 4.00-3.96 (m, 2H), 3.92 (s, 3H), 3.89-3.86 (m, 4H), 3.26-3.17 (m, 5H), 3.11-2.99 (m, 2H), 1.98-1.95 (m, 1H), 1.88-1.85 (m, 1H), 1.77-1.72 (m, 2H). LCMS (ESI): Rt=3.371 min, m/z 469.2 $[M+H]^+$; purity: 99.50% @ 254 nm, 99.09% @ 214 nm.

Example 121: Synthesis of (1-(cyclohexylsulfonyl) piperidin-3-yl)(4-(quinolin-4-yl)piperazin-1-yl) methanone

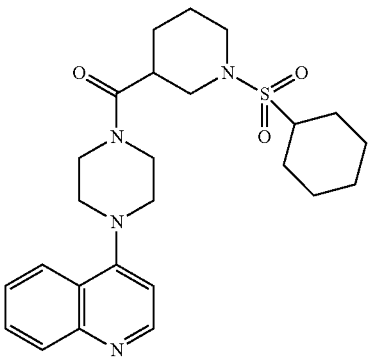 [SMILES: O=C(C1CCCN(S(=O)(=O)C2CCCCC2)C1)N1CCN(c2ccnc3ccccc23)CC1]

Piperidin-3-yl(4-(quinolin-4-yl)piperazin-1-yl)methanone (180 mg, 0.56 mmol) and cyclohexanesulfonyl chloride (200 mg, 0.11 mmol) were used in the same manner as in the method of Example 117 to obtain the title compound (50 mg, 19% yield) as a white solid.

$^1H$ NMR (400 MHz, $CDCl_3$): δ 8.77 (d, J=4.8 Hz, 1H), 8.09 (d, J=8.4 Hz, 1H), 8.02 (d, J=8.4 Hz, 1H), 7.70 (t, J=8.0 Hz, 1H), 7.53 (t, J=8.0 Hz, 1H), 6.86 (d, J=5.2 Hz, 1H), 3.90-3.81 (m, 6H), 3.25-3.20 (m, 4H), 3.12-3.06 (m, 1H), 2.95-2.85 (m, 3H), 2.12-2.09 (m, 2H), 2.00-1.98 (m, 1H), 1.90-1.86 (m, 2H), 1.82-1.72 (m, 4H), 1.53-1.44 (m, 2H), 1.31-1.17 (m, 3H). LC-MS (ESI): Rt=3.315 min, m/z 471.3 $[M+H]^+$; purity: 95.57% @ 254 nm, 95.62% @ 214 nm.

Example 122: Synthesis of (1-(cyclopropylsulfonyl) piperidin-3-yl)(4-(quinolin-4-yl)piperazin-1-yl) methanone

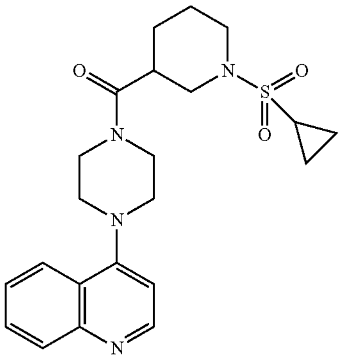 [SMILES: O=C(C1CCCN(S(=O)(=O)C2CC2)C1)N1CCN(c2ccnc3ccccc23)CC1]

Piperidin-3-yl(4-(quinolin-4-yl)piperazin-1-yl)methanone (80 mg, 0.25 mmol) and cyclopropanesulfonyl chloride (42 mg, 0.30 mmol) were used in the same manner as in the method of Example 117 to obtain the title compound (55 mg, 52% yield) as a white solid.

$^1H$ NMR (400 MHz, $CDCl_3$): δ 8.77 (d, J=5.2 Hz, 1H), 8.11 (d, J=8.8 Hz, 1H), 8.02 (d, J=7.6 Hz, 1H), 7.72-7.69 (m, 1H), 7.56-7.52 (m, 1H), 6.87 (d, J=5.2 Hz, 1H), 3.92-3.84 (m, 6H), 3.28-3.23 (m, 4H), 3.05 (t, J=12.0 Hz, 1H), 2.93-2.87 (m, 1H), 2.83-2.78 (m, 1H), 2.33-2.26 (m, 1H), 1.98-1.96 (m, 1H), 1.90-1.87 (m, 1H), 1.73-1.67 (m, 2H), 1.20-1.16 (m, 2H), 1.03-0.97 (m, 2H). LC-MS (ESI): Rt=3.374 min, m/z 429.2 $[M+H]^+$; purity: 98.56% @ 254 nm, 99.40% @ 214 nm.

Example 123: Synthesis of (4-(7-chloroquinolin-4-yl)piperazin-1-yl)(1-(furan-2-ylsulfonyl)piperidin-3-yl)methanone

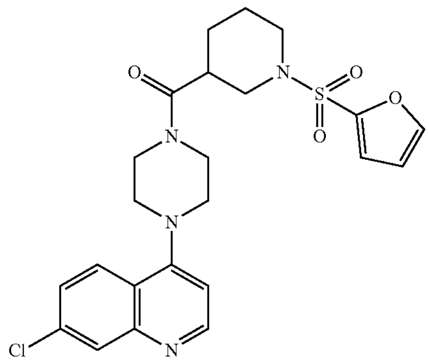 [SMILES: O=C(C1CCCN(S(=O)(=O)c2ccco2)C1)N1CCN(c2ccnc3cc(Cl)ccc23)CC1]

Piperidin-3-yl(4-(quinolin-4-yl)piperazin-1-yl)methanone (80 mg, 0.22 mmol) and furan-2-sulfonyl chloride (41 mg, 0.25 mmol) were used in the same manner as in the method of Example 117 to obtain the title compound (50 mg, 46% yield) as a white solid.

$^1H$ NMR (400 MHz, $CDCl_3$): δ 8.76 (d, J=4.8 Hz, 1H), 8.08 (d, J=2.0 Hz, 1H), 7.95 (d, J=8.8 Hz, 1H), 7.58 (s, 1H), 7.47 (dd, J=8.8, 2.0 Hz, 1H), 7.02 (d, J=3.2 Hz, 1H), 6.86 (d, J=4.8 Hz, 1H), 6.53-6.52 (m, 1H), 3.94-3.82 (m, 6H), 3.25-3.18 (m, 4H), 2.92-2.86 (m, 1H), 2.83-2.77 (m, 1H), 2.61-2.55 (m, 1H), 1.93-1.85 (m, 2H), 1.74-1.65 (m, 1H). LC-MS (ESI): Rt=4.090 min, m/z 489.1 $[M+H]^+$; purity: 98.26% @ 254 nm, 98.47% @ 214 nm.

Example 124: Synthesis of (4-(7-chloroquinolin-4-yl)piperazin-1-yl)(1-(pyridin-4-ylsulfonyl)piperidin-3-yl)methanone

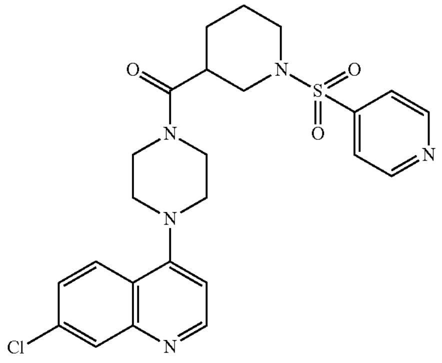 [SMILES: O=C(C1CCCN(S(=O)(=O)c2ccncc2)C1)N1CCN(c2ccnc3cc(Cl)ccc23)CC1]

(4-(7-Chloroquinolin-4-yl)piperazin-1-yl)(piperidin-3-yl) methanone (80 mg, 0.22 mmol) and pyridine-4-sulfonyl chloride (46 mg, 0.26 mmol) were used in the same manner as in the method of Example 117 to obtain the title compound (58 mg, 53% yield) as a white solid.

$^1$H NMR (400 MHz, $CDCl_3$): δ 8.88-8.87 (dd, J=4.4, 1.6 Hz, 2H), 8.77 (d, J=5.2 Hz, 1H), 8.08 (d, J=2.0 Hz, 1H), 7.95 (d, J=9.2 Hz, 1H), 7.61 (dd, J=8.8, 1.6 Hz, 2H), 7.48 (dd, J=8.8, 2.0 Hz, 1H), 6.86 (d, J=4.8 Hz, 1H), 3.93-3.82 (m, 6H), 3.28-3.19 (m, 4H), 2.95-2.89 (m, 1H), 2.63 (t, J=11.2 Hz, 1H), 2.37-2.31 (m, 1H), 1.95-1.86 (m, 2H), 1.80-1.69 (m, 1H), 1.57-1.47 (m, 1H). LC-MS (ESI): Rt=3.664 min, m/z 500.1 $[M+H]^+$; purity: 98.15% @ 254 nm, 97.97% @ 214 nm.

Example 125: Synthesis of (4-(2-methylquinolin-4-yl)piperazin-1-yl)(1-(pyridin-3-ylsulfonyl)piperidin-3-yl)methanone

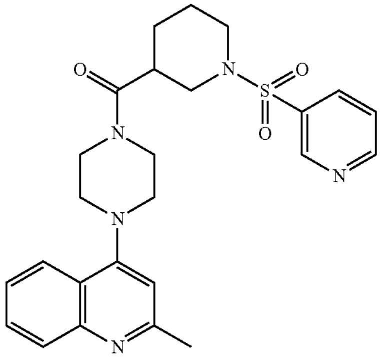 [SMILES: Cc1cc(N2CCN(C(=O)C3CCCN(S(=O)(=O)c4cccnc4)C3)CC2)c2ccccc2n1]

(4-(2-Methylquinolin-4-yl)piperazin-1-yl)(piperidin-3-yl)methanone (80 mg, 0.24 mmol) and pyridine-3-sulfonyl chloride (46 mg, 0.26 mmol) were used in the same manner as in the method of Example 117 to obtain the title compound (60 mg, 52% yield) as a white solid.

$^1$HNMR (400 MHz, $CDCl_3$): δ 9.00 (d, J=1.5 Hz, 1H), 8.84 (dd, J=4.4. 1.5 Hz, 1H), 8.07-8.04 (m, 1H), 8.00 (d, J=8.0 Hz, 1H), 7.96 (d, J=8.0 Hz, 1H), 7.65 (td, J=8.4, 1.5 Hz, 1H), 7.51-7.44 (m, 2H), 6.75 (s, 1H), 3.93-3.82 (m, 6H), 3.27-3.18 (m, 4H), 2.96-2.90 (m, 1H), 2.69 (s, 3H), 2.59 (t, J=11.2 Hz, 1H), 2.33 (td, J=12.0, 2.8 Hz, 1H), 1.94-86 (m, 2H), 1.78-1.74 (m, 1H), 1.58-1.50 (m, 1H). LC-MS (ESI): Rt=2.723 min, m/z 480.3 $[M+H]^+$; purity: 99.28% @ 254 nm, 99.86% @ 214 nm.

Example 126: Synthesis of (4-(2-methylquinolin-4-yl)piperazin-1-yl)(1-(pyridin-4-ylsulfonyl)piperidin-3-yl)methanone

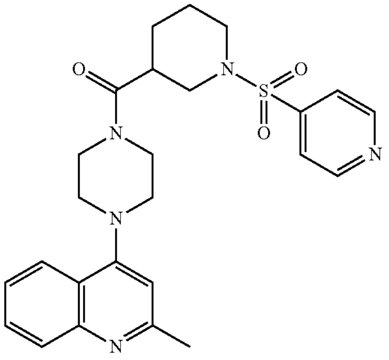 [SMILES: Cc1cc(N2CCN(C(=O)C3CCCN(S(=O)(=O)c4ccncc4)C3)CC2)c2ccccc2n1]

(4-(2-Methylquinolin-4-yl)piperazin-1-yl)(piperidin-3-yl)methanone (80 mg, 0.24 mmol) and pyridine-4-sulfonyl chloride (46 mg, 0.26 mmol) were used in the same manner as in the method of Example 117 to obtain the title compound (55 mg, 48% yield) as a white solid.

$^1$H NMR (400 MHz, $CDCl_3$): δ 8.88 (dd, J=4.4, 1.6 Hz, 2H), 8.01-7.95 (m, 2H), 7.68-7.64 (m, 1H), 7.62-7.61 (m, 2H), 7.47 (t, J=8.0 Hz, 1H), 6.75 (s, 1H), 3.94-3.82 (m, 6H), 3.29-3.18 (m, 4H), 2.96-2.89 (m, 1H), 2.70 (s, 3H), 2.63 (t, J=11.2 Hz, 1H), 2.37-2.31 (m, 1H), 1.95-1.86 (m, 2H), 1.80-1.73 (m, 1H), 1.58-1.47 (m, 1H). LC-MS (ESI): Rt=3.493 min, m/z 480.2 $[M+H]^+$; purity: 98.62% @ 254 nm, 98.57% @ 214 nm.

Example 127: Synthesis of (4-(2-methylquinolin-4-yl)piperazin-1-yl)(1-(thiophen-2-ylsulfonyl)piperidin-3-yl)methanone

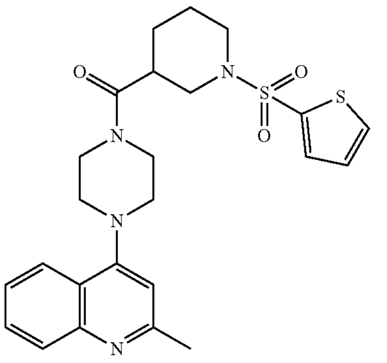 [SMILES: Cc1cc(N2CCN(C(=O)C3CCCN(S(=O)(=O)c4cccs4)C3)CC2)c2ccccc2n1]

(4-(2-Methylquinolin-4-yl)piperazin-1-yl)(piperidin-3-yl)methanone (44 mg, 0.14 mmol) and thiophene-2-sulfonyl chloride (33 mg, 0.18 mmol) were used in the same manner as in the method of Example 117 to obtain the title compound (30 mg, 44% yield) as a white solid.

$^1$H NMR (600 MHz, $CDCl_3$) δ 7.98 (d, J=8.4 Hz, 1H), 7.95 (dd, J=8.4 Hz, 1.2 Hz, 1H), 7.65 (td, J=8.4 Hz, 1.2 Hz, 1H), 7.62 (dd, J=4.8 Hz, 1.2 Hz, 1H), 7.54 (dd, J=3.6 Hz, 1.2 Hz, 1H), 7.45 (td, J=8.4 Hz, 1.2 Hz, 1H), 7.14 (t, J=4.8 Hz, 1H), 6.74 (s, 1H), 3.93-3.74 (m, 6H), 3.28-3.12 (m, 4H), 2.94 (tt, J=11.6 Hz, 3.6 Hz, 1H), 2.69 (s, 3H), 2.59 (t, J=11.4 Hz, 1H), 2.34 (t, J=12.3 Hz, 3.0 Hz, 1H), 1.88 (t, J=16.8 Hz, 2H), 1.76-1.66 (m, 1H), 1.52 (qd, J=12.6 Hz, 3.6 Hz, 1H). LC-MS (ESI): Rt=16.20 min, m/z 485.00 $[M+H]^+$ purity: 99.0% @ 254 nm, 365 nm Example 128: Synthesis of (1-(pyridin-4-ylsulfonyl)piperidin-3-yl)(4-(2-(trifluoromethyl)quinolin-4-yl)piperazin-1-yl)methanone

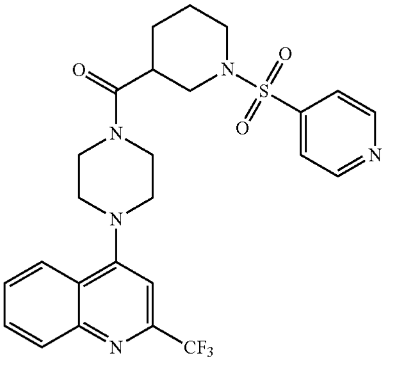 [SMILES: O=C(C1CCCN(S(=O)(=O)c2ccncc2)C1)N1CCN(c2cc(C(F)(F)F)nc3ccccc23)CC1]

Piperidin-3-yl(4-(2-(trifluoromethyl)quinolin-4-yl)piperazin-1-yl)methanone (80 mg, 0.20 mmol) and pyridine-4-sulfonyl chloride (40 mg, 0.22 mmol) were used in the same manner as in the method of Example 117 to obtain the title compound (65 mg, 58% yield) as a white solid.

$^1$H NMR (400 MHz, $CDCl_3$): δ 8.89-8.87 (dd, J=4.4, 1.6 Hz, 2H), 8.21 (d, J=8.4 Hz, 1H), 8.05 (d, J=8.0 Hz, 1H), 7.81-7.77 (m, 1H), 7.66-7.61 (m, 3H), 7.16 (s, 1H), 3.94-3.85 (m, 6H), 3.40-3.28 (m, 4H), 2.96-2.89 (m, 1H), 2.63 (t, J=11.2 Hz, 1H), 2.38-2.31 (m, 1H), 1.96-1.87 (m, 2H), 1.80-1.71 (m, 1H), 1.55-1.48 (m, 1H). LC-MS (ESI): Rt=3.463 min, m/z 534.2 $[M+H]^+$; purity: 99.09% @ 254 nm, 99.18% @ 214 nm.

Example 129: Synthesis of (1-(pyridin-3-ylsulfonyl)piperidin-3-yl)(4-(2-(trifluoromethyl)quinolin-4-yl)piperazin-1-yl)methanone

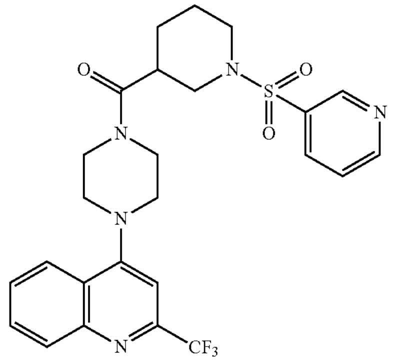 [SMILES: O=C(C1CCCN(S(=O)(=O)c2cccnc2)C1)N1CCN(c2cc(C(F)(F)F)nc3ccccc23)CC1]

Piperidin-3-yl(4-(2-(trifluoromethyl)quinolin-4-yl)piperazin-1-yl)methanone (80 mg, 0.20 mmol) and pyridine-3-sulfonyl chloride (40 mg, 0.22 mmol) were used in the same manner as in the method of Example 117 to obtain the title compound (70 mg, 62% yield) as a white solid.

$^1$H NMR (400 MHz, $CDCl_3$): δ 9.00 (d, J=2.0 Hz, 1H), 8.84 (dd, J=4.8, 1.6 Hz, 1H), 8.20 (d, J=8.4 Hz, 1H), 8.07-8.04 (m, 2H), 7.79 (td, J=6.8, 0.8 Hz, 1H), 7.64 (t, J=7.2 Hz, 1H), 7.51-7.48 (m, 1H), 7.16 (s, 1H), 3.93-3.85 (m, 6H), 3.37-3.28 (m, 4H), 2.96-2.91 (m, 1H), 2.60 (t, J=12.0 Hz, 1H), 2.34 (td, J=12.0, 2.8 Hz, 1H), 1.95-1.86 (m, 2H), 1.78-1.74 (m, 1H), 1.55-1.51 (m, 1H). LC-MS (ESI): Rt=3.925 min, m/z 534.2 $[M+H]^+$; purity: 99.95% @ 254 nm, 99.92% @ 214 nm.

Example 130: Synthesis of methyl 3-((3-(4-(7-fluoroquinolin-4-yl)piperazine-1-carbonyl)piperidin-1-yl)sulfonyl)propanoate

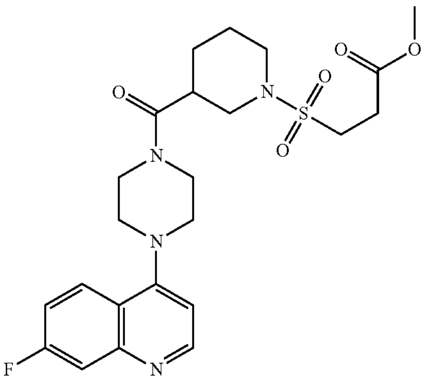 [SMILES: COC(=O)CCS(=O)(=O)N1CCCC(C(=O)N2CCN(c3ccnc4cc(F)ccc34)CC2)C1]

(4-(7-Fluoroquinolin-4-yl)piperazin-1-yl)(piperidin-3-yl)methanone (220 mg, 0.64 mmol) and methyl-3-(chlorosulfonyl)propanoate (180 mg, 0.96 mmol) were used in the same manner as in the method of Example 117 to obtain the title compound (170 mg, 54% yield) as a white solid.

LCMS (ESI): Rt=1.48 min, m/z 493.2 $[M+H]^+$; purity: 100% @254 nm, 98% @214 nm.

Example 131: Synthesis of (4-(7-fluoroquinolin-4-yl)piperazin-1-yl)(1-((3-hydroxypropyl)sulfonyl)piperidin-3-yl)methanone

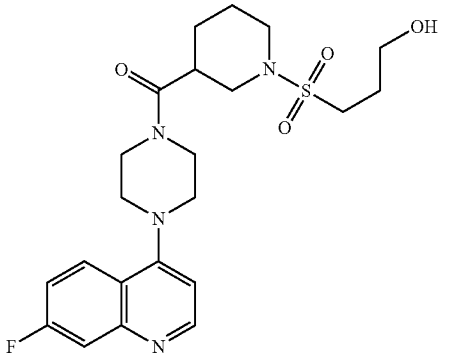 [SMILES: O=C(C1CCCN(S(=O)(=O)CCCO)C1)N1CCN(c2ccnc3cc(F)ccc23)CC1]

According to Reaction Scheme 1-5, methyl 3-((3-(4-(7-fluoroquinolin-4-yl)piperazine-1-carbonyl)piperidin-1-yl)sulfonyl)propanoate (170 mg, 0.34 mmol, Example 130) was dissolved in methanol (10 mL) at 10° C., and $NaBH_4$ (66 mg, 1.72 mmol) was slowly added thereto. The reaction mixture was stirred at room temperature for 4 hours, and purified water (20 mL) was then added and extraction was carried out with dichloromethane (10 mL×3). The organic layer was dried over $Na_2SO_4$, filtered and concentrated under reduced pressure. The residue was purified by C18 chromatography using 20-90% $CH_3CN$ aqueous solution as a developing solvent to obtain the title compound (80 mg, 50% yield) as a white solid.

$^1$HNMR (400 MHz, $CDCl_3$): δ 8.76 (d, J=4.8 Hz, 1H), 8.04-8.00 (m, 1H), 7.71 (dd, J=13.2, 6.0 Hz, 1H), 7.33-7.28 (m, 1H), 6.84 (d, J=5.2 Hz, 1H), 3.89-3.83 (m, 6H), 3.80-

3.77 (m, 2H), 3.25-3.19 (m, 4H), 3.09 (t, J=7.6 Hz, 2H), 3.02 (t, J=12.4 Hz, 1H), 2.91-2.88 (m, 1H), 2.82-2.77 (m, 1H), 2.09-2.04 (m, 2H), 1.99-1.97 (m, 1H), 1.88-1.85 (m, 2H), 1.82-1.68 (m, 2H).

LCMS (ESI): Rt=3.047 min, m/z 465.2 $[M+H]^+$; purity: 97.95% @254 nm, 97.94% @214 nm.

Example 132: Synthesis of methyl 3-((3-(4-(quinolin-4-yl)piperazine-1-carbonyl)piperidin-1-yl)sulfonyl)propanoate

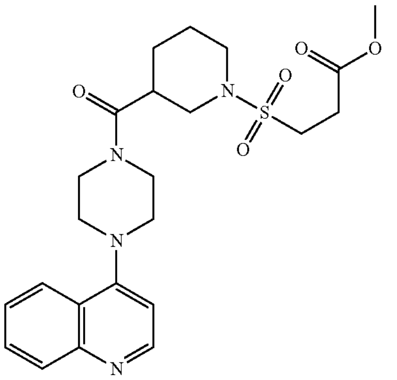 [SMILES: COC(=O)CCS(=O)(=O)N1CCCC(C(=O)N2CCN(c3ccnc4ccccc34)CC2)C1]

Piperidin-3-yl(4-(quinolin-4-yl)piperazin-1-yl)methanone (200 mg, 0.62 mmol) was used in the same manner as in the method of Example 120 to obtain the title compound (130 mg, 44% yield) as a white solid.

LCMS (ESI): Rt=1.44 min, m/z 475.3 $[M+H]^+$; purity: 100% @ 254 nm, 100% @ 214 nm.

Example 133: Synthesis of (1-((3-hydroxypropyl)sulfonyl)piperidin-3-yl)(4-(quinolin-4-yl)piperazin-1-yl)methanone

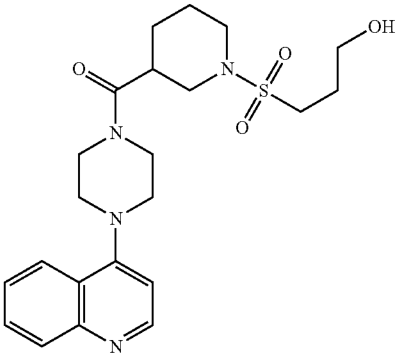 [SMILES: O=C(C1CCCN(S(=O)(=O)CCCO)C1)N1CCN(c2ccnc3ccccc23)CC1]

$NaBH_4$ (48 mg, 1.26 mmol) and 3-((3-(4-(quinolin-4-yl)piperazine-1-carbonyl)piperidin-1-yl)sulfonyl)propanoate (120 mg, 0.25 mmol, Example 132) were used in the same manner as in the method of Example 120 to obtain the title compound (50 mg, 44% yield) as a white solid.

$^1$HNMR (400 MHz, $CDCl_3$): δ 8.76 (d, J=4.8 Hz, 1H), 8.08 (d, J=8.4 Hz, 1H), 8.02 (d, J=8.0 Hz, 1H), 7.69 (t, J=7.2 Hz, 1H), 7.53 (t, J=7.6 Hz, 1H), 6.86 (d, J=5.2 Hz, 1H), 3.90-3.83 (m, 5H), 3.78 (t, J=6.0 Hz, 2H), 3.26-3.20 (m, 4H), 3.09 (t, J=7.2 Hz, 2H), 3.03 (t, J=12.8 Hz, 1H), 2.92-2.89 (m, 1H), 2.82-2.76 (m, 1H), 2.09-2.02 (m, 2H), 1.99-1.97 (m, 1H), 1.88-1.85 (m, 2H), 1.77-1.68 (m, 3H). LCMS (ESI): Rt=2.841 min, m/z 447.2 $[M+H]^+$; purity: 95.00% @ 254 nm, 97.35% @214 nm.

Example 134: Synthesis of (R)-(1-((1H-1,2,4-triazol-5-yl)sulfonyl)pyrrolidin-3-yl)(4-(7-fluoroquinolin-4-yl)piperazin-1-yl)methanone

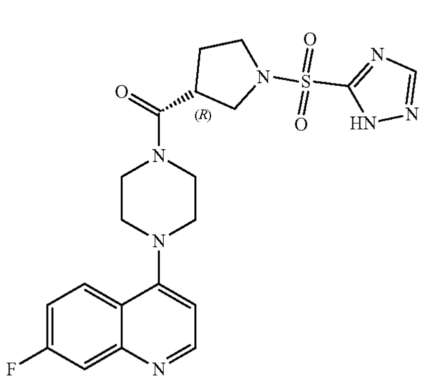

(R)-(4-(7-fluoroquinolin-4-yl)piperazin-1-yl)(pyrrolidin-3-yl)methanone (100 mg, 0.30 mmol) and 1H-1,2,4-triazole-5-sulfonyl chloride (60 mg, 0.36 mmol) were used in the same manner as in the method of Example 5 to obtain the title compound (60 mg, 36% yield) as a white solid.

$^1$H NMR (400 MHz, DMSO-$d_6$): δ 8.71 (d, J=5.2 Hz, 1H), 8.15 (dd, J=9.2, 6.0 Hz, 1H), 8.10 (s, 1H), 7.68 (dd, J=10.4, 2.4 Hz, 1H), 7.50-7.45 (m, 1H), 7.00 (d, J=4.8 Hz, 1H), 3.74-3.73 (m, 3H), 3.64-3.59 (m, 2H), 3.39-3.35 (m, 1H), 3.32-3.28 (m, 2H), 3.23-3.12 (m, 5H), 1.95-1.84 (m, 2H). LC-MS (ESI): Rt=2.688 min, m/z 460.2 $[M+H]^+$; purity: 96.72% @254 nm, 97.90% @214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 230 nm, Rt=9.636 min, 99.89% ee.

Example 135: Synthesis of (1-((1H-1,2,4-triazol-5-yl)sulfonyl)piperidin-4-yl)(4-(7-fluoroquinolin-4-yl)piperazin-1-yl)methanone

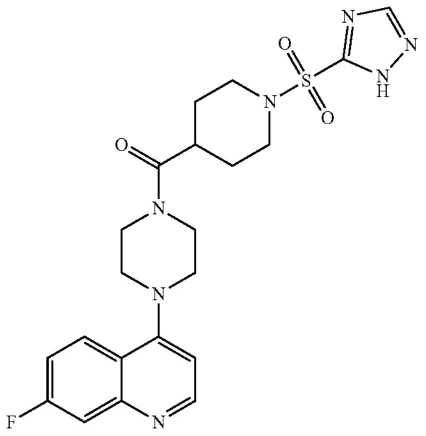 [SMILES: O=C(C1CCN(S(=O)(=O)c2ncn[nH]2)CC1)N1CCN(c2ccnc3cc(F)ccc23)CC1]

(4-(7-Fluoroquinolin-4-yl)piperazin-1-yl)(piperidin-4-yl)methanone (80 mg, 0.23 mmol) and 1H-1,2,4-triazole-5-sulfonyl chloride (47 mg, 0.28 mmol) were used in the same manner as in the method of Example 5 to obtain the title compound (50 mg, 46% yield) as a white solid.

$^1$HNMR (400 MHz, DMSO-$d_6$): δ 8.79 (s, 1H), 8.72-8.71 (m, 1H), 8.14 (dd, J=9.6, 6.4 Hz, 1H), 7.68 (dd, J=10.4, 2.4 Hz, 1H), 7.50-7.45 (m, 1H), 6.98 (d, J=5.2 Hz, 1H), 3.78-3.69 (m, 6H), 3.19-3.08 (m, 4H), 2.81-2.75 (m, 3H), 1.77-1.74 (m, 2H), 1.63-1.53 (m, 2H). LC-MS (ESI): Rt=2.367 min, m/z 540.1 [M+H]$^+$; purity: 95.79% @ 254 nm, 95.22% @ 214 nm. chiral HPLC: Column: Chiralpak IC 5 um 4.6×250 mm; Mobile Phase: HEX:EtOH:DEA=50:50:0.2 at 1 mL/min; Temp: 30° C.; Wavelength: 230 nm, Rt=27.701 min, 99.70% ee.

Example 136: Synthesis of (S)-(1-((1H-1,2,4-triazol-5-yl)sulfonyl)pyrrolidin-3-yl)(4-(6-fluoroquinolin-4-yl)piperazin-1-yl)methanone

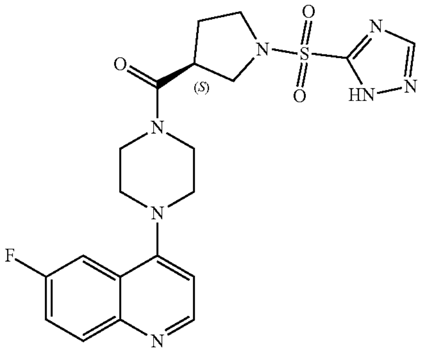

(S)-(4-(6-fluoroquinolin-4-yl)piperazin-1-yl)(pyrrolidin-3-yl)methanone (100 mg, 0.30 mmol) and 1H-1,2,4-triazole-5-sulfonyl chloride (60 mg, 0.36 mmol) were used in the same manner as in the method of Example 5 to obtain the title compound (60 mg, 36% yield) as a white solid.

$^1$H NMR (400 MHz, DMSO-$d_6$): δ 8.86 (s, 1H), 8.71 (d, J=5.2 Hz, 1H), 8.05 (dd, J=9.2, 5.6 Hz, 1H), 7.73 (dd, J=10.4, 3.2 Hz, 1H), 7.67-7.62 (m, 1H), 7.06 (d, J=5.2 Hz, 1H), 3.77-3.73 (m, 4H), 3.63-3.58 (m, 1H), 3.48-3.41 (m, 3H), 3.39-3.35 (m, 1H), 3.15-3.09 (m, 4H), 2.07-1.99 (m, 1H), 1.94-1.86 (m, 1H). LC-MS (ESI): Rt=3.299 min, m/z 460.2 [M+H]$^+$; purity: 99.55% @ 254 nm, 99.41% @ 214 nm. chiral HPLC: Column: Chiralpak IC 5 um 4.6×250 mm; Mobile Phase: HEX:EtOH:DEA=50:50:0.2 at 1 mL/min; Temp: 30° C.; Wavelength: 230 nm, Rt=27.701 min, 99.70% ee.

Example 137: Synthesis of (1-((1H-1,2,4-triazol-5-yl)sulfonyl)azetidin-3-yl)(4-(7-fluoroquinolin-4-yl)piperazin-1-yl)methanone

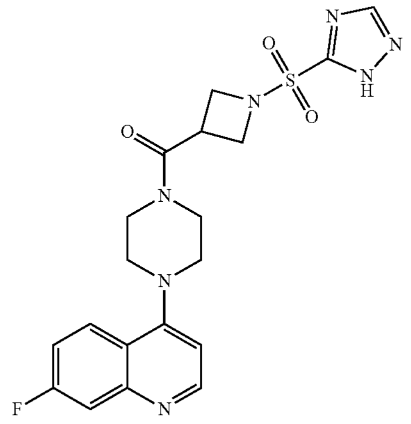 [SMILES: O=C(C1CN(S(=O)(=O)c2ncn[nH]2)C1)N1CCN(c2ccnc3cc(F)ccc23)CC1]

Azetidin-3-yl(4-(7-fluoroquinolin-4-yl)piperazin-1-yl)methanone (100 mg, 0.32 mmol) and 1H-1,2,4-triazole-5-sulfonyl chloride (64 mg, 0.38 mmol) were used in the same manner as in the method of Example 65 to obtain the title compound (100 mg, 70% yield) as a white solid.

$^1$H NMR (400 MHz, DMSO-$d_6$): δ 8.90 (s, 1H), 8.72 (d, J=5.2 Hz, 1H), 8.12 (dd, J=9.2, 6.4 Hz, 1H), 7.68 (dd, J=10.4, 2.4 Hz, 1H), 7.50-7.45 (m, 1H), 6.98 (d, J=5.2 Hz, 1H), 4.13-4.04 (m, 4H), 3.72-3.64 (m, 3H), 3.52-3.45 (m, 2H), 3.15-3.07 (m, 4H). LC-MS (ESI): Rt=2.864 min, m/z 446.2 [M+H]$^+$; purity: 96.79% @ 254 nm, 97.52% @ 214 nm.

Example 138: Synthesis of (S)-(1-((1H-1,2,4-triazol-5-yl)sulfonyl)pyrrolidin-3-yl)(4-(8-fluoroquinolin-4-yl)piperazin-1-yl)methanone

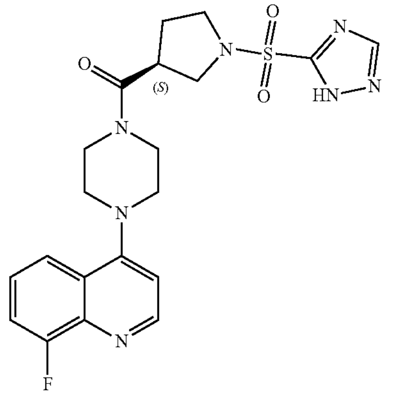

(S)-(4-(8-fluoroquinolin-4-yl)piperazin-1-yl)(pyrrolidin-3-yl)methanone (200 mg, 0.61 mmol, Preparation Example 5) and 4H-1,2,4-triazole-3-sulfonyl chloride (123 mg, 0.73 mmol) were used in the same manner as in the method of Example 5 to obtain the title compound (130 mg, 46% yield) as a white solid.

$^1$H NMR (400 MHz, DMSO-$d_6$): δ 8.84 (s, 1H), 8.74 (d, J=4.8 Hz, 1H), 7.90-7.87 (m, 1H), 7.56-7.53 (m, 2H), 7.10-7.09 (m, 1H), 3.80-3.68 (m, 4H), 3.62-3.58 (m, 1H), 3.51-3.37 (m, 3H), 3.34-3.32 (m, 1H), 3.22-3.09 (m, 4H), 2.07-1.99 (m, 1H), 1.94-1.85 (m, 1H). LC-MS (ESI): Rt=3.161 min., m/z 460.2 $[M+H]^+$; purity: 97.66% @ 254 nm, 98.66% @ 214 nm. Chiral HPLC: Column: Chiralpak IG 5 um 4.6×250 mm; Mobile Phase: Hex:EtOH=60:40 at 1 mL/min; Temp: 30° C.; Wavelength: 230 nm, Rt=10.787 min, 100% ee.

Example 139: Synthesis of (S)-(4-(7-fluoroquinolin-4-yl)piperazin-1-yl)(1-((1-methyl-1H-1,2,4-triazol-3-yl)sulfonyl)pyrrolidin-3-yl)methanone

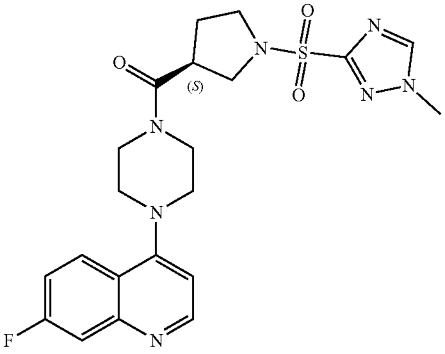

According to Reaction Scheme 6, (S)-(1-((1H-1,2,4-triazol-3-yl)sulfonyl)pyrrolidin-3-yl)(4-(7-fluoroquinolin-4-yl)piperazin-1-yl)methanone (300 mg, 0.65 mmole) was dissolved in acetonitrile (5 ml), and potassium carbonate (270 mg, 19.9 mmol) and methyl iodide (Mel, 110 mg, 0.78 mmol) were added thereto and stirred at room temperature for 4 hours. The reaction solution was concentrated and diluted in dichloromethane (20 mL), saturated aqueous sodium bicarbonate solution (20 mL) was added, and extraction was carried out three times using a mixed solvent (20 ml) of dichloromethane:methanol=10:1. The organic layer was dried over $Na_2SO_4$, filtered and concentrated under reduced pressure. The residue was first purified by prep-TLC (dichloromethane: methanol=20-10:1), and then purified by C18 chromatography using 10-70% $CH_3CN$ aqueous solution as a developing solvent to obtain the title compound (80 mg, 26% yield). as a white solid.

$^1H$ NMR (400 MHz, $CDCl_3$): δ 8.76 (d, J=4.8 Hz, 1H), 8.14 (s, 1H), 8.04-8.00 (m, 1H), 7.74-7.71 (m, 1H), 7.34-7.26 (m, 1H), 6.83 (d, J=4.8 Hz, 1H), 4.03 (s, 3H), 3.94-3.84 (m, 3H), 3.80-3.68 (m, 2H), 3.66-3.59 (m, 1H), 3.57-3.53 (m, 2H), 3.39-3.28 (m, 1H), 3.23-3.18 (m, 4H), 2.29-2.21 (m, 1H), 2.16-2.08 (m, 1H). LC-MS (ESI): Rt=3.188 min, m/z 474.2 $[M+H]^+$; purity: 97.66% @ 254 nm, 97.97% @ 214 nm. chiral HPLC: Column: Chiralpak IG 5 um 4.6×250 mm; Mobile Phase: Hexane:EtOH=40:60 at 1 mL/min; Temp: 30° C.; Wavelength: 230 nm, Rt=14.238 min, 100% ee.

Example 140: Synthesis of (S)-(4-(7-fluoroquinolin-4-yl)piperazin-1-yl)(1-((1-(2-hydroxyethyl)-1H-1,2,4-triazol-3-yl)sulfonyl)pyrrolidin-3-yl)methanone

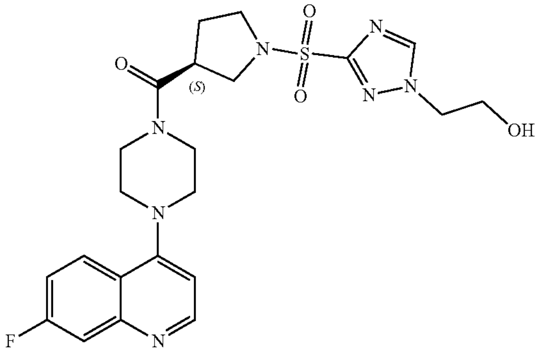

(S)-(1-((1H-1,2,4-triazol-3-yl)sulfonyl)pyrrolidin-3-yl)(4-(7-fluoroquinolin-4-yl)piperazin-1-yl)methanone (50 mg, 0.11 mmole) and 2-bromoethanol (28 mg, 0.22 mmol) were used in the same manner as in the method of Example 139 to obtain the title compound (40 mg, 73% yield) as a white solid.

$^1H$ NMR (400 MHz, $CDCl_3$): δ 8.73 (d, J=4.8 Hz, 1H), 8.24 (s, 1H), 7.98 (dd, J=9.2, 6.4 Hz, 1H), 7.69 (dd, J=10.0, 2.0 Hz, 1H), 7.32-7.30 (m, 1H), 6.82 (d, J=4.8 Hz, 1H), 4.38-4.36 (m, 2H), 4.06-3.98 (m, 2H), 3.75-3.54 (m, 8H), 3.35-3.16 (m, 5H), 2.22-2.13 (m, 1H), 2.01-1.96 (m, 1H). LC-MS (ESI): Rt=2.508 min, m/z 504.2 $[M+H]^+$; purity: 97.61% @ 254 nm, 97.79% @214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 141: Synthesis of (S)-(4-(7-fluoroquinolin-4-yl)piperazin-1-yl)(1-((1-isopropyl)-1H-1,2,4-triazol-3-yl)sulfonyl)pyrrolidin-3-yl)methanone

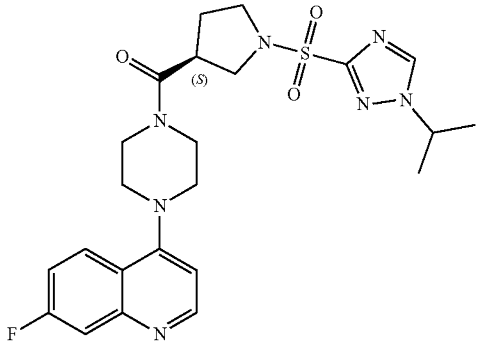

(S)-(1-((1H-1,2,4-triazol-3-yl)sulfonyl)pyrrolidin-3-yl)(4-(7-fluoroquinolin-4-yl)piperazin-1-yl)methanone (100 mg, 0.22 mmole) and 2-iodopropane (74 mg, 0.44 mmol) were used in the same manner as in the method of Example 139 to obtain the title compound (83 mg, 53% yield) as a white solid.

$^1H$ NMR (400 MHz, $CDCl_3$): δ 8.76 (d, J=4.4 Hz, 1H), 8.19 (s, 1H), 8.02 (dd, J=9.2, 6.0 Hz, 1H), 7.70 (dd, J=10.0, 2.4 Hz, 1H), 7.33-7.29 (m, 1H), 6.83 (d, J=4.8 Hz, 1H), 4.69-4.62 (m, 1H), 3.89-3.79 (m, 5H), 3.70-3.64 (m, 1H), 3.61-3.52 (m, 2H), 3.41-3.33 (m, 1H), 3.23-3.14 (m, 4H), 2.29-2.19 (m, 1H), 2.16-2.08 (m, 1H), 1.61 (d, J=6.8 Hz, 6H). LC-MS (ESI): Rt=2.360 min, m/z 502.3 $[M+H]^+$; purity: 98.64% @ 254 nm, 98.97% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 142: Synthesis of (S)-1-(3-((3-(4-(7-fluoroquinolin-4-yl)piperazine-1-carbonyl)pyrrolidin-1-yl)sulfonyl)-1H-1,2,4-triazol-1-yl)propan-2-one

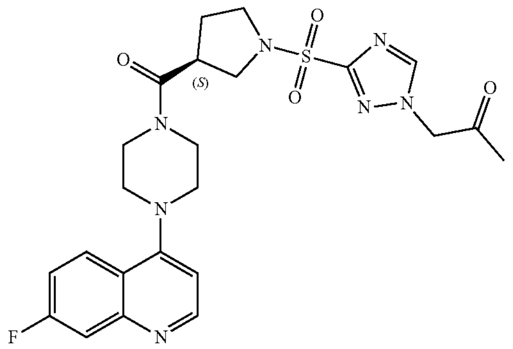

(S)-(1-((1H-1,2,4-triazol-3-yl)sulfonyl)pyrrolidin-3-yl)(4-(7-fluoroquinolin-4-yl)piperazin-1-yl)methanone (100 mg, 0.22 mmole) and 1-bromopropan-2-one (36 mg, 0.26 mmol) were used in the same manner as in the method of Example 139 to obtain the title compound (50 mg, 44% yield) as a white solid.

$^1$H NMR (400 MHz, $CDCl_3$): δ 8.75 (d, J=4.8 Hz, 1H), 8.28 (s, 1H), 8.02 (dd, J=9.2, 6.0 Hz, 1H), 7.69 (dd, J=10.0, 2.4 Hz, 1H), 7.33-7.28 (m, 1H), 6.83 (d, J=4.8 Hz, 1H), 5.18 (s, 2H), 3.88-3.76 (m, 5H), 3.68-3.51 (m, 3H), 3.28-3.18 (m, 5H), 2.31 (s, 3H), 2.24-2.17 (m, 1H), 2.13-2.07 (m, 1H). LC-MS (ESI): Rt=2.813 min, m/z 516.2 $[M+H]^+$; purity: 91.93% @254 nm, 92.85% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 143: Synthesis of (S)-(4-(7-fluoroquinolin-4-yl)piperazin-1-yl)(1-((1-(2-methoxyethyl)-1H-1,2,4-triazol-3-yl)sulfonyl)pyrrolidin-3-yl)methanone

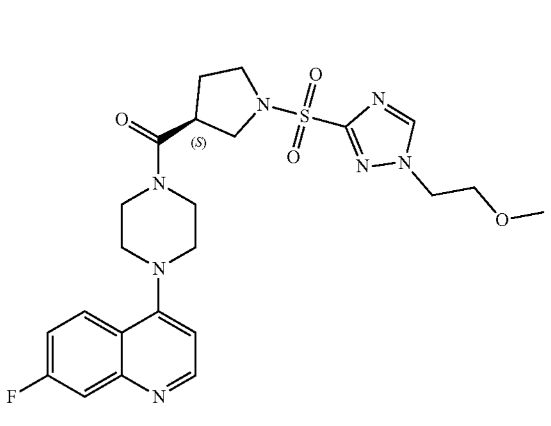

(S)-(1-((1H-1,2,4-triazol-3-yl)sulfonyl)pyrrolidin-3-yl)(4-(7-fluoroquinolin-4-yl)piperazin-1-yl)methanone (100 mg, 0.22 mmole) and 1-bromo-2-methoxyethane (36 mg, 0.26 mmol) were used in the same manner as in the method of Example 139 to obtain the title compound (58 mg, 51% yield) as a white solid.

$^1$H NMR (400 MHz, $CDCl_3$): δ 8.76 (d, J=4.8 Hz, 1H), 8.25 (s, 1H), 8.02 (dd, J=9.2, 6.0 Hz, 1H), 7.70 (dd, J=10.0, 2.4 Hz, 1H), 7.33-7.28 (m, 1H), 6.83 (d, J=5.2 Hz, 1H), 4.42 (t, J=5.2 Hz, 2H), 3.92-3.78 (m, 5H), 3.77-3.74 (m, 2H), 3.70-3.64 (m, 1H), 3.61-3.52 (m, 2H), 3.39-3.33 (m, 4H), 3.26-3.16 (m, 4H), 2.30-2.20 (m, 1H), 2.15-2.07 (m, 1H). LC-MS (ESI): Rt=4.100 min, m/z 518.0 $[M+H]^+$; purity: 91.55% @ 254 nm, 93.53% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 144: Synthesis of (S)-(1-((1-(2-aminoethyl)-1H-1,2,4-triazol-3-yl)sulfonyl)pyrrolidin-3-yl)(4-(7-fluoroquinolin-4-yl)piperazin-1-yl)methanone

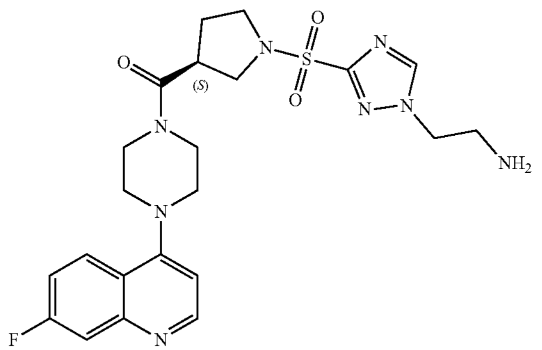

(S)-(1-((1H-1,2,4-triazol-3-yl)sulfonyl)pyrrolidin-3-yl)(4-(7-fluoroquinolin-4-yl)piperazin-1-yl)methanone (200 mg, 0.44 mmole) and benzyl (2-bromoethyl)carbamate (135 mg, 0.52 mmol) were used in the same manner as in the method of Example 139 to obtain (S)-benzyl (2-(3-((3-(4-(7-fluoroquinolin-4-yl)piperazine-1-carbonyl)pyrrolidin-1-yl)sulfonyl)-1H-1,2,4-triazol-1-yl)ethyl)carbamate (150 mg, 54% yield), and the compound was confirmed through NMR.

$^1$H NMR (400 MHz, $CDCl_3$): δ 8.74 (d, J=4.8 Hz, 1H), 8.09 (s, 1H), 7.88 (dd, J=9.2, 6.4 Hz, 1H), 7.74-7.71 (m, 1H), 7.32-7.29 (m, 1H), 7.25-7.24 (m, 2H), 7.19-7.15 (m, 2H), 7.09-7.06 (m, 1H), 6.74-6.71 (m, 1H), 6.65 (d, J=4.8 Hz, 1H), 5.11-5.02 (m, 2H), 4.49-4.35 (m, 2H), 3.76-3.49 (m, 10H), 3.32-3.28 (m, 1H), 3.16-3.14 (m, 1H), 3.08-3.01 (m, 1H), 2.70-2.61 (m, 2H), 2.20-2.13 (m, 1H), 1.93-1.87 (m, 1H) The obtained (S)-benzyl (2-(3-((3-(4-(7-fluoroquinolin-4-yl)piperazine-1-carbonyl)pyrrolidin-1-yl)sulfonyl)-1H-1,2,4-triazol-1-yl)ethyl)carbamate (100 mg, 1.16 mmol) was dissolved in methanol (4 ml), and palladium on charcoal (10% wt., 100 mg, 0.94 mmol) was added thereto. The hydrogenation reaction was carried out for 12 hours by injection hydrogen.

The reaction product was filtered, and the filtrate was depressurized to remove the solvent. The residue was first purified by prep-TLC (dichloromethane: methanol=20-10:1) and finally purified by C18 chromatography using 10-70%

$CH_3CN$ aqueous solution as a developing solvent to obtain the title compound (60 mg, 75% yield) as a white solid.

$^1H$ NMR (400 MHz, $CDCl_3$): δ 8.76 (d, J=5.2 Hz, 1H), 8.28 (s, 1H), 8.01 (dd, J=9.2, 6.0 Hz, 1H), 7.70 (dd, J=10.4, 2.8 Hz, 1H), 7.33-7.28 (m, 1H), 6.82 (d, J=5.2 Hz, 1H), 4.31-4.29 (m, 2H), 3.84-3.77 (m, 5H), 3.67-3.54 (m, 3H), 3.38-3.31 (m, 1H), 3.24-3.14 (m, 6H), 2.21-2.10 (m, 2H). LC-MS (ESI): Rt=2.714 min, m/z 503.2 $[M+H]^+$; purity: 98.70% @254 nm, 99.19% @214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 145: Synthesis of (S)-(4-(7-fluoroquinolin-4-yl)piperazin-1-yl)(1-((1-(2-hydroxyethyl)-1H-1,2,4-triazol-5-yl)sulfonyl)pyrrolidin-3-yl)methanone

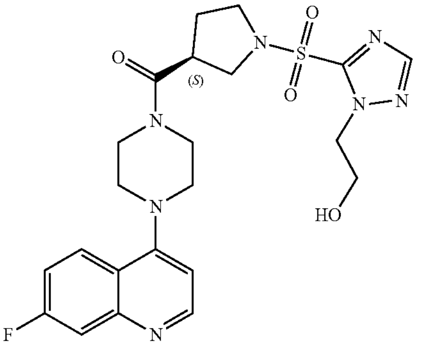

(S)-(1-((1H-1,2,4-triazol-3-yl)sulfonyl)pyrrolidin-3-yl)(4-(7-fluoroquinolin-4-yl)piperazin-1-yl)methanone (100 mg, 0.22 mmole) and 2-bromoethanol (28 mg, 0.22 mmol) were used in the same manner as in the method of Example 139 to obtain the title compound (18 mg, 16% yield) as a white solid.

$^1H$ NMR (400 MHz, $CDCl_3$): δ 8.75 (d, J=4.8 Hz, 1H), 8.01 (dd, J=9.6, 6.4 Hz, 1H), 7.96 (s, 1H), 7.72 (dd, J=10.0, 2.4 Hz, 1H), 7.34-7.29 (m, 1H), 6.82 (d, J=5.2 Hz, 1H), 4.72-4.64 (m, 2H), 4.11-4.08 (m, 2H), 3.90-3.80 (m, 7H), 3.65-3.60 (m, 1H), 3.53-3.46 (m, 1H), 3.28-3.19 (m, 4H), 2.38-2.31 (m, 1H), 2.29-2.23 (m, 1H). LC-MS (ESI): Rt=3.024 min, m/z 504.2 $[M+H]^+$; purity: 98.93% @ 254 nm, 98.75% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 146: Synthesis of (S)-(1-((1H-imidazol-2-yl)sulfonyl)pyrrolidin-3-yl)(4-(7-fluoroquinolin-4-yl)piperazin-1-yl)methanone

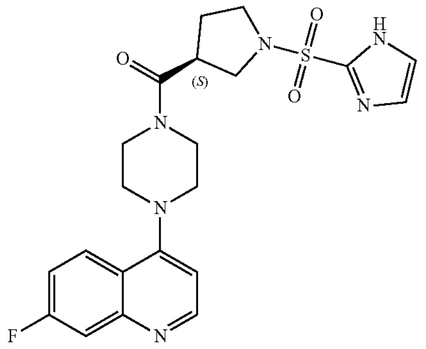

(S)-(4-(7-fluoroquinolin-4-yl)piperazin-1-yl)(pyrrolidin-3-yl)methanone (200 mg, 0.61 mmol) and 1H-imidazole-2-sulfonyl chloride (122 mg, 0.73 mmol) were used in the same manner as in the method of Example 5 to obtain the title compound (240 mg, 86% yield) as a white solid.

$^1H$ NMR (400 MHz, $CDCl_3$): δ 8.77 (d, J=5.2 Hz, 1H), 8.02 (dd, J=9.2, 6.0 Hz, 1H), 7.71 (dd, J=10.0, 2.8 Hz, 1H), 7.34-7.32 (m, 1H), 7.24 (s, 2H), 6.84 (d, J=5.2 Hz, 1H), 3.91-3.76 (m, 5H), 3.72-3.68 (m, 1H), 3.63-3.51 (m, 2H), 3.36-3.29 (m, 1H), 3.25-3.18 (m, 4H), 2.23-2.13 (m, 2H). LC-MS (ESI): Rt=2.484 min, m/z 459.2 $[M+H]^+$; purity: 96.66% @ 254 nm, 97.56% @ 214 nm. chiral HPLC: Column: Chiralpak IG 5 um 4.6×250 mm; Mobile Phase: ACN:IPA=80:20 at 1 mL/min; Temp: 30° C.; Wavelength: 254 nm, Rt=4.839 min, 94.71% ee.

Example 147: Synthesis of (R)-(1-((1H-imidazol-2-yl)sulfonyl)pyrrolidin-3-yl)(4-(7-fluoroquinolin-4-yl)piperazin-1-yl)methanone

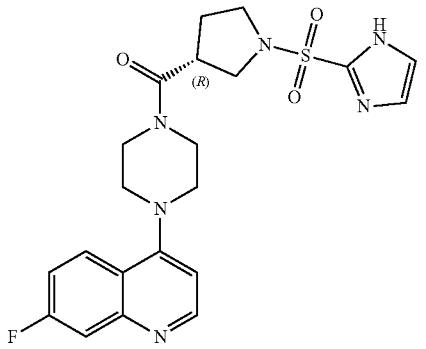

(R)-(4-(7-fluoroquinolin-4-yl)piperazin-1-yl)(pyrrolidin-3-yl)methanone (200 mg, 0.61 mmol) and 1H-imidazole-2-sulfonyl chloride (122 mg, 0.73 mmol) were used in the same manner as in the method of Example 5 to obtain the title compound (76 mg, 21% yield) as a white solid.

$^1H$ NMR (400 MHz, $CDCl_3$): δ 8.77-8.76 (m, 1H), 8.04-8.00 (m, 1H), 7.72-7.69 (m, 1H), 7.34-7.29 (m, 1H), 7.24 (s, 2H), 6.84-6.83 (m, 1H), 3.95-3.77 (m, 5H), 3.72-3.67 (m, 1H), 3.63-3.49 (m, 2H), 3.35-3.26 (m, 1H), 3.23-3.15 (m, 4H), 2.21-2.13 (m, 2H). LC-MS (ESI): Rt=2.918 min, m/z 459.2 [M+H]$^+$; purity: 99.05% @ 254 nm, 97.68% @ 214 nm. chiral HPLC: Column: Chiralpak IG 5 um 4.6×250 mm; Mobile Phase: ACN:IPA=80:20 at 1 mL/min; Temp: 30° C.; Wavelength: 254 nm, Rt=6.410 min, 100% ee.

Example 148: Synthesis of (S)-(4-(7-fluoroquinolin-4-yl)piperazin-1-yl)(1-((1-(2-hydroxyethyl)-1H-imidazol-2-yl)sulfonyl)pyrrolidin-3-yl)methanone

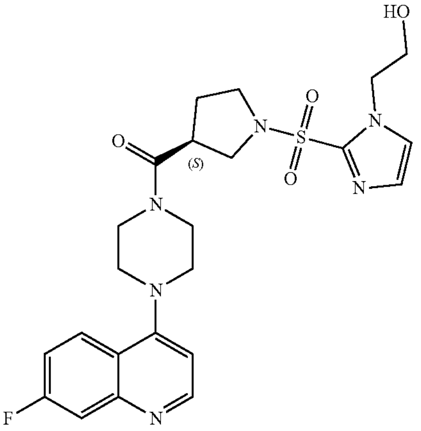

According to Reaction Scheme 7, (S)-(1-((1-1H-imidazol-2-yl)sulfonyl)pyrrolidin-3-yl)(4-(7-fluoroquinolin-4-yl)piperazin-1-yl)methanone (150 mg, 0.33 mmol) was dissolved in acetonidrile (2 ml), and potassium carbonate (136 mg, 0.98 mmol) and 2-bromoethanol (563 mg, 3.27 mmol) were added thereto and stirred at room temperature for 12 hours. The reaction solution was concentrated and diluted in dichloromethane (20 mL), saturated aqueous sodium bicarbonate solution (20 mL) was added, and extraction was a carried out three times using a mixed solvent (20 ml) of dichloromethane:methanol=10:1. The organic layer was dried over $Na_2SO_4$, filtered and concentrated under reduced pressure. The residue was first purified by prep-TLC (dichloromethane: methanol=20-10:1), and then purified by C18 chromatography using 10-70% $CH_3CN$ aqueous solution as a developing solvent to obtain the title compound (40 mg, 24% yield). as a white solid.

$^1$H NMR (400 MHz, $CDCl_3$): δ 8.75 (d, J=5.2 Hz, 1H), 8.02 (dd, J=9.2, 6.4 Hz, 1H), 7.70 (dd, J=10.0, 2.8 Hz, 1H), 7.34-7.29 (m, 1H), 7.15-7.13 (m, 1H), 7.06-7.05 (m, 1H), 6.83 (d, J=4.8 Hz, 1H), 4.47-4.44 (m, 2H), 4.01-3.98 (m, 2H), 3.95-3.90 (m, 3H), 3.86-3.73 (m, 4H), 3.65-3.54 (m, 2H), 3.28-3.6 (m, 4H), 2.43-2.33 (m, 1H), 2.27-2.22 (m, 1H). LC-MS (ESI): Rt=2.772 min, m/z 503.3 [M+H]$^+$; purity: 96.07% @ 254 nm, 96.27% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 149: Synthesis of (S)-(4-(7-fluoroquinolin-4-yl)piperazin-1-yl)(1-((1-(2-methoxyethyl)-1H-imidazol-2-yl)sulfonyl)pyrrolidin-3-yl)methanone

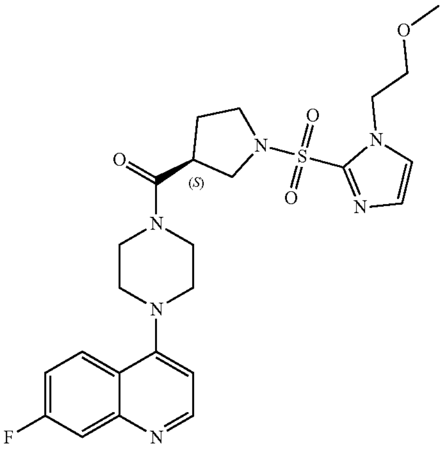

(S)-(1-((1-1H-imidazol-2-yl)sulfonyl)pyrrolidin-3-yl)(4-(7-fluoroquinolin-4-yl)piperazin-1-yl)methanone (100 mg, 0.55 mmole) and 1-bromo-2-methoxyethane (300 mg, 2.17 mmol) were used in the same manner as in the method of Example 147 to obtain the title compound (60 mg, 53% yield) as a white solid.

$^1$H NMR (400 MHz, $CDCl_3$): δ 8.75 (d, J=5.2 Hz, 1H), 8.03 (dd, J=9.2, 6.0 Hz, 1H), 7.70 (dd, J=10.0, 2.4 Hz, 1H), 7.34-7.29 (m, 1H), 7.15-7.13 (m, 1H), 7.06-7.05 (m, 1H), 6.83 (d, J=4.8 Hz, 1H), 4.51-4.40 (m, 2H), 4.00-3.90 (m, 3H), 3.85-3.83 (m, 2H), 3.77-3.67 (m, 4H), 3.65-3.57 (m, 2H), 3.34 (s, 3H), 3.25-3.16 (m, 4H), 2.47-2.37 (m, 1H), 2.27-2.19 (m, 1H). LC-MS (ESI): Rt=3.293 min, m/z 517.2 [M+H]$^+$; purity: 99.10% @ 254 nm, 99.03% @ 214 nm. chiral HPLC: Column: Chiralpak IG 5 um 4.6×250 mm; Mobile Phase: Hex:EtOH:DEA=50:50:0.2 at 1 mL/min; Temp: 30° C.; Wavelength: 254 nm, Rt=6.456 min, 100% ee.

Example 150: Synthesis of (S)-(1-((1-(2-aminoethyl)-1H-imidazol-2-yl)sulfonyl)pyrrolidin-3-yl)(4-(7-fluoroquinolin-4-yl)piperazin-1-yl)methanone

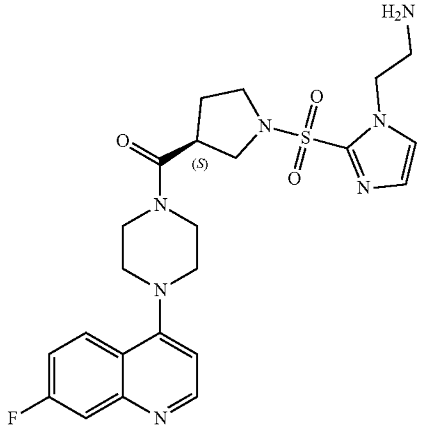

(S)-(1-((1-1H-imidazol-2-yl)sulfonyl)pyrrolidin-3-yl)(4-(7-fluoroquinolin-4-yl)piperazine-1-yl)methanone (100 mg, 0.22 mmol) and benzyl (2-bromoethyl)carbamide (68 mg, 0.26 mmol) were used in the same manner as in the method of Example 143 to obtain the intermediate, (S)-benzyl (2-(2-((3-(4-(7-fluoroquinolin-4-yl)piperazine-1-carbonyl) pyrrolidin-1-yl)sulfonyl)-1H-imidazol-1-yl)ethyl)carbamate (110 mg, 68% yield) was obtained as a white solid ($^1$H NMR (400 MHz, $CDCl_3$): δ 8.75 (d, J=4.8 Hz, 1H), 8.01 (dd, J=9.6, 6.0 Hz, 1H), 7.71 (dd, J=10.0, 2.4 Hz, 1H), 7.39-7.27 (m, 6H), 7.02-7.00 (m, 1H), 6.95 (s, 1H), 6.82 (d, J=4.8 Hz, 1H), 5.27-5.21 (m, 1H), 5.09 (s, 1H), 4.47-4.40 (m, 2H), 3.94-3.80 (m, 5H), 3.77-3.70 (m, 2H), 3.65-3.52 (m, 4H), 3.25-3.13 (m, 4H), 2.43-2.33 (m, 1H), 2.26-2.17 (m, 1H)).

Hydrogenation reaction was carried out using the intermediate (100 mg, 0.16 mmol) to obtain the title compound (30 mg, 38% yield) as a white solid.

$^1$H NMR (400 MHz, $CDCl_3$): δ 8.75 (d, J=5.2 Hz, 1H), 8.03 (dd, J=9.2, 6.0 Hz, 1H), 7.70 (dd, J=10.0, 2.4 Hz, 1H), 7.34-7.29 (m, 1H), 7.11-7.10 (m, 1H), 7.06-7.05 (m, 1H), 6.83 (d, J=5.2 Hz, 1H), 4.38-4.30 (m, 2H), 3.99-3.84 (m, 5H), 3.77-3.69 (m, 2H), 3.65-3.57 (m, 2H), 3.24-3.12 (m, 6H), 2.46-2.36 (m, 1H), 2.27-2.20 (m, 1H). LC-MS (ESI): Rt=2.733 min, m/z 502.2 $[M+H]^+$; purity: 97.95% @ 254 nm, 98.03% @ 214 nm. chiral HPLC: Column: Chiralpak IG 5 um 4.6×250 mm; Mobile Phase: ACN:IPA=80:20 at 1 mL/min; Temp: 30° C.; Wavelength: 254 nm, Rt=4.947 min, 98.25% ee.

Example 151: Synthesis of (S)-(4-(quinolin-4-yl) piperazin-1-yl)(1-((1,3,5-trimethyl-1H-pyrazol-4-yl) sulfonyl)pyrrolidin-3-yl)methanone

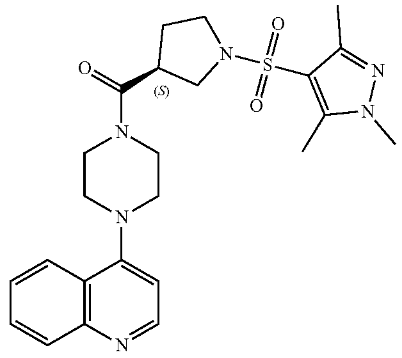

(S)-pyrrolidin-3-yl(4-(quinolin-4-yl)piperazin-1-yl) methanone (100 mg, 0.32 mmol) and 1,3,5-trimethyl-1H-pyrazole-4-sulfonyl chloride (72 mg, 0.31 mmol) were used in the same manner as in the method of Example 5 to obtain the title compound (66 mg, 43% yield) as a white solid.

$^1$H NMR (400 MHz, $CDCl_3$): δ 8.77 (d, J=4.8 Hz, 1H), 8.10-8.08 (m, 1H), 8.02-8.00 (m, 1H), 7.72-7.68 (m, 1H), 7.55-7.51 (m, 1H), 6.86 (d, J=4.8 Hz, 1H), 3.94-3.86 (m, 2H), 3.80-3.78 (m, 2H), 3.76 (s, 3H), 3.68-3.65 (m, 1H), 3.49-3.43 (m, 1H), 3.37-3.24 (m, 2H), 3.20-3.15 (m, 5H), 2.50 (s, 3H), 2.41 (s, 3H), 2.22-2.13 (m, 2H). LC-MS (ESI): Rt=3.067 min., m/z 483.3 $[M+H]^+$; purity: 97.82% @ 254 nm, 99.72% @ 214 nm. Chiral HPLC: Column: Chiralpak IE 5 um 4.6×250 mm; Mobile Phase: ACN:IPA:DEA=70:30:0.2 at 1 mL/min; Temp: 30° C.; Wavelength: 230 nm, Rt=6.932 min, 100% ee.

Example 152: Synthesis of (R)-(4-(quinolin-4-yl) piperazin-1-yl)(1-((1,3,5-trimethyl-1H-pyrazol-4-yl) sulfonyl)pyrrolidin-3-yl)methanone

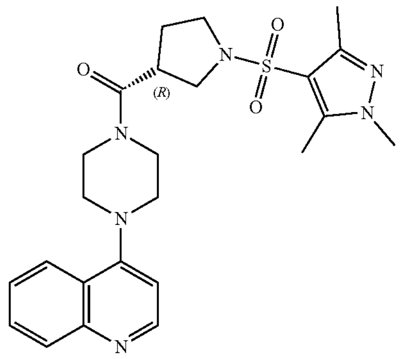

(R)-pyrrolidin-3-yl(4-(quinolin-4-yl)piperazin-1-yl) methanone (80 mg, 0.26 mmol) and 1,3,5-trimethyl-1H-pyrazole-4-sulfonyl chloride (58 mg, 0.25 mmol) were used in the same manner as in the method of Example 5 to obtain the title compound (48 mg, 39% yield) as a white solid.

$^1$H NMR (400 MHz, $CDCl_3$): δ 8.77 (d, J=4.8 Hz, 1H), 8.10-8.08 (m, 1H), 8.03-8.00 (m, 1H), 7.72-7.68 (m, 1H), 7.55-7.51 (m, 1H), 6.85 (d, J=4.8 Hz, 1H), 3.93-3.86 (m, 2H), 3.81-3.78 (m, 2H), 3.76 (s, 3H), 3.68-3.6 (m, 1H), 3.49-3.43 (m, 1H), 3.37-3.24 (m, 2H), 3.24-3.18 (m, 5H), 2.50 (s, 3H), 2.41 (s, 3H), 2.22-2.13 (m, 2H). LC-MS (ESI): Rt=3.444 min., m/z 483.3 $[M+H]^+$; purity: 95.01% @ 254 nm, 99.18% @214 nm. Chiral HPLC: Column: Chiralpak IE 5 um 4.6×250 mm; Mobile Phase: ACN:IPA:DEA=70:30:0.2 at 1 mL/min; Temp: 30° C.; Wavelength: 230 nm, Rt=7.968 min, 100% ee.

Example 153: Synthesis of (1-(4-nitrobenzyl)pyrrolidin-3-yl)(4-(quinolin-4-yl)piperazin-1-yl)methanone

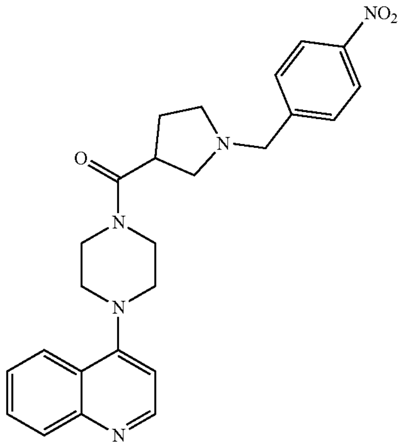 [SMILES: O=C(C1CCN(Cc2ccc([N+](=O)[O-])cc2)C1)N1CCN(c2ccnc3ccccc23)CC1]

According to Reaction Scheme 1-8, pyrrolidin-3-yl(4-(quinolin-4-yl)piperazin-1-yl)methanone (100 mg, 0.25 mmol) and 60% sodium hydride (NaH, 12 mg, 0.13 mmol) were added to DMF (3 mL), and then 1-(bromomethyl)-4-nitrobenzene (68 mg, 0.31 mmol) diluted in DMF (1 mL)

was slowly added thereto at room temperature. The reaction mixture was stirred at room temperature for 4 hours, and the solvent was concentrated under reduced pressure. The residue was purified by silica gel chromatography using a developing solvent of DCM:MeOH=20-10:1 to obtain the title compound (48 mg, 41% yield) as a yellow solid.

$^1$H NMR (400 MHz, $CDCl_3$): δ 8.76 (d, J=4.8 Hz, 1H), 8.20-8.18 (m, 2H), 8.10-8.08 (m, 1H), 8.03-8.01 (m, 1H), 7.71-7.67 (m, 1H), 7.58-7.50 (m, 3H), 6.85 (d, J=5.2 Hz, 1H), 3.98-3.90 (m, 2H), 3.85-3.74 (m, 4H), 3.34-3.30 (m, 1H), 3.23-3.20 (m, 4H), 2.99-2.95 (m, 1H), 2.88-2.82 (m, 2H), 2.64-2.58 (m, 1H), 2.20-2.15 (m, 2H). LC-MS (ESI): Rt=2.800 min, m/z 446.2 $[M+H]^+$; purity: 99.23% @254 nm, 99.36% @214 nm.

Example 154: Synthesis of (S)-(4-(7-fluoroquinolin-4-yl)piperazin-1-yl)(1-((4-methyl-4H-1,2,4-triazol-3-yl)methyl)pyrrolidin-3-yl)methanone

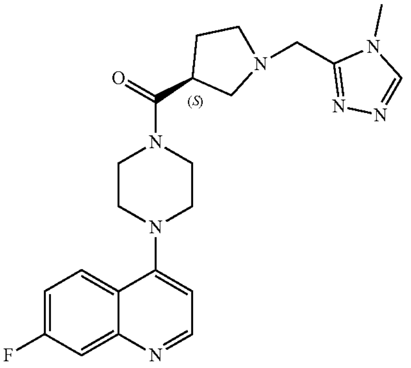

(S)-(4-(7-fluoroquinolin-4-yl)piperazin-1-yl)(pyrrolidin-3-yl)methanone (100 mg, 0.31 mmol) and 3-(chloromethyl)-4-methyl-4H-1,2,4-triazole (49 mg, 0.37 mmol) were used in the same manner as in the method of Example 152 to obtain the title compound (40 mg, 31% yield) as a white solid.

1H NMR (400 MHz, DMSO-$d_6$): δ 8.71 (d, J=4.8 Hz, 1H), 8.39 (s, 1H), 8.15 (dd, J=9.2, 6.4 Hz, 1H), 7.68 (dd, J=10.4, 2.8 Hz, 1H), 7.50-7.45 (m, 1H), 6.99 (d, J=4.8 Hz, 1H), 3.80-3.70 (m, 6H), 3.66 (s, 3H), 3.21-3.09 (m, 4H), 2.78 (t, J=8.8 Hz, 1H), 2.65-2.57 (m, 2H), 2.49-2.45 (m, 2H), 2.04-1.91 (m, 2H). LC-MS (ESI): Rt=3.097 min, m/z 424.3 $[M+H]^+$; purity: 91.90% @ 254 nm, 92.53% @ 214 nm. chiral HPLC: Column: Chiralpak IA 5 um 4.6×250 mm; Mobile Phase: HEX:EtOH=40:60 at 1 mL/min; Temp: 30° C.; Wavelength: 230 nm, Rt=9.175 min, 95.63% ee.

Example 155: Synthesis of (1-((1H-tetrazol-5-yl)methyl)pyrrolidin-3-yl)(4-(7-fluoroquinolin-4-yl)piperazin-1-yl)methanone

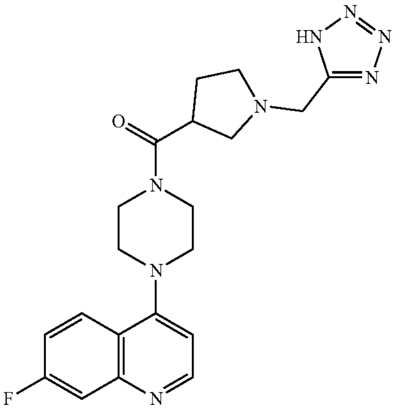 [SMILES: O=C(C1CCN(Cc2nnn[nH]2)C1)N1CCN(c2ccnc3cc(F)ccc23)CC1]

(4-(7-Fluoroquinolin-4-yl)piperazin-1-yl)(pyrrolidin-3-yl)methanone (1,000 mg, 9.17 mmol) and 3-(chloromethyl)-4-methyl-4H-1,2,4-triazole (350 mg, 11.9 mmol) were used in the same manner as in the method of Example 152 to obtain the title compound (220 mg, 23% yield) as a white solid.

$^1$H NMR (400 MHz, $CDCl_3$): δ 8.76 (d, J=4.8 Hz, 1H), 8.03-7.99 (m, 1H), 7.73-7.69 (m, 1H), 7.34-7.29 (m, 1H), 6.83 (d, J=4.8 Hz, 1H), 4.72-4.69 (m, 1H), 4.59-4.56 (m, 1H), 3.95-3.77 (m, 5H), 3.70-3.66 (m, 1H), 3.52-3.45 (m, 2H), 3.39-3.33 (m, 1H), 3.28-3.16 (m, 4H), 2.67-2.59 (m, 1H), 2.29-2.11 (m, 1H). LC-MS (ESI): Rt=2.750 min., m/z 411.3 $[M+H]^+$; purity: 97.44% @ 254 nm, 98.12% @ 214 nm.

Example 156: Synthesis of (S)-(4-(7-fluoroquinolin-4-yl)piperazin-1-yl)(1-(pyridin-3-ylsulfonyl)pyrrolidin-3-yl)methanone

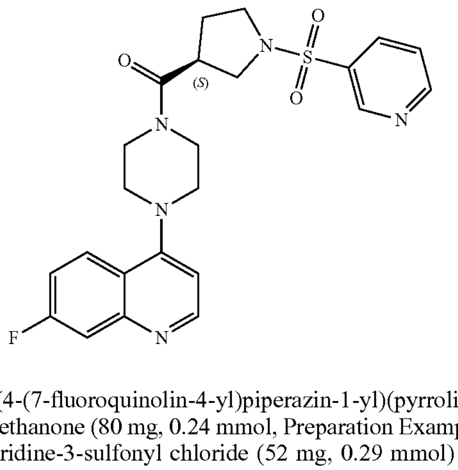

(S)-(4-(7-fluoroquinolin-4-yl)piperazin-1-yl)(pyrrolidin-3-yl)methanone (80 mg, 0.24 mmol, Preparation Example 5) and pyridine-3-sulfonyl chloride (52 mg, 0.29 mmol) were used in the same manner as in the method of Example 5 to obtain the title compound (35 mg, 31% yield) as a white solid.

$^1$H NMR (400 MHz, $CDCl_3$): δ 9.08 (d, J=2.0 Hz, 1H), 8.85 (d, J=4.8 Hz, 1H), 8.76 (d, J=4.8 Hz, 1H), 8.17-8.15 (m, 1H), 8.00 (dd, J=6.4, 9.2 Hz, 1H), 7.70 (dd, J=2.4, 10.0 Hz,

1H), 7.51 (dd, J=4.8, 8.0 Hz, 1H), 7.33-7.28 (m, 1H), 6.82 (d, J=4.8 Hz, 1H), 3.88-3.83 (m, 2H), 3.80-3.70 (m, 3H), 3.56-3.50 (m, 1H), 3.45-3.40 (m, 1H), 3.35-3.27 (m, 2H), 3.24-3.13 (m, 4H), 2.20-2.05 (m, 2H). LC-MS (ESI): Rt=3.243 min, m/z 470.2 $[M+H]^+$; purity: 99.14% @ 254 nm, 99.08% @214 nm.

Example 157: Synthesis of (S)-(4-(7-fluoroquinolin-4-yl)piperazin-1-yl)(1-(pyridin-2-ylsulfonyl)pyrrolidin-3-yl)methanone

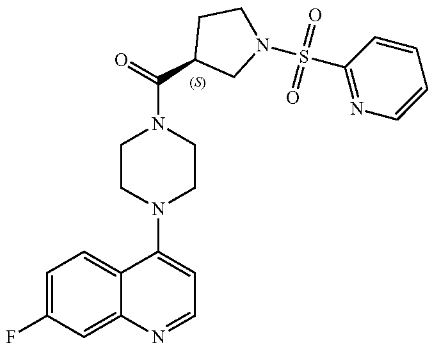

(S)-(4-(7-fluoroquinolin-4-yl)piperazin-1-yl)(pyrrolidin-3-yl)methanone (200 mg, 0.61 mmol) and pyridine-2-sulfonyl chloride (130 mg, 0.73 mmol) were used in the same manner as in the method of Example 5 to obtain the title compound (35 mg, 310% yield) as a white solid.

$^1$H NMR (400 MHz, $CDCl_3$): δ 8.75 (d, J=4.8 Hz, 1H), 8.71 (d, J=5.6 Hz, 1H), 8.04-7.98 (m, 2H), 7.95-7.91 (m, 1H), 7.71 (dd, J=2.4, 10.0, 1H), 7.53-7.49 (m, 1H), 7.34-7.29 (m, 1H), 6.83-6.82 (d, J=4.8 Hz, 1H), 3.97-3.94 (m, 1H), 3.92-3.79 (m, 4H), 3.66-3.51 (m, 3H), 3.37-3.28 (m, 1H), 3.23-3.11 (m, 4H), 2.30-2.20 (m, 1H), 2.14-2.05 (m, 1H). LC-MS (ESI): Rt=3.250 min, m/z 470.2 $[M+H]^+$; purity: 97.50% @ 254 nm, 97.95% @ 214 nm.

Example 158: Synthesis of (S)-(4-(7-fluoroquinolin-4-yl)piperazin-1-yl)(1-((4-nitrophenyl)sulfonyl)pyrrolidin-3-yl)methanone

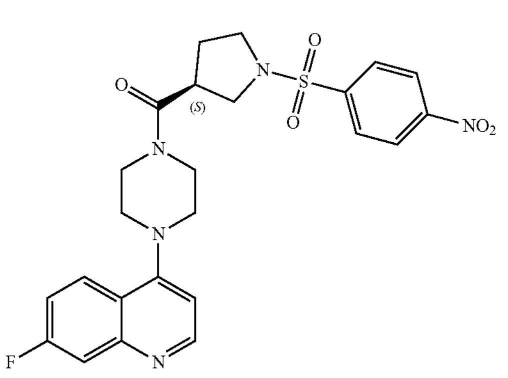

(S)-(4-(7-fluoroquinolin-4-yl)piperazin-1-yl)(pyrrolidin-3-yl)methanone (80 mg, 0.24 mmol) and 4-nitrobenzene-1-sulfonyl chloride (64 mg, 0.29 mmol) were used in the same manner as in the method of Example 5 to obtain the title compound (36 mg, 29% yield) as a white solid.

$^1$H NMR (400 MHz, $CDCl_3$): δ 8.76 (d, J=4.8 Hz, 1H), 8.41-8.39 (m, 2H), 8.07-8.04 (m, 2H), 8.00 (dd, J=6.0, 9.2 Hz, 1H), 7.71 (dd, J=2.4, 10.0 Hz, 1H), 7.33-7.28 (m, 1H), 6.82 (d, J=4.8 Hz, 1H), 3.85-3.81 (m, 2H), 3.76-3.70 (m, 3H), 3.59-3.53 (m, 1H), 3.49-3.44 (m, 1H), 3.37-3.27 (m, 2H), 3.21-3.14 (m, 4H), 2.21-2.16 (m, 1H), 2.08-2.01 (m, 1H). LC-MS (ESI): Rt=3.274 min, m/z 514.3 $[M+H]^+$; purity: 98.50% @ 254 nm, 99.06% @ 214 nm.

Example 159: Synthesis of (S)-(1-((1H-imidazol-2-yl)sulfonyl)pyrrolidin-3-yl)(4-(6-fluoroquinolin-4-yl)piperazin-1-yl)methanone

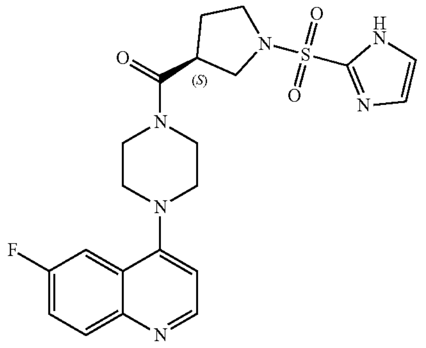

(S)-(4-(6-fluoroquinolin-4-yl)piperazin-1-yl)(pyrrolidin-3-yl)methanone (200 mg, 0.61 mmol) and 1H-imidazole-2-sulfonyl chloride (122 mg, 0.73 mmol) were used in the same manner as in the method of Example 5 to obtain the title compound (120 mg, 35% yield) as a white solid.

1H NMR (400 MHz, DMSO-$d_6$) δ 13.52 (s, 1H), 8.71 (d, J=4.8 Hz, 1H), 8.04 (dd, J=5.6, 9.2 Hz, 1H), 7.73 (dd, J=2.8, 10.4 Hz, 1H), 7.66-7.61 (m, 1H), 7.30 (s, 2H), 7.06 (d, J=5.2 Hz, 1H), 3.75-3.73 (m, 4H), 3.60-3.56 (m, 1H), 3.46-3.34 (m, 4H), 3.17-3.06 (m, 4H), 2.01-1.92 (m, 1H), 1.92-1.80 (m, 1H). LC-MS (ESI): Rt=2.32 min., m/z 459.1 $[M+H]^+$; purity: 95.6% @ 214 nm, 97.3% @ 254 nm.

Example 160: Synthesis of (S)-(4-(6-fluoroquinolin-4-yl)piperazin-1-yl)(1-((1-(2-hydroxyethyl)-1H-imidazol-2-yl)sulfonyl)pyrrolidin-3-yl)methanone

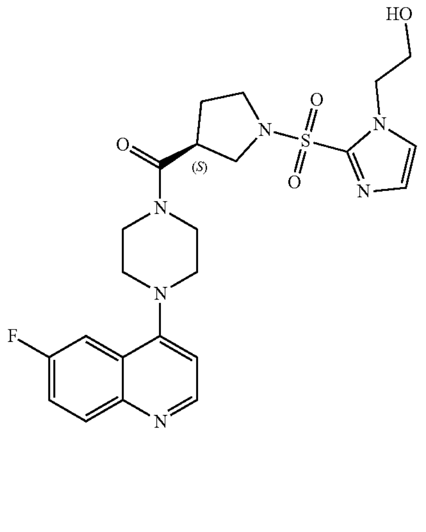

(S)-(1-((1-1H-imidazol-2-yl)sulfonyl)pyrrolidin-3-yl)(4-(6-fluoroquinolin-4-yl)piperazin-1-yl)methanone (100 mg, 0.22 mmole) and 2-bromoethanol (76 mg, 0.44 mmol) were used in the same manner as in the method of Example 147 to obtain the title compound (33 mg, 30% yield) as a white solid.

1H NMR (400 MHz, $CDCl_3$) δ 8.73 (d, J=5.2 Hz, 1H), 8.10-8.07 (m, 1H), 7.61 (dd, J=2.8, 10.0 Hz, 1H), 7.49-7.42 (m, 1H), 7.14 (s, 1H), 7.06 (s, 1H), 6.89 (d, J=5.2 Hz, 1H), 4.46 (t, J=5.2 Hz, 1H), 4.04-3.98 (m, 2H), 3.92-3.71 (m, 8H), 3.65-3.54 (m, 2H), 3.25-3.13 (m, 4H), 2.43-2.35 (m, 1H), 2.28-2.18 (m, 1H). LC-MS (ESI): Rt=2.37 min., m/z 503.2.1 $[M+H]^+$; purity: 99.2% @ 254 nm, 99.4% @ 214 nm.

Example 161: Synthesis of (S)-(1-(4H-1,2,4-triazole-3-carbonyl)pyrrolidin-3-yl)(4-(7-fluoroquinolin-4-yl)piperazin-1-yl)methanone

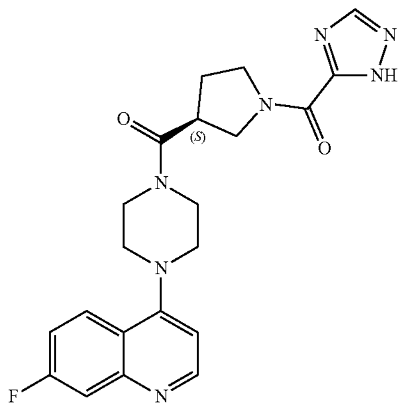

(S)-(4-(7-fluoroquinolin-4-yl)piperazin-1-yl)(pyrrolidin-3-yl)methanone (100 mg, 0.31 mmol) and 1H-1,2,4-triazole-5-carboxylic acid (41 mg, 0.37 mmol) were used in the same manner as in the method of Example 83 to obtain the title compound (30 mg, 22% yield) as a white solid.

$^1$H NMR (400 MHz, $CDCl_3$): δ 8.78 (d, J=4.8 Hz, 1H), 8.14-8.10 (m, 1H), 8.07-8.02 (m, 1H), 7.75-7.71 (m, 1H), 7.34-7.30 (m, 1H), 6.85 (d, J=6.8 Hz, 1H), 4.60-4.21 (m, 2H), 4.07-3.73 (m, 6H), 3.49-3.31 (m, 1H), 3.27-3.19 (m, 4H), 2.46-2.21 (m, 2H). LC-MS (ESI): Rt=2.982 min, m/z 424.2 $[M+H]^+$; purity: 99.130% @ 254 nm, 99.226% @ 214 nm. chiral HPLC: Column: Chiralpak IG 5 um 4.6×250 mm; Mobile Phase: Hex:EtOH:DEA=75:25:0.2 at 1 mL/min; Temp: 30° C.; Wavelength: 254 nm, Rt=20.233 min, 100% ee.

Example 162: Synthesis of (S)-(1-(2H-tetrazole-5-carbonyl)pyrrolidin-3-yl)(4-(7-fluoroquinolin-4-yl)piperazin-1-yl)methanone

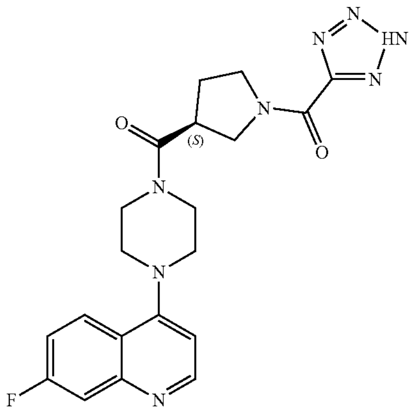

(S)-(4-(7-fluoroquinolin-4-yl)piperazin-1-yl)(pyrrolidin-3-yl)methanone (100 mg, 0.31 mmol) and 2H-tetrazole-5-carboxylic acid (42 mg, 0.37 mmol) were used in the same manner as in the method of Example 83 to obtain the title compound (47 mg, 36% yield) as a white solid.

$^1$H NMR (400 MHz, $CD_4O$): δ 8.64-8.61 (m, 1H), 8.35-8.29 (m, 1H), 7.66-7.62 (m, 1H), 7.52-7.49 (m, 1H), 7.15-7.11 (m, 1H), 4.22-3.61 (m, 13H), 2.31-2.23 (m, 2H). LC-MS (ESI): Rt=2.615 min, m/z 425.2 $[M+H]^+$; purity: 97.61% @ 254 nm, 98.10% @ 214 nm. chiral HPLC: Column: Chiralpak IG 5 um 4.6×250 mm; Mobile Phase: Hex:EtOH:DEA=60:40:0.2 at 1 mL/min; Temp: 30° C.; Wavelength: 254 nm, Rt=19.787 min, 100% ee.

Example 163: Synthesis of (S)-(1-((1H-1,2,4-triazol-5-yl)sulfonyl)pyrrolidin-3-yl)(4-(7-methylquinolin-4-yl)piperazin-1-yl)methanone

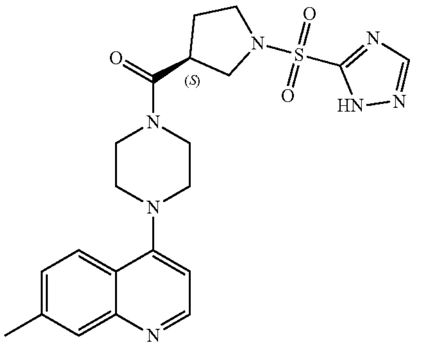

(S)-(4-(7-methylquinolin-4-yl)piperazin-1-yl)(pyrrolidin-3-yl)methanone (100 mg, 0.31 mmol) and 1H-1,2,4-triazole-5-sulfonyl chloride (62 mg, 0.37 mmol) were used in the same manner as in the method of Example 5 to obtain the title compound (100 mg, 36% yield) as a white solid.

$^1$H NMR (400 MHz, DMSO-$d_6$): δ 8.85 (s, 1H), 8.65 (d, J=5.2 Hz, 1H), 7.98-7.95 (m, 1H), 7.75 (s, 1H), 7.41-7.39 (m, 1H), 6.93 (d, J=4.8 Hz, 1H), 3.76-3.71 (m, 4H), 3.62-3.58 (m, 1H), 3.49-3.43 (m, 3H), 3.41-3.33 (m, 2H), 3.17-3.10 (m, 4H), 2.50 (s, 3H), 2.07-1.99 (m, 1H), 1.93-1.85 (m,

1H). LC-MS (ESI): Rt=3.340 min, m/z 456.1 $[M+H]^+$; purity: 99.41% @254 nm, 99.61% @214 nm. chiral HPLC: Column: Chiralpak IA 5 um 4.6×250 mm; Mobile Phase: HEX:EtOH=50:50 at 1 mL/min; Temp: 30° C.; Wavelength: 230 nm, Rt=7.083 min, 100% ee.

Example 164: Synthesis of (S)-(1-((1H-1,2,4-triazol-5-yl)sulfonyl)pyrrolidin-3-yl)(4-(7-hydroxyquinolin-4-yl)piperazin-1-yl)methanone

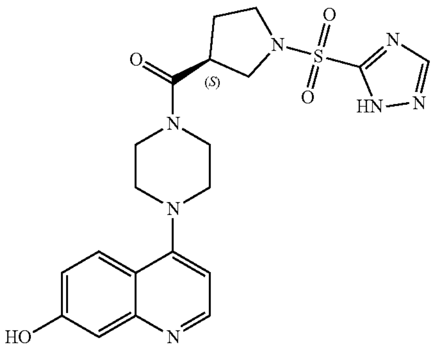

(S)-(4-(7-hydroxyquinolin-4-yl)piperazin-1-yl)(pyrrolidin-3-yl)methanone (75 mg, 0.23 mmol) and 1H-1,2,4-triazole-5-sulfonyl chloride (46 mg, 0.28 mmol) were used in the same manner as in the method of Example 5 to obtain the title compound (13 mg, 12% yield) as a yellow solid.

$^1H$ NMR (400 MHz, DMSO-$d_6$): δ 10.11 (s, 1H), 8.73 (s, 1H), 8.55-8.54 (m, 1H), 7.93-7.91 (m, 1H), 7.19-7.18 (m, 1H), 7.12-7.09 (m, 1H), 6.79-6.78 (m, 1H), 3.79-3.66 (m, 4H), 3.62-3.58 (m, 1H), 3.48-3.37 (m, 4H), 3.16-3.01 (m, 4H), 2.05-1.96 (m, 1H), 1.92-1.84 (m, 1H). LC-MS (ESI): Rt=2.750 min., m/z 458.2 $[M+H]^+$; purity: 97.88% @254 nm, 97.05% @214 nm. chiral HPLC: Column: IB N-5×230 mm; Mobile Phase: CO2:MeOH:DEA=60:40:0.2 at 1 mL/min; Temp: 40° C.; Wavelength: 230 nm, Rt=9.59 min, 99.57% ee.

Example 165: Synthesis of (S)-(1-((1H-1,2,4-triazol-5-yl)sulfonyl)pyrrolidin-3-yl)(4-(7-methoxyquinolin-4-yl)piperazin-1-yl)methanone

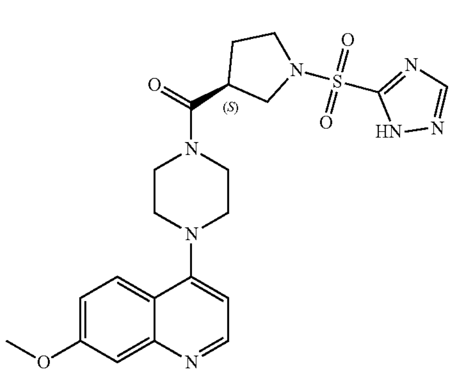

(S)-(4-(7-methoxyquinolin-4-yl)piperazin-1-yl)(pyrrolidin-3-yl)methanone (100 mg, 0.29 mmol) and 1H-1,2,4-triazole-5-sulfonyl chloride (59 mg, 0.35 mmol) were used in the same manner as in the method of Example 5 to obtain the title compound (33 mg, 24% yield) as a yellow solid.

$^1H$ NMR (400 MHz, DMSO-$d_6$): δ 8.83 (s, 1H), 8.63-8.62 (m, 1H), 7.98-7.96 (m, 1H), 7.34-7.33 (m, 1H), 7.21-7.18 (m, 1H), 6.88-6.86 (m, 1H), 3.90 (s, 3H), 3.78-3.65 (m, 4H), 3.62-3.56 (m, 1H), 3.48-3.32 (m, 4H), 3.18-3.06 (m, 4H), 2.05-2.00 (m, 1H), 1.93-1.86 (m, 1H). LC-MS (ESI): Rt=2.796 min., m/z 472.2 $[M+H]^+$; purity: 99.07% @ 254 nm, 99.43% @ 214 nm. Chiral HPLC: Column: Chiralpak IG 5 um 4.6×250 mm; Mobile Phase: Hex:EtOH:DEA=40:60:0.2 at 1 mL/min; Temp: 30° C.; Wavelength: 254 nm, Rt=15.055 min, 100% ee.

Example 166: Synthesis of (S)-(4-(7-fluoroquinolin-4-yl)piperazin-1-yl)(1-((5-methyl-1H-1,2,4-triazol-3-yl)sulfonyl)pyrrolidin-3-yl)methanone

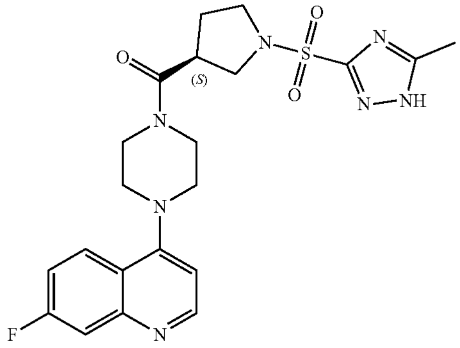

(S)-(4-(7-fluoroquinolin-4-yl)piperazin-1-yl)(pyrrolidin-3-yl)methanone (100 mg, 0.31 mmol) and 5-methyl-1H-1,2,4-triazole-3-sulfonyl chloride (70 mg, 0.38 mmol) were used in the same manner as in the method of Example 83 to obtain the title compound (42 mg, 30% yield) as a white solid.

$^1H$ NMR (400 MHz, $CDCl_3$) δ 8.68 (d, J=4.8 Hz, 1H), 7.94 (dd, J=6.0, 9.2 Hz, 1H), 7.63 (dd, J=2.0, 10.0 Hz, 1H), 7.27-7.19 (m, 1H), 6.76 (d, J=5.2 Hz, 1H), 3.82-3.73 (m, 5H), 3.57-3.54 (m, 2H), 3.51-3.45 (m, 1H), 3.34-3.26 (m, 1H), 3.20-3.08 (m, 4H), 2.50 (s, 3H), 2.23-2.18 (m, 1H), 2.08-2.03 (m, 1H). LC-MS (ESI): Rt=2.776 min. m/z 474.2 $[M+H]^+$; purity: 99.10% @ 254 nm, 99.66% @ 214 nm.

Example 167: Synthesis of (S)-(1-((1H-1,2,4-triazol-5-yl)sulfonyl)pyrrolidin-3-yl)(4-(2-(trifluoromethyl)quinolin-4-yl)piperazin-1-yl)methanone

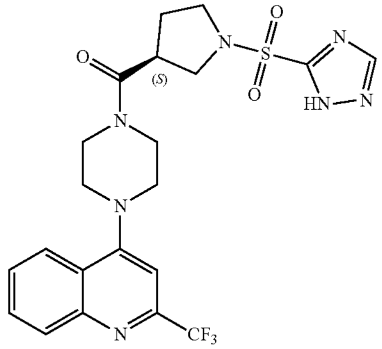

(S)-pyrrolidin-3-yl(4-(2-trifluoromethylquinolin-4-yl)piperazin-1-yl)methanone (170 mg, 0.49 mmol) and 1H-1,2,4-triazole-5-sulfonyl chloride (102 mg, 0.61 mmol) were used in the same manner as in the method of Example 5 to obtain the title compound (86 mg, 33% yield) as a yellow solid.

$^1$H NMR (400 MHz, DMSO-$d_6$) δ 8.79 (s, 1H), 8.17 (d, J=8.0 Hz, 1H), 8.10 (d, J=8.4 Hz, 1H), 7.86 (t, J=7.2H, 1H), 7.86 (t, J=7.2H, 1H), 7.72 (t, J=7.2H, 1H), 7.29 (s, 1H), 3.79-3.70 (m, 4H), 3.64-3.60 (m, 1H), 3.49-3.44 (m, 4H), 3.42-3.27 (m, 4H), 2.05-2.00 (m, 1H), 1.93-1.88 (m, 1H). LC-MS (ESI): Rt=3.22 min., m/z 510.1[M+H]$^+$; purity: 97.7% @ 214 nm.

Example 168: Synthesis of (S)-(1-((1H-1,2,4-triazol-5-yl)sulfonyl)pyrrolidin-3-yl)(4-(6,7-difluoroquinolin-4-yl)piperazin-1-yl)methanone

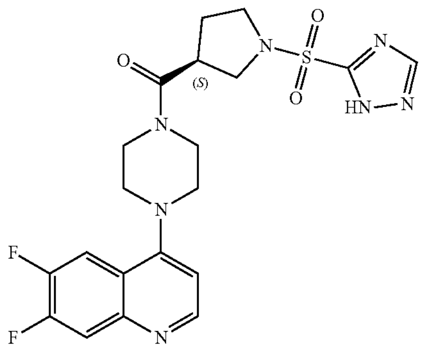

(S)-(4-(6,7-difluoroquinolin-4-yl)piperazin-1-yl)(pyrrolidin-3-yl)methanone (83 mg, 0.24 mmol) and 1H-1,2,4-triazole-5-sulfonyl chloride (49 mg, 0.26 mmol) were used in the same manner as in the method of Example 5 to obtain the title compound (40 mg, 32% yield) as a white solid.

1H NMR (400 MHz DMSO-$d_6$) δ 8.82 (s, 1H), 8.73 (d, J=5.2 Hz, 1H), 8.00-7.94 (m, 2H), 7.07 (d, J=4.8 Hz, 1H), 3.76-3.72 (m, 4H), 3.60 (s, 1H), 3.43-3.46 (m, 3H), 3.41-3.36 (m, 3H), 3.14-3.09 (m, 4H), 2.04-1.86 (m, 2H). LC-MS (ESI): Rt=2.445 min. m/z 479.1 [M+H]$^+$; purity: 99.71% @ 254 nm, 99.33% @ 214 nm. chiral HPLC: Column: Chiralpak IE 5 um 4.6×250 mm; Mobile Phase: Hex:EtOH:DEA=60:40:0.2 at 1 mL/min; Temp: 30° C.; Wavelength: 254 nm, Rt=12.426 min, 99.55% ee.

Example 169: Synthesis of (S)-(1-((1H-imidazol-2-yl)sulfonyl)pyrrolidin-3-yl)(4-(6,7-difluoroquinolin-4-yl)piperazin-1-yl)methanone

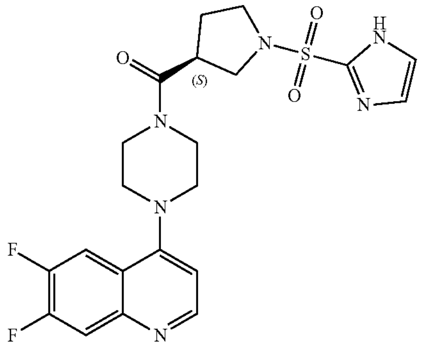

(S)-(4-(6,7-difluoroquinolin-4-yl)piperazin-1-yl)(pyrrolidin-3-yl)methanone (83 mg, 0.24 mmol) and 1H-imidazole-2-sulfonyl chloride (53 mg, 0.32 mmol) were used in the same manner as in the method of Example 5 to obtain the title compound (42 mg, 34% yield) as a white solid.

1H NMR (400 MHz DMSO-$d_6$) δ 12.35 (s, 1H), 8.73 (d, J=5.2 Hz, 1H), 7.94-8.00 (m, 2H), 7.29 (s, 2H), 7.07 (d, J=4.8 Hz, 1H), 3.72-3.76 (m, 4H), 3.58 (t, J=10 Hz, 1H), 3.40-3.43 (m, 4H), 3.09-3.14 (m, 4H), 1.95-2.00 (m, 1H), 1.82-1.87 (m, 1H). LC-MS (ESI): Rt=2.032 min. m/z 477.0 [M+H]$^+$; purity: 99.80% @ 254 nm, 99.83% @ 214 nm. chiral HPLC: Column: Chiralpak IE 5 um 4.6×250 mm; Mobile Phase: Hex:EtOH:DEA=30:70:0.2 at 1 mL/min; Temp: 30° C.; Wavelength: 254 nm, Rt=14.198 min, 99.76% ee.

Experimental Example 1: Measurement of CYP4A Inhibitory Activity

The CYP4A inhibitory activity of the above compounds of the examples was measured. The reagents used in the experiment were commercially available, and were prepared and used when necessary. The device used for measuring activity was SpectraMax of MOLECULAR DEVICES.

CYP4A bactosome and the compounds to be evaluated (5 μM) were each diluted in assay buffer (100 mM $KPO_4$, 0.1% BSA, 1 mM DTT) and mixed in a 384 well plate (white opaque polystyrene nontreated flat-bottom well), and reaction was carried out at room temperature for 15 minutes. To induce CYP4A reaction, 5 mM Luciferin-ME, NADPH Regeneration system (10× sol. A, 20× sol. B in assay buffer, Cat. Number: V865B, Promega) were sequentially added and mixed, and the reaction was carried out at room temperature for 30 minutes. Then, Luciferin Detection reagent was added thereto and reacted at room temperature for 15 minutes to stop the CYP4A reaction and induce a luminescence reaction. Finally, after measuring the luminescence value using a microplate reader, the inhibition of CYP4A activity by the compounds was evaluated by comparing the luminescence value from each well.

The results are represented in Table 1 along with the result for HET-0016 (N-hydroxy-N'-(4-butyl-2-methylphenyl)-formamidine), which is known as a strong CYP inhibitor.

TABLE 1

| CYP4A enzyme assay (Compound concentration 5 μM) % Inhibition | | | | |
|---|---|---|---|---|
| Example No. | Less than 50% | 50%-70% | 70%-90% | Greater than 90% |
| HET-0016 | | | | ○ |
| Example 1 | | | | ○ |
| Example 2 | | | | ○ |
| Example 3 | | | | ○ |
| Example 4 | | | | ○ |
| Example 5 | | | | ○ |
| Example 6 | | | | ○ |
| Example 7 | | | | ○ |
| Example 8 | | | | ○ |
| Example 9 | | | | ○ |
| Example 10 | | | | ○ |
| Example 11 | | | | ○ |
| Example 12 | | | | ○ |
| Example 13 | | | | ○ |
| Example 14 | | | | ○ |
| Example 15 | | | | ○ |
| Example 16 | | | ○ | |
| Example 17 | | | | ○ |
| Example 18 | | | | ○ |
| Example 19 | | | | ○ |
| Example 20 | | | | ○ |
| Example 21 | | | | ○ |
| Example 22 | | | | ○ |
| Example 23 | | | | ○ |
| Example 24 | | | ○ | |
| Example 25 | | | | ○ |
| Example 26 | | | | ○ |
| Example 27 | | | | ○ |
| Example 28 | | | | ○ |
| Example 29 | | | | ○ |
| Example 30 | | | | ○ |
| Example 31 | | | ○ | |
| Example 32 | | | | ○ |
| Example 33 | | | | ○ |
| Example 34 | | | | ○ |
| Example 35 | | | | ○ |
| Example 36 | | | ○ | |
| Example 37 | | | ○ | |
| Example 38 | | | | ○ |
| Example 39 | | | | ○ |
| Example 40 | | | | ○ |
| Example 41 | | | ○ | |
| Example 42 | | | | ○ |
| Example 43 | | | | ○ |
| Example 44 | | | | ○ |
| Example 45 | | | | ○ |
| Example 46 | | | | ○ |
| Example 47 | | | | ○ |
| Example 48 | | | | ○ |
| Example 49 | | | | ○ |
| Example 50 | | | ○ | |
| Example 51 | | | ○ | |
| Example 52 | | | | ○ |
| Example 53 | | | ○ | |
| Example 54 | | | | ○ |
| Example 55 | | | | ○ |
| Example 56 | | | ○ | |
| Example 57 | | | | 0 |
| Example 58 | | | | ○ |
| Example 59 | | | | ○ |
| Example 60 | | | | ○ |
| Example 61 | | | | ○ |
| Example 62 | | | | ○ |
| Example 63 | | | ○ | |
| Example 64 | | | | ○ |
| Example 65 | | | | ○ |
| Example 66 | | | | ○ |
| Example 67 | | | | ○ |
| Example 68 | | ○ | | |
| Example 69 | | | | ○ |
| Example 70 | | | | ○ |
| Example 71 | | | | ○ |
| Example 72 | | | ○ | |
| Example 73 | | | | ○ |
| Example 74 | | | ○ | |
| Example 75 | | ○ | | |
| Example 76 | | | ○ | |
| Example 77 | | | ○ | |
| Example 78 | | | ○ | |
| Example 79 | | ○ | | |
| Example 80 | ○ | | | |
| Example 81 | | ○ | | |
| Example 82 | | ○ | | |
| Example 83 | | | | ○ |
| Example 84 | | | ○ | |
| Example 85 | | | ○ | |
| Example 86 | | ○ | | |
| Example 87 | | | ○ | |
| Example 88 | | ○ | | |
| Example 89 | | | ○ | |
| Example 90 | | | ○ | |
| Example 91 | | ○ | | |
| Example 92 | | ○ | | |
| Example 93 | | | ○ | |
| Example 94 | | ○ | | |
| Example 95 | | ○ | | |
| Example 96 | | ○ | | |
| Example 97 | ○ | | | |
| Example 98 | | ○ | | |
| Example 99 | | ○ | | |
| Example 100 | | ○ | | |
| Example 101 | | ○ | | |
| Example 102 | | ○ | | |
| Example 103 | ○ | | | |
| Example 104 | | ○ | | |
| Example 105 | | | ○ | |
| Example 106 | | | ○ | |
| Example 107 | | | ○ | |
| Example 108 | | ○ | | |
| Example 109 | | | ○ | |
| Example 110 | | | ○ | |
| Example 111 | | | ○ | ○ |
| Example 112 | | | ○ | |
| Example 113 | | ○ | | |
| Example 114 | ○ | | | |
| Example 115 | | | ○ | |
| Example 116 | | | ○ | |
| Example 117 | | | ○ | |
| Example 118 | | | | ○ |
| Example 119 | | ○ | | |
| Example 120 | | | | ○ |
| Example 121 | | | ○ | |
| Example 122 | | ○ | | |
| Example 123 | | ○ | | |
| Example 124 | | | ○ | |
| Example 125 | | ○ | | |
| Example 126 | | ○ | | |
| Example 127 | | ○ | | |
| Example 128 | | ○ | | |
| Example 129 | | ○ | | |
| Example 130 | | ○ | | |
| Example 131 | | ○ | | |
| Example 132 | | ○ | | |
| Example 133 | | ○ | | |
| Example 134 | | | | ○ |
| Example 135 | | | ○ | |
| Example 136 | | | | ○ |
| Example 137 | | | | ○ |
| Example 138 | | | ○ | |
| Example 139 | | | ○ | |
| Example 140 | | | | ○ |
| Example 141 | | | ○ | |
| Example 142 | | | | ○ |
| Example 143 | | | | ○ |
| Example 144 | | | ○ | |
| Example 145 | | | ○ | |
| Example 146 | | | | ○ |
| Example 147 | | | | ○ |
| Example 148 | | | | ○ |
| Example 149 | | | | ○ |

TABLE 1-continued

| CYP4A enzyme assay (Compound concentration 5 μM) % Inhibition | | | | |
|---|---|---|---|---|
| Example No. | Less than 50% | 50%-70% | 70%-90% | Greater than 90% |
| Example 150 | | | ○ | |
| Example 151 | | | ○ | |
| Example 152 | | | ○ | |
| Example 153 | | ○ | | |
| Example 154 | | ○ | | |
| Example 155 | | | ○ | |
| Example 156 | | | | ○ |
| Example 157 | | | | ○ |
| Example 158 | | | | ○ |
| Example 159 | | | | ○ |
| Example 160 | | | | ○ |
| Example 161 | | | | ○ |
| Example 162 | | | | ○ |
| Example 163 | | | ○ | |
| Example 164 | | | | ○ |
| Example 165 | | | | ○ |
| Example 166 | | | | ○ |
| Example 167 | | | ○ | |
| Example 168 | | | | ○ |
| Example 169 | | | | ○ |
| HET-0016 | | | | ○ |

As can be seen from Table 1, it was confirmed that the compounds according to the present invention have the inhibitory activity against CYP4A.

Experimental Example 2: Confirmation of Effect according to Induction of Endoplasmic Reticulum Stress in Hepatocytes

Experimental Example 2-1: Glucose Uptake Promoting Effect

HepG2 cells, a human liver cell line, were incubated in a high-glucose DMEM (Dulbecco's modified Eagle's medium) containing 10% fetal bovine serum (FBS), and then glucose uptake experiments were carried out as follows.

First, HepG2 cells were dispensed into a 96-well plate (black, clear bottom culture plate) at $2\times10^4$ cells/well and incubated in a 37° C., 5% $CO_2$ incubator for 24 hours. After washing with PBS (phosphate buffered saline), the medium was changed to a glucose-free medium, and thapsigargin (1 μM, Thap), which induces endoplasmic reticulum stress, and the compounds (5 μM) synthesized in the above Examples were treated together and reacted in the 37° C., 5% $CO_2$ incubator for 24 hours.

After that, the glucose uptake experiment was carried out using a glucose uptake assay kit (Promega Cat. Number J1342). 2DG (1 mM) was reacted at room temperature for 10 minutes, and the stop buffer and neutralization buffer were then sequentially added and mixed lightly. After mixing the 2DG6P Detection Reagent, a luminescence reaction was induced by reacting at room temperature for 30 minutes. Finally, after measuring the luminescence value using a microplate reader, the luminescence value from each well was compared to evaluate the degree of effect of improving glucose absorption by the compounds of the present invention, and the results are represented in FIG. 1.

As can be seen from FIG. 1, in the control group treated only with thapsigargin without treatment with the test compound, glucose uptake was decreased compared to the negative control group, but when thapsigargin and the compound of the present invention were treated, glucose intake was improved to the level of the negative control group, and this effect was confirmed to be equal to or greater than that of HET-0016.

Experiment Example 2-2: Fat Accumulation Improvement Effect

After culturing HepG2 cells, a human liver cell line, in a high glucose DMEM (Dulbecco's modified Eagle's medium) containing 10% fetal bovine serum (FBS), an experiment was carried out to measure fat accumulation in the following way.

First, HepG2 cells were dispensed into a 96-well plate (black, clear bottom culture plate) at $5\times10^3$ cells/well and incubated in a 37° C., 5% $CO_2$ incubator for 24 hours. Thapsigargin (1 μM, Thap) and the compounds (5 μM) synthesized in the above Examples were treated together and reacted in the 37° C., 5% $CO_2$ incubator for 24 hours. After that, 4% paraformaldehyde was added and reacted at room temperature for 15 minutes for fixation, and then Nile-Red solution was added, light was blocked, and reaction was carried out at 37° C. for 10 minutes. After the reaction time was over, fluorescence was measured using a microplate reader (Excitation: 530 nm, Emission: 635 nm), and then the fluorescence values from each well were compared to evaluate the degree of effect of improving fat accumulation by the compounds of the present invention, and the results are represented in FIG. 2.

As can be seen from FIG. 2, it was confirmed that a large amount of fat was accumulated in the control cells treated with thapsigargin without the test compound as compared to the negative control group. In contrast, in the test group treated with the compounds of the present invention, it can be known that the accumulation of fat in the liver cells was reduced to HET-0016 or more.

Experimental Example 2-3: Active Oxygen Scavenging Capacity

After culturing HepG2 cells, a human liver cell line, in high glucose concentration DMEM (Dulbecco's modified Eagle's medium) containing 10% FBS (fetal bovine serum), an experiment was conducted to measure the active oxygen scavenging capacity in the following way.

First, HepG2 cells were dispensed into a 96-well plate (black, clear bottom culture plate) at $1\times10^4$ cells/well by the above method and incubated in a 37° C., 5% $CO_2$ incubator for 24 hours. Thapsigargin (1 μM, Thap) and the compounds (5 μM) synthesized in the above Examples were treated together and reacted in the 37° C., 5% $CO_2$ incubator for 24 hours. To measure active oxygen, 5 μM H2DCFDA (cell-permeant 2',7'-dichlorodihydrofluorescein diacetate) was added and reacted for 30 minutes in the 37° C., 5% $CO_2$ incubator. Thereafter, after washing with PBS, the 96-well plate was placed in the 37° C., 5% $CO_2$ incubator for 30 minutes to induce luminescent reaction. After measuring the fluorescence with a microplate reader (Excitation: 488 nm, Emission: 508 nm), the fluorescence value from each well was compared to evaluate the degree of active oxygen scavenging capacity by the compound of the present invention, and the results are represented in FIG. 3.

As can be seen from FIG. 3, it was confirmed that the amount of ROS was sharply increased in the control group treated with thapsigargin only compared to the negative control group. In contrast, the group treated with the compounds of the present invention confirmed that the amount of ROS was significantly lowered, and it was confirmed that ROS generation was reduced to a level similar to that of the negative control group.

Based on the above results, it was confirmed that the compounds of the present invention have effects on factors such as promoting glucose uptake in hepatocytes and improving lipid accumulation and oxidative stress under the condition of endoplasmic reticulum stress, which are important causes of metabolic diseases. Specifically, it was confirmed that the compounds of the present invention have the effect of treating/improving diabetes by lowering blood sugar and improving insulin resistance by promoting glucose uptake, and can also be effective in fatty liver disease by improving fat accumulation and oxidative stress in liver cells.

The invention claimed is:

1. A compound of the following Formula (1), or a racemate, a diastereomer, a geometric isomer, a stereoisomer, a tautomer, a hydrate or a pharmaceutically acceptable salt thereof:

[Formula (1)]

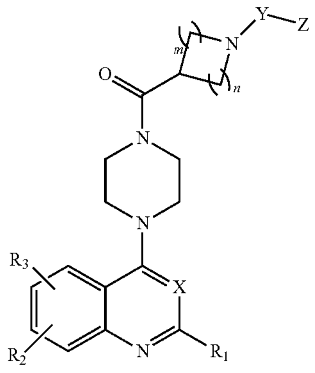

wherein $R_1$ and $R_2$ are each independently hydrogen, hydroxy, halo, amino, alkyl, haloalkyl or alkoxy;

$R_3$ is hydrogen or halo;

X is CH or N;

m and n are each independently an integer of 1 to 3;

Y is —S(═O)$_2$—, —C(═O)—, —S(═O)— or alkylene; wherein the alkylene may be substituted with one or more substituents selected from hydroxy, alkyl and alkoxy; and Z is alkyl, cycloalkyl, aryl or heteroaryl; wherein the alkyl, cycloalkyl, aryl and heteroaryl may be substituted with one or more substituents selected from halo; hydroxy; nitro; amino; alkyl; haloalkyl; hydroxyalkyl; alkylamino; dialkylamino; alkoxy; alkylcarbonyl; aminocarbonyl; carboxy; carboxyamino; carboxyalkyl; alkoxycarbonyl; alkoxyalkyl; aminoalkyl; alkylcarbonylamino; alkylcarbonylalkyl; alkylaminocarbonyl; dialkylaminocarbonyl; alkylaminoalkyl; dialkylaminoalkyl; aminocarbonylalkyl; alkylaminocarbonylalkyl; dialkylaminocarbonylalkyl; aryl unsubstituted or substituted with hydroxy, amino or alkyl; heterocycloalkyl unsubstituted or substituted with hydroxy, amino, alkyl, hydroxyalkyl, alkylcarbonyl or alkylcarbonyloxy; and heteroaryl unsubstituted or substituted with hydroxy or alkyl; and wherein the heteroaryl and heterocycloalkyl have one or more heteroatoms selected from N, O and S;

provided that when m or n is 3, Y is —S(═O)$_2$— and Z is phenyl; X is N.

2. The compound, or a racemate, a diastereomer, a geometric isomer, a stereoisomer, a tautomer, a hydrate or a pharmaceutically acceptable salt thereof according to claim 1, wherein $R_1$ and $R_2$ are each independently hydrogen, hydroxy, halo, amino, $C_1$-$C_7$ alkyl, halo-$C_1$-$C_7$ alkyl or $C_1$-$C_7$ alkoxy;

$R_3$ is hydrogen or halo;

X is CH or N;

m and n are each independently an integer of 1 to 3;

Y is —S(═O)$_2$—, —C(═O)—, —S(═O)— or $C_1$-$C_7$ alkylene; wherein the alkylene may be substituted with 1 to 4 substituents selected from hydroxy, $C_1$-$C_7$ alkyl and $C_1$-$C_7$ alkoxy;

Z is $C_1$-$C_7$ alkyl, $C_3$-$C_{10}$ cycloalkyl, $C_6$-$C_{10}$ aryl or 5- to 10-membered heteroaryl; wherein the alkyl, cycloalkyl, aryl and heteroaryl may be substituted with 1 to 4 substituents selected from halo; hydroxy; nitro; amino; $C_1$-$C_7$ alkyl; halo-$C_1$-$C_7$ alkyl; hydroxy-$C_1$-$C_7$ alkyl; $C_1$-$C_7$ alkylamino; di($C_1$-$C_7$ alkyl)amino; $C_1$-$C_7$ alkoxy; $C_1$-$C_7$ alkylcarbonyl; aminocarbonyl; carboxy; carboxyamino; carboxy-$C_1$-$C_7$ alkyl; $C_1$-$C_7$ alkoxycarbonyl; $C_1$-$C_7$ alkoxy-$C_1$-$C_7$ alkyl; amino-$C_1$-$C_7$ alkyl; $C_1$-$C_7$ alkylcarbonylamino; $C_1$-$C_7$ alkylcarbonyl-$C_1$-$C_7$ alkyl; $C_1$-$C_7$ alkylaminocarbonyl; di($C_1$-$C_7$ alkyl)aminocarbonyl; $C_1$-$C_7$ alkylamino-$C_1$-$C_7$ alkyl; di($C_1$-$C_7$ alkyl)amino-$C_1$-$C_7$ alkyl; aminocarbonyl-$C_1$-$C_7$ alkyl; $C_1$-$C_7$ alkylaminocarbonyl-$C_1$-$C_7$ alkyl; di($C_1$-$C_7$ alkyl)aminocarbonyl-$C_1$-$C_7$ alkyl; $C_6$-$C_{10}$ aryl unsubstituted or substituted with hydroxy, amino or $C_1$-$C_7$ alkyl; 5- to 10-membered heterocycloalkyl unsubstituted or substituted with hydroxy, amino, $C_1$-$C_7$ alkyl, hydroxy-$C_1$-$C_7$ alkyl, $C_1$-$C_7$ alkylcarbonyl or $C_1$-$C_7$ alkylcarbonyloxy; and 5- to 10-membered heteroaryl unsubstituted or substituted with hydroxy or $C_1$-$C_7$ alkyl; and wherein the heteroaryl and heterocycloalkyl have 1 to 4 heteroatoms selected from N, O and S;

provided that when m or n is 3, Y is —S(═O)$_2$— and Z is phenyl; X is N.

3. The compound, or a racemate, a diastereomer, a geometric isomer, a stereoisomer, a tautomer, a hydrate or a pharmaceutically acceptable salt thereof according to claim 1, wherein $R_1$ is hydrogen, halo, $C_1$-$C_5$alkyl or halo-$C_1$-$C_5$ alkyl.

4. The compound, or a racemate, a diastereomer, a geometric isomer, a stereoisomer, a tautomer, a hydrate or a pharmaceutically acceptable salt thereof according to claim 1, wherein $R_2$ is hydrogen, hydroxy, halo, $C_1$-$C_5$ alkyl or $C_1$-$C_5$ alkoxy.

5. The compound, or a racemate, a diastereomer, a geometric isomer, a stereoisomer, a tautomer, a hydrate or a pharmaceutically acceptable salt thereof according to claim 1, wherein Y is —S(═O)$_2$—, —C(═O)—, —S(═O)— or $C_1$-$C_5$ alkylene; wherein the alkylene is unsubstituted or substituted with 1 to 3 substituents selected from hydroxy, $C_1$-$C_5$ alkyl and $C_1$-$C_5$ alkoxy.

6. The compound, or a racemate, a diastereomer, a geometric isomer, a stereoisomer, a tautomer, a hydrate or a pharmaceutically acceptable salt thereof according to claim 1, wherein Z is $C_1$-$C_5$ alkyl, $C_3$-$C_8$ cycloalkyl, $C_6$-$C_{10}$ aryl or 5- to 9-membered heteroaryl; wherein the alkyl, cycloalkyl, aryl and heteroaryl are unsubstituted or substituted with 1 to 3 substituents selected from halo; hydroxy; nitro; amino; $C_1$-$C_5$ alkyl; halo-$C_1$-$C_5$ alkyl; hydroxy-$C_1$-$C_5$ alkyl; $C_1$-$C_5$ alkylamino; di($C_1$-$C_5$ alkyl)amino; $C_1$-$C_5$ alkoxy; $C_1$-$C_5$ alkylcarbonyl; aminocarbonyl; carboxy; carboxyamino; carboxy-$C_1$-$C_5$ alkyl; $C_1$-$C_5$ alkoxycarbonyl; $C_1$-$C_5$ alkoxy-$C_1$-$C_5$ alkyl; amino-$C_1$-$C_5$ alkyl; $C_1$-$C_5$ alkylcarbonylamino; $C_1$-$C_5$ alkylcarbonyl-$C_1$-$C_5$ alkyl; $C_1$-$C_5$ alkylaminocarbonyl; di($C_1$-$C_5$ alkyl)aminocarbonyl; $C_1$-$C_5$ alkylamino-$C_1$-$C_5$ alkyl; di($C_1$-$C_5$ alkyl)amino-$C_1$-$C_5$ alkyl; aminocarbonyl-$C_1$-$C_5$ alkyl; $C_1$-$C_5$ alkylaminocarbonyl-$C_1$-$C_5$ alkyl; di($C_1$-$C_5$ alkyl)aminocarbonyl-$C_1$-$C_5$ alkyl; $C_6$-$C_{10}$ aryl unsubstituted or substituted with hydroxy, amino or $C_1$-$C_5$ alkyl; 5- to 9-membered heterocycloalkyl unsubstituted or substituted with hydroxy, amino, $C_1$-$C_5$ alkyl, hydroxy-$C_1$-$C_5$ alkyl, $C_1$-$C_5$ alkylcarbonyl or $C_1$-$C_5$ alkylcarbonyloxy; and 5- to 9-membered heteroaryl unsubstituted or substituted with hydroxy or $C_1$-$C_5$ alkyl; and wherein the heteroaryl and heterocycloalkyl have 1 to 3 heteroatoms selected from N, O and S.

7. The compound, or a racemate, a diastereomer, a geometric isomer, a stereoisomer, a tautomer, a hydrate or a pharmaceutically acceptable salt thereof according to claim 6, wherein the aryl is phenyl; and the heteroaryl is selected from imidazolyl, triazolyl, tetrazolyl, pyrazolyl, pyridinyl, thienyl, oxazolyl, isoxazolyl, thiazolyl, furyl and pyrimidinyl.

8. The compound, or a racemate, a diastereomer, a geometric isomer, a stereoisomer, a tautomer, a hydrate or a pharmaceutically acceptable salt thereof according to claim 1, wherein the compound of Formula (1) is selected from the group consisting of:

N-(4-((3-(4-(7-fluoroquinolin-4-yl) piperazine-1-carbonyl) pyrrolidin-1-yl)sulfonyl)phenyl)acetamide;
(R)—N-(4-((3-(4-(7-fluoroquinolin-4-yl) piperazine-1-carbonyl) pyrrolidin-1-yl)sulfonyl)phenyl)acetamide;
(1-((4-(dimethylamino)phenyl) sulfonyl) pyrrolidin-3-yl) (4-(7-fluoroquinolin-4-yl) piperazin-1-yl) methanone;
(4-(7-fluoroquinolin-4-yl) piperazin-1-yl) (1-((4-hydroxyphenyl) sulfonyl) pyrrolidin-3-yl) methanone;
(4-(7-fluoroquinolin-4-yl) piperazin-1-yl) (1-((1-methyl-1H-imidazol-2-yl) sulfonyl) pyrrolidin-3-yl) methanone;
(R)-(4-(7-fluoroquinolin-4-yl) piperazin-1-yl) (1-((1-methyl-1H-imidazol-2-yl) sulfonyl) pyrrolidin-3-yl) methanone;
(S)-(4-(7-fluoroquinolin-4-yl) piperazin-1-yl) (1-((1-methyl-1H-imidazol-2-yl) sulfonyl) pyrrolidin-3-yl) methanone;
(4-(7-fluoroquinolin-4-yl) piperazin-1-yl) (1-((4-nitrophenyl) sulfonyl) pyrrolidin-3-yl) methanone;
N-(3-((3-(4-(7-fluoroquinolin-4-yl) piperazine-1-carbonyl) pyrrolidin-1-yl)sulfonyl)phenyl)acetamide;
(1-((1H-1,2,4-triazol-5-yl) sulfonyl) pyrrolidin-3-yl) (4-(7-fluoroquinolin-4-yl) piperazin-1-yl) methanone;
(1-((3,5-dimethyl-1H-pyrazol-4-yl) sulfonyl) pyrrolidin-3-yl) (4-(7-fluoroquinolin-4-yl) piperazin-1-yl) methanone;
(4-(7-fluoroquinolin-4-yl) piperazin-1-yl) (1-((1,3,5-trimethyl-1H-pyrazol-4-yl) sulfonyl) pyrrolidin-3-yl) methanone;
(1-((1H-imidazol-2-yl) sulfonyl) pyrrolidin-3-yl) (4-(7-fluoroquinolin-4-yl) piperazin-1-yl) methanone;
(4-(7-fluoroquinolin-4-yl) piperazin-1-yl) (1-((1-methyl-1H-imidazol-5-yl) sulfonyl) pyrrolidin-3-yl) methanone;
(4-(7-fluoroquinolin-4-yl) piperazin-1-yl) (1-((4-(oxazol-5-yl)phenyl) sulfonyl) pyrrolidin-3-yl) methanone;
(1-((4-bromophenyl) sulfonyl) pyrrolidin-3-yl) (4-(7-fluoroquinolin-4-yl) piperazin-1-yl) methanone;
(4-(7-fluoroquinolin-4-yl) piperazin-1-yl) (1-((4-(pyridin-4-yl)phenyl) sulfonyl) pyrrolidin-3-yl) methanone;
(R)-(4-(7-fluoroquinolin-4-yl) piperazin-1-yl) (1-((4-(pyridin-4-yl)phenyl) sulfonyl) pyrrolidin-3-yl) methanone;
(S)-(1-((1H-1,2,4-triazol-5-yl) sulfonyl) pyrrolidin-3-yl) (4-(7-fluoroquinolin-4-yl) piperazin-1-yl) methanone;
(1-((5-(tert-butyl)-4/-1,2,4-triazol-3-yl) sulfonyl) pyrrolidin-3-yl) (4-(7-fluoroquinolin-4-yl) piperazin-1-yl) methanone;
N-(4-((3-(4-(quinolin-4-yl) piperazine-1-carbonyl) pyrrolidin-1-yl)sulfonyl)phenyl)acetamide;
(R)—N-(4-((3-(4-(quinolin-4-yl) piperazine-1-carbonyl) pyrrolidin-1-yl)sulfonyl)phenyl)acetamide;
(S)—N-(4-((3-(4-(quinolin-4-yl) piperazine-1-carbonyl) pyrrolidin-1-yl)sulfonyl)phenyl)acetamide;
(1-((6-chloropyridin-3-yl) sulfonyl) pyrrolidin-3-yl) (4-(quinolin-4-yl) piperazin-1-yl) methanone;
(1-((6-phenylpyridin-3-yl) sulfonyl) pyrrolidin-3-yl) (4-(quinolin-4-yl) piperazin-1-yl) methanone;
(1-([2,4'-bipyridin]-5-ylsulfonyl) pyrrolidin-3-yl) (4-(quinolin-4-yl) piperazin-1-yl) methanone;
(1-((6-(3-hydroxyphenyl)pyridin-3-yl) sulfonyl) pyrrolidin-3-yl) (4-(quinolin-4-yl) piperazin-1-yl) methanone;
(1-((6-(4-hydroxyphenyl)pyridin-3-yl) sulfonyl) pyrrolidin-3-yl) (4-(quinolin-4-yl) piperazin-1-yl) methanone;
(1-([2,3'-bipyridin]-5-ylsulfonyl) pyrrolidin-3-yl) (4-(quinolin-4-yl) piperazin-1-yl) methanone;
N-(5-((3-(4-(quinolin-4-yl) piperazine-1-carbonyl) pyrrolidin-1-yl) sulfonyl)pyridin-2-yl) acetamide;
(1-((4-bromophenyl) sulfonyl) pyrrolidin-3-yl) (4-(quinolin-4-yl) piperazin-1-yl) methanone;
(1-((4-(pyridin-3-yl)phenyl) sulfonyl) pyrrolidin-3-yl) (4-(quinolin-4-yl) piperazin-1-yl) methanone;
(1-((4-(2-methylpyrimidin-5-yl)phenyl) sulfonyl) pyrrolidin-3-yl) (4-(quinolin-4-yl) piperazin-1-yl) methanone;
(1-((4-(6-hydroxypyridin-3-yl)phenyl) sulfonyl) pyrrolidin-3-yl) (4-(quinolin-4-yl) piperazin-1-yl) methanone;
(1-((4-morpholinophenyl) sulfonyl) pyrrolidin-3-yl) (4-(quinolin-4-yl) piperazin-1-yl) methanone;
(4-(quinolin-4-yl) piperazin-1-yl) (1-(thiophen-2-ylsulfonyl) pyrrolidin-3-yl) methanone;
(1-((5-methylthiophen-2-yl) sulfonyl) pyrrolidin-3-yl) (4-(quinolin-4-yl) piperazin-1-yl) methanone;
(4-(quinolin-4-yl) piperazin-1-yl) (1-((1,3,5-trimethyl-1H-pyrazol-4-yl) sulfonyl) pyrrolidin-3-yl) methanone;
(1-((3,5-dimethylisoxazol-4-yl) sulfonyl) pyrrolidin-3-yl) (4-(quinolin-4-yl) piperazin-1-yl) methanone;
(1-((2,4-dimethylthiazol-5-yl) sulfonyl) pyrrolidin-3-yl) (4-(quinolin-4-yl) piperazin-1-yl) methanone;
(4-(quinolin-4-yl) piperazin-1-yl) (1-((5-(trifluoromethyl) pyridin-2-yl) sulfonyl) pyrrolidin-3-yl) methanone;
(1-((1H-imidazol-2-yl) sulfonyl) pyrrolidin-3-yl) (4-(quinolin-4-yl) piperazin-1-yl) methanone;
(1-((1H-1,2,4-triazol-5-yl) sulfonyl) pyrrolidin-3-yl) (4-(quinolin-4-yl) piperazin-1-yl) methanone;
(1-((1-methyl-1H-pyrazol-4-yl) sulfonyl) pyrrolidin-3-yl) (4-(quinolin-4-yl) piperazin-1-yl) methanone;
(1-((3,5-dimethyl-1H-pyrazol-4-yl) sulfonyl) pyrrolidin-3-yl) (4-(quinolin-4-yl) piperazin-1-yl) methanone;
(1-((1-methyl-1H-imidazol-4-yl) sulfonyl) pyrrolidin-3-yl) (4-(quinolin-4-yl) piperazin-1-yl) methanone;

N-(4-methyl-5-((3-(4-(quinolin-4-yl) piperazine-1-carbonyl) pyrrolidin-1-yl) sulfonyl) thiazol-2-yl) acetamide;

(R)—N-(4-methyl-5-((3-(4-(quinolin-4-yl) piperazine-1-carbonyl) pyrrolidin-1-yl) sulfonyl) thiazol-2-yl) acetamide;

(S)—N-(4-methyl-5-((3-(4-(quinolin-4-yl) piperazine-1-carbonyl) pyrrolidin-1-yl) sulfonyl) thiazol-2-yl) acetamide;

methyl 3-((3-(4-(quinolin-4-yl) piperazine-1-carbonyl) pyrrolidin-1-yl) sulfonyl)thiophene-2-carboxylate;

(1-((6-methoxypyridin-3-yl) sulfonyl) pyrrolidin-3-yl) (4-(quinolin-4-yl) piperazin-1-yl) methanone;

(1-((6-fluoropyridin-2-yl) sulfonyl) pyrrolidin-3-yl) (4-(quinolin-4-yl) piperazin-1-yl) methanone;

(4-(7-fluoroquinolin-4-yl) piperazin-1-yl) (1-(4-nitrobenzyl) pyrrolidin-3-yl) methanone;

(4-(7-fluoroquinolin-4-yl) piperazin-1-yl) (1-((4-nitrophenyl) sulfonyl) piperidin-4-yl) methanone;

N-(3-((4-(4-(7-fluoroquinolin-4-yl) piperazine-1-carbonyl) piperidin-1-yl)sulfonyl)phenyl)acetamide;

(1-((4-bromophenyl) sulfonyl) piperidin-4-yl) (4-(7-fluoroquinolin-4-yl) piperazin-1-yl) methanone;

(4-(7-fluoroquinolin-4-yl) piperazin-1-yl) (1-((4-(pyridin-4-yl)phenyl) sulfonyl) piperidin-4-yl) methanone;

(4-(7-fluoroquinolin-4-yl) piperazin-1-yl) (1-((4-(pyridin-3-yl)phenyl) sulfonyl) piperidin-4-yl) methanone;

(1-((6-chloropyridin-3-yl) sulfonyl) piperidin-3-yl) (4-(7-fluoroquinolin-4-yl) piperazin-1-yl) methanone;

N-(5-((3-(4-(7-fluoroquinolin-4-yl) piperazine-1-carbonyl) piperidin-1-yl) sulfonyl)pyridin-2-yl) acetamide;

(4-(7-fluoroquinolin-4-yl) piperazin-1-yl) (1-((6-morpholinopyridin-3-yl) sulfonyl) piperidin-3-yl) methanone;

(4-(7-fluoroquinolin-4-yl) piperazin-1-yl) (1-((6-(4-methylpiperazin-1-yl) pyridin-3-yl) sulfonyl) piperidin-3-yl) methanone;

(1-((4-bromophenyl) sulfonyl) piperidin-4-yl) (4-(quinolin-4-yl) piperazin-1-yl) methanone;

(1-((4-(pyridin-4-yl)phenyl) sulfonyl) piperidin-4-yl) (4-(quinolin-4-yl) piperazin-1-yl) methanone;

N-(4-((3-(4-(7-fluoroquinolin-4-yl) piperazine-1-carbonyl) azetidin-1-yl)sulfonyl)phenyl)acetamide;

(4-(7-fluoroquinolin-4-yl) piperazin-1-yl) (1-((4-hydroxyphenyl) sulfonyl) azetidin-3-yl) methanone;

(4-(7-fluoroquinolin-4-yl) piperazin-1-yl) (1-((4-nitrophenyl) sulfonyl) azetidin-3-yl) methanone;

(1-((4-bromophenyl) sulfonyl) azetidin-3-yl) (4-(7-fluoroquinolin-4-yl) piperazin-1-yl) methanone;

(4-(7-fluoroquinolin-4-yl) piperazin-1-yl) (1-((4-(pyridin-4-yl)phenyl) sulfonyl) azetidin-3-yl) methanone;

N-(4-((3-(4-(quinolin-4-yl) piperazine-1-carbonyl) azetidin-1-yl)sulfonyl)phenyl)acetamide;

(4-(7-fluoroquinolin-4-yl) piperazin-1-yl) (1-((3-nitrophenyl) sulfonyl) azetidin-3-yl) methanone;

(1-((3-aminophenyl) sulfonyl) azetidin-3-yl) (4-(7-fluoroquinolin-4-yl) piperazin-1-yl) methanone;

N-(3-((3-(4-(7-fluoroquinolin-4-yl) piperazine-1-carbonyl) azetidin-1-yl)sulfonyl)phenyl)acetamide;

N-(4-((3-(4-(quinazolin-4-yl) piperazine-1-carbonyl) piperidin-1-yl)sulfonyl)phenyl)acetamide;

(4-(quinazolin-4-yl) piperazin-1-yl) (1-tosylpiperidin-3-yl) methanone;

(1-((4-fluorophenyl) sulfonyl) piperidin-3-yl) (4-(quinazolin-4-yl) piperazin-1-yl) methanone;

1-((4-(dimethylamino)phenyl) sulfonyl) piperidin-3-yl) (4-(quinazolin-4-yl) piperazin-1-yl) methanone;

(1-((4-hydroxyphenyl) sulfonyl) piperidin-3-yl) (4-(quinazolin-4-yl) piperazin-1-yl) methanone;

N-(4-(3-(1-(2-methylquinazolin-4-yl) piperazine-4-carbonyl) piperidin-1-ylsulfonyl)phenyl) acetamide;

(4-(2-methylquinazolin-4-yl) piperazin-1-yl) (1-tosylpiperidin-3-yl) methanone;

(1-(4-fluorophenylsulfonyl) piperidin-3-yl) (4-(2-methylquinazolin-4-yl) piperazin-1-yl) methanone;

(1-(4-(dimethylamino)phenylsulfonyl) piperidin-3-yl) (4-(2-methylquinazolin-4-yl) piperazin-1-yl) methanone;

N-(4-(3-(1-(7-chloroquinolin-4-yl) piperazine-4-carbonyl) piperidine-1-carbonyl)phenyl) acetamide;

(4-(7-chloroquinolin-4-yl) piperazin-1-yl) (1-(4-fluorophenylcarbonyl) piperidin-3-yl) methanone;

(4-(7-chloroquinolin-4-yl) piperazin-1-yl) (1-(phenylcarbonyl) piperidin-3-yl) methanone;

(4-(7-chloroquinolin-4-yl) piperazin-1-yl) (1-(cyclohexylcarbonyl) piperidin-3-yl) methanone;

(4-(7-chloroquinolin-4-yl) piperazin-1-yl) (1-(pyridine-4-ylcarbonyl) piperidin-3-yl) methanone;

(4-(7-chloroquinolin-4-yl) piperazin-1-yl) (1-(4-methoxyphenylcarbonyl) piperidin-3-yl) methanone;

N-(4-(3-(4-(7-methoxyquinolin-4-yl) piperazine-1-carbonyl) piperidine-1-carbonyl)phenyl) acetamide;

(1-(4-fluorobenzoyl) piperidin-3-yl) (4-(7-methoxyquinolin-4-yl) piperazin-1-yl) methanone;

(1-benzoylpiperidin-3-yl) (4-(7-methoxyquinolin-4-yl) piperazin-1-yl) methanone;

(4-(7-methoxyquinolin-4-yl) piperazin-1-yl) (1-(cyclohexylcarbonyl) piperidin-3-yl) methanone;

(4-(7-methoxyquinolin-4-yl) piperazin-1-yl) (1-(pyridine-4-ylcarbonyl) piperidin-3-yl) methanone;

(4-(7-methoxyquinolin-4-yl) piperazin-1-yl) (1-(4-methoxyphenylcarbonyl) piperidin-3-yl) methanone;

N-(4-(3-(1-(2-(trifluoromethyl) quinolin-4-yl) piperazine-4-carbonyl) piperidine-1-carbonyl)phenyl) acetamide;

(1-(4-fluorobenzoyl) piperidin-3-yl) (4-(2-(trifluoromethyl) quinolin-4-yl) piperazin-1-yl) methanone;

(1-(cyclohexylcarbonyl) piperidin-3-yl) (4-(2-(trifluoromethyl) quinolin-4-yl) piperazin-1-yl) methanone;

(1-isonicotinoylpiperidin-3-yl) (4-(2-(trifluoromethyl) quinolin-4-yl) piperazin-1-yl) methanone;

(1-(4-methoxybenzoyl) piperidin-3-yl) (4-(2-(trifluoromethyl) quinolin-4-yl) piperazin-1-yl) methanone;

N-(4-(3-(1-(2-methylquinolin-4-yl) piperazine-4-carbonyl) piperidine-1-carbonyl)phenyl) acetamide;

(1-(4-fluorobenzoyl) piperidin-3-yl) (4-(2-methylquinolin-4-yl) piperazin-1-yl) methanone;

(1-benzoylpiperidin-3-yl) (4-(2-methylquinolin-4-yl) piperazin-1-yl) methanone;

(1-(cyclohexylcarbonyl) piperidin-3-yl) (4-(2-methylquinolin-4-yl) piperazin-1-yl) methanone;

(1-isonicotinoylpiperidin-3-yl) (4-(2-methylquinolin-4-yl) piperazin-1-yl) methanone;

N-(4-(3-(4-(7-fluoroquinolin-4-yl) piperazine-1-carbonyl) piperidine-1-carbonyl)phenyl) acetamide;

(1-(4-fluorobenzoyl) piperidin-3-yl) (4-(7-fluoroquinolin-4-yl) piperazin-1-yl) methanone;

(1-benzoylpiperidin-3-yl) (4-(7-fluoroquinolin-4-yl) piperazin-1-yl) methanone;

(1-(cyclohexylcarbonyl) piperidin-3-yl) (4-(7-fluoroquinolin-4-yl) piperazin-1-yl) methanone;

(4-(7-fluoroquinolin-4-yl) piperazin-1-yl) (1-isonicotinoylpiperidin-3-yl) methanone;

(4-(7-fluoroquinolin-4-yl) piperazin-1-yl) (1-(4-methoxybenzoyl) piperidin-3-yl) methanone;

N-(4-(3-(1-(quinolin-4-yl) piperazine-4-carbonyl) piperidine-1-carbonyl)phenyl) acetamide;
(1-(4-fluorophenylcarbonyl) piperidin-3-yl) (4-(quinolin-4-yl) piperazin-1-yl) methanone;
(1-benzoylpiperidin-3-yl) (4-(quinolin-4-yl) piperazin-1-yl) methanone;
(1-(cyclohexylcarbonyl) piperidin-3-yl) (4-(quinolin-4-yl) piperazin-1-yl) methanone;
(1-isonicotinoylpiperidin-3-yl) (4-(quinolin-4-yl) piperazin-1-yl) methanone;
(1-(4-methoxyphenylcarbonyl) piperidin-3-yl) (4-(quinolin-4-yl) piperazin-1-yl) methanone;
(1-(cyclohexylsulfonyl) piperidin-3-yl) (4-(7-fluoroquinolin-4-yl) piperazin-1-yl) methanone;
(4-(7-fluoroquinolin-4-yl) piperazin-1-yl) (1-(1-methyl-1H-imidazol-2-ylsulfonyl) piperidin-3-yl) methanone;
(1-(cyclopropylsulfonyl) piperidin-3-yl) (4-(7-fluoroquinolin-4-yl) piperazin-1-yl) methanone;
(1-(1-methyl-1H-imidazol-2-ylsulfonyl) piperidin-3-yl) (4-(quinolin-4-yl) piperazin-1-yl) methanone;
(1-(cyclohexylsulfonyl) piperidin-3-yl) (4-(quinolin-4-yl) piperazin-1-yl) methanone;
(1-(cyclopropylsulfonyl) piperidin-3-yl) (4-(quinolin-4-yl) piperazin-1-yl) methanone;
(4-(7-chloroquinolin-4-yl) piperazin-1-yl) (1-(furan-2-ylsulfonyl) piperidin-3-yl) methanone;
(4-(7-chloroquinolin-4-yl) piperazin-1-yl) (1-(pyridin-4-ylsulfonyl) piperidin-3-yl) methanone;
(4-(2-methylquinolin-4-yl) piperazin-1-yl) (1-(pyridin-3-ylsulfonyl) piperidin-3-yl) methanone;
(4-(2-methylquinolin-4-yl) piperazin-1-yl) (1-(pyridin-4-ylsulfonyl) piperidin-3-yl) methanone;
(4-(2-methylquinolin-4-yl) piperazin-1-yl) (1-(thiophen-2-ylsulfonyl) piperidin-3-yl) methanone;
(1-(pyridin-4-ylsulfonyl) piperidin-3-yl) (4-(2-(trifluoromethyl) quinolin-4-yl) piperazin-1-yl) methanone;
(1-(pyridin-3-ylsulfonyl) piperidin-3-yl) (4-(2-(trifluoromethyl) quinolin-4-yl) piperazin-1-yl) methanone;
methyl 3-((3-(4-(7-fluoroquinolin-4-yl) piperazine-1-carbonyl) piperidin-1-yl) sulfonyl) propanoate;
(4-(7-fluoroquinolin-4-yl) piperazin-1-yl) (1-((3-hydroxypropyl) sulfonyl) piperidin-3-yl) methanone;
methyl 3-((3-(4-(quinolin-4-yl) piperazine-1-carbonyl) piperidin-1-yl) sulfonyl) propanoate;
(1-((3-hydroxypropyl) sulfonyl) piperidin-3-yl) (4-(quinolin-4-yl) piperazin-1-yl) methanone;
(R)-(1-((1H-1,2,4-triazol-5-yl) sulfonyl) pyrrolidin-3-yl) (4-(7-fluoroquinolin-4-yl) piperazin-1-yl) methanone;
(1-((1H-1,2,4-triazol-5-yl) sulfonyl) piperidin-4-yl) (4-(7-fluoroquinolin-4-yl) piperazin-1-yl) methanone;
(S)-(1-((1H-1,2,4-triazol-5-yl) sulfonyl) pyrrolidin-3-yl) (4-(6-fluoroquinolin-4-yl) piperazin-1-yl) methanone;
(1-((1H-1,2,4-triazol-5-yl) sulfonyl) azetidin-3-yl) (4-(7-fluoroquinolin-4-yl) piperazin-1-yl) methanone;
(S)-(1-((1H-1,2,4-triazol-5-yl) sulfonyl) pyrrolidin-3-yl) (4-(8-fluoroquinolin-4-yl) piperazin-1-yl) methanone;
(S)-(4-(7-fluoroquinolin-4-yl) piperazin-1-yl) (1-((1-methyl-1H-1,2,4-triazol-3-yl) sulfonyl) pyrrolidin-3-yl) methanone;
(S)-(4-(7-fluoroquinolin-4-yl) piperazin-1-yl) (1-((1-(2-hydroxyethyl)-1H-1,2,4-triazol-3-yl) sulfonyl) pyrrolidin-3-yl) methanone;
(S)-(4-(7-fluoroquinolin-4-yl) piperazin-1-yl) (1-((1-isopropyl)-1H-1,2,4-triazol-3-yl) sulfonyl) pyrrolidin-3-yl) methanone;
(S)-1-(3-((3-(4-(7-fluoroquinolin-4-yl) piperazine-1-carbonyl) pyrrolidin-1-yl) sulfonyl)-1H-1,2,4-triazol-1-yl) propan-2-one;
(S)-(4-(7-fluoroquinolin-4-yl) piperazin-1-yl) (1-((1-(2-methoxyethyl)-1H-1,2,4-triazol-3-yl) sulfonyl) pyrrolidin-3-yl) methanone;
(S)-(1-((1-(2-aminoethyl)-1H-1,2,4-triazol-3-yl) sulfonyl) pyrrolidin-3-yl) (4-(7-fluoroquinolin-4-yl) piperazin-1-yl) methanone;
(S)-(4-(7-fluoroquinolin-4-yl) piperazin-1-yl) (1-((1-(2-hydroxyethyl)-1H-1,2,4-triazol-5-yl) sulfonyl) pyrrolidin-3-yl) methanone;
(S)-(1-((1H-imidazol-2-yl) sulfonyl) pyrrolidin-3-yl) (4-(7-fluoroquinolin-4-yl) piperazin-1-yl) methanone;
(R)-(1-((1H-imidazol-2-yl) sulfonyl) pyrrolidin-3-yl) (4-(7-fluoroquinolin-4-yl) piperazin-1-yl) methanone;
(S)-(4-(7-fluoroquinolin-4-yl) piperazin-1-yl) (1-((1-(2-hydroxyethyl)-1H-imidazol-2-yl) sulfonyl) pyrrolidin-3-yl) methanone;
(S)-(4-(7-fluoroquinolin-4-yl) piperazin-1-yl) (1-((1-(2-methoxyethyl)-1H-imidazol-2-yl) sulfonyl) pyrrolidin-3-yl) methanone;
(S)-(1-((1-(2-aminoethyl)-1H-imidazol-2-yl) sulfonyl) pyrrolidin-3-yl) (4-(7-fluoroquinolin-4-yl) piperazin-1-yl) methanone;
(S)-(4-(quinolin-4-yl) piperazin-1-yl) (1-((1,3,5-trimethyl-1H-pyrazol-4-yl) sulfonyl) pyrrolidin-3-yl) methanone;
(R)-(4-(quinolin-4-yl) piperazin-1-yl) (1-((1,3,5-trimethyl-1H-pyrazol-4-yl) sulfonyl) pyrrolidin-3-yl) methanone;
(1-(4-nitrobenzyl) pyrrolidin-3-yl) (4-(quinolin-4-yl) piperazin-1-yl) methanone;
(S)-(4-(7-fluoroquinolin-4-yl) piperazin-1-yl) (1-((4-methyl-4H-1,2,4-triazol-3-yl)methyl) pyrrolidin-3-yl) methanone;
(1-((1H-tetrazol-5-yl)methyl) pyrrolidin-3-yl) (4-(7-fluoroquinolin-4-yl) piperazin-1-yl) methanone;
(S)-(4-(7-fluoroquinolin-4-yl) piperazin-1-yl) (1-(pyridin-3-ylsulfonyl) pyrrolidin-3-yl) methanone;
(S)-(4-(7-fluoroquinolin-4-yl) piperazin-1-yl) (1-(pyridin-2-ylsulfonyl) pyrrolidin-3-yl) methanone;
(S)-(4-(7-fluoroquinolin-4-yl) piperazin-1-yl) (1-((4-nitrophenyl) sulfonyl) pyrrolidin-3-yl) methanone;
(S)-(1-((1H-imidazol-2-yl) sulfonyl) pyrrolidin-3-yl) (4-(6-fluoroquinolin-4-yl) piperazin-1-yl) methanone;
(S)-(4-(6-fluoroquinolin-4-yl) piperazin-1-yl) (1-((1-(2-hydroxyethyl)-1H-imidazol-2-yl) sulfonyl) pyrrolidin-3-yl) methanone;
(S)-(1-(4H-1,2,4-triazole-3-carbonyl) pyrrolidin-3-yl) (4-(7-fluoroquinolin-4-yl) piperazin-1-yl) methanone;
(S)-(1-(2H-tetrazole-5-carbonyl) pyrrolidin-3-yl) (4-(7-fluoroquinolin-4-yl) piperazin-1-yl) methanone;
(S)-(1-((1H-1,2,4-triazol-5-yl) sulfonyl) pyrrolidin-3-yl) (4-(7-methylquinolin-4-yl) piperazin-1-yl) methanone;
(S)-(1-((1H-1,2,4-triazol-5-yl) sulfonyl) pyrrolidin-3-yl) (4-(7-hydroxyquinolin-4-yl) piperazin-1-yl) methanone;
(S)-(1-((1H-1,2,4-triazol-5-yl) sulfonyl) pyrrolidin-3-yl) (4-(7-methoxyquinolin-4-yl) piperazin-1-yl) methanone;
(S)-(4-(7-fluoroquinolin-4-yl) piperazin-1-yl) (1-((5-methyl-1H-1,2,4-triazol-3-yl) sulfonyl) pyrrolidin-3-yl) methanone;
(S)-(1-((1H-1,2,4-triazol-5-yl) sulfonyl) pyrrolidin-3-yl) (4-(2-(trifluoromethyl) quinolin-4-yl) piperazin-1-yl) methanone;

(S)-(1-((1H-1,2,4-triazol-5-yl) sulfonyl) pyrrolidin-3-yl) (4-(6,7-difluoroquinolin-4-yl) piperazin-1-yl) methanone; and (S)-(1-((1H-imidazol-2-yl) sulfonyl) pyrrolidin-3-yl) (4-(6,7-difluoroquinolin-4-yl) piperazin-1-yl) methanone.

9. A pharmaceutical composition for the prevention or treatment of metabolic disease comprising a compound of Formula (1), or a racemate, a diastereomer, a geometric isomer, a stereoisomer, a tautomer, a hydrate or a pharmaceutically acceptable salt thereof as defined in claim 1 as an active ingredient, together with a pharmaceutically acceptable carrier.

10. The pharmaceutical composition according to claim 9, wherein the metabolic disease is diabetes or fatty liver disease.

11. The pharmaceutical composition according to claim 10, wherein the diabetes is type 2 diabetes.

12. The pharmaceutical composition according to claim 10, wherein the diabetes is derived from obesity.

13. The pharmaceutical composition according to claim 10, wherein the fatty liver disease is selected from the group consisting of fatty liver, steatohepatitis and fatty liver-associated liver cirrhosis.

* * * * *